(12) United States Patent
Tesar

(10) Patent No.: US 10,702,353 B2
(45) Date of Patent: Jul. 7, 2020

(54) SURGICAL VISUALIZATIONS SYSTEMS AND DISPLAYS

(71) Applicant: CAMPLEX, INC., Germantown, TN (US)

(72) Inventor: John Tesar, Tucson, AZ (US)

(73) Assignee: CAMPLEX, INC., Germantown, TN (US)

( * ) Notice: Subject to any disclaimer, the term of this patent is extended or adjusted under 35 U.S.C. 154(b) by 0 days.

(21) Appl. No.: 14/960,276

(22) Filed: Dec. 4, 2015

(65) Prior Publication Data

US 2016/0220324 A1 Aug. 4, 2016

Related U.S. Application Data

(60) Provisional application No. 62/088,470, filed on Dec. 5, 2014, provisional application No. 62/098,297, filed
(Continued)

(51) Int. Cl.
*A61B 90/00* (2016.01)
*H04N 5/232* (2006.01)
(Continued)

(52) U.S. Cl.
CPC .......... *A61B 90/361* (2016.02); *A61B 90/20* (2016.02); *A61B 90/25* (2016.02);
(Continued)

(58) Field of Classification Search
CPC .............. A61B 2576/00; A61B 90/361; G02B 21/0012; H04N 5/23293
See application file for complete search history.

(56) References Cited

U.S. PATENT DOCUMENTS

| 497,064 A | 5/1893 | Van Meter |
|---|---|---|
| 2,826,114 A | 3/1958 | Bryan |

(Continued)

FOREIGN PATENT DOCUMENTS

| CN | 2336380 Y | 9/1999 |
|---|---|---|
| CN | 101518438 | 9/2009 |

(Continued)

OTHER PUBLICATIONS

"Portion", Definition, American Heritage® Dictionary of the English Language, Fifth Edition, 2016, Retrieved Apr. 12, 2018 from https://www.thefreedictionary.com/portion in 1 page.
(Continued)

*Primary Examiner* — Mainul Hasan
(74) *Attorney, Agent, or Firm* — Knobbe, Martens, Olson & Bear, LLP

(57) ABSTRACT

A medical apparatus is configured to provide visualization of a surgical site. The medical apparatus includes an electronic display disposed within a display housing. The medical apparatus includes a display optical system disposed within the display housing, the display optical system comprising a plurality of lens elements disposed along an optical path. The display optical system is configured to receive images from the electronic display. The medical apparatus can include proximal cameras mounted on a frame, the cameras configured to provide a view of a surgical site from outside the surgical site. The display housing can have a height that is larger than its depth.

31 Claims, 54 Drawing Sheets

Related U.S. Application Data on Dec. 30, 2014, provisional application No. 62/099,422, filed on Jan. 2, 2015, provisional application No. 62/260,220, filed on Nov. 25, 2015, provisional application No. 62/183,148, filed on Jun. 22, 2015, provisional application No. 62/184,222, filed on Jun. 24, 2015, provisional application No. 62/184,838, filed on Jun. 25, 2015, provisional application No. 62/187,796, filed on Jul. 1, 2015.

(51) Int. Cl.
*A61B 90/25* (2016.01)
*H04N 7/18* (2006.01)
*G02B 21/00* (2006.01)
*A61B 90/20* (2016.01)
*A61B 90/50* (2016.01)
*A61B 34/20* (2016.01)

(52) U.S. Cl.
CPC ..... *G02B 21/0012* (2013.01); *H04N 5/23293* (2013.01); *H04N 7/183* (2013.01); *A61B 90/50* (2016.02); *A61B 2034/2048* (2016.02); *A61B 2034/2055* (2016.02); *A61B 2090/365* (2016.02); *A61B 2090/371* (2016.02); *A61B 2090/373* (2016.02); *A61B 2090/3933* (2016.02); *A61B 2090/3941* (2016.02); *A61B 2090/502* (2016.02); *A61B 2576/00* (2013.01)

(56) References Cited

U.S. PATENT DOCUMENTS

| | | |
|---|---|---|
| 3,050,870 A | 8/1962 | Heilig |
| 3,108,781 A | 10/1963 | Saffir |
| 3,128,988 A | 4/1964 | Mandroian |
| 3,141,650 A | 7/1964 | Saffir |
| 3,405,990 A | 10/1968 | Nothnagle et al. |
| 3,409,346 A | 11/1968 | Stapsy |
| 3,664,330 A | 5/1972 | Deutsch |
| 4,056,310 A | 11/1977 | Shimizu et al. |
| 4,063,557 A | 12/1977 | Wuchinich et al. |
| 4,087,198 A | 5/1978 | Theis, Jr. |
| 4,167,302 A | 9/1979 | Karasawa |
| 4,176,453 A | 12/1979 | Abbott |
| 4,223,676 A | 9/1980 | Wuchinich et al. |
| 4,226,228 A | 10/1980 | Shin et al. |
| 4,344,746 A | 8/1982 | Leonard |
| 4,354,734 A | 10/1982 | Nkahashi |
| 4,395,731 A | 7/1983 | Schoolman |
| 4,562,832 A | 1/1986 | Wilder et al. |
| 4,651,201 A | 3/1987 | Schoolman |
| 4,655,557 A | 4/1987 | Takahashi |
| 4,665,391 A | 5/1987 | Spani |
| 4,684,224 A | 8/1987 | Yamashita et al. |
| 4,703,314 A | 10/1987 | Spani |
| 4,750,488 A | 6/1988 | Wuchinich et al. |
| 4,750,902 A | 6/1988 | Wuchinich et al. |
| 4,779,968 A | 10/1988 | Sander |
| 4,783,156 A | 11/1988 | Yokota |
| 4,786,155 A | 11/1988 | Fantone et al. |
| 4,813,927 A | 3/1989 | Morris et al. |
| 4,873,572 A | 10/1989 | Miyazaki et al. |
| 4,900,301 A | 2/1990 | Morris et al. |
| 4,905,670 A | 3/1990 | Adair |
| 4,920,336 A | 4/1990 | Meijer |
| 4,922,902 A | 5/1990 | Wuchinich et al. |
| 4,986,622 A | 1/1991 | Martinez |
| 4,989,452 A | 2/1991 | Toon et al. |
| 5,032,111 A | 7/1991 | Morris et al. |
| 5,047,009 A | 9/1991 | Morris et al. |
| 5,098,426 A | 3/1992 | Sklar et al. |
| 5,143,054 A | 9/1992 | Adair |
| 5,151,821 A | 9/1992 | Marks |
| 5,176,677 A | 1/1993 | Wuchinich et al. |
| 5,201,325 A | 4/1993 | McEwen et al. |
| 5,221,282 A | 6/1993 | Wuchinich |
| 5,251,613 A | 10/1993 | Adair |
| 5,327,283 A | 7/1994 | Zobel |
| 5,354,314 A | 10/1994 | Hardy et al. |
| 5,417,210 A | 5/1995 | Funda |
| 5,441,059 A | 8/1995 | Dannan |
| 5,464,008 A | 11/1995 | Kim |
| 5,523,810 A | 6/1996 | Volk |
| 5,537,164 A | 7/1996 | Smith |
| 5,553,995 A | 9/1996 | Martinez |
| 5,575,789 A | 11/1996 | Bell et al. |
| 5,584,796 A | 12/1996 | Cohen |
| 5,593,402 A | 1/1997 | Patrick |
| 5,601,549 A * | 2/1997 | Miyagi ............. A61B 1/00193 606/4 |
| 5,625,493 A | 4/1997 | Matsumura et al. |
| 5,634,790 A | 6/1997 | Pathmanabhan et al. |
| 5,667,481 A | 9/1997 | Villalta et al. |
| 5,697,891 A | 12/1997 | Hori |
| 5,712,995 A | 1/1998 | Cohn |
| 5,716,326 A | 2/1998 | Dannan |
| 5,743,731 A | 4/1998 | Lares et al. |
| 5,743,846 A | 4/1998 | Takahashi et al. |
| 5,747,824 A | 5/1998 | Jung et al. |
| 5,751,341 A | 5/1998 | Chaleki |
| 5,797,403 A | 8/1998 | DiLorenzo |
| 5,803,733 A | 9/1998 | Trott et al. |
| 5,822,036 A | 10/1998 | Massie et al. |
| 5,825,534 A | 10/1998 | Strahle |
| 5,835,266 A * | 11/1998 | Kitajima ................ G02B 7/001 359/384 |
| 5,841,510 A | 11/1998 | Roggy |
| 5,861,983 A | 1/1999 | Twisselman |
| 5,889,611 A | 3/1999 | Zonneveld |
| 5,897,491 A | 4/1999 | Kastenbauer et al. |
| 5,909,380 A | 6/1999 | Dubois |
| 5,913,818 A | 6/1999 | Co et al. |
| 5,928,139 A | 7/1999 | Koros et al. |
| 5,949,388 A | 9/1999 | Atsumi |
| 5,982,532 A | 11/1999 | Mittelstadt et al. |
| 6,016,607 A | 1/2000 | Morimoto et al. |
| 6,023,638 A | 2/2000 | Swanson |
| 6,088,154 A | 7/2000 | Morita |
| 6,139,493 A | 10/2000 | Koros et al. |
| 6,152,736 A | 11/2000 | Schmidinger |
| 6,152,871 A | 11/2000 | Foley et al. |
| 6,176,825 B1 | 1/2001 | Chin et al. |
| 6,217,188 B1 | 4/2001 | Wainwright et al. |
| 6,246,898 B1 | 6/2001 | Vesely et al. |
| 6,293,911 B1 | 9/2001 | Imaizumi et al. |
| 6,317,260 B1 | 11/2001 | Ito |
| 6,319,223 B1 | 11/2001 | Wortrich et al. |
| 6,340,363 B1 | 1/2002 | Bolger et al. |
| 6,350,235 B1 | 2/2002 | Cohen et al. |
| 6,354,992 B1 | 3/2002 | Kato |
| 6,398,721 B1 | 6/2002 | Nakamura |
| 6,405,072 B1 | 6/2002 | Cosman |
| 6,434,329 B1 | 8/2002 | Dube et al. |
| 6,443,594 B1 | 9/2002 | Marshall et al. |
| 6,450,706 B1 | 9/2002 | Chapman |
| 6,450,950 B2 | 9/2002 | Irion |
| 6,491,661 B1 | 12/2002 | Boukhny et al. |
| 6,508,759 B1 * | 1/2003 | Taylor ................ A61B 1/00149 359/381 |
| 6,517,207 B2 | 2/2003 | Chapman |
| 6,525,310 B2 | 2/2003 | Dunfield |
| 6,525,878 B1 | 2/2003 | Takahashi |
| 6,527,704 B1 | 3/2003 | Chang et al. |
| 6,538,665 B2 | 3/2003 | Crow et al. |
| 6,549,341 B2 | 4/2003 | Nomura et al. |
| 6,561,999 B1 | 5/2003 | Nazarifar et al. |
| 6,582,358 B2 | 6/2003 | Akui et al. |
| 6,587,711 B1 | 7/2003 | Alfano et al. |
| 6,589,168 B2 | 7/2003 | Thompson |
| 6,618,207 B2 | 9/2003 | Lei |
| 6,626,445 B2 | 9/2003 | Murphy et al. |
| 6,633,328 B1 | 10/2003 | Byrd et al. |
| 6,635,010 B1 | 10/2003 | Lederer |

(56) References Cited

U.S. PATENT DOCUMENTS

| | | |
|---|---|---|
| 6,636,254 B1 | 10/2003 | Onishi et al. |
| 6,661,571 B1 | 12/2003 | Shioda et al. |
| 6,668,841 B1 | 12/2003 | Chou |
| 6,698,886 B2 | 3/2004 | Pollack et al. |
| 6,720,988 B1 | 4/2004 | Gere et al. |
| 6,757,021 B1 | 6/2004 | Nguyen-Nhu |
| 6,805,127 B1 | 10/2004 | Karasic |
| 6,817,975 B1 | 11/2004 | Farr et al. |
| 6,824,525 B2 | 11/2004 | Nazarifar et al. |
| 6,847,336 B1 | 1/2005 | Lemelson et al. |
| 6,869,398 B2 | 3/2005 | Obenchain et al. |
| 6,873,867 B2 | 3/2005 | Vilsmeier |
| 6,892,597 B2 | 5/2005 | Tews |
| 6,903,883 B2 | 6/2005 | Amanai |
| 6,908,451 B2 | 6/2005 | Brody et al. |
| 6,985,765 B2 | 1/2006 | Morita |
| 6,996,460 B1 | 2/2006 | Krahnstoever et al. |
| 7,034,983 B2 | 4/2006 | Desimone et al. |
| 7,050,225 B2 | 5/2006 | Nakamura |
| 7,050,245 B2 | 5/2006 | Tesar et al. |
| 7,054,076 B2 | 5/2006 | Tesar et al. |
| 7,116,437 B2 | 10/2006 | Weinstein et al. |
| 7,125,119 B2 | 10/2006 | Farberov |
| 7,150,713 B2 | 12/2006 | Shener et al. |
| 7,150,714 B2 | 12/2006 | Myles |
| 7,154,527 B1 | 12/2006 | Goldstein et al. |
| 7,155,316 B2 | 12/2006 | Sutherland |
| 7,163,543 B2 | 1/2007 | Smedley et al. |
| 7,226,451 B2 | 6/2007 | Shluzas et al. |
| 7,244,240 B2 | 7/2007 | Nazarifar et al. |
| 7,278,092 B2 | 10/2007 | Krzanowski |
| 7,298,393 B2 | 11/2007 | Morita |
| 7,306,559 B2 | 12/2007 | Williams |
| 7,307,799 B2 | 12/2007 | Minefuji |
| 7,326,183 B2 | 2/2008 | Nazarifar et al. |
| 7,471,301 B2 | 12/2008 | Lefevre |
| 7,480,872 B1 | 1/2009 | Ubillos |
| 7,494,463 B2 | 2/2009 | Nehls |
| 7,518,791 B2 | 4/2009 | Sander |
| 7,537,565 B2 | 5/2009 | Bass |
| 7,538,939 B2 | 5/2009 | Zimmerman et al. |
| 7,559,887 B2 | 7/2009 | Dannan |
| 7,621,868 B2 | 11/2009 | Breidenthal et al. |
| 7,633,676 B2 | 12/2009 | Brunner et al. |
| 7,644,889 B2 | 1/2010 | Johnson |
| 7,651,465 B1 | 1/2010 | Sperling et al. |
| 7,713,237 B2 | 5/2010 | Nazarifar et al. |
| 7,764,370 B2 | 7/2010 | Williams et al. |
| 7,766,480 B1 | 8/2010 | Graham et al. |
| 7,777,941 B2 | 8/2010 | Zimmer |
| 7,785,253 B1 | 8/2010 | Arambula |
| 7,786,457 B2 | 8/2010 | Gao |
| 7,806,865 B1 | 10/2010 | Wilson |
| 7,844,320 B2 | 11/2010 | Shahidi |
| 7,872,746 B2 | 1/2011 | Gao et al. |
| 7,874,982 B2 | 1/2011 | Selover et al. |
| 7,896,839 B2 | 3/2011 | Nazarifar et al. |
| 7,907,336 B2 | 3/2011 | Abele et al. |
| 7,927,272 B2 | 4/2011 | Bayer et al. |
| 7,932,925 B2 | 4/2011 | Inbar et al. |
| 7,956,341 B2 | 6/2011 | Gao |
| 8,009,141 B1 | 8/2011 | Chi et al. |
| 8,012,089 B2 | 9/2011 | Bayat |
| 8,018,523 B2 | 9/2011 | Choi |
| 8,018,579 B1 | 9/2011 | Krah |
| 8,027,710 B1 | 9/2011 | Dannan |
| 8,038,612 B2 | 10/2011 | Paz |
| 8,070,290 B2 | 12/2011 | Gille et al. |
| 8,088,066 B2 | 1/2012 | Grey et al. |
| 8,136,779 B2 | 3/2012 | Wilson et al. |
| 8,149,270 B1 | 4/2012 | Yaron et al. |
| 8,159,743 B2 | 4/2012 | Abele et al. |
| 8,169,468 B2 | 5/2012 | Scott et al. |
| 8,187,167 B2 | 5/2012 | Kim |
| 8,187,180 B2 | 5/2012 | Pacey |
| 8,194,121 B2 | 6/2012 | Blumzvig et al. |
| 8,221,304 B2 | 7/2012 | Shioda et al. |
| 8,229,548 B2 | 7/2012 | Frangioni |
| 8,294,733 B2 | 10/2012 | Eino |
| 8,295,693 B2 | 10/2012 | McDowall |
| 8,358,330 B2 | 1/2013 | Riederer |
| 8,405,733 B2 | 3/2013 | Saijo |
| 8,408,772 B2 | 4/2013 | Li |
| 8,409,088 B2 | 4/2013 | Grey et al. |
| 8,419,633 B2 | 4/2013 | Koshikawa et al. |
| 8,419,634 B2 | 4/2013 | Nearmann et al. |
| 8,430,840 B2 | 4/2013 | Nazarifar et al. |
| 8,439,830 B2 | 5/2013 | McKinley et al. |
| 8,460,184 B2 | 6/2013 | Nearman et al. |
| 8,464,177 B2 | 6/2013 | Ben-Yoseph et al. |
| 8,482,606 B2 | 7/2013 | Razzaque |
| 8,498,695 B2 | 7/2013 | Westwick et al. |
| 8,521,331 B2 | 8/2013 | Itkowitz |
| 8,702,592 B2 | 4/2014 | Langlois et al. |
| 8,702,602 B2 | 4/2014 | Berci et al. |
| 8,734,328 B2 | 5/2014 | McDowall |
| 8,786,946 B2 | 7/2014 | Nakamura |
| 8,827,899 B2 | 9/2014 | Farr et al. |
| 8,827,902 B2 | 9/2014 | Dietze, Jr. et al. |
| 8,836,723 B2 | 9/2014 | Tsao et al. |
| 8,858,425 B2 | 10/2014 | Farr et al. |
| 8,876,711 B2 | 11/2014 | Lin et al. |
| 8,878,924 B2 | 11/2014 | Farr |
| 8,882,662 B2 | 11/2014 | Charles |
| 8,976,238 B2 | 3/2015 | Ernsperger et al. |
| 8,979,301 B2 | 3/2015 | Moore |
| 9,033,870 B2 | 5/2015 | Farr et al. |
| 9,216,068 B2 | 12/2015 | Tesar |
| 9,492,065 B2 | 11/2016 | Tesar et al. |
| 9,615,728 B2 | 4/2017 | Charles et al. |
| 9,629,523 B2 | 4/2017 | Tesar et al. |
| 9,642,606 B2 | 5/2017 | Charles et al. |
| 9,681,796 B2 | 6/2017 | Tesar et al. |
| 9,723,976 B2 | 8/2017 | Tesar |
| 9,782,159 B2 | 10/2017 | Tesar |
| 9,936,863 B2 | 4/2018 | Tesar |
| 10,022,041 B2 | 7/2018 | Charles et al. |
| 10,028,651 B2 | 7/2018 | Tesar |
| 10,231,607 B2 | 3/2019 | Charles et al. |
| 2001/0055062 A1 | 12/2001 | Shioda et al. |
| 2002/0013514 A1 | 1/2002 | Brau |
| 2002/0049367 A1 | 4/2002 | Irion et al. |
| 2002/0065461 A1 | 5/2002 | Cosman |
| 2002/0082498 A1 | 6/2002 | Wendt et al. |
| 2003/0055410 A1 | 3/2003 | Evans et al. |
| 2003/0059097 A1 | 3/2003 | Abovitz et al. |
| 2003/0078494 A1 | 4/2003 | Panescu et al. |
| 2003/0088179 A1 | 5/2003 | Seeley et al. |
| 2003/0102819 A1 | 6/2003 | Min et al. |
| 2003/0103191 A1 | 6/2003 | Staurenghi et al. |
| 2003/0142204 A1 | 7/2003 | Rus et al. |
| 2003/0147254 A1 | 8/2003 | Yoneda et al. |
| 2004/0017607 A1 | 1/2004 | Hauger et al. |
| 2004/0027652 A1 | 2/2004 | Erdogan et al. |
| 2004/0036962 A1* | 2/2004 | Brunner ............ G02B 21/0012 359/368 |
| 2004/0070822 A1 | 4/2004 | Shioda et al. |
| 2004/0087833 A1 | 5/2004 | Bauer et al. |
| 2004/0111183 A1 | 6/2004 | Sutherland |
| 2004/0196553 A1 | 10/2004 | Banju et al. |
| 2004/0230191 A1 | 11/2004 | Frey et al. |
| 2005/0018280 A1 | 1/2005 | Richardson |
| 2005/0019722 A1 | 1/2005 | Schmid et al. |
| 2005/0026104 A1 | 2/2005 | Takahashi |
| 2005/0031192 A1 | 2/2005 | Sieckmann |
| 2005/0033117 A1 | 2/2005 | Ozaki et al. |
| 2005/0052527 A1 | 3/2005 | Remy et al. |
| 2005/0063047 A1 | 3/2005 | Obrebski et al. |
| 2005/0064936 A1 | 3/2005 | Pryor |
| 2005/0065435 A1 | 3/2005 | Rauch et al. |
| 2005/0095554 A1 | 5/2005 | Wilkinson |
| 2005/0107808 A1 | 5/2005 | Evans et al. |
| 2005/0171551 A1 | 8/2005 | Sukovich et al. |
| 2005/0215866 A1 | 9/2005 | Kim |

(56) References Cited

U.S. PATENT DOCUMENTS

| | | |
|---|---|---|
| 2005/0228232 A1 | 10/2005 | Gillinov et al. |
| 2005/0279355 A1 | 12/2005 | Loubser |
| 2006/0004261 A1 | 1/2006 | Douglas |
| 2006/0020213 A1 | 1/2006 | Whitman et al. |
| 2006/0025656 A1 | 2/2006 | Buckner et al. |
| 2006/0069315 A1 | 3/2006 | Miles et al. |
| 2006/0069316 A1 | 3/2006 | Dorfman et al. |
| 2006/0085969 A1 | 4/2006 | Bennett et al. |
| 2006/0092178 A1 | 5/2006 | Tanguya, Jr. et al. |
| 2006/0114411 A1 | 6/2006 | Wei et al. |
| 2006/0129140 A1 | 6/2006 | Todd et al. |
| 2006/0152516 A1 | 7/2006 | Plummer |
| 2006/0235279 A1 | 10/2006 | Hawkes et al. |
| 2006/0236264 A1 | 10/2006 | Cain et al. |
| 2006/0241499 A1 | 10/2006 | Irion et al. |
| 2006/0276693 A1 | 12/2006 | Pacey |
| 2006/0293557 A1 | 12/2006 | Chuanggui et al. |
| 2007/0010716 A1 | 1/2007 | Malandain |
| 2007/0019916 A1 | 1/2007 | Takami |
| 2007/0038080 A1 | 2/2007 | Salisbury, Jr. et al. |
| 2007/0086205 A1 | 4/2007 | Krupa et al. |
| 2007/0129719 A1 | 6/2007 | Kendale et al. |
| 2007/0153541 A1 | 7/2007 | Bennett et al. |
| 2007/0173853 A1 | 7/2007 | MacMillan |
| 2007/0238932 A1 | 10/2007 | Jones et al. |
| 2007/0282171 A1 | 12/2007 | Karpowicz et al. |
| 2008/0015417 A1 | 1/2008 | Hawkes et al. |
| 2008/0058606 A1 | 3/2008 | Miles et al. |
| 2008/0081947 A1 | 4/2008 | Irion et al. |
| 2008/0091066 A1 | 4/2008 | Sholev |
| 2008/0094583 A1 | 4/2008 | Williams et al. |
| 2008/0096165 A1 | 4/2008 | Virnicchi et al. |
| 2008/0097467 A1 | 4/2008 | Gruber et al. |
| 2008/0123183 A1 | 5/2008 | Awdeh |
| 2008/0151041 A1 | 6/2008 | Shafer et al. |
| 2008/0183038 A1 | 7/2008 | Tilson et al. |
| 2008/0195128 A1 | 8/2008 | Orbay et al. |
| 2008/0221394 A1 | 9/2008 | Melkent et al. |
| 2008/0221591 A1 | 9/2008 | Farritor et al. |
| 2008/0266840 A1 | 10/2008 | Nordmeyer et al. |
| 2008/0269564 A1 | 10/2008 | Gelnett |
| 2008/0269730 A1 | 10/2008 | Dotson |
| 2008/0278571 A1 | 11/2008 | Mora |
| 2008/0300465 A1 | 12/2008 | Feigenwinter et al. |
| 2008/0303899 A1 | 12/2008 | Berci |
| 2008/0310181 A1 | 12/2008 | Gurevich et al. |
| 2008/0319266 A1 | 12/2008 | Poll et al. |
| 2009/0030436 A1 | 1/2009 | Charles |
| 2009/0034286 A1 | 2/2009 | Krupa et al. |
| 2009/0040783 A1 | 2/2009 | Krupa et al. |
| 2009/0105543 A1 | 4/2009 | Miller et al. |
| 2009/0137893 A1 | 5/2009 | Seibel et al. |
| 2009/0137989 A1 | 5/2009 | Kataoka |
| 2009/0149716 A1 | 6/2009 | Diao et al. |
| 2009/0156902 A1 | 6/2009 | Dewey et al. |
| 2009/0185392 A1 | 7/2009 | Krupa et al. |
| 2009/0190209 A1 | 7/2009 | Nakamura |
| 2009/0190371 A1 | 7/2009 | Root et al. |
| 2009/0209826 A1 | 8/2009 | Sanders et al. |
| 2009/0238442 A1 | 9/2009 | Upham et al. |
| 2009/0244259 A1 | 10/2009 | Kojima et al. |
| 2009/0245600 A1 | 10/2009 | Hoffman et al. |
| 2009/0248036 A1* | 10/2009 | Hoffman ............ A61B 1/045 606/130 |
| 2009/0258638 A1 | 10/2009 | Lee |
| 2009/0304582 A1 | 12/2009 | Rousso et al. |
| 2009/0318756 A1 | 12/2009 | Fisher et al. |
| 2009/0326322 A1 | 12/2009 | Diolaiti |
| 2009/0326331 A1 | 12/2009 | Rosen |
| 2010/0013910 A1 | 1/2010 | Farr |
| 2010/0013971 A1 | 1/2010 | Amano |
| 2010/0081919 A1 | 4/2010 | Hyde et al. |
| 2010/0107118 A1 | 4/2010 | Pearce |
| 2010/0128350 A1 | 5/2010 | Findlay et al. |
| 2010/0161129 A1 | 6/2010 | Costa et al. |
| 2010/0182340 A1 | 7/2010 | Bachelder et al. |
| 2010/0198014 A1 | 8/2010 | Poll et al. |
| 2010/0198241 A1 | 8/2010 | Gerrah et al. |
| 2010/0208046 A1 | 8/2010 | Takahashi |
| 2010/0245557 A1 | 9/2010 | Luley, III et al. |
| 2010/0249496 A1 | 9/2010 | Cardenas et al. |
| 2010/0286473 A1 | 11/2010 | Roberts |
| 2010/0305409 A1 | 12/2010 | Chang |
| 2010/0312069 A1 | 12/2010 | Sutherland et al. |
| 2010/0318099 A1 | 12/2010 | Itkowitz et al. |
| 2010/0331855 A1 | 12/2010 | Zhao et al. |
| 2011/0034781 A1 | 2/2011 | Loftus |
| 2011/0038040 A1 | 2/2011 | Abele et al. |
| 2011/0042452 A1 | 2/2011 | Cormack |
| 2011/0063734 A1 | 3/2011 | Sakaki |
| 2011/0065999 A1 | 3/2011 | Manzanares |
| 2011/0071359 A1 | 3/2011 | Bonadio et al. |
| 2011/0080536 A1 | 4/2011 | Nakamura et al. |
| 2011/0115882 A1 | 5/2011 | Shahinian et al. |
| 2011/0115891 A1 | 5/2011 | Trusty |
| 2011/0144436 A1 | 6/2011 | Nearman et al. |
| 2011/0178395 A1 | 7/2011 | Miesner et al. |
| 2011/0184243 A1 | 7/2011 | Wright et al. |
| 2011/0190588 A1 | 8/2011 | McKay |
| 2011/0234841 A1 | 9/2011 | Akeley et al. |
| 2011/0249323 A1 | 10/2011 | Tesar et al. |
| 2011/0257488 A1 | 10/2011 | Koyama et al. |
| 2011/0263938 A1 | 10/2011 | Levy |
| 2011/0264078 A1 | 10/2011 | Lipow et al. |
| 2011/0288560 A1 | 11/2011 | Shohat et al. |
| 2011/0298704 A1 | 12/2011 | Krah |
| 2011/0301421 A1 | 12/2011 | Michaeli et al. |
| 2011/0316994 A1 | 12/2011 | Lemchen |
| 2012/0029280 A1 | 2/2012 | Kucklick |
| 2012/0035423 A1 | 2/2012 | Sebastian et al. |
| 2012/0035638 A1 | 2/2012 | Mathaneswaran et al. |
| 2012/0040305 A1 | 2/2012 | Karazivan et al. |
| 2012/0041272 A1 | 2/2012 | Dietze, Jr. et al. |
| 2012/0059222 A1 | 3/2012 | Yoshida |
| 2012/0065468 A1 | 3/2012 | Levy et al. |
| 2012/0087006 A1 | 4/2012 | Signaigo |
| 2012/0088974 A1 | 4/2012 | Maurice |
| 2012/0089093 A1 | 4/2012 | Trusty |
| 2012/0097567 A1 | 4/2012 | Zhao et al. |
| 2012/0108900 A1 | 5/2012 | Viola et al. |
| 2012/0116173 A1 | 5/2012 | Viola |
| 2012/0127573 A1 | 5/2012 | Robinson et al. |
| 2012/0130399 A1 | 5/2012 | Moll et al. |
| 2012/0134028 A1 | 5/2012 | Maruyama |
| 2012/0157775 A1 | 6/2012 | Yamaguchi |
| 2012/0157787 A1 | 6/2012 | Weinstein et al. |
| 2012/0157788 A1 | 6/2012 | Serowski et al. |
| 2012/0158015 A1 | 6/2012 | Fowler et al. |
| 2012/0190925 A1 | 7/2012 | Luiken |
| 2012/0197084 A1 | 8/2012 | Drach et al. |
| 2012/0230668 A1 | 9/2012 | Vogt |
| 2012/0232352 A1 | 9/2012 | Lin et al. |
| 2012/0245432 A1 | 9/2012 | Karpowicz et al. |
| 2012/0265023 A1 | 10/2012 | Berci et al. |
| 2012/0320102 A1 | 12/2012 | Jorgensen |
| 2012/0330129 A1 | 12/2012 | Awdeh |
| 2013/0012770 A1 | 1/2013 | Su |
| 2013/0027516 A1 | 1/2013 | Hart et al. |
| 2013/0041226 A1 | 2/2013 | McDowall |
| 2013/0041368 A1 | 2/2013 | Cunningham et al. |
| 2013/0060095 A1 | 3/2013 | Bouquet |
| 2013/0066304 A1 | 3/2013 | Belson et al. |
| 2013/0072917 A1 | 3/2013 | Kaschke et al. |
| 2013/0077048 A1 | 3/2013 | Mirlay |
| 2013/0085337 A1 | 4/2013 | Hess et al. |
| 2013/0159015 A1 | 6/2013 | O'Con |
| 2013/0197313 A1 | 8/2013 | Wan |
| 2013/0245383 A1 | 9/2013 | Friedrich et al. |
| 2013/0298208 A1 | 11/2013 | Ayed |
| 2013/0331730 A1 | 12/2013 | Fenech et al. |
| 2014/0005484 A1* | 1/2014 | Charles ............ A61B 17/02 600/201 |
| 2014/0005485 A1 | 1/2014 | Tesar et al. |
| 2014/0005486 A1 | 1/2014 | Charles |

(56) References Cited

U.S. PATENT DOCUMENTS

| | | |
|---|---|---|
| 2014/0005488 A1 | 1/2014 | Charles et al. |
| 2014/0005489 A1 | 1/2014 | Charles |
| 2014/0005555 A1 | 1/2014 | Tesar |
| 2014/0081659 A1 | 3/2014 | Nawana et al. |
| 2014/0168785 A1 | 6/2014 | Belgum |
| 2014/0168799 A1 | 6/2014 | Hurbert et al. |
| 2014/0179998 A1 | 6/2014 | Pacey et al. |
| 2014/0187859 A1 | 7/2014 | Leeuw et al. |
| 2014/0198190 A1 | 7/2014 | Okumu |
| 2014/0247482 A1* | 9/2014 | Doi ............... G02B 21/0012 359/363 |
| 2014/0275801 A1 | 9/2014 | Menchaca et al. |
| 2014/0276008 A1 | 9/2014 | Steinbach et al. |
| 2014/0285403 A1 | 9/2014 | Kobayashi |
| 2014/0316209 A1 | 10/2014 | Overes et al. |
| 2014/0327742 A1 | 11/2014 | Kiening et al. |
| 2014/0347395 A1 | 11/2014 | Tsao et al. |
| 2014/0362228 A1 | 12/2014 | McCloskey et al. |
| 2014/0378843 A1 | 12/2014 | Valdes et al. |
| 2015/0018622 A1 | 1/2015 | Tesar |
| 2015/0025324 A1 | 1/2015 | Wan |
| 2015/0080982 A1 | 3/2015 | Van Funderburk |
| 2015/0085095 A1* | 3/2015 | Tesar ............... A61B 90/361 348/77 |
| 2015/0087918 A1 | 3/2015 | Vasan |
| 2015/0094533 A1 | 4/2015 | Kleiner et al. |
| 2015/0112148 A1 | 4/2015 | Bouquet |
| 2015/0141755 A1 | 5/2015 | Tesar |
| 2015/0141759 A1 | 5/2015 | Charles |
| 2015/0238073 A1 | 8/2015 | Charles |
| 2015/0272694 A1 | 10/2015 | Charles |
| 2015/0297311 A1 | 10/2015 | Tesar |
| 2015/0300816 A1 | 10/2015 | Yang et al. |
| 2016/0018598 A1 | 1/2016 | Hansson |
| 2016/0089026 A1* | 3/2016 | Heeren ............... A61B 3/0025 |
| 2016/0100908 A1 | 4/2016 | Tesar |
| 2016/0139039 A1 | 5/2016 | Ikehara et al. |
| 2017/0020627 A1 | 1/2017 | Tesar |
| 2017/0143442 A1 | 5/2017 | Tesar |
| 2018/0055348 A1 | 3/2018 | Tesar et al. |
| 2018/0055502 A1 | 3/2018 | Charles et al. |
| 2018/0064316 A1 | 3/2018 | Charles et al. |
| 2018/0064317 A1 | 3/2018 | Tesar |
| 2018/0070804 A1 | 3/2018 | Tesar |
| 2018/0256145 A1 | 9/2018 | Tesar |
| 2018/0318033 A1 | 11/2018 | Tesar |
| 2018/0353059 A1 | 12/2018 | Tesar |
| 2018/0368656 A1 | 12/2018 | Austin et al. |
| 2019/0046021 A1 | 2/2019 | Charles et al. |
| 2019/0053700 A1 | 2/2019 | Tesar |

FOREIGN PATENT DOCUMENTS

| | | |
|---|---|---|
| CN | 102495463 | 6/2012 |
| CN | 202920720 | 11/2012 |
| DE | 103 41 125 | 4/2005 |
| DE | 10 2010 030 285 | 12/2011 |
| DE | 10 2010 044 502 | 3/2012 |
| EP | 0 293 228 | 11/1988 |
| EP | 0 233 940 | 11/1993 |
| EP | 0 466 705 | 6/1996 |
| EP | 1 175 106 | 1/2002 |
| EP | 1 333 305 | 8/2003 |
| EP | 2 641 561 | 9/2013 |
| JP | 49-009378 | 3/1974 |
| JP | 03-018891 | 1/1991 |
| JP | 06-315487 | 11/1994 |
| JP | 07-261094 | 10/1995 |
| JP | 08-131399 | 5/1996 |
| JP | 2001-087212 | 4/2001 |
| JP | 2001-117049 | 4/2001 |
| JP | 2001-161638 | 6/2001 |
| JP | 2002-011022 | 1/2002 |
| JP | 3402797 | 5/2003 |
| JP | 2003-322803 | 11/2003 |
| JP | 2004-024835 | 1/2004 |
| JP | 3549253 | 8/2004 |
| JP | 2007-068876 | 3/2007 |
| JP | 2009-288296 | 12/2009 |
| JP | 4503748 | 7/2010 |
| JP | 2010-206495 | 9/2010 |
| JP | 2011-118741 | 6/2011 |
| WO | WO 87/001276 | 3/1987 |
| WO | WO 91/012034 | 8/1991 |
| WO | WO 99/017661 | 4/1999 |
| WO | WO 00/078372 | 12/2000 |
| WO | WO 01/072209 | 10/2001 |
| WO | WO 2007/047782 | 4/2007 |
| WO | WO 2008/073243 | 6/2008 |
| WO | WO 2009/051013 | 4/2009 |
| WO | WO 2010/079817 | 7/2010 |
| WO | WO 2010/114843 | 10/2010 |
| WO | WO 2010/123578 | 10/2010 |
| WO | WO 2011/069469 | 6/2011 |
| WO | WO 2012/047962 | 4/2012 |
| WO | WO 2012/078989 | 6/2012 |
| WO | WO 2013/049679 | 4/2013 |
| WO | WO 2013/109966 | 7/2013 |
| WO | WO 2013/116489 | 8/2013 |
| WO | WO 2014/004717 | 1/2014 |
| WO | WO 2014/060412 | 4/2014 |
| WO | WO 2014/189969 | 11/2014 |
| WO | WO 2015/042460 | 3/2015 |
| WO | WO 2015/042483 | 5/2015 |
| WO | WO 2015/100310 | 7/2015 |
| WO | WO 2016/090336 | 6/2016 |
| WO | WO 2016/154589 | 9/2016 |
| WO | WO 2017/091704 | 6/2017 |
| WO | WO 2018/208691 | 11/2018 |
| WO | WO 2018/217951 | 11/2018 |

OTHER PUBLICATIONS

Amendment in U.S. Appl. No. 14/411,068, dated Feb. 16, 2018.
Office Action in U.S. Appl. No. 14/411,068, dated Apr. 6, 2018.
Notice of Decision or Rejection in Japanese Application No. 2015-520471, dated Jul. 24, 2018.
Office Action in U.S. Appl. No. 15/483,995, dated Mar. 9, 2018.
Amendment in U.S. Appl. No. 15/483,995, dated Sep. 7, 2018.
Office Action in U.S. Appl. No. 15/645,589, dated Feb. 9, 2018.
Amendment in U.S. Appl. No. 15/645,589, dated Aug. 7, 2018.
Office Action in U.S. Appl. No. 15/626,516, dated Mar. 14, 2018.
Amendment in U.S. Appl. No. 15/589,058, dated Jun. 7, 2018.
Final Office Action in U.S. Appl. No. 15/589,058, dated Aug. 27, 2018.
Official Communication in European Application No. 14846410.0, dated Jul. 18, 2018.
Official Communication in Japanese Application No. 2016-544032, dated Jun. 26, 2018.
Restriction Requirement and Election of Species Response in U.S. Appl. No. 14/581,779, dated Jan. 2, 2018.
Office Action in U.S. Appl. No. 14/581,779, dated Apr. 24, 2018.
Extended European Search Report in European Application No. 15865454.1, dated Jun. 27, 2018.
Office Action in U.S. Appl. No. 15/081,653, dated Mar. 28, 2018.
Office Action in U.S. Appl. No. 15/360,565, dated Aug. 10, 2018.
International Preliminary Report on Patentability and Written Opinion in PCT Application No. PCT/US2016/063549, dated Jun. 7, 2018.
International Search Report and Written Opinion in PCT Application No. PCT/US2018/034227, dated Jul. 30, 2018.
Preliminary Amendment in U.S. Appl. No. 14/411,068, dated Aug. 13, 2015.
Office Action in U.S. Appl. No. 14/411,068, dated Aug. 17, 2017.
Official Communication in European Application No. 13808996.6, dated Apr. 14, 2016.
Official Communication in European Application No. 13808996.6, dated Feb. 21, 2017.

(56) References Cited

OTHER PUBLICATIONS

Official Communication in European Application No. 13808996.6, dated Jun. 6, 2017.
Official Communication in Japanese Application No. 2015-520471, dated May 9, 2017.
Official Communication in Japanese Application No. 2015-520471, dated Nov. 21, 2017.
Preliminary Amendment in U.S. Appl. No. 15/483,995, dated Nov. 21, 2017.
Response to Final Office Action in U.S. Appl. No. 13/802,635, dated Jul. 13, 2016.
Office Action in U.S. Appl. No. 13/802,635, dated Sep. 27, 2016.
Amendment and Response to Office Action in U.S. Appl. No. 13/802,635, dated Mar. 24, 2017.
Notice of Allowance in U.S. Appl. No. 13/802,635, dated Apr. 27, 2017.
Notice of Allowance in U.S. Appl. No. 13/802,635, dated Aug. 15, 2017.
Amendment in U.S. Appl. No. 15/589,058, dated Nov. 15, 2017.
Office Action in U.S. Appl. No. 15/589,058, dated Dec. 8, 2017.
Office Action in U.S. Appl. No. 13/802,577, dated Sep. 30, 2016.
Response to Office Action in U.S. Appl. No. 13/802,577, dated Mar. 29, 2017.
Notice of Allowance in U.S. Appl. No. 13/802,577, dated Apr. 24, 2017.
Amendment in U.S. Appl. No. 13/802,577, dated May 25, 2017.
Office Action in U.S. Appl. No. 13/802,577, dated Jun. 20, 2017.
Amendment in U.S. Appl. No. 13/802,577, dated Nov. 20, 2017.
Notice of Allowance in U.S. Appl. No. 13/802,577, dated Dec. 6, 2017.
Official Communication in European Application No. 14800423.7, dated Feb. 8, 2017.
Preliminary Amendment in U.S. Appl. No. 14/491,827, dated Nov. 25, 2014.
Office Action in U.S. Appl. No. 14/491,827, dated Mar. 1, 2017.
Amendment in U.S. Appl. No. 14/491,827, dated Aug. 1, 2017.
Notice of Allowance in U.S. Appl. No. 14/491,827, dated Sep. 25, 2017.
Preliminary Amendment in U.S. Appl. No. 14/491,935, dated Feb. 5, 2015.
Restriction Requirement in U.S. Appl. No. 14/491,935, dated Sep. 8, 2017.
Restriction Requirement and Election of Species Response in U.S. Appl. No. 14/491,935, dated Jan. 8, 2018.
Partial Supplementary European Search Report in European Application No. 14845427.5, dated May 4, 2017.
Extended European Search Report in European Application No. 14845427.5, dated Aug. 8, 2017.
European Search Report in European Application No. 14846410.0, dated Jun. 23, 2017.
Preliminary Amendment in U.S. Appl. No. 14/581,779, dated Jul. 6, 2015.
Restriction Requirement in U.S. Appl. No. 14/581,779, dated Oct. 31, 2017.
Extended European Search Report in European Application No. 14873324.9, dated Aug. 25, 2017.
International Preliminary Report on Patentability and Written Opinion in PCT Application No. PCT/US2014/072121, dated Jul. 7, 2016.
International Preliminary Report on Patentability and Written Opinion in PCT Application No. PCT/US2015/064133, dated Jun. 15, 2017.
Preliminary Amendment in U.S. Appl. No. 15/081,653, dated Oct. 11, 2016.
International Search Report and Written Opinion in PCT Application No. PCT/US2016/024330, dated Jul. 1, 2016.
International Preliminary Report on Patentability and Written Opinion in PCT Application No. PCT/US2016/024330, dated Oct. 5, 2017.
Preliminary Amendment in U.S. Appl. No. 15/360,565, dated Feb. 6, 2017.
Invitation to Pay Additional Fees in PCT Application No. PCT/US2016/063549, dated Feb. 2, 2017.
International Search Report and Written Opinion in PCT Application No. PCT/US2016/063549, dated Apr. 14, 2017.
Aesculap Inc.; Aesculap Neurosurgery Pneumatic Kerrison; http://www.aesculapusa.com/assets/base/doc/doc763-pneumatic_kerrison_brochure.pdf; 2008; pp. 12.
Aliaga, Daniel G. "Image Morphing and Warping"; Department of Computer Science; Purdue University; Spring 2010; in 61 pages.
"ARRI Medical Shows SeeFront 3D Display with HD 3D Surgical Microscope"; dated Jun. 9, 2013; downloaded from http://www.seefront.com/news-events/article/arri-medical-shows-seefront-3d-display-with-hd-3d-surgical-microscope/ in 2 pages.
"ARRISCOPE: A New Era in Surgical Microscopy"; Arriscope Brochure published May 20, 2014 in 8 pages.
AustriaMicroSystems; "AS5050: Smallest Magnetic Rotary Encoder for µA Low Power Applications"; www.austriamicrosystems.com/AS5050 printed Nov. 2012 in 2 pages.
Bayonet Lock Video; 00:16 in length; Date Unknown; [Screenshots captured at 00:00, 00:02, 00:05, 00:08, and 00:16].
BellowsTech; "Actuators"; www.bellowstech.com/metal-bellows/actuators/ printed Jul. 17, 2012 in 4 pages.
"Carl Zeiss Unveils $99 VR One Virtual Reality Headset"; www.electronista.com/articles/14/10/10/zeiss.vr.one.able.to.accept.variety.of.smartphones.using.custom.trays printed Oct. 13, 2014 in 2 pages.
Designboom; "Bright LED"; http://www.designboom.com/project/fiber-optics-light-glove/; Sep. 28, 2007.
Fei-Fei, Li; Lecture 10 Multi-View Geometry; Stanford Vision Lab; Oct. 24, 2011; pp. 89.
"Fuse™. Full Spectrum Endoscopy™"; http://www.endochoice.com/Fuse printed Oct. 7, 2013 in 3 pages.
Hardesty, Larry; "3-D Cameras for Cellphones: Clever math could enable a high-quality 3-D camera so simple, cheap and power-efficient that it could be incorporated into handheld devices"; MIT News Office; http://web.mit.edu/newsoffice/2011/lidar-3d-camera-cellphones-0105.html; Jan. 5, 2012; pp. 4.
Hartley et al.; "Multiple View Geometry in Computer Vision: Chapter 9—Epipolar Geometry and the Fundamental Matrix"; http://www.robots.ox.ac.uk/~vgg/hzbook/hzbook2/HZepipolar.pdf; Mar. 2004; 2nd Edition; Ch. 9; pp. 239-261.
Heidelberg Engineering; "MultiColor: Scanning Laser Imaging"; http://www.heidelbergengineering.com/us/products/spectralis-models/imaging-modes/multicolor/; Copyright © 2013; printed Apr. 5, 2013.
Kramer, Jennifer; "The Right Filter Set Gets the Most out of a Microscope"; Biophotonics International; Jan./Feb. 1999; vol. 6; pp. 54-58.
Krishna, Golden; "Watch: What Good is a Screen?"; http://www.cooper.com/author/golden_krishna as printed Jul. 9, 2014 in 62 pages.
Lang et al.; "ZEISS Microscopes for Microsurgery"; Springer-Verlag; Berlin, Heidelberg; 1981.
Leica Microsystems; "Images TrueVision Integrated 3D"; http://www.leica-microsystems.com/products/surgical-microscopes/neurosurgery-spine/details/product/truevision-integrated-3d/gallery/; Nov. 26, 2014; pp. 3.
Leica Microsystems; "Leica Microsystems' Ophthalmic Surgical Microscopes with TrueVision 3D Technology Available Globally"; http://www.leica-microsystems.com/products/surgical-microscopes/neurosurgery-spine/details/product/truevision-integrated-3d/news/; Sep. 18, 2014; pp. 5.
Lutze et al.; "Microsystems Technology for Use in a Minimally Invasive Endoscope Assisted Neurosurgical Operating System—MINOP II"; 2005; http://web.archive.org/web/20151120215151/http://www.meditec.hia.rwth-aachen.de/fileadmin/content/meditec/bilder/forschung/aktuelle_projekte/robotische/Excoscope_Aesculap.pdf; Nov. 20, 2015 in 4 pages.
Male Bayonet Video; 00:04 in length; Date Unknown; [Screenshots captured at 00:00, 00:01, 00:02, 00:03, and 00:04].

(56) References Cited

OTHER PUBLICATIONS

MediTec; "MINOP II—Robotical Microscope Platform"; http://web.archive.org/web/20151120213932/http://www.meditec.hia.rwth-aachen.de/en/research/former-projects/minop-ii/; Nov. 20, 2015 in 3 pages.
Melexis; "MLX75031 Optical Gesture and Proximity Sensing IC"; http://melexis.com/optical-sensors/optical-sensing.mlx75031-815.aspx?sta printed Mar. 15, 2013 in 1 page.
MMR Technologies; "Micro Miniature Refrigerators"; http://www.mmr-tech.com/mmr_overview.php; Copyright © 2011; printed Feb. 11, 2013.
Moog; "Surgical Handpieces: Therapeutic Ultrasonic Devices"; http://www.moog.com/products/surgical-hpieces/ printed Sep. 25, 2013 in 1 page.
Morita; "TwinPower Turbine® High Speed Handpieces Standard, 45°, and Ultra Series Head Designs"; J. Morita Mfg. Corp., http://www.morita.com/usa/root/img/pool/pdf/product_brochures/twinpower_brochure_I-264_0512_web.pdf; May 2012; pp. 20.
"Narrow Band Imaging"; http://web.archive.org/web/20150701233623/https://en.wikipedia.org/wiki/Narrow_band_imaging printed Jul. 1, 2015 in 1 page.
Olympus; "Olympus Introduces the World's First and Only Monopolar, Disposable Tonsil Adenoid Debrider (DTAD)"; http://www.olympusamerica.com/corporate/corp_presscenter_headline.asp?pressNo=926; Sep. 11, 2012; pp. 2.
OmniVision; "OV2722 full HD (1080p) product brief: ⅙-Inch Native 1080p HD CameraChip Sensor for Ultra-Compact Applications"; http://web.archive.org/web/20120730043057/http://www.ovt.com/download_document.php?type=sensor&sensorid=119; May 2012 in 2 pages.
Orthofix; "ProView MAP System Retractors"; www.us.orthofix.com/products/proviewretractors.asp?cid=39; Copyright © 2010; printed Apr. 1, 2013.
OrtusTech; "Sample Shipment Start: World's Smallest Size Full-HD Color TFT LCD"; http://ortustech.co.jp/english/notice/20120427.html printed May 22, 2012 in 2 pages.
Rustum, Dr. Abu; "ICG Mapping Endometrial Cancer"; Pinpoint Endometrium Ca Lenfedenektomi MSKCC May 2013; Memorial Sloan Kettering Cancer Center; May 2013; Published to YouTube.com Sep. 1, 2013, pp. 2, http://web.archive.org/web/20150402210857/https://www.youtube.com/watch?v=DhChvaUCe4I.
Purcher, Jack; "Apple Wins a Patent for an Oculus Rift-Like Display System"; http://www.patentlyapple.com/patently-apple/2014/09/apple-wins-a-patent-for-an-oculus-rift-like-display-system.html; Sep. 9, 2014.
Saab, Mark; "Applications of High-Pressure Balloons in the Medical Device Industry"; http://www.ventionmedical.com/documents/medicalballoonpaper.pdf; Copyright © 1999; pp. 19.
Savage, Lynn; "Sound and Light, Signifying Improved Imaging"; www.photonics.com/Article.aspx?AID=45039; Nov. 1, 2010; pp. 6.
Sun et al.; "Neurotoxin-Directed Synthesis and in Vitro Evaluation of Au Nanoclusters"; RSC Advances, 2015; vol. 5, No. 38; pp. 29647-29652.
Timm, Karl Walter; "Real-Time View Morphing of Video Streams"; University of Illinois; Chicago, Illinois; 2003; pp. 168.
TrueVision Microscopes; http://truevisionmicroscopes.com/images/productsnew/081a-f.jpg; printed Nov. 26, 2014 in 1 page.
TrueVision; "About TrueVision"; http://web.archive.org/web/20071208125103/http://www.truevisionsys.com/about.html; as viewed Dec. 8, 2007 in 2 pages.
TrueVision; "Leica Microsystems and TrueVision® 3D Surgical create the first 3D digital hybrid microscope"; Press Release; Oct. 5, 2012; pp. 2.
TrueVision; "TrueVision Technology"; http://web.archive.org/web/20071208125125/http://www.truevisionsys.com/technology.html; as viewed Dec. 8, 2007 in 2 pages.
Whitney et al.; "Pop-up book MEMS"; Journal of Micromechanics and Microengineering; Oct. 14, 2011; vol. 21; No. 115021; pp. 7.
Wikipedia; "Zoom Lens"; http://en.wikipedia.org/wiki/Optical_Zoom; printed Oct. 7, 2014 in 3 pages.
Zeiss. "Informed for Medical Professionals, Focus: Fluorescence"; Carl Zeiss; 2nd Issue; Oct. 2006; 30-801-LBW-GFH-X-2006; Printed in Germany; pp. 32.
Zeiss. "Ophthalmic Surgery in Its Highest Form, OPMI® VISU 210"; Carl Zeiss, 2005, 30-097/III-e/USA Printed in Germany AW-TS-V/2005 Uoo; pp. 19.
Zeiss. "SteREO Discovery. V12, Expanding the Boundaries"; Carl Zeiss, Sep. 2004; 46-0008 e 09.2004, pp. 6.
Zeiss; "Stereomicroscopes Stemi SV 6, SV 11, SV 11 Apo"; The Profile; 1999; pp. 30.
Zeiss. "Time for a Change: OPMI® pico for ENT"; Carl Zeiss, 2005, 30-451/III-e Printed in Germany LBW-TS-V/2005 Uoo, pp. 8.
Zhang, Michael; "LIFX: A WiFi-Enabled LED Bulb that May Revolutionize Photographic Lighting"; http://www.petapixel.com/2012/09/22/lifx-a-wifi-enabled-led-bulb-that-may-revolutionize-photographic-lighting/ printed Sep. 28, 2012 in 9 pages.
Zhang, Sarah; "The Obscure Neuroscience Problem That's Plaguing VR"; http://web.archive.org/web/20150812172934/http://www.wired.com/2015/08/obscure-neuroscience-problem-thats-plaguing-vr/; Aug. 11, 2015 in 5 pages.
Restriction Requirement in U.S. Appl. No. 13/802,362, dated Oct. 23, 2013.
Office Action in U.S. Appl. No. 13/802,362, dated Dec. 17, 2013.
Final Office Action in U.S. Appl. No. 13/802,362, dated Apr. 7, 2014.
Office Action in U.S. Appl. No. 13/802,362, dated Jan. 27, 2015.
Final Office Action in U.S. Appl. No. 13/802,362, dated Jul. 21, 2015.
Notice of Allowance in U.S. Appl. No. 13/802,362, dated Mar. 11, 2016.
Official Communication in European Application No. 13808996.6, dated Jan. 4, 2016.
International Search Report and Written Opinion in PCT Application No. PCT/US2013/047972, dated Jan. 3, 2014.
International Preliminary Report on Patentability in PCT Application No. PCT/US2013/047972, dated Jan. 8, 2015.
Office Action in U.S. Appl. No. 13/802,162, dated Feb. 12, 2015.
Final Office Action in U.S. Appl. No. 13/802,162, dated Sep. 1, 2015.
Office Action in U.S. Appl. No. 13/802,485, dated Jun. 20, 2014.
Notice of Allowance in U.S. Appl. No. 13/802,485, dated Apr. 14, 2015.
Notice of Allowance in U.S. Appl. No. 13/802,485, dated Aug. 19, 2015.
Office Action in U.S. Appl. No. 14/975,490, dated Feb. 26, 2016.
Restriction Requirement in U.S. Appl. No. 13/802,635, dated May 28, 2014.
Office Action in U.S. Appl. No. 13/802,635, dated Mar. 27, 2015.
Final Office Action in U.S. Appl. No. 13/802,635, dated Jan. 14, 2016.
Office Action in U.S. Appl. No. 13/802,509, dated Sep. 9, 2013.
Notice of Allowance in U.S. Appl. No. 13/802,509, dated Apr. 16, 2014.
Notice of Allowance in U.S. Appl. No. 13/802,509, dated Aug. 29, 2014.
Office Action in U.S. Appl. No. 14/537,524, dated Mar. 26, 2015.
Office Action in U.S. Appl. No. 14/537,524, dated Nov. 6, 2015.
Restriction Requirement in U.S. Appl. No. 13/802,582, dated Oct. 23, 2013.
Office Action in U.S. Appl. No. 13/802,582, dated Dec. 16, 2013.
Office Action in U.S. Appl. No. 13/802,582, dated Apr. 16, 2014.
Office Action in U.S. Appl. No. 13/802,582, dated Jan. 29, 2015.
Notice of Allowance in U.S. Appl. No. 13/802,582, dated Nov. 10, 2015.
Notice of Allowance in U.S. Appl. No. 13/802,582, dated Mar. 14, 2016.
Office Action in U.S. Appl. No. 14/215,826, dated Apr. 13, 2016.
International Search Report and Written Opinion in PCT Application No. PCT/US2014/038839, dated Oct. 17, 2014.
International Preliminary Report on Patentability in PCT Application No. PCT/US2014/038839, dated Dec. 3, 2015.

(56) References Cited

OTHER PUBLICATIONS

International Search Report and Written Opinion in PCT Application No. PCT/US2014/056643, dated Dec. 11, 2014.
International Preliminary Report and Written Opinion in PCT Application No. PCT/US2014/056643, dated Mar. 31, 2016.
Invitation to Pay Additional Fees in PCT Application No. PCT/US2014/056681, dated Jan. 14, 2015.
International Search Report and Written Opinion in PCT Application No. PCT/US2014/056681, dated Mar. 20, 2015.
International Preliminary Report and Written Opinion in PCT Application No. PCT/US2014/056681, dated Mar. 31, 2016.
Invitation to Pay Additional Fees in PCT Application No. PCT/US2014/072121, dated Mar. 2, 2015.
International Search Report and Written Opinion in PCT Application No. PCT/US2014/072121, dated May 1, 2015.
International Search Report and Written Opinion in PCT Application No. PCT/US2015/064133, dated Feb. 9, 2016.
Preliminary Amendment in U.S. Appl. No. 16/357,081, dated Sep. 4, 2019.
Official Communication in European Application No. 13808996.6, dated Jun. 15, 2018.
Official Communication in European Application No. 13808996.6, dated May 13, 2019.
Final Office Action in U.S. Appl. No. 15/483,995, dated Nov. 29, 2018.
Amendment in U.S. Appl. No. 15/483,995, dated May 28, 2019.
Office Action in U.S. Appl. No. 15/483,995, dated Jun. 13, 2019.
Final Office Action in U.S. Appl. No. 15/645,589, dated Nov. 28, 2018.
Amendment in U.S. Appl. No. 15/645,589, dated May 28, 2019.
Office Action in U.S. Appl. No. 15/645,589, dated Jun. 13, 2019.
Preliminary Amendment filed in U.S. Appl. No. 16/036,665, dated Nov. 1, 2018.
Preliminary Amendment filed in U.S. Appl. No. 16/036,665, dated Sep. 5, 2019.
Office Action in U.S. Appl. No. 16/036,665, dated Sep. 26, 2019.
Amendment in U.S. Appl. No. 15/626,516, dated Sep. 13, 2018.
Final Office Action in U.S. Appl. No. 15/626,516, dated Jan. 15, 2019.
Response in U.S. Appl. No. 15/626,516, dated Jul. 15, 2019.
Restriction Requirement in U.S. Appl. No. 15/495,484, dated May 14, 2019.
Response to Restriction Requirement in U.S. Appl. No. 15/495,484, dated Nov. 13, 2019.
Office Action in U.S. Appl. No. 15/495,484, dated Nov. 27, 2019.
Amendment in U.S. Appl. No. 15/589,058, dated Feb. 26, 2019.
Office Action in U.S. Appl. No. 15/589,058, dated Mar. 5, 2019.
Amendment in U.S. Appl. No. 15/589,058, dated Sep. 5, 2019.
Notice of Allowance in U.S. Appl. No. 15/589,058, dated Sep. 25, 2019.
Preliminary Amendment filed in U.S. Appl. No. 15/724,100, dated Jun. 5, 2018.
Office Action in U.S. Appl. No. 15/724,100, dated Oct. 9, 2019.
Preliminary Amendment in U.S. Appl. No. 16/042,318, dated Nov. 8, 2018.
Office Action in U.S. Appl. No. 16/042,318, dated May 8, 2019.
Amendment in U.S. Appl. No. 16/042,318, dated Sep. 9, 2019.
Notice of Allowance in U.S. Appl. No. 16/042,318, dated Oct. 9, 2019.
Office Action in U.S. Appl. No. 14/491,935, dated May 13, 2019.
Amendment in U.S. Appl. No. 14/491,935, dated Nov. 13, 2019.
Official Communication in European Application No. 14846410.0, dated Mar. 20, 2019.
Amendment in U.S. Appl. No. 14/581,779, dated Sep. 24, 2018.
Final Office Action in U.S. Appl. No. 14/581,779, dated Jan. 4, 2019.
Amendment in U.S. Appl. No. 14/581,779, dated Jul. 2, 2019.
Office Action in U.S. Appl. No. 14/581,779, dated Aug. 5, 2019.
Official Communication in Japanese Application No. 2016-542194, dated Nov. 6, 2018.
Decision of Rejection in Japanese Application No. 2016-542194, dated May 14, 2019.
Amendment in U.S. Appl. No. 15/081,653, dated Sep. 27, 2018.
Final Office Action in U.S. Appl. No. 15/081,653, dated Nov. 16, 2018.
Final Amendment in U.S. Appl. No. 15/081,653, dated May 15, 2019.
Office Action in U.S. Appl. No. 15/081,653, dated Jul. 12, 2019.
Extended European Search Report in European Application No. 16769809.1, dated Nov. 23, 2018.
Amendment in U.S. Appl. No. 15/360,565, dated Feb. 8, 2019.
Office Action in U.S. Appl. No. 15/360,565, dated May 22, 2019.
Amendment in U.S. Appl. No. 15/360,565, dated Nov. 21, 2019.
Extended European Search Report in European Application No. 16869253.1, dated May 29, 2019.
Office Action in U.S. Appl. No. 15/973,433, dated Jun. 28, 2019.
Amendment in U.S. Appl. No. 15/973,433, dated Sep. 30, 2019.
International Search Report and Written Opinion in PCT Application No. PCT/US2018/031442, dated Sep. 14, 2018.
International Preliminary Report on Patentability and Written Opinion in PCT Application No. PCT/US2018/031442, dated Nov. 21, 2019.
International Preliminary Report on Patentability and Written Opinion in PCT/US2018/034227, dated Dec. 5, 2019.

* cited by examiner

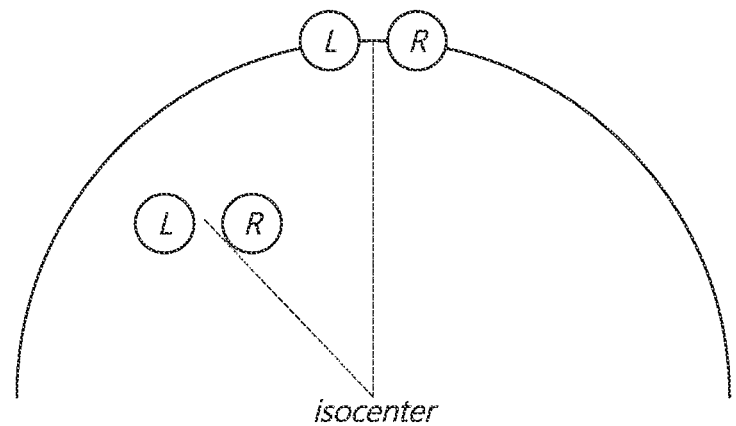
The display provides a horizon consistent with an ergonomically advantageous viewing position for the user. The isocenter is defined as the postion bewtween the two eyes parallel to the display's horizon.
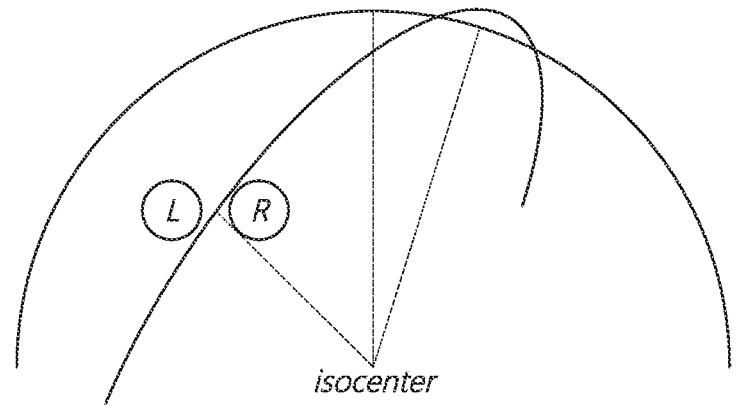
FIG. 3B

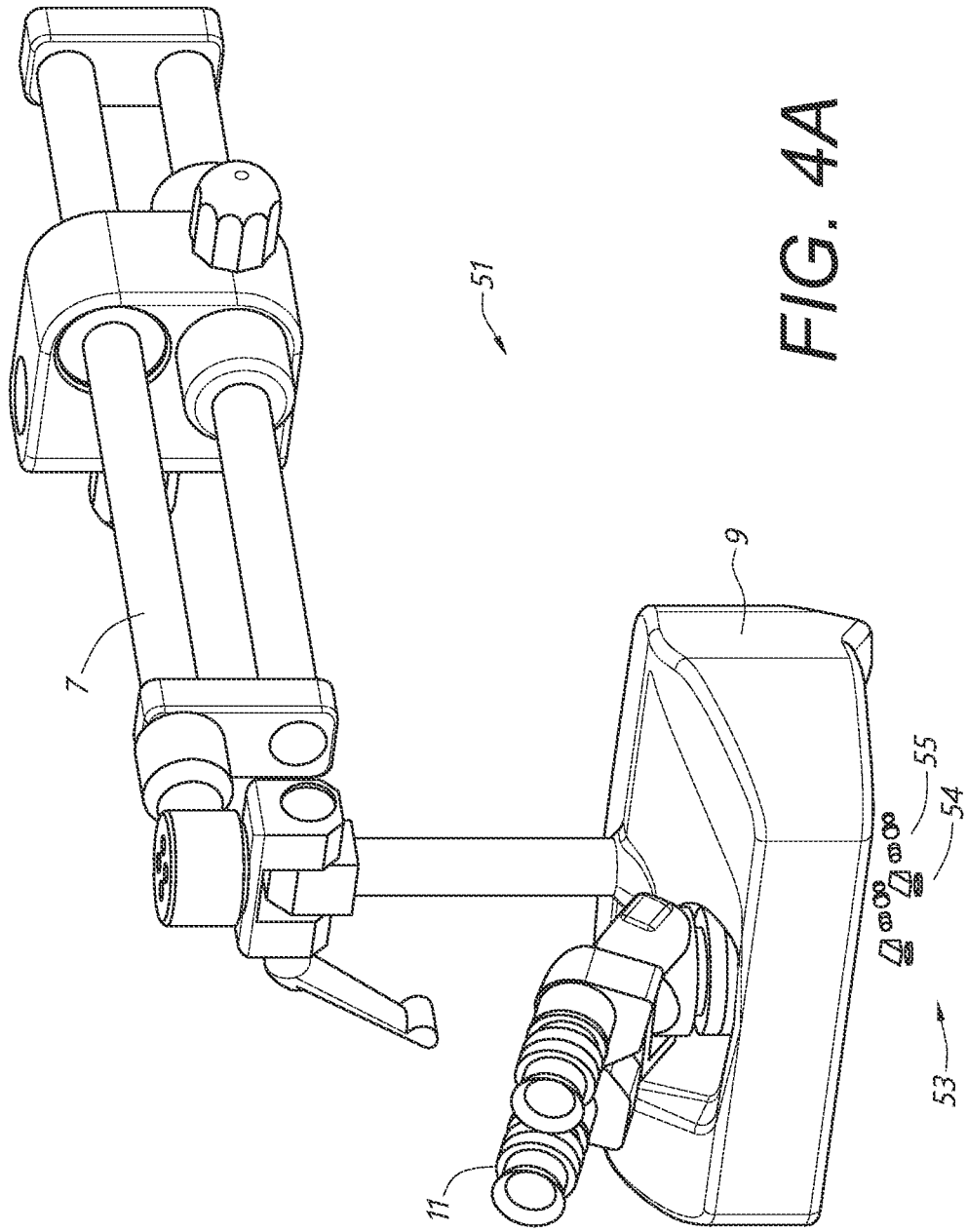

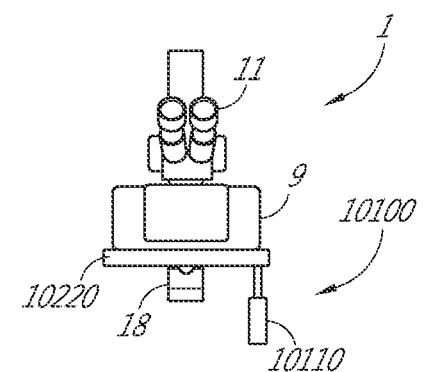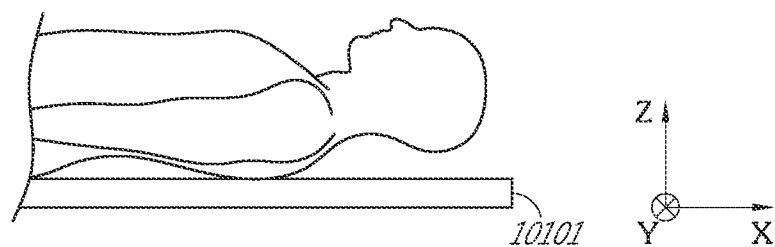
FIG. 6A
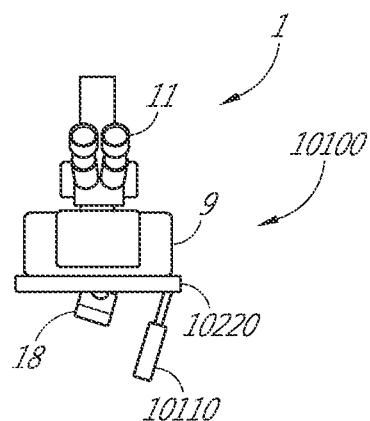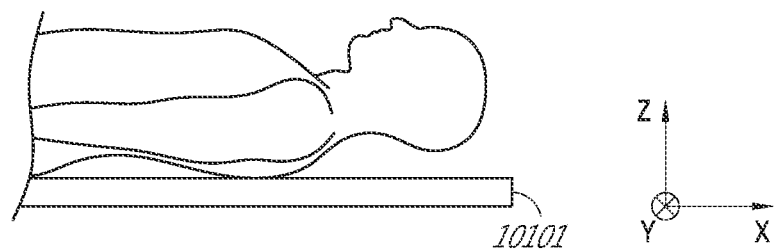
FIG. 6B

Side View
173.2
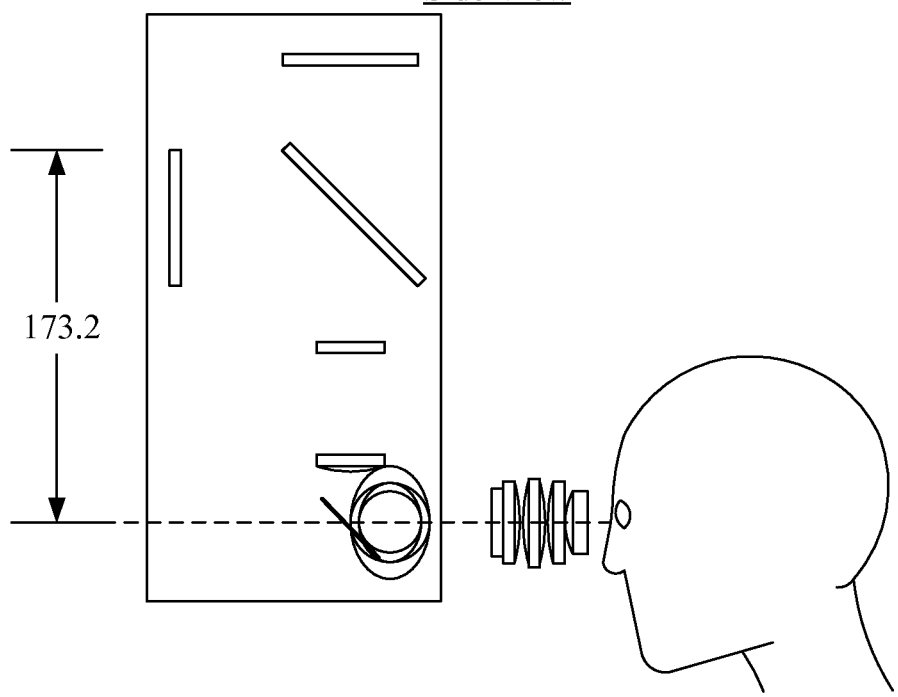
341.5
140
61.5
67
67.2
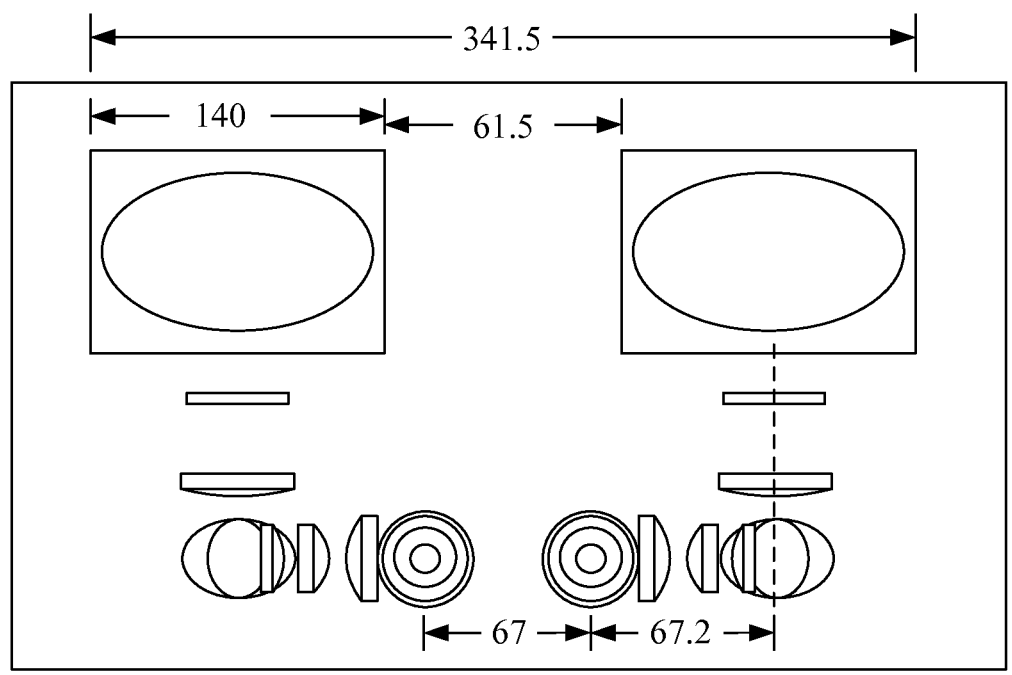
Front View
FIG. 14B1

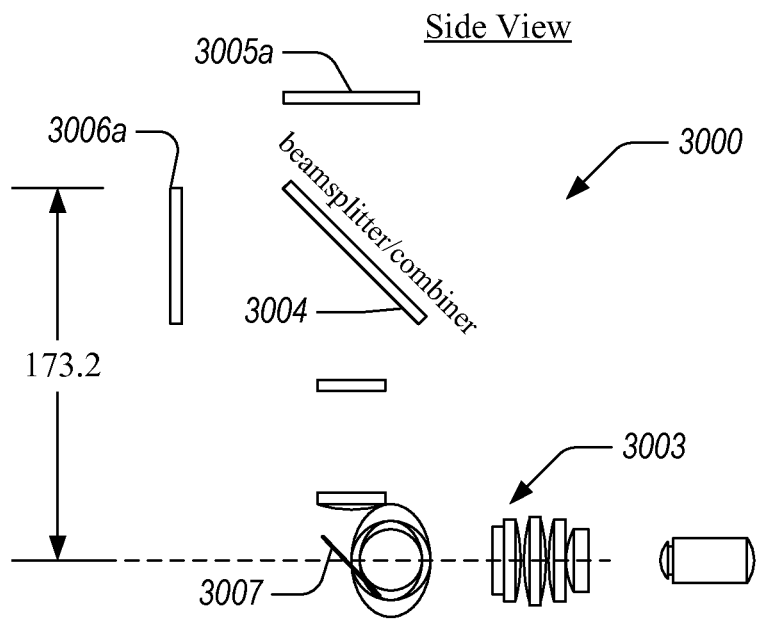
FIG. 14B1-a
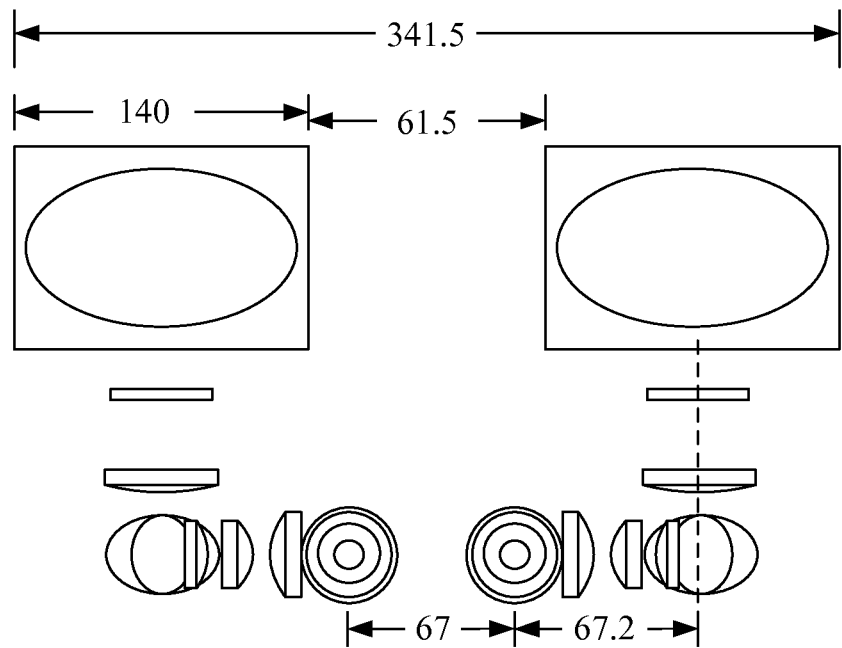
Front View
FIG. 14B1-b

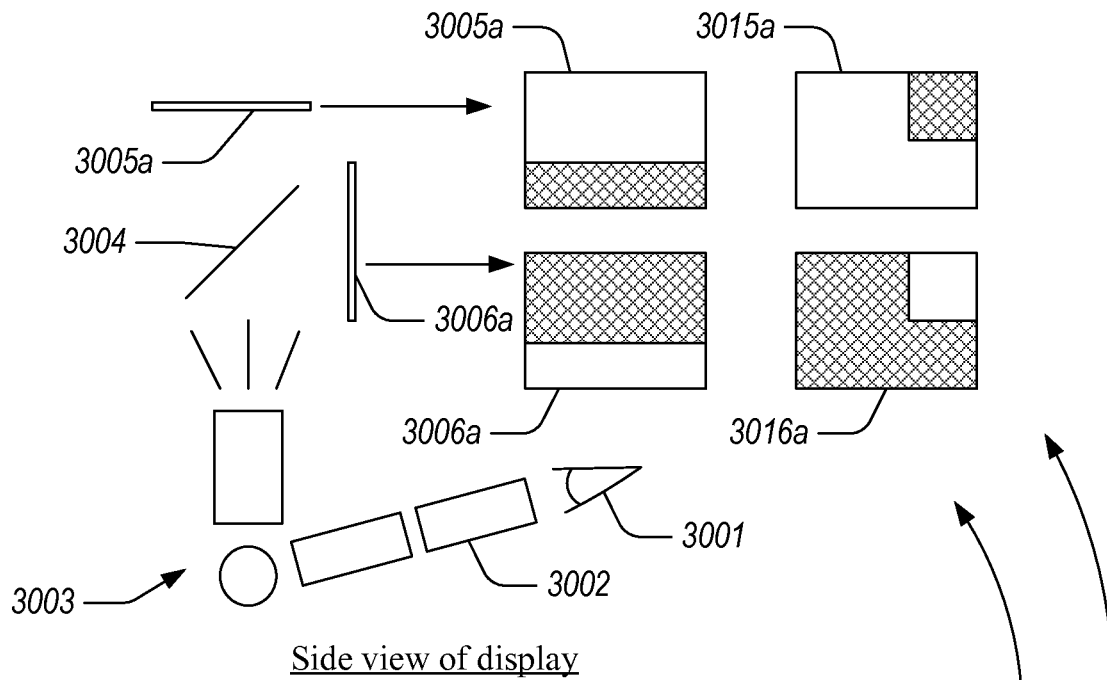
Side view of display
FIG. 14B1-c
one eye's view shown from side
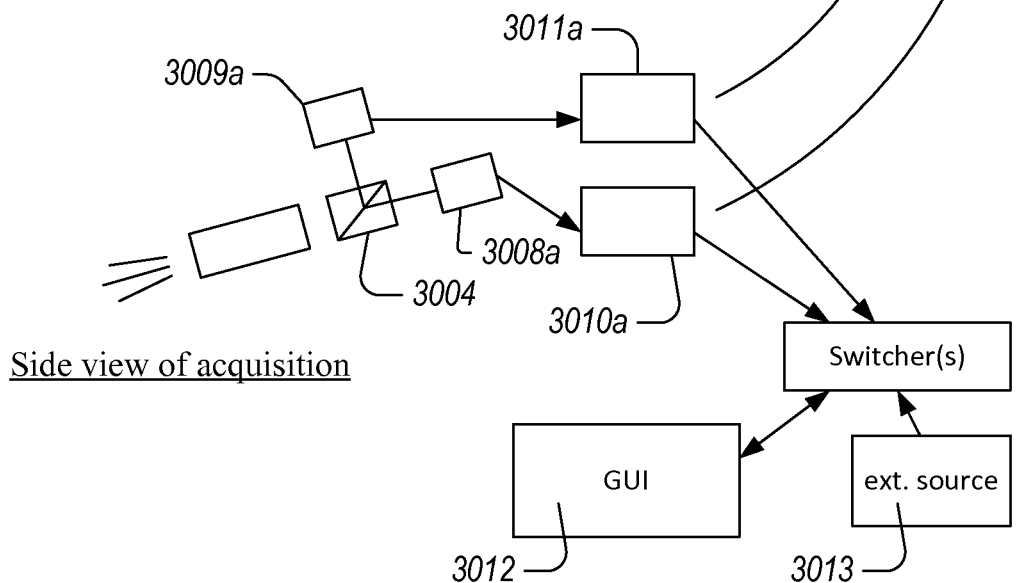
Side view of acquisition
FIG. 14B1-d

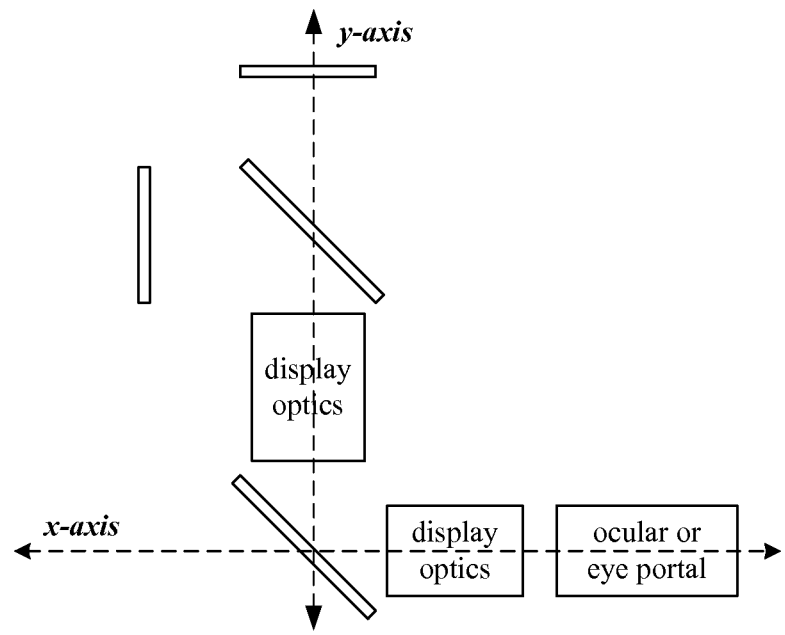
FIG. 14B1-e
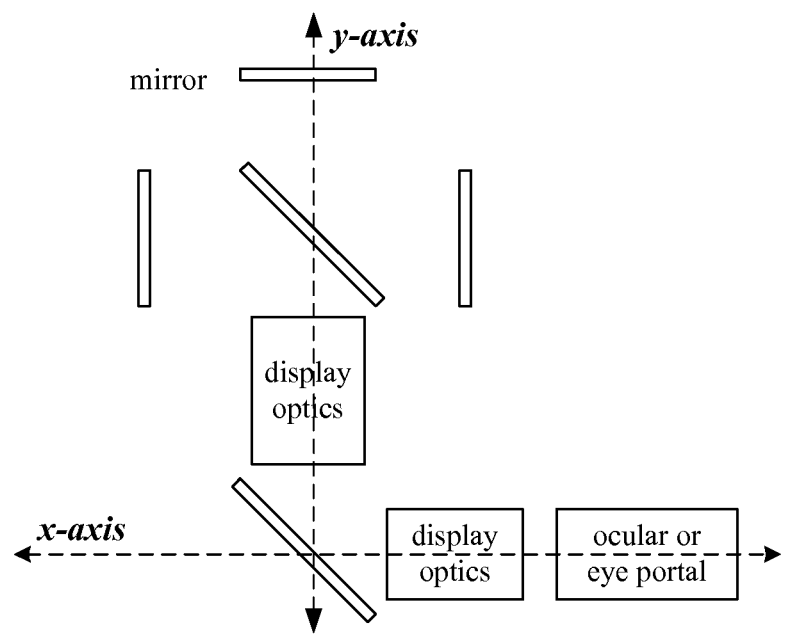
FIG. 14B1-f

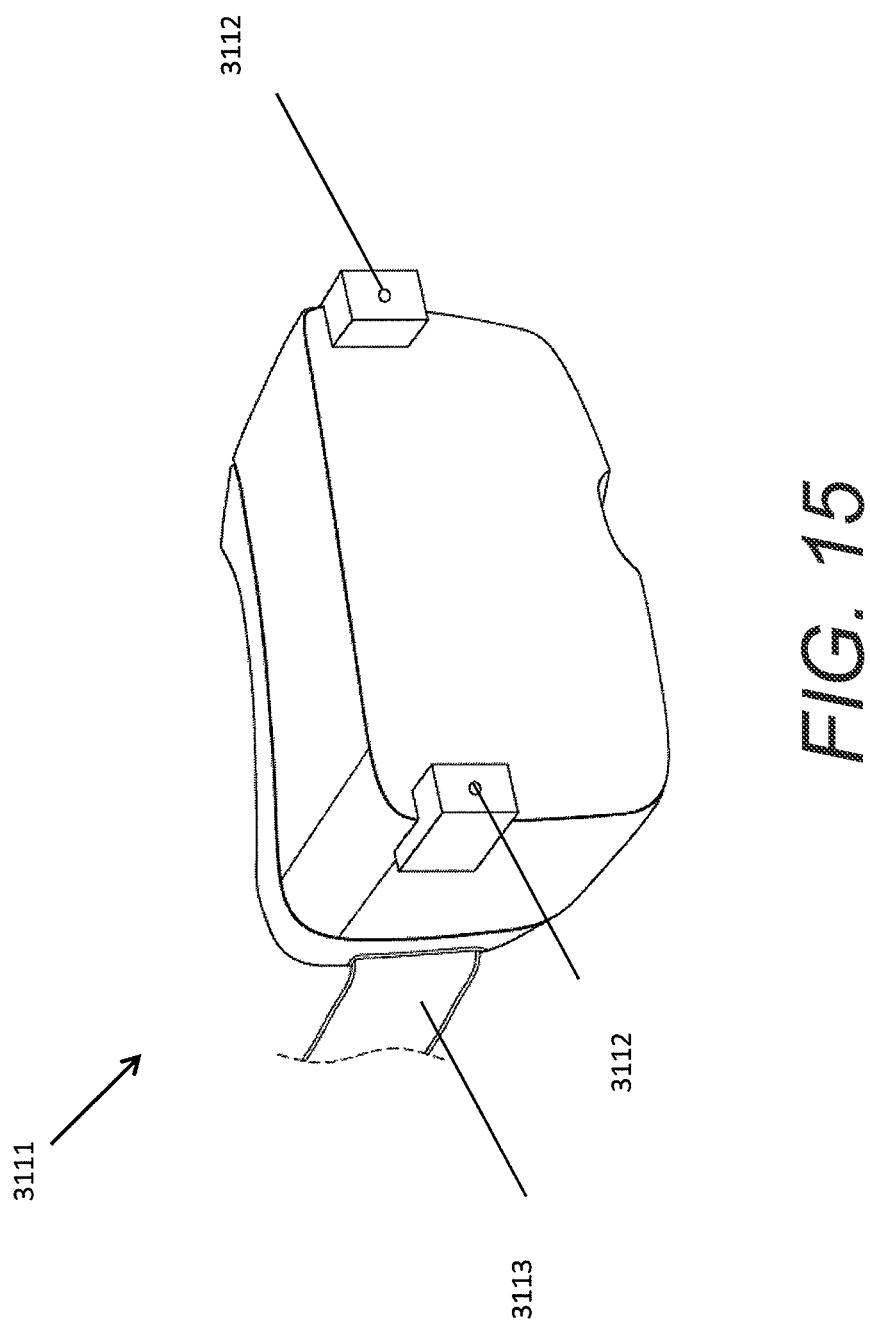

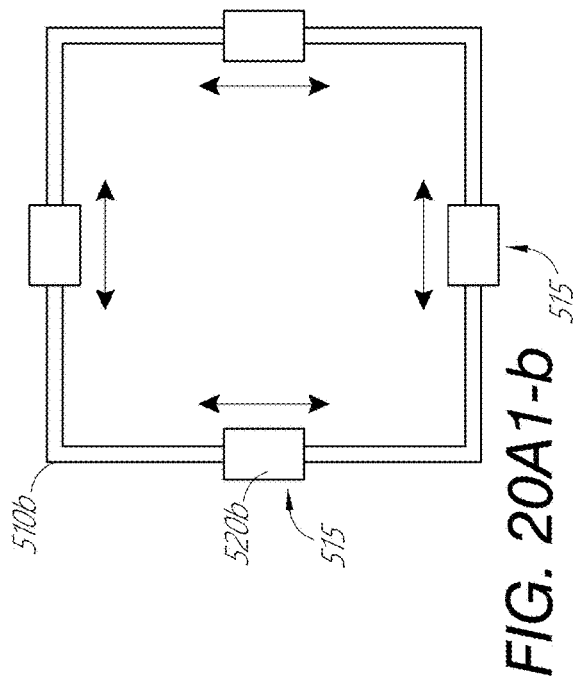
FIG. 20A1-b
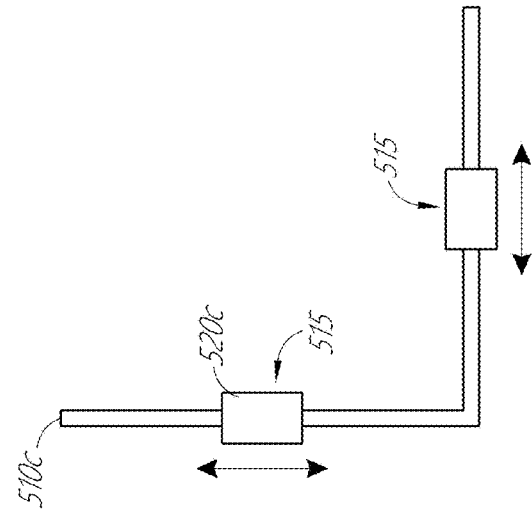
FIG. 20A1-c
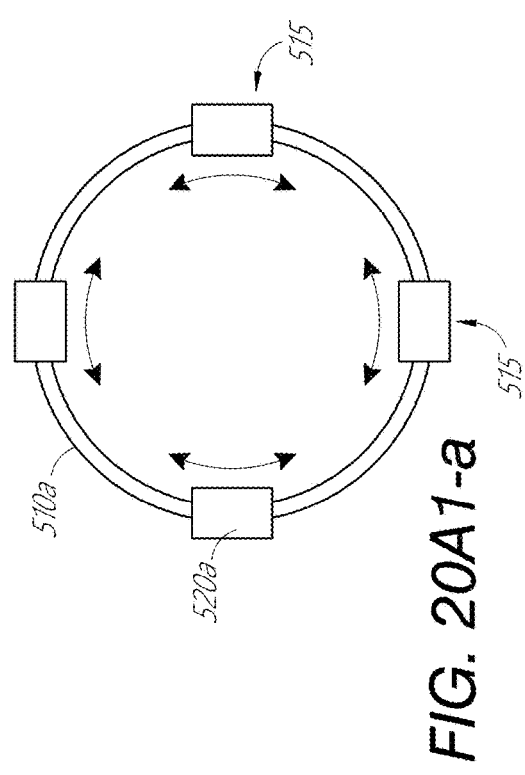
FIG. 20A1-a

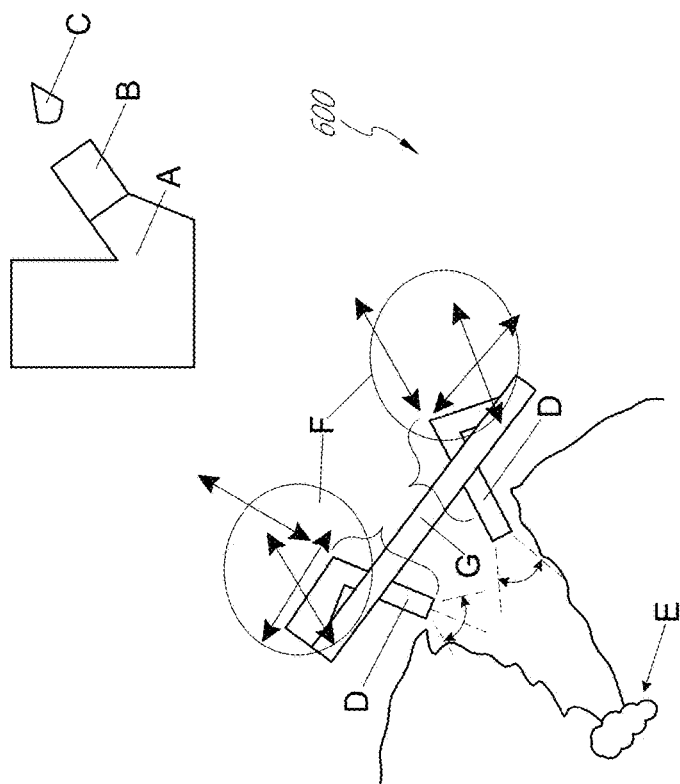
FIG. 20B1-b
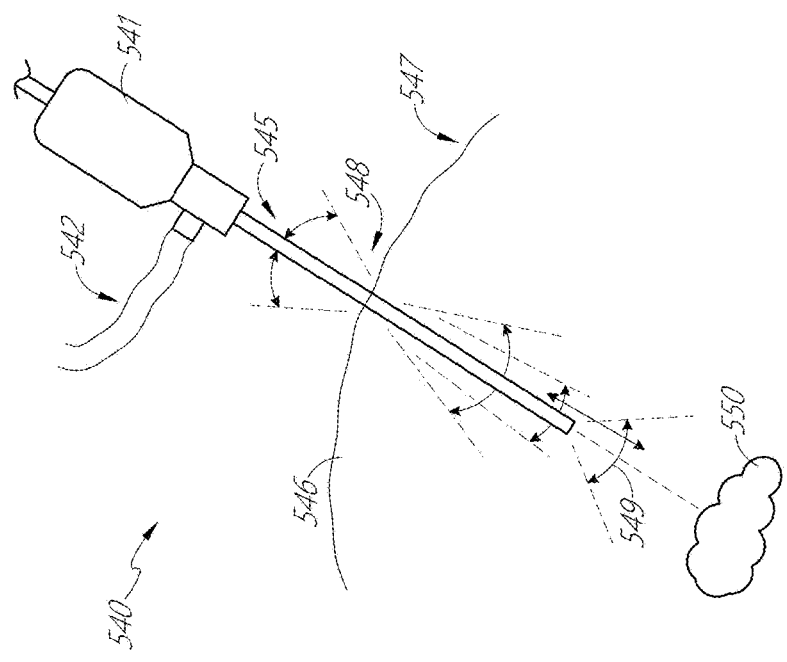
FIG. 20B1-a

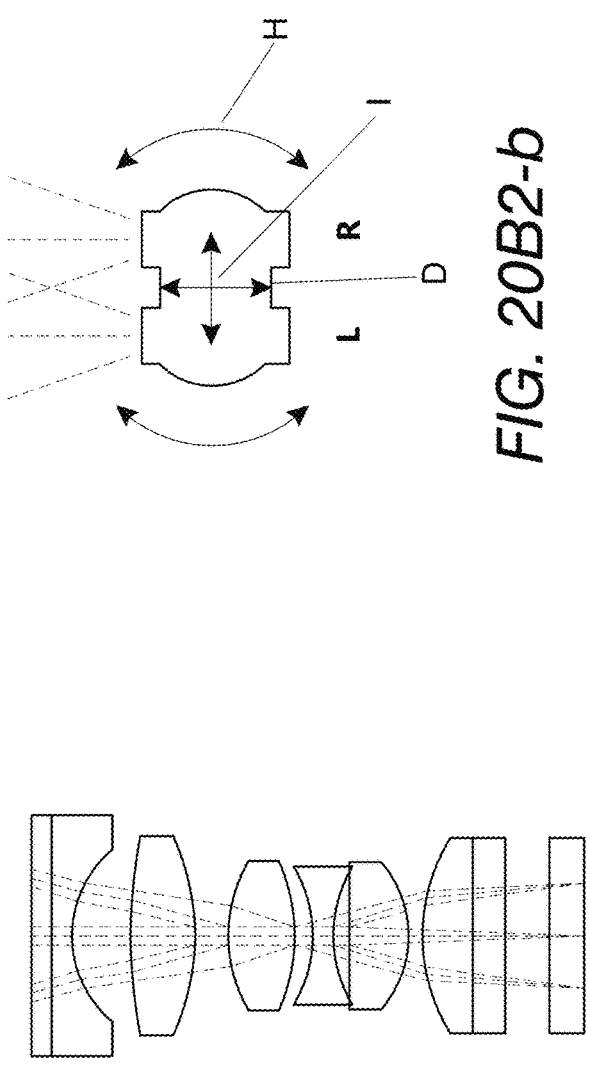
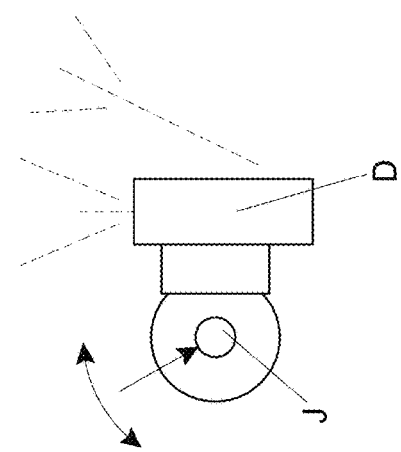
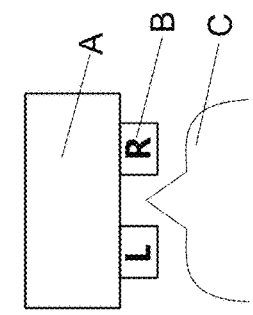
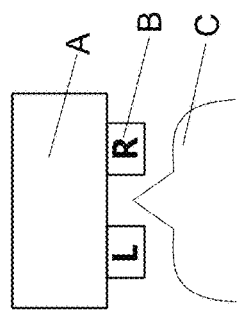
FIG. 20B2-a
FIG. 20B2-b
FIG. 20B2-c
FIG. 20B2-d
FIG. 20B2-e

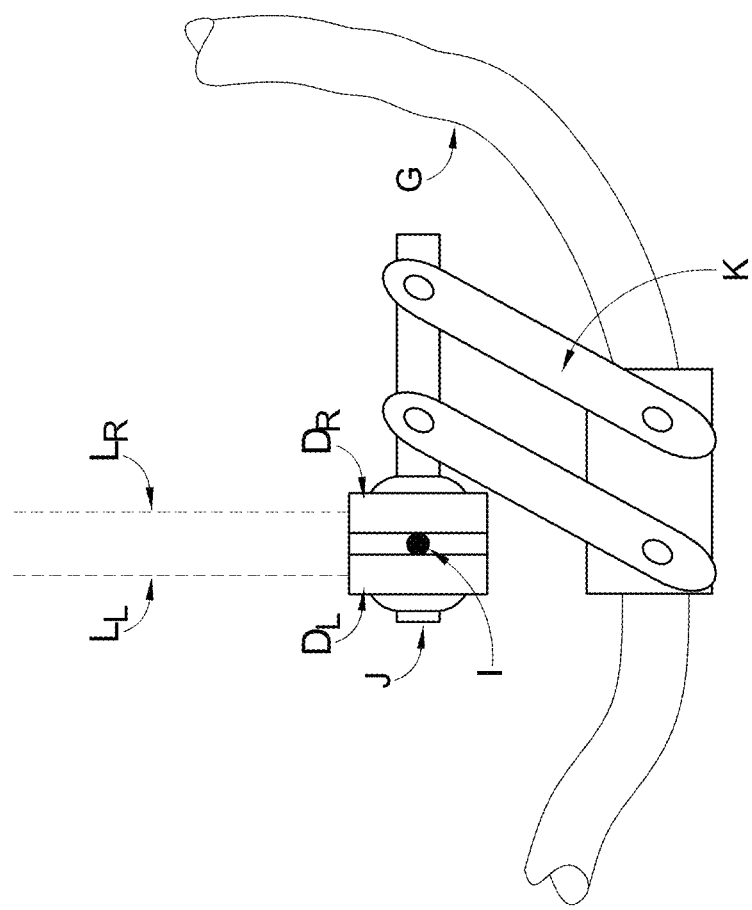
FIG. 20B2-f

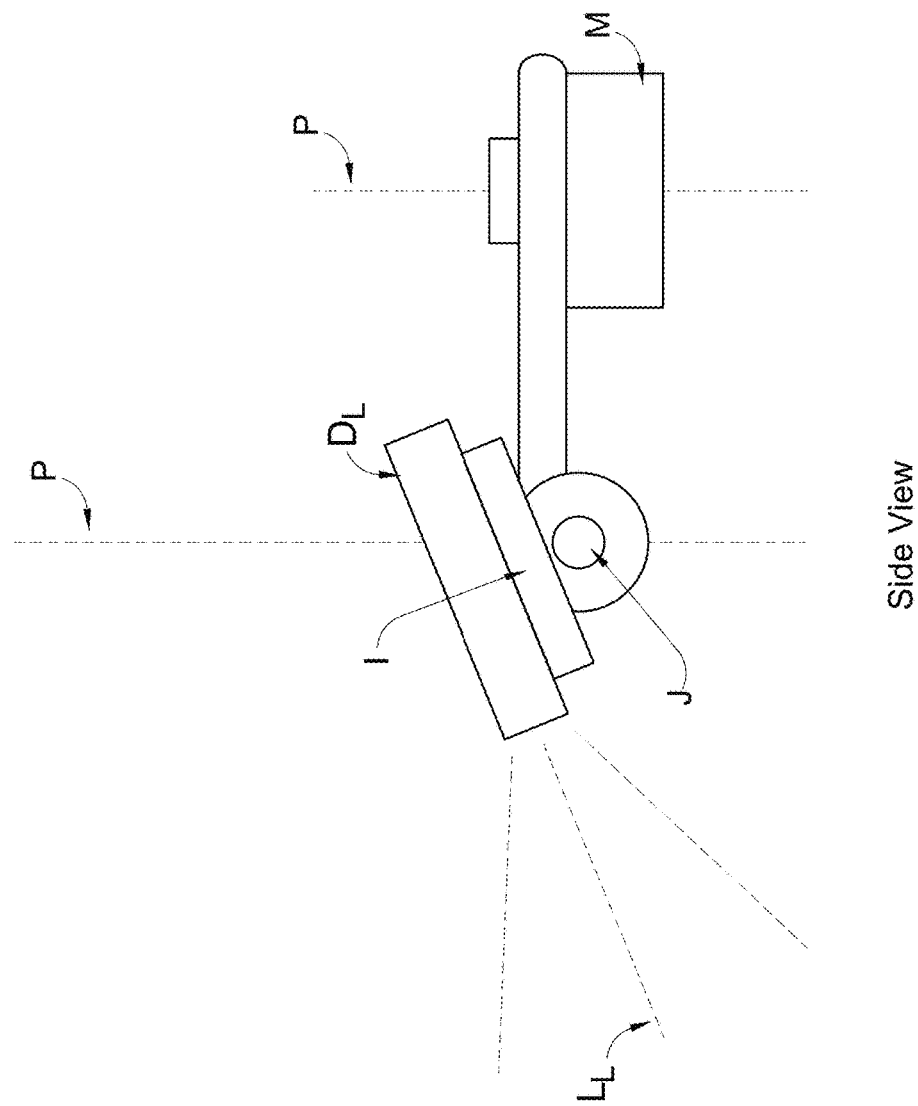
FIG. 20B2-g

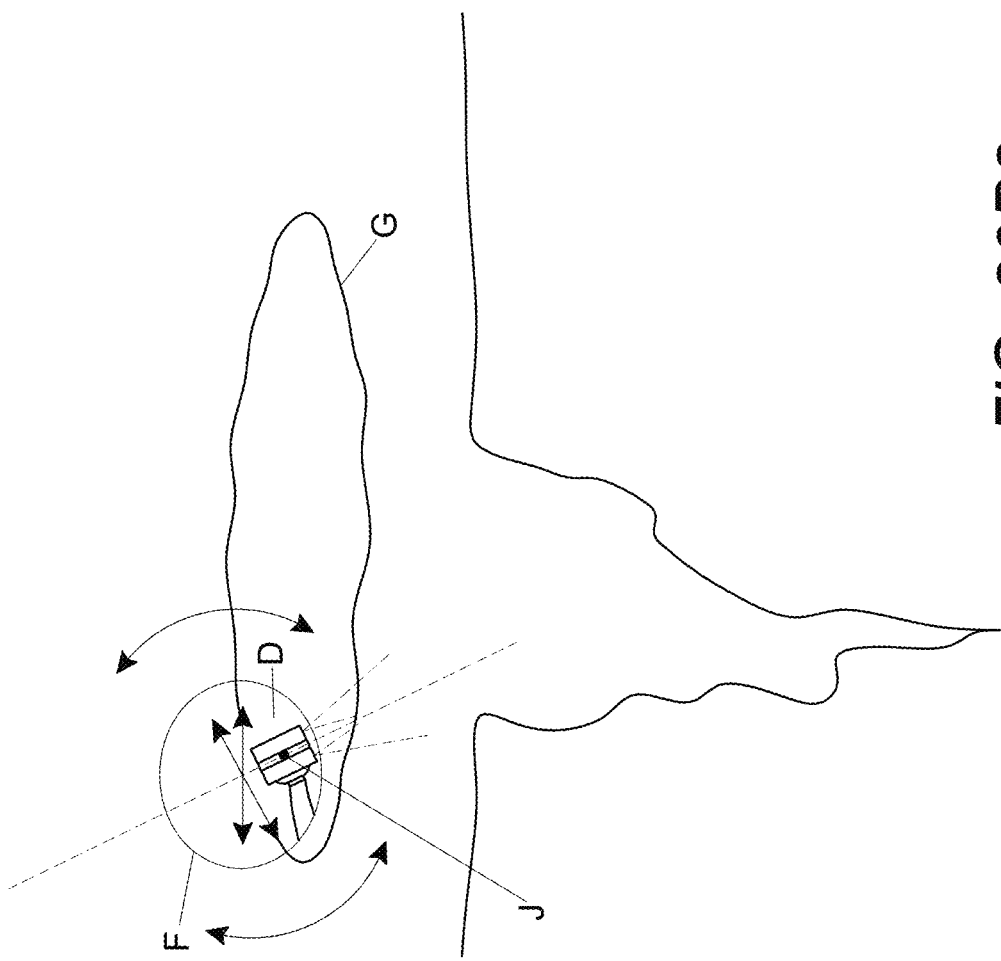
FIG. 20B3

SURGICAL VISUALIZATIONS SYSTEMS AND DISPLAYS

CROSS-REFERENCE TO RELATED APPLICATIONS

This application claims the benefit of priority to U.S. Provisional Application No. 62/088,470, entitled "SURGICAL VISUALIZATION SYSTEMS AND DISPLAYS," filed Dec. 5, 2014, to U.S. Provisional Application No. 62/098,297, entitled "SURGICAL VISUALIZATION SYSTEMS AND DISPLAYS," filed Dec. 30, 2014, to U.S. Provisional Application No. 62/099,422, entitled "SURGICAL VISUALIZATION SYSTEMS AND DISPLAYS," filed Jan. 2, 2015, and to U.S. Provisional Application No. 62/260,220, entitled "SURGICAL VISUALIZATION SYSTEMS AND DISPLAYS," filed Nov. 25, 2015, to U.S. Provisional Application No. 62/183,148, entitled "SURGICAL VISUALIZATION SYSTEMS AND DISPLAYS," filed Jun. 22, 2015, to U.S. Provisional Application No. 62/184,222, entitled "SURGICAL VISUALIZATION SYSTEMS AND DISPLAYS," filed Jun. 24, 2015, to U.S. Provisional Application No. 62/184,838, entitled "SURGICAL VISUALIZATION SYSTEMS AND DISPLAYS," filed Jun. 25, 2015, and to U.S. Provisional Application No. 62/187,796, entitled "SURGICAL VISUALIZATION SYSTEMS AND DISPLAYS," filed Jul. 1, 2015. The entirety of each application referenced in this paragraph is incorporated herein by reference.

BACKGROUND

Field

Embodiments of the present disclosure relate to visualization systems and displays for use during surgery.

Description of Related Art

Some surgical operations involve the use of large incisions. These open surgical procedures provide ready access for surgical instruments and the hand or hands of the surgeon, allowing the user to visually observe and work in the surgical site, either directly or through an operating microscope or with the aid of loupes. Open surgery is associated with significant drawbacks, however, as the relatively large incisions result in pain, scarring, and the risk of infection as well as extended recovery time. To reduce these deleterious effects, techniques have been developed to provide for minimally invasive surgery. Minimally invasive surgical techniques, such as endoscopy, laparoscopy, arthroscopy, pharyngo-laryngoscopy, as well as small incision procedures utilizing an operating microscope for visualization, utilize a significantly smaller incision than typical open surgical procedures. Specialized tools may then be used to access the surgical site through the small incision. However, because of the small access opening, the surgeon's view and workspace of the surgical site is limited. In some cases, visualization devices such as endoscopes, laparoscopes, and the like can be inserted percutaneously through the incision to allow the user to view the surgical site.

The visual information available to a user without the aid of visualization systems and/or through laparoscopic or endoscopic systems contains trade-offs in approach. Accordingly, there is a need for improved visualization systems, for use in open and/or minimally invasive surgery.

SUMMARY

Disclosed herein are systems, devices, and methods for surgery and surgical visualization and display. Image acquisition and image display, for example, are described. Such image acquisition may be performed by, such as for example but not limited to, one or more cameras on a surgical tool, frame or support just a few centimeters above the patient's body and/or surgical site, as well as camera systems farther from the patient including camera systems from about 15 cm to about 45 cm from the patient's body and/or the surgical site. In various embodiments, these cameras may be stereo or mono cameras. A variety of camera designs may be employed. Different types of displays and display designs including binocular displays may also be used. Various combinations of components and features are possible. For example, one or more embodiment or feature described or referenced in any one or more of the different sections of the present disclosure may be used with, combined with, incorporated into, and/or are otherwise compatible with one or more embodiments and features described in any one or more other of the sections of the present disclosure. For example, the head mounted display(s) described herein can be used in combination with the surgical visualization systems, cameras providing surgical microscope views, proximal cameras located just above the surgical site and/or patient, and/or one or more cameras on a surgical tool(s) such as described in any one or more of the other sections. Additionally, any of the features or embodiments described in connection with the surgical tools, surgical visualization systems and components thereof, may be used with, combined with, incorporated into, be applicable to, and/or are otherwise compatible with one or more embodiments of the proximal cameras disposed above the patient and/or surgical site described herein. Similarly, embodiments or features described or referenced in any section of the present disclosure may be used with, combined with, incorporated into, and/or are otherwise compatible with any other embodiment or feature also described or referenced in that section. Additionally any one or more embodiments or features described or referenced in any section may be used with, combined with, incorporated into, be applicable to, and/or are otherwise compatible with a wide range of medical or surgical devices which may or may not be introduced into the body including but not limited to endoscopes, laparoscopes, and arthroscopes. Use of the various features and embodiments and combination thereof with other medical devices is also possible.

In certain aspects, a medical apparatus is provided. The medical apparatus can include a frame configured to be disposed above a surgical site of a patient. The frame can be configured to be mounted to a bed or to the patient and anchored outside surgical site of the patient. The medical apparatus can also include one or more cameras mounted to the frame. The one or more cameras can be configured to image the surgical site. The medical apparatus can also include a surgical microscope camera configured to provide a surgical microscope view of the surgical site. In various embodiments, the surgical microscope camera is not coupled to a direct view surgical microscope. The medical apparatus can further include a viewing assembly comprising a housing and separate left and right eye portals for left and right eyes of a viewer. The left and right eye portals can be configured to provide views of at least one display disposed in the housing. Furthermore, the medical apparatus can include an image processing system in communication with the one or more cameras, the surgical microscope camera, and the at least one display. The image processing system can comprise processing electronics. The image processing system can be configured to receive images acquired by the one or more cameras and the surgical microscope camera, and to present output images based on the received images on the at least one display so that the output images can be viewable through the separate left and right eye portals.

In various embodiments, the one or more cameras can comprise first and second cameras configured to move relative to the surgical site and to maintain a same horizontal orientation with respect to each other. The medical apparatus can further include one or more gimbals connecting the one or more cameras to the frame. The one or more gimbals can be configured to move the one or more cameras relative to the frame. The one or more cameras can be configured to move electronically. In some embodiments, the one or more cameras can be configured to move with respect to an x direction, a y direction, or a z direction. The one or more cameras can be configured to move with respect to a pitch or yaw. For example, the one or more cameras can be configured to move with respect to a pitch and/or yaw, and without roll. In some embodiments, the one or more cameras can comprise cameras to provide a left-eye view and a right-eye view. For example, the cameras can be configured to provide stereo imaging.

In some embodiments, the one or more cameras can comprise four cameras mounted to the frame at 3 o'clock, 6 o'clock, 9 o'clock, and 12 o'clock positions. The frame can have a cross-sectional shape comprising a circle, a square, or an L-shape. In some embodiments, the frame can be configured to be disposed 10 to 50 mm above the surgical site; or the frame can be configured to be disposed 10 to 50 mm above the patient. In some embodiments, the frame can be configured to be disposed 50 to 150 mm above the surgical site; or the frame can be configured to be disposed 50 to 150 mm above the patient. In some embodiments, the frame can be configured to be disposed 100 to 200 mm above the surgical site; or the frame can be configured to be disposed 100 to 200 mm above the patient.

In some embodiments, the frame can be configured to provide a stereotactic planning system. The frame can be configured to be mounted to a gurney. The frame can be configured to be mounted to a bed rail. The frame can be configured to be mounted to the bed or to the patient via a Mayfield clamp.

In some embodiments, the separate left and right eye portals include a plurality of oculars. In some embodiments, at least one of the one or more cameras can include a stereo camera and the separate left and right eye portals can provide a stereo view providing 3D visualization.

In some embodiments, the image processing system can include separate electronics for each of the one or more cameras. Also, in some embodiments, the at least one display can include a first display configured to display a first image from a first camera of the one or more cameras. The at least one display can also include a second display configured to display a second image from the surgical microscope camera. The medical apparatus further can include a beam combiner configured to receive the first and second images from the first and second displays and to combine the first and second images for viewing.

In a first aspect, a surgical visualization system comprising a stereo optical assembly comprising a stereo camera configured to provide a stereo surgical microscope view of a surgical site; a binocular head mounted display viewing assembly configured to be worn by a user having left and right eyes, the binocular head mounted display comprising left and right display portions for displaying images viewable by the left and right eyes, respectively; and an image processing system in communication with the stereo optical assembly and the display portions, the image processing system comprising processing electronics, wherein the image processing system is configured to: receive video images acquired by the stereo camera, provide output video images based on the received video images, and present the output video images on the display portions so that the output video images are viewable on the display portions of the head mounted display.

In some embodiments, a surgical visualization system is provided wherein the head mounted display comprises eyewear, eyeglasses, goggles, or a mask. In some embodiments, a surgical visualization system further comprises an orientation sensing system configured to provide orientation information regarding the orientation of the head mounted display with movement of the head mounted display, the image processing system configured to alter the output video images on the display portions based on orientation information sensed by the orientation sensing system. In some embodiments, a surgical visualization system is provided wherein the orientation sensing system comprises one or more of the following: one or more gyroscopes, one or more accelerometers, one or more inertial measurement units (IMUs), or a tracking system. In some embodiments, a surgical visualization system is provided wherein the orientation sensing system comprises one or more accelerometers, gyroscopes, inertial measurement units (IMUs) or combinations thereof.

In some embodiments, a surgical visualization system is provided wherein the orientation sensing system comprises a tracking system. In some embodiments, a surgical visualization system is provided wherein the tracking system comprises fiducial markers on the head mounted display and an optical imaging system for imaging the fiducial markers. In some embodiments, a surgical visualization system is provided wherein the tracking system comprises a transmitter on the head mounted display and a receiver on a remote display assembly. In some embodiments, a surgical visualization system is provided wherein the tracking system comprises a receiver on the head mounted display and a transmitter on a remote display assembly. In some embodiments, a surgical visualization system is provided wherein the binocular head mounted display is opaque so as to block the view of the left and right eyes along the line of sight of the respective left and right eyes through the head mounted display. In some embodiments, a surgical visualization system further comprises one or more cameras disposed on the head mounted display. In some embodiments, a surgical visualization system further comprises one or more cameras having a field of view that moves with movement head mounted display. In some embodiments, a surgical visualization system is provided wherein the image processing system is configured to replace output video images of the surgical microscope view with output video images from one or more cameras on the head mounted display based on orientation information. In some embodiments, a surgical visualization system is provided wherein the image processing system is configured to replace output video images of the surgical microscope view with an unmagnified view forward the head mounted display. In some embodiments, a surgical visualization system is provided wherein the output video images of the surgical microscope view are presented on the display portions together with output video images from at least one camera on the head mounted display. In some embodiments, a surgical visualization system is provided wherein the orientation sensing system is configured to control the relative sizes of (i) the output video images of a surgical microscope view and (ii) the output video image from the at least one camera on the head mounted display that are presented on the display portions. In some embodiments, a surgical visualization system is provided wherein the output video images of the surgical microscope view are presented on the display portions together with an unmagnified view forward the head mounted display. In some embodiments, a surgical visualization system is provided wherein the orientation sensing system is configured to control the size and percentage of the output video images of a surgical microscope view with respect to the size and percentage of the view forward the head mounted display that are presented on the display portions.

In some embodiments, a surgical visualization system is provided wherein the head mounted display is at least partially transparent along the line of sight of the respective left and right eyes such that the left and right eyes can see through the head mounted display along the line of site of the left and right eyes when the head mounted display is worn by the user. In some embodiments, a surgical visualization system is provided wherein the display portions comprise a transparent material configured to provide a view therethrough along the line of sight of the left and right eyes. In some embodiments, a surgical visualization system is provided wherein the display portions comprises at least one heads-up projection display comprising an at least partially transparent window and at least one projector configured to project an image into the left and right eyes such that a view through the window and the projected image are viewable by the left and right eyes. In some embodiments, a surgical visualization system is provided wherein the image processing system is configured to attenuate output video images of the surgical microscope view on the head mounted display with respect to the view through the transparent window along the line of sight of the left and right eyes.

In some embodiments, a surgical visualization system is provided wherein the image processing system is configured to attenuate output video images of the surgical microscope view such that the output video images of the surgical microscope view are not visible while the view forward the head mounted display is visible. In some embodiments, a surgical visualization system the output video images of the surgical microscope view and a view forward the head mounted display are visible at the same time by user. In some embodiments, a surgical visualization system is provided wherein the orientation sensing system is configured to control the relative sizes with respect to each other of (i) the output video images of a surgical microscope view and (ii) the view forward the head mounted display. In some embodiments, a surgical visualization system is provided wherein the output video images of the surgical microscope view are visible together a view along the line of sight of the left and right eyes. In some embodiments, a surgical visualization system is provided wherein an orientation sensing system is configured to control the size and percentage of the output video images of a surgical microscope view with respect to the size and percentage of the view through the window along the line of sight of the left and right eyes of the user of the head mounted display. In some embodiments, a surgical visualization system is provided wherein the orientation sensing system is configured to control the amount of transparency of the display portions. In some embodiments, a surgical visualization system is provided wherein the display portion for the right eye comprises a display, a spatial light modulator, and a beam combiner, the beam combiner and the spatial light modulator forming a first optical path and the display and the beam combiner forming a second optical path. In some embodiments, a surgical visualization system is provided wherein the line of sight is directed through the beam combiner and the spatial light modulator along the first path, the spatial light modulator being configured to provide selected transmission therethrough. In some embodiments, a surgical visualization system is provided wherein the beam combiner and display are disposed with respect to each other and the line of sight of the right eye such that output video images displayed on the display are viewable by the right eye. In some embodiments, a surgical visualization system is provided wherein the spatial light modulator comprises a liquid crystal spatial light modulator configured to control the amount of light permitted to pass therethrough. In some embodiments, a surgical visualization system is provided wherein the display comprises a light emitting diode display or a liquid crystal display. In some embodiments, a surgical visualization system is provided wherein an orientation sensing system is configured to control the amount of light passing through the spatial light modulator. In some embodiments, a surgical visualization system further comprises a camera configured to provide a surgical tool view. In some embodiments, a surgical visualization system further comprises a surgical tool. In some embodiments, a surgical visualization system further comprises additional cameras configured to provide view of the surgical site.

In another aspect, a surgical visualization system comprising a stereo optical assembly comprising a stereo camera configured to provide a surgical tool view of a surgical site; a binocular head mounted display viewing assembly configured to be worn by a user having left and right eyes, the binocular head mounted display comprising left and right display portions for displaying images viewable by the left and right eyes, respectively; and an image processing system in communication with the stereo optical assembly and the display portions, the image processing system comprising processing electronics, wherein the image processing system is configured to: receive video images acquired by the stereo camera, provide output video images based on the received video images, and present the output video images on the display portions so that the output video images are viewable on the display portions of the head mounted display.

In some embodiments, a surgical visualization system is provided wherein the head mounted display comprises eyewear, eyeglasses, goggles, or a mask. In some embodiments, a surgical visualization system further comprises an orientation sensing system configured to provide orientation information regarding the orientation of the head mounted display with movement of the head mounted display, the image processing system configured to alter the output video images on the display portions based on orientation information sensed by the orientation sensing system. In some embodiments, a surgical visualization system is provided wherein the orientation sensing system comprises one or more of the following: one or more gyroscopes, one or more accelerometers, one or more inertial measurement units (IMUs), or a tracking system. In some embodiments, a surgical visualization system is provided wherein the orientation sensing system comprises one or more accelerometers, gyroscopes, inertial measurement units (IMUs) or combinations thereof.

In some embodiments, a surgical visualization system is provided wherein the orientation sensing system comprises a tracking system. In some embodiments, a surgical visualization system is provided wherein the tracking system comprises fiducial markers on the head mounted display and an optical imaging system for imaging the fiducial markers. In some embodiments, a surgical visualization system is provided wherein the tracking system comprises a transmitter on the head mounted display and a receiver on a remote display assembly. In some embodiments, a surgical visualization system is provided wherein the tracking system comprises a receiver on the head mounted display and a transmitter on a remote display assembly. In some embodiments, a surgical visualization system is provided wherein the binocular head mounted display is opaque so as to block the view of the left and right eyes along the line of sight of the respective left and right eyes through the head mounted display. In some embodiments, a surgical visualization system further comprises one or more cameras disposed on the head mounted display. In some embodiments, a surgical visualization system further comprises one or more cameras having a field of view that moves with movement head mounted display. In some embodiments, a surgical visualization system is provided wherein the image processing system is configured to replace output video images of the surgical tool view with output video images from one or more cameras on the head mounted display based on orientation information. In some embodiments, a surgical visualization system is provided wherein the image processing system is configured to replace output video images of the surgical tool view with an unmagnified view forward the head mounted display. In some embodiments, a surgical visualization system is provided wherein the output video images of the surgical tool view are presented on the display portions together with output video images from at least one camera on the head mounted display.

In some embodiments, a surgical visualization system is provided wherein the orientation sensing system is configured to control the relative sizes of (i) the output video images of a surgical tool view and (ii) the output video image from the at least one camera on the head mounted display that are presented on the display portions. In some embodiments, a surgical visualization system is provided wherein the output video images of the surgical tool view are presented on the display portions together with an unmagnified view forward the head mounted display. In some embodiments, a surgical visualization system is provided wherein the orientation sensing system is configured to control the size and percentage of the output video images of a surgical tool view with respect to the size and percentage of the view forward the head mounted display that are presented on the display portions. In some embodiments, a surgical visualization system is provided wherein the head mounted display is at least partially transparent along the line of sight of the respective left and right eyes such that the left and right eyes can see through the head mounted display along the line of site of the left and right eyes when the head mounted display is worn by the user. In some embodiments, a surgical visualization system is provided wherein the display portions comprises a transparent material configured to provide a view therethrough along the line of sight of the left and right eyes. In some embodiments, a surgical visualization system is provided wherein the display portions comprises at least one heads-up projection display comprising an at least partially transparent window and at least one projector configured to project an image into the left and right eyes such that a view through the window and the projected image are viewable by the left and right eyes. In some embodiments, a surgical visualization system is provided wherein the image processing system is configured to attenuate output video images of the surgical tool view on the head mounted display with respect to the view through the transparent window along the line of sight of the left and right eyes. In some embodiments, a surgical visualization system is provided wherein the image processing system is configured to attenuate output video images of the surgical tool view such that the output video images of the surgical tool view are not visible while the view forward the head mounted display is visible. In some embodiments, a surgical visualization system is provided wherein the output video images of the surgical tool view and a view forward the head mounted display are visible at the same time by user. In some embodiments, a surgical visualization system is provided wherein the orientation sensing system is configured to control the relative sizes with respect to each other of (i) the output video images of a surgical tool view and (ii) the view forward the head mounted display. In some embodiments, a surgical visualization system is provided wherein the output video images of the surgical tool view are visible together a view along the line of sight of the left and right eyes.

In some embodiments, a surgical visualization system is provided wherein an orientation sensing system is configured to control the size and percentage of the output video images of a surgical tool view with respect to the size and percentage of the view through the window along the line of sight of the left and right eyes of the user of the head mounted display. In some embodiments, a surgical visualization system is provided wherein the orientation sensing system is configured to control the amount of transparency of the display portions. In some embodiments, a surgical visualization system is provided wherein the display portion for the right eye comprises a display, a spatial light modulator, and a beam combiner, the beam combiner and the spatial light modulator forming a first optical path and the display and the beam combiner forming a second optical path. In some embodiments, a surgical visualization system is provided wherein the line of sight is directed through the beam combiner and the spatial light modulator along the first path, the spatial light modulator being configured to provide selected transmission therethrough. In some embodiments, a surgical visualization system is provided wherein the beam combiner and display are disposed with respect to each other and the line of sight of the right eye such that output video images displayed on the display are viewable by the right eye. In some embodiments, a surgical visualization system is provided wherein the spatial light modulator comprises a liquid crystal spatial light modulator configured to control the amount of light permitted to pass therethrough. In some embodiments, a surgical visualization system is provided wherein the display comprises a light emitting diode display or a liquid crystal display. In some embodiments, a surgical visualization system is provided wherein an orientation sensing system is configured to control the amount of light passing through the spatial light modulator. In some embodiments, a surgical visualization system further comprises a surgical tool.

In another aspect, a surgical visualization system comprising a stereo optical assembly comprising a stereo camera configured to provide a surgical device view of a surgical site; a binocular head mounted display viewing assembly configured to be worn by a user having left and right eyes, the binocular head mounted display comprising left and right display portions for displaying images viewable by the left and right eyes, respectively; and an image processing system in communication with the stereo optical assembly and the display portions, the image processing system comprising processing electronics, wherein the image processing system is configured to: receive video images acquired by the stereo camera, provide output video images based on the received video images, and present the output video images on the display portions so that the output video images are viewable on the display portions of the head mounted display.

In various aspects, a medical apparatus is provided. The medical apparatus can include a first display portion configured to display a first image and a second display portion configured to display a second image. The medical apparatus can also include electronics configured to receive one or more signals corresponding to images from a plurality of sources and to drive the first and second display portions to produce the first and second images based at least in part on the images from the plurality of sources. The medical apparatus can further include a first beam combiner configured to receive the first and second images from the first and second display portions and to combine the first and second images for viewing.

In certain embodiments, the first and second display portions can include first and second displays. The medical apparatus can further include imaging optics disposed to collect light from both the first and second display portions. The imaging optics can be configured to form images at infinity. The medical apparatus can further include a housing and a first ocular for viewing the combined first and second images within the housing. The medical apparatus can also further include a second ocular for viewing an additional image within the housing.

In some embodiments, the plurality of sources can include at least one camera providing a surgical microscope view. For example, the medical apparatus can further include the at least one camera providing the surgical microscope view. In some embodiments, the plurality of sources can include at least one camera disposed on a surgical tool. For example, the medical apparatus can further include the at least one camera disposed on the surgical tool. In some embodiments, the plurality of sources can include at least one source providing data, a computed tomography scan, a computer aided tomography scan, magnetic resonance imaging, an x-ray, or ultrasound imaging. For example, the medical apparatus can further include the at least one source providing the data, computed tomography scan, computer aided tomography scan, magnetic resonance imaging, x-ray, or ultrasound imaging. In various embodiments, the first image can include a fluorescence image and the second image can include a non-fluorescence image.

In various embodiments, the medical apparatus can further comprise a third display portion configured to display a third image and a fourth display portion configured to display a fourth image. The medical apparatus can further include a second beam combiner configured to receive the third and fourth images from the third and fourth display portions and to combine the third and fourth images for viewing. The third and fourth display portions can comprise third and fourth displays. The medical apparatus can further include additional electronics configured to receive one or more signals corresponding to images from another plurality of sources and to drive the third and fourth display portions to produce the third and fourth images based at least in part on the images from the another plurality of sources.

Some embodiments of the medical apparatus can further include imaging optics disposed to collect light from both the third and fourth display portions. The imaging optics can be configured to form images at infinity. The medical apparatus can further include a housing, a first ocular for viewing the combined first and second images within the housing, and a second ocular for viewing the combined third and fourth images within the housing.

In some embodiments, the another plurality of sources can include at least one camera providing a surgical microscope view. For example, the medical apparatus can further include the at least one camera providing the surgical microscope view. In some embodiments, the another plurality of sources can include at least one camera disposed on a surgical tool. For example, the medical apparatus can further include the at least one camera disposed on the surgical tool. In some embodiments, the another plurality of sources can include at least one source providing data, a computed tomography scan, a computer aided tomography scan, magnetic resonance imaging, an x-ray, or ultrasound imaging. For example, the medical apparatus can further include the at least one source providing the data, computed tomography scan, computer aided tomography scan, magnetic resonance imaging, x-ray, or ultrasound imaging. In various embodiments, the third image can include a fluorescence image and the fourth image can include a non-fluorescence image. In some embodiments, the medical apparatus can provide 3D viewing of a surgical field.

In certain embodiments of the medical apparatus, the combined first and second images for viewing can include a composite image of the first and second images. For example, the first beam combiner can be configured to produce the first image as a background image of the composite image, and to produce the second image as a picture-in-picture (PIP) of the composite image. Furthermore, in some embodiments, the combined third and fourth images for viewing can include a composite image of the third and fourth images. For example, the second beam combiner can be configured to produce the third image as a background image of the composite image, and to produce the fourth image as a picture-in-picture (PIP) of the composite image.

In various aspects, a binocular display for viewing a surgical field is provided. The binocular display can comprise one or more cameras configured to produce images of the surgical field, a left-eye view channel, and a right-eye view channel. The left-eye view channel can include a first display configured to display a left-eye view image of the surgical field and one or more first processing electronics. The right-eye view channel can include a second display configured to display a right-eye view image of the surgical field and one or more second processing electronics. Each of the first and second processing electronics can be configured to receive one or more user inputs, receive one or more input signals corresponding to the images from the one or more camera, select which image of the images from the one or more cameras to display, resize, rotate, or reposition the selected image based at least in part on the one or more user inputs, and produce one or more output signals to drive the first or second display to produce the left-eye or right-eye image. In some embodiments, each of the first and second processing electronics can include a microprocessor, a field programmable gate array (FPGA), or an application specific integrated circuit (ASIC).

In some embodiments of the binocular display, the one or more cameras can comprise at least one camera providing a surgical microscope view. In some embodiments, the one or more cameras can comprise at least one camera disposed on a surgical tool. In some embodiments, the one or more cameras can comprise a camera configured to produce a fluorescence image and a camera configured to produce a non-fluorescence image. In some embodiments, the binocular display can further include one or more sources providing data, a computed tomography scan, a computer aided tomography scan, magnetic resonance imaging, an x-ray, or ultrasound imaging. The binocular display can in some embodiments, provide 3D viewing of the surgical field.

Furthermore, in various embodiments of the binocular display, the one or more first processing electronics can include separate processing electronics for each of the one or more cameras configured to produce images on the first display. In some embodiments, the one or more second processing electronics can include separate processing electronics for each of the one or more cameras configured to produce images on the second display.

In accordance with another aspect, a medical apparatus is provided that includes a display housing, an opening in the display housing, an electronic display disposed within the display housing, the electronic display comprising a plurality of pixels configured to produce a two-dimensional image. The medical apparatus includes oculars configured to provide a view of the display within the display housing and an imaging system disposed on the display housing, the imaging system configured to generate images of a surgical site from outside the surgical site. The view of the display within the housing through the oculars can be configured to provide a stereoscopic image to a viewer.

The imaging system includes an objective lens configured to collimate light from the surgical site, imaging optics to form an image of the surgical site at an image plane, a camera configured to generate a video stream based on the image at the image plane, and a fiber illumination source comprising an optical fiber and a source of light, the fiber illumination source configured to generate illumination directed through the objective lens so that the illumination provides light at a portion of the surgical site being imaged. In some embodiments, the fiber illumination source is attached to a gimbal configured to adjust a pitch or orientation of the fiber illumination source. In some embodiments light provided at the portion of the surgical site is configured to change in intensity based at least in part on a relative position or orientation of the optical fiber and the objective lens.

In accordance with another aspect, a medical apparatus is provided that includes a display housing, an opening in the display housing, at least two chambers within the display housing, and at least one electronic display disposed the display housing, each of the at least one electronic display comprising a plurality of pixels configured to produce a two-dimensional image. The display housing is further configured to separate a right eye path from a left eye path to the at least one electronic display so that light intended to be viewed with a right eye from the at least one electronic display does not travel down the left eye path and vice versa. The medical apparatus includes an imaging system disposed on the display housing, the imaging system configured to generate images of a surgical site from outside the surgical site. The view of the display within the housing can be configured to provide a stereoscopic image to a viewer. In some embodiments, the housing further includes lenses and/or a transparent plate between the eyes of a viewer and the at least one electronic display. In some embodiments, the housing further includes a baffle or other structure to separate the left eye path and the right eye path. In some embodiments, each chamber is baffled to prevent light from one channel to communicate to the other eye path.

In a second aspect, a medical apparatus is provided that includes a display housing and an opening in the display housing. The medical apparatus also includes an electronic display disposed within the display housing, the electronic display comprising a plurality of pixels configured to produce a two-dimensional image. The medical apparatus also includes a display optical system disposed within the display housing, the display optical system comprising a plurality of lens elements disposed along an optical path. The display optical system is configured to receive the two-dimensional image from the electronic display, produce a beam with a cross-section that remains substantially constant along the optical path, and produce a collimated beam exiting the opening in the display housing.

In some embodiments of the second aspect, the display optical system further comprises an optical redirection element configured to fold the optical path. In a further embodiment of the second aspect the optical redirection element comprises a mirror or a prism. In another embodiment of the second aspect, the display optical system is configured to direct light received from the electronic display to the opening in the display housing while reducing stray light.

In some embodiments of the second aspect, the display optical system further comprises a baffle configured to reduce stray light. In a further embodiment, the display optical system comprises less than or equal to four baffles. In a further embodiment, the display optical system comprises less than or equal to four mirrors. In a further embodiment, a first baffle is positioned between the electronic display and a first baffle along the optical path, the first mirror positioned prior to the plurality of lens elements along the optical path from the display to the opening. In another further embodiment, at least three baffles are positioned prior to the plurality of lens elements along the optical path from the display to the opening. In another further embodiment, at least two mirrors are positioned prior to the plurality of lens elements along the optical path from the display to the opening.

In some embodiments of the second aspect, the display optical system has an exit pupil and the electronic display is not parallel to the exit pupil. In some embodiments of the second aspect, the opening in the display housing comprises a mounting interface configured to mate with a binocular assembly for a surgical microscope. In a further embodiment, an exit pupil of the display optical system is of a same size or smaller than an entrance pupil of oculars in the binocular assembly.

In some embodiments of the second aspect, the medical apparatus further comprises a second electronic display and a second display optical system configured to provide a stereo view. In some embodiments of the second aspect, the medical apparatus further comprises processing electronics configured to communicate with the electronic display to provide images for the electronic display. In a further embodiment, the processing electronics are configured to receive images from one or more cameras on a surgical device. In a further embodiment, the processing electronics are configured to receive images from one or more cameras that provide a surgical microscope view.

In some embodiments of the second aspect, the optical path is less than or equal to 16.2 inches and a light-emitting portion of the electronic display has a diagonal measurement that is greater than or equal to 5 inches. In some embodiments of the second aspect, the optical path is less than or equal to 18.7 inches and a light-emitting portion of the electronic display has a diagonal measurement that is greater than or equal to 8 inches. In some embodiments of the second aspect, the display optical system further comprises a converging mirror. In some embodiments of the second aspect, the medical apparatus further comprises a viewing assembly comprising an objective lens, beam positioning optics, and an ocular, the viewing assembly configured to receive the collimated beam exiting the opening in the display housing. In some embodiments of the second aspect, the electronic display has a diagonal light-emitting portion between 4 inches and 9 inches. In some embodiments of the second aspect, an optical path length from the electronic display to a last element of the display optical system is at least 9 inches. In a further embodiment, the optical path length from the electronic display to the last element of the display optical system is less than 20 inches.

In a third aspect, a medical apparatus is provided that includes a viewing assembly comprising a housing and an ocular, the ocular configured to provide a view an electronic display disposed in the housing. The medical assembly includes an optical assembly disposed on the viewing assembly, the optical assembly configured to provide a surgical microscope view of a surgical site. The optical assembly includes an auxiliary video camera and a gimbal configured to couple the auxiliary video camera to the viewing assembly and configured to change an orientation of the auxiliary video camera relative to the viewing assembly. The medical apparatus includes an image processing system in communication with the optical assembly and the electronic display, the image processing system comprising at least one physical processor. The image processing system is configured to receive video images acquired by the auxiliary video camera, provide output video images based on the received video images, and present the output video images on the electronic display so that the output video images are viewable through the ocular. The gimbal is configured to adjust a pitch of the auxiliary video camera between a first position and a second position, wherein the auxiliary video camera has a first viewing angle perpendicular to a floor in the first position and a second viewing angle that is within about 10 degrees of parallel to the floor in the second position.

In some embodiments of the third aspect, the gimbal comprises two pivots. In a further embodiment, a first pivot is configured to adjust a pitch of the auxiliary video camera and a second pivot is configured to rotate the auxiliary video camera around an axis perpendicular to the floor.

In some embodiments of the third aspect, the gimbal is configured to adjust a pitch of the auxiliary video camera between the first position and a third position, wherein the auxiliary video camera has a third viewing angle in the third position that is less than or equal to 180 degrees from the first viewing angle. In some embodiments of the third aspect, the gimbal is electronically controlled. In some embodiments of the third aspect, the optical assembly is configured to provide an oblique view of a portion of a patient. In a further embodiment, an orientation of the ocular of the viewing assembly is configured to remain stationary when an orientation of the auxiliary video camera changes to provide the oblique view of the portion of the patient.

In some embodiments of the third aspect, the gimbal is configured to smoothly adjust the viewing angle of the auxiliary video camera between the first position and the second position. In some embodiments of the third aspect, the auxiliary video camera comprises a stereo video camera and the ocular comprises a pair of oculars. In some embodiments of the third aspect, the medical apparatus further comprises a camera arm attached to the viewing assembly.

In a fourth aspect, a medical apparatus is provided that includes a display housing. The medical apparatus includes a plurality of electronic displays disposed within the display housing, each of the plurality of electronic displays comprising a plurality of pixels configured to produce a two-dimensional image. The plurality of electronic displays are configured to present superimposed images in a field of view of a person's eye.

In some embodiments of the fourth aspect, the medical apparatus further comprises a binocular viewing assembly coupled to the display housing. In some embodiments of the fourth aspect, at least one of the plurality of electronic displays comprises a transmissive display panel. In some embodiments of the fourth aspect, the superimposed images comprise a video of a first portion of a surgery site that is superimposed on a video of a second portion of the surgery site, the first portion contained within the second portion. In a further embodiment, the video of the first portion is magnified relative to the video of the second portion.

In some embodiments, a medical apparatus can include a camera having a field of view that can be designed to include a surgical site, wherein the camera is designed to provide a surgical microscope view of the surgical site. In some embodiments, the medical apparatus can include a binocular viewing assembly having a housing and a plurality of oculars, the plurality of oculars designed to provide views of at least one display disposed in the housing. In some embodiments, the medical apparatus can include an image processing system designed to receive images acquired by the camera and present the output video images on the at least one display. In some embodiments, the medical apparatus can include a movement control system designed to move the camera relative to the binocular viewing assembly, the movement control system having a control member operatively coupled to the movement control system to translate the camera relative to the binocular viewing assembly along at least a first axis and a second axis and to rotate the camera relative to the binocular viewing assembly.

In a fifth aspect a medical apparatus is provided wherein a movement control system can include a translation system having a moveable platform to which the camera is attached, the moveable platform being positioned between the binocular viewing assembly and the camera and being moveable relative to the binocular viewing assembly along at least a first axis and a second axis. In some embodiments, the translation system can include an electromechanical device operatively coupled to the moveable platform.

In some embodiments of the fifth aspect, the movement control system can include a pitch-yaw adjustment system having an electromechanical device to which the camera can be attached, the pitch-yaw adjustment system designed to rotate the camera relative to the binocular viewing assembly around an axis parallel to the first axis and rotate the camera around an axis parallel to the second axis. In some embodiments, the control member is operatively coupled to the movement control system via sensors designed to detect movement of the control member, the sensors in communication with components of the movement control system In some embodiments, the control member can be operatively coupled to the movement control system via a gimbal having one or more sensors designed to detect movement of the control member, the sensors in communication with one or more components of the movement control system.

In some embodiments of the fifth aspect, the movement control system can be attached to the binocular viewing assembly. In some embodiments, the movement control system can be attached to an articulated arm. In some embodiments, the camera can be attached to the movement control system via an arm. In some embodiments, the medical apparatus can include a control system for controlling one or more electromechanical devices operatively coupled to the movement control system. In some embodiments, the control system can includes one or more pre-set positions for the movement control system In a sixth aspect, a medical apparatus is provided that includes a display, a plurality of cameras and a processor, at least one of the cameras providing a surgical microscope view, the plurality of cameras comprising a first camera configured to image fluorescence in a surgical field and a second camera configured to produce a non-fluorescence image of the surgical field, a processor configured to receive video from the plurality of cameras and to display on the display a first fluorescence video from the first of the cameras and display a second non-fluorescence video from the second of the cameras.

In some embodiments of the sixth aspect, the first and second cameras have different spectral responses. In certain embodiments of the sixth aspect, one of the first and second cameras is sensitive to infrared and the other is not.

The systems, methods and devices of the disclosure each have innovative aspects, no single one of which is solely responsible for the desirable attributes disclosed herein.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIGS. 3A and 3B illustrate an example surgical viewing system that includes an isocenter positioning system attached to the binocular viewing platform.

FIGS. 4A and 4B illustrate an embodiment of a surgical visualization system having an optical imaging system mounted under the binocular viewing platform.

FIG. 6A is a front view of an embodiment of a surgical visualization system, a movement control system, and an imager.

FIG. 6B is a front view of the embodiment of FIG. 6A with the movement control system and imager shifted.

FIG. 14B1 shows an illustration of an example medical apparatus according to certain embodiments described herein.

FIG. 14B1-*a* shows a larger view of the side view of FIG. 14B1.

FIG. 14B1-*b* shows a larger view of the front view of FIG. 14B1.

FIG. 14B1-*c* shows the example medical apparatus of FIG. 14B1.

FIG. 14B1-*d* shows an illustration of a beam combiner, a first camera, and a second camera.

FIGS. 14B1-*e* and 14B1-*f* illustrate example display units and optical paths of a medical apparatus.

FIGS. 15-16 illustrate the head mounted display with the pair of cameras.

FIG. 20A1-*a*, FIG. 20A1-*b*, and FIG. 20A1-*c* schematically illustrates cameras mounted to a circular frame, a square frame, or a L-shaped frame respectively.

FIG. 20B1-*a* shows an illustration of an imaging system comprising a camera, fiber optics, and a laparoscope.

FIG. 20B1-*b* shows an illustration of certain embodiments of a medical apparatus having one or more proximal camera D on a frame.

FIG. 20B2-*a* schematically illustrates imaging optics of an example imaging system compatible with certain embodiments of cameras as described herein.

FIG. 20B2-*b* shows an illustration of an example top-down view of certain embodiments disclosed herein.

FIG. 20B2-*c* shows an illustration of an example side-view of one optical channel of the apparatus shown in FIG. 20B2-*b*.

FIG. 20B2-*d* shows an illustration of an example proximal camera arrangement in accordance with certain embodiments described herein.

FIG. 20B2-*e* schematically illustrates a display viewable through portals.

FIG. 20B2-*f* shows an illustration of an example planar four-bar mechanism.

FIG. 20B2-*g* shows an illustration of the side-view of FIG. 20B2-*f*.

FIG. 20B3 shows an illustration of an oblique camera orientation.

DETAILED DESCRIPTION

The following description is directed to certain embodiments for the purposes of describing the innovative aspects of this disclosure. However, a person having ordinary skill in the art will readily recognize that the teachings herein can be applied in a multitude of different ways. The described embodiments may be implemented in any device or system that can be configured to provide visualization of a surgical site. Thus, the teachings are not intended to be limited to the embodiments depicted solely in the figures and described herein, but instead have wide applicability as will be readily apparent to one having ordinary skill in the art.

Surgical Visualization System

To provide improved visualization of a surgical site, a surgical device can be provided with multiple integrated cameras. Each of the cameras may capture a distinct view of the surgical site. In some embodiments, imagery from the plurality of cameras may be displayed to facilitate operation in a surgical site. Tiled, individual, and/or stitched imagery from the multiple cameras can provide the user with a view of the surgical site. The user can select the imagery to be displayed and the manner in which it is displayed for enhanced utility during surgery. As used herein, the term imagery and images includes video and/or images captured from one or more video cameras. Images from video are often referred to as video images or simply images. The term images may also refer to still images or snap shots. Video feed or video stream may also be used to describe the video images such as video images from a camera.

The video cameras may comprise, for example, CCD or CMOS sensor arrays or other types of detector arrays. A frame grabber may be configured to capture data from the cameras. For example, the frame grabber may be a Matrox Solios eA/XA, 4 input analog frame grabber board. Image processing of the captured video may be undertaken. Such image processing can be performed by, for example, the Matrox Supersight E2 with Matrox Supersight SHB-5520 with two Intel Six Core Xeon E5645 2.4 GHz processors with DDR3-1333SDRAM. This system can be designed to support eight or more camera inputs using two Matrox Solios eA/XA, 4 input, analog frame grabber boards. More or fewer cameras may be employed. In some implementations, a field programmable gate array ("FPGA") can be used to capture and/or process video received from the cameras. For example, the image processing can be performed by Xilinx series 7 FPGA boards. Other hardware devices can be used as well, including ASIC, DSP, computer processors, a graphics board, and the like. The hardware devices can be standalone devices or they can be expansion cards integrated into a computing system through a local computer bus, e.g., a PCI card or PCIe card.

Figure 1:
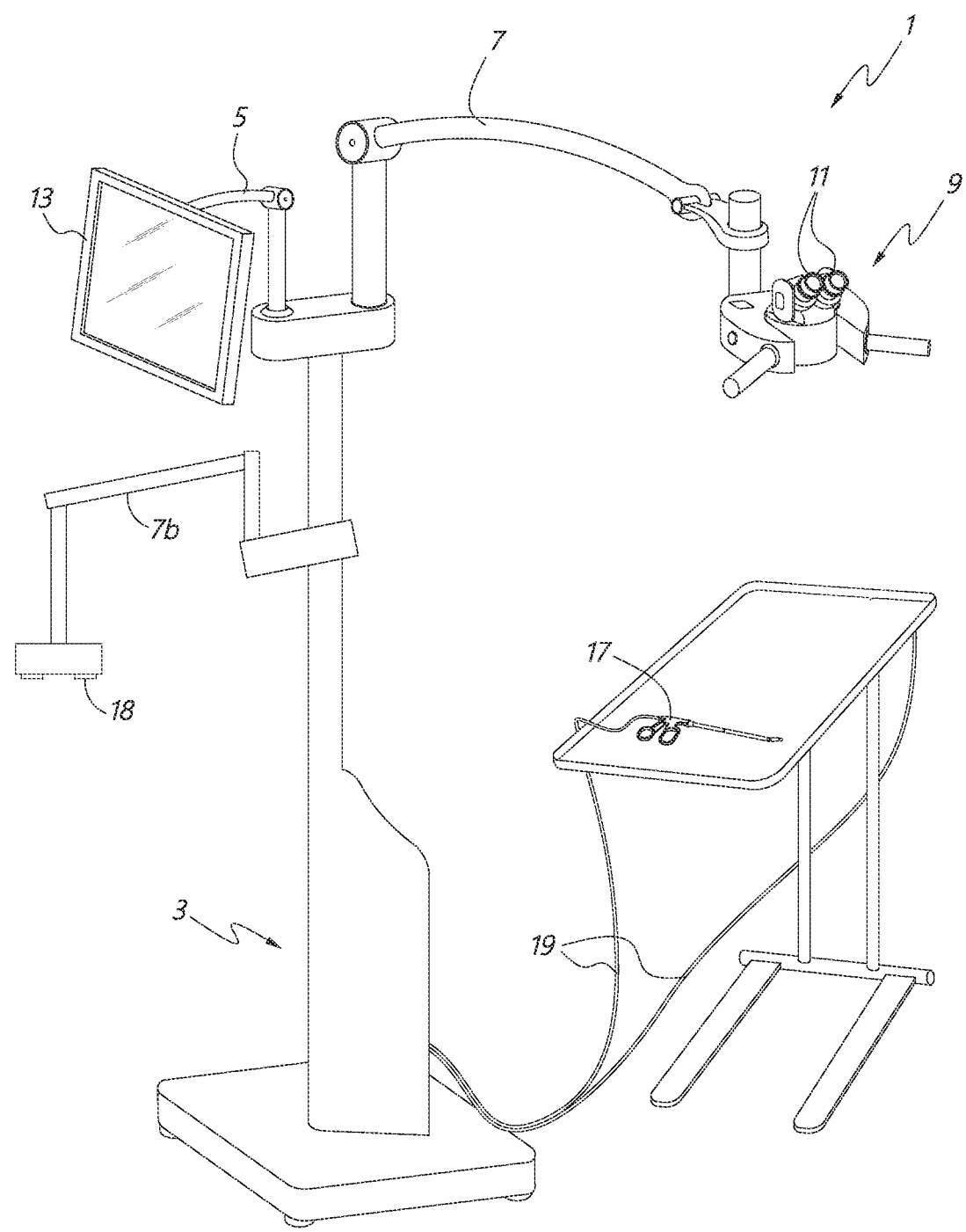
FIG. 1 illustrates an embodiment of the surgical visualization system having an imaging system that can be configured to provide imagery similar to a direct-view surgery microscope.

FIG. 1 shows an example embodiment of a surgical visualization system 1. As illustrated, the system 1 includes a console and electronics 3 from which three arms 5, 7 and 7*b* extend. The first arm 5 has mounted to its distal end a viewing platform 9. The viewing platform may include two oculars 11 and be configured similarly to a standard surgical microscope viewing platform. In some embodiments, however, unlike a conventional surgical microscope or a head mounted display the viewing platform 9 is not a direct view device where the surgeon or other user sees directly through the platform, e.g., an aperture in the platform. In some embodiments, regardless whether the user can view directly through the viewing platform, the surgical visualization system 1 can be configured to display video in a manner that the video displayed is decoupled from movement of the surgical microscope cameras such that a user can adjust the position and/or orientation of the surgical microscope cameras without moving the oculars 11 or the user adjusting position. As discussed in more detail below, the viewing platform 9 may include displays that receive signals from cameras that the surgeon or user employs to view the surgical site.

In some embodiments, cameras can be mounted to the viewing platform 9 and the cameras can be configured to provide imagery of the surgical site. Accordingly, the cameras can be used to provide imagery similar to a conventional surgical microscope. For example, the cameras on the viewing platform 9 can be configured to provide a working distance, or a distance from the viewing platform 9 to the patient, that can vary using zooming. The virtual working distance can vary, where the working distance can be at least about 150 mm and/or less than or equal to about 450 mm, at least about 200 mm and/or less than or equal to about 400 mm, or at least about 250 mm and/or less than or equal to about 350 mm. The working distance can be selected and/or changed by the surgeon. In some embodiments, changing the working distance does not affect the position and/or orientation of the oculars 11 with respect to the user or surgeon. In various embodiments, different objectives having different work distances can be employed for different procedures. One objective can be switched out for another objective to provide a different work distance for a different procedure. In some embodiments, zoom lens systems are included to provide the ability to vary working distance. In some embodiments, the cameras mounted on the viewing platform 9 can be used to provide gesture recognition to allow a surgeon to virtually interact with imagery provided by the display using the surgeon's hands, a surgical tool, or both, as described in greater detail herein.

The second arm 5 has mounted to its distal end an input and display device 13. In some embodiments, the input and display device 13 comprises a touchscreen display having various menu and control options available to a user. In some embodiments, the touchscreen can be configured to receive multi-touch input from ten fingers simultaneously, allowing for a user to interact with virtual objects on the display. For example, an operator may use the input device 13 to adjust various aspects of the displayed image. In various embodiments, the surgeon display incorporating a video camera providing a surgical microscope view may be mounted on a free standing arm, from the ceiling, on a post, or the like. The flat panel display touch screen 13 may be positioned on a tilt/rotate device on top of the electronics console.

A surgical tool 17 can be connected to the console 3 by electrical cable 19. The surgical tool 17 includes, for example, a cutting tool, a cleaning tool, a device used to cut patients, or other such devices. In other embodiments, the surgical tool 17 may be in wireless communication with the console 3, for example via WiFi (e.g., IEEE 802.11a/b/g/n), Bluetooth, NFC, WiGig (e.g., IEEE 802.11ad), etc. The surgical tool 17 may include one or more cameras configured to provide imagery, e.g., image and/or video data. In various embodiments, video data can be transmitted to a video switcher, camera control unit (CCU), video processor, or image processing module positioned, for example, within the console 3. The video switching module may then output a display video to the viewing platform 9. The operator may then view the displayed video through the oculars 11 of the viewing platform 9. In some embodiments, the binoculars permit 3D viewing of the displayed video. As discussed in more detail below, the displayed video viewed through the viewing platform 9 may comprise a composite video formed (e.g., stitched or tiled) from two or more of the cameras on the surgical tool 17.

In use, an operator may use the surgical tool 17 to perform open and/or minimally invasive surgery. The operator may view the surgical site by virtue of the displayed video in the viewing platform 9. Accordingly, the viewing platform (surgeon display system) 9 may be used in a manner similar to a standard surgical microscope although, as discussed above, the viewing platform 9 need not be a direct view device wherein the user sees directly through the platform 9 to the surgical site via an optical path from the ocular through an aperture at the bottom of the viewing platform 9. Rather, in various embodiments, the viewing platform 9 includes a plurality of displays, such as liquid crystal or light emitting diode displays (e.g., LCD, AMLCD, LED, OLED, etc.) that form an image visible to the user by peering into the ocular. Accordingly, one difference, however, is that the viewing platform 9 itself need not necessarily include a microscope objective or a detector or other image-capturing mechanisms. Rather, the image data can be acquired via the cameras of the surgical tool 17. The image data can then be processed by a camera control unit, video processor, video switcher or image processor within the console 3 and displayed imagery may then be viewable by the operator at the viewing platform 9 via the display devices, e.g., liquid crystal or LED displays, contained therein. In some embodiments, the viewing platform 9 can provide a view similar to a standard surgical microscope using cameras and displays and can be used in addition to or in conjunction with a standard surgical microscope optical pathway in the viewing platform. In certain embodiments, the viewing platform 9 can provide a surgical microscope view wherein changes in the viewing angle, viewing distance, work distance, zoom setting, focal setting, or the like is decoupled from movement of the viewing platform 9. In certain embodiments, changes in the position, pitch, yaw, and/or roll of the imaging system 18 are decoupled from the viewing platform 9 such that the imaging system 18 can move and/or re-orient while the surgeon can remain stationary while viewing video through the oculars 11.

The third arm 7b can include an imaging system 18 that can be configured to provide video similar to a direct-view surgery microscope. The imaging system 18 can be configured, then, to provide a surgical imaging system configured to provide an electronic microscope-like view that can comprise video of the work site or operational site from a position above the site (e.g., about 15-45 cm above the surgical site) or from another desired angle. By decoupling the imagers 18 from the display, the surgeon can manipulate the surgical imaging system to provide a desired or selected viewpoint without having to adjust the viewing oculars. This can advantageously provide an increased level of comfort, capability, and consistency to the surgeon compared to traditional direct-view operating microscope systems. In some embodiments, as described herein, the imagers 18 can be located on the viewing platform 9, on a dedicated arm 7b, on a display arm 5, on a separate post, a separate stand, supported from an overhead structure, supported from the ceiling or wall, or detached from other systems. The imagers 18 can comprise a camera configured to be adjustable to provide varying levels of magnification, viewing angles, monocular or stereo imagery, convergence angles, working distance, or any combination of these.

The viewing platform 9 can be equipped with wide field-of-view oculars 11 that are adjustable for refractive error and presbyopia. In some embodiments, the oculars 11, or eyepieces, may additionally include polarizers in order to provide for stereoscopic vision. The viewing platform 9 can be supported by the arm 7 or 7b, such that it may be positioned for the user to comfortably view the display 13 through the oculars 11 while in position to perform surgery. For example, the user can pivot and move the arm 7 or 7b to re-orient and/or re-position the viewing platform 9. In some embodiments, the viewing platform 9 can be positioned above the patient while in use by the surgeon or other user. The surgeon can then be positioned next to the patient while performing surgery.

In some embodiments, the image processing system and the display system are configured to display imagery placed roughly at infinity to reduce or eliminate accommodation and/or convergence when viewing the display. For example, the display system can be configured with sufficient eye relief for the user to reduce fatigue associated with using the display system. A display optical system can include one or more lenses and one or more redirection elements (e.g., mirrors, prisms) and can be configured to provide light from the display that can be imaged by a binocular viewing assembly comprising a pair of oculars, objectives, and/or turning prisms or mirrors. The display devices such as liquid crystal displays can be imaged with the objective and the pair of oculars and display optical system within the viewing platform 9. The binocular assembly and display optical system can be configured to produce an image of the displays at infinity. Such arrangements may potentially reduce the amount of accommodation by the surgeon. The oculars can also have adjustments (e.g., of focus or power) to address myopia or hyperopia of the surgeon. Accordingly, the surgeon or other users may view the displays through the oculars without wearing glasses even if ordinarily prescription glasses were worn for other activities.

In certain implementations, the display optical system does not include a pair of oculars but instead includes two or more chambers that are optically separate to form left and right eye paths. In such implementations, the display optical system can be baffled to prevent light communication between the left and right eye channels. To adjust for different accommodations, the displays within the display system can be configured to move toward and/or away from the viewer along the optical path. This can have an effect similar to varying focal lengths of lenses in an ocular system. In some embodiments, the display housing with the electronic displays can change to move the displays closer or further from the viewer along the optical path. In some embodiments, both the display housing and the electronic displays are configured to be adjustable along the optical path to adjust for accommodation.

Figure 2:
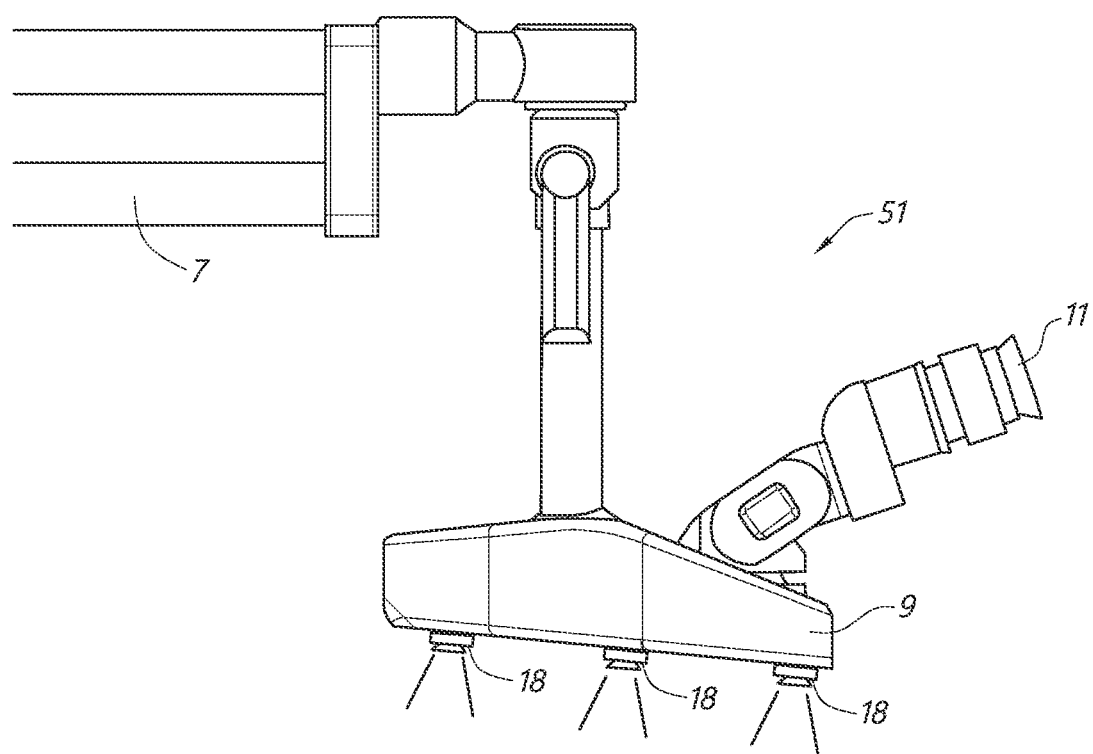
FIG. 2 illustrates an example surgical viewing system attached to an articulating arm, the system including one or more cameras mounted on a binocular viewing platform.

In some embodiments, the viewing platform 9 can include one or more imagers configured to provide electronic microscope-like imaging capabilities. FIG. 2 illustrates an example surgical imaging system 51 attached to an arm 7, the system 51 including one or more cameras 18 mounted on a viewing platform 9. The cameras 18 can be configured to provide imagery of a worksite. The image data can be presented on a display that the user can view using oculars 11 mounted on the viewing platform 9. This design can be used to mimic other direct-view microscopes, but it can also be configured to provide additional capabilities. For example, the surgical imaging system 51 can be configured to have a variable working distance without adjusting the viewing platform 9 or the articulating arm 7. In some embodiments, the working distance can be adjusted by adjusting one or more elements of imaging optics of the camera(s) 18 mounted on the viewing platform 9. In certain implementations, the working distance can be adjusted by adjusting a zoom or focal length of a zoom optical apparatus. The surgical imaging system 51 can be configured to provide image processing capabilities such as electronic zooming and/or magnification, image rotation, image enhancement, stereoscopic imagery, and the like. Furthermore, the imagery from the cameras 18 can be combined with imagery from cameras on the surgical device 17. In some embodiments, the surgical imaging system 51 can provide fluorescence images.

Although the discussion considers images from surgical tools, numerous embodiments may involve at least one auxiliary video camera 18 and one or more other cameras that are not disposed on surgical tools but are disposed on other medical devices. These medical devices may include devices introduced into the body such as endoscopes, laparoscopes, arthroscopes, etc.

Accordingly, one or more displays such as the at least one display 13 included in the viewing platform 9 may be used to provide a surgical microscope view using one or more cameras such as the auxiliary video camera(s) 18 as well as to display views from one or more cameras located on such medical devices other than surgical tools. In some embodiments, cameras from a variety of sources, e.g., surgical tools and other medical devices, in any combination, may be viewed on the display(s) on the surgical platform together with the surgical microscope view from the auxiliary video cameras 18. As described herein, the displays may provide 3D thus any of the images and graphics may be provided in 3D.

In various embodiments, a virtual touchscreen may be provided by the auxiliary video cameras 18 or other virtual touchscreen cameras mounted to the viewing platform 9. Accordingly, in some embodiments a user may provide a gesture in the field of view of the auxiliary video cameras and/or virtual touchscreen cameras and the processing module can be configured to recognize the gesture as an input. Although the virtual display has been described in the context of the auxiliary video cameras 18, other cameras, e.g., virtual reality input cameras, possibly in addition to the auxiliary video cameras 18 may be used. These cameras may be disposed on the viewing platform 9 or elsewhere, such as the third arm 7b. As described herein the displays may provide 3D thus the virtual reality interface may appear in 3D. This may increase the immersive quality of the viewing experience, enhancing the detail and/or realistic presentation of video information on the display.

Figure 3A:
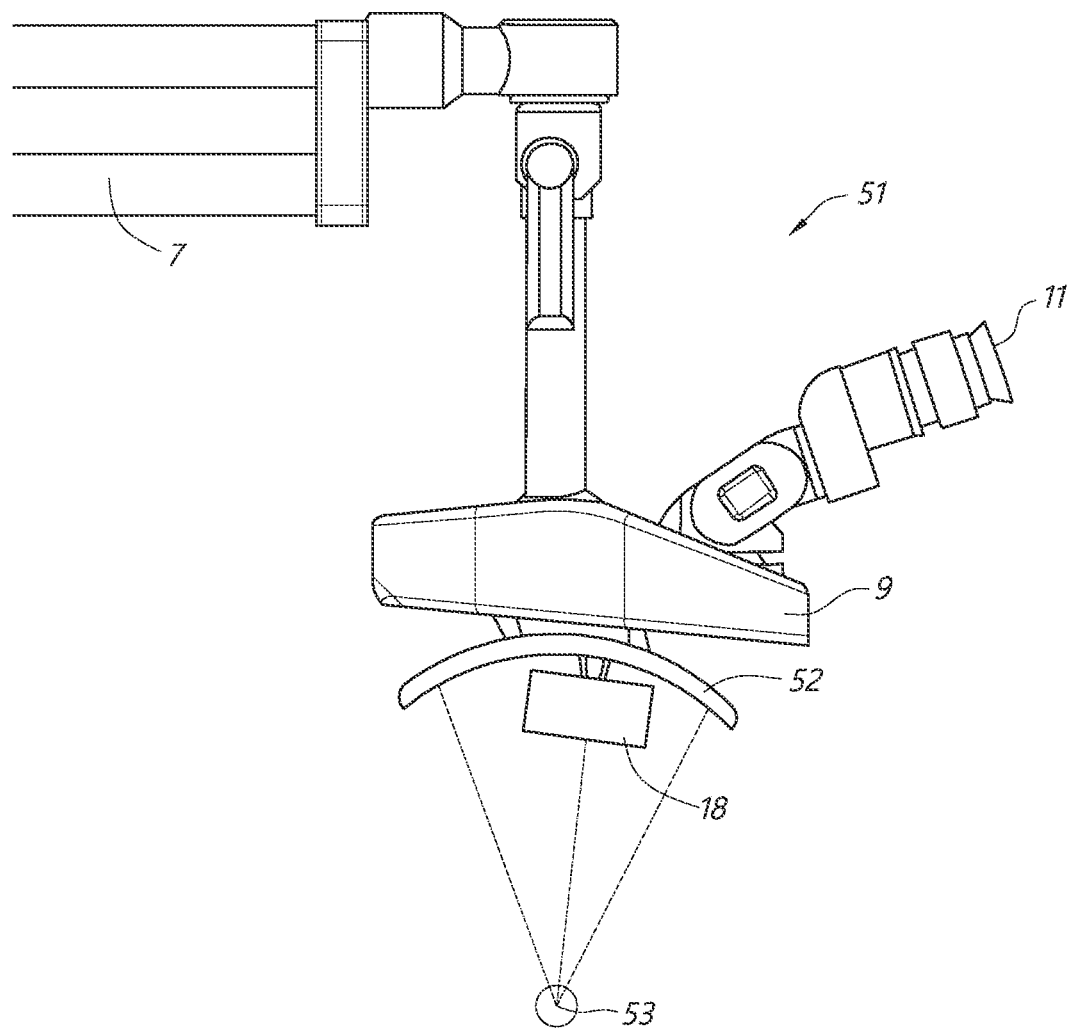

In some embodiments, as illustrated in FIG. 3A, the surgical imaging system 51 includes an isocenter positioning system 52 attached to the viewing platform 9. The isocenter positioning system 52 can include a single track or guide configured to move and orient the cameras 18 such that they are substantially pointed at a single point 53, the isocenter. In some embodiments, a second track or guide can be attached to the first guide in an orthogonal manner to provide movement along two dimensions while substantially maintaining the pointing angle towards the isocenter 53. Other configurations can be used to provide isocenter pointing capabilities, such as articulating arms, electro-mechanical elements, curved friction plates, etc. In some embodiments, as illustrated in FIG. 3B, the imaging system is configured to move in an isocenter manner. This can be used to enhance dexterity of the user of the system because hand-eye coordination is increased or maximized. Such enhanced dexterity can be vital for prolonged and/or difficult surgery. In the displayed embodiment, the horizons of the acquisition systems are configured to be horizontal to match the horizon of the display system and the user. As shown in FIG. 3B, in various embodiments, a stereo imaging system may be maintained in a horizontal configuration as it is moved across a range of locations to avoid confusion for the user viewing the video from the stereo camera. By maintaining a common relative horizon between the display and the acquisition system, the user can relatively easily translate hand motion to manipulation of objects in the display, which may not be the case where translation of the acquisition system is accompanied by a relative rotation between the display and the acquisition system.

In the embodiments illustrated in FIGS. 3A and 3B, the isocenter assemblies can be a part of the display system or a separate, independent system. For example, the viewing platform 9 can be mounted on a separate arm from the cameras 18. Thus, the display and the image acquisition of the surgical imaging system can be decoupled, similar to the embodiment illustrated in FIG. 1. By decoupling the isocenter cameras 18 from the display ergonomic benefits are provided such as, for example, the surgeon does not need to be looking through binoculars for an extended period of time or at an uncomfortable position or angle. In various embodiments, a common relative horizon for both the display and the acquisition system may also be employed.

In some embodiments, the distance between the surgical site of interest and the imagers, e.g., the working distance, can be at least about 20 cm and/or less than or equal to about 450 cm, at least about 10 cm and/or less than or equal to about 50 cm, or at least about 5 cm and/or less than or equal to about 1 m, although values outside this range are possible.

The user can interact with the surgical imaging system 51 to select a working distance, which can be fixed throughout the procedure or which can be adjusted at any point in time. Changing the working distance can be accomplished using elements on a user interface, such as a graphical user interface, or using physical elements such as rotatable rings, knobs, pedals, levers, buttons, etc. In some embodiments, the working distance is selected by the system based at least in part on the cables and/or tubing being used in the surgical visualization system. For example, the cables and/or tubing can include an RFID chip or an EEPROM or other memory storage that is configured to communicate information to the surgical imaging system 51 about the kind of procedure to be performed. For an ENT/Head/Neck procedure, the typical working distance can be set to about 40 cm. In some embodiments, the user's past preferences are remembered and used, at least in part, to select a working distance.

In some embodiments, the working distance can be changed by translating an imaging lens or imaging lenses along a longitudinal axis (e.g., a z-axis parallel to gravity). The imaging lens(es) can be translated in an orthogonal and/or transverse direction (e.g., x- and/or y-axis) to adjust a convergence angle with changes in the working distance. In this way, the viewing platform 9 and/or the position of the cameras 18 can remain relatively fixed with changes in working distance. This can also provide for stereoscopic image acquisition, thereby providing 3D video to the surgeon while being able to change working distance.

In some embodiments, gross focus adjustment can be accomplished manually by positioning the cameras 18 and arm 7. The fine focus adjustment can be done using other physical elements, such as a fine focusing ring, or it can be accomplished electronically.

In some embodiments, the magnification of the surgical imaging system 51 can be selected by the user using physical or virtual user interface elements. The magnification can change and can range between about 1× and about 6×, between about 1× and about 4×, or between about 1× and about 2.5×. Embodiments may be able to change between any of these such as between 2.5× and 6× or between 2.5× and 6×. Values outside these ranges are also possible. For example, the system 51 can be configured to provide magnification and demagnification and image inversion, with a range from about −2× to about 10×, from about −2× to about 8×, from about −2× to about 4×, from about −0.5× to about 4×, or from about −0.5× to about 10×. The surgical imaging system 51 can be configured to decouple zoom features and focus adjustments, to overcome problems with traditional operating room microscopes. In some embodiments, the surgical visualization system 51 can be used to provide surgical microscope views. In some embodiments, the surgical imaging system 51 can decouple instrument myopia by providing an electronic display instead of a direct view of a scene. The electronic displays can be configured to be focused at varying levels of magnification allowing the user to view the displays without adjusting the oculars between magnification adjustments. Moreover, in various embodiments, the oculars can be configured to provide continuous views at infinity. In some embodiments, however, the principal user of the surgical imaging system may select an accommodation level for the oculars, rather than using a relaxed view provided by the electronic displays. The electronic displays, in various embodiments, however, can remain in focus and the ocular adjustments do not affect the focus of the various video acquisition systems. Thus, adjustments by the principal user do not affect the views of the other users of the system viewing, for example, other displays showing the video, as the cameras/acquisition systems can remain focused. In some embodiments, the surgical imaging system 51 can be focused at a relatively close working distance (e.g., a distance with a relatively narrow depth of field) such that the image remains focused when moving to larger working distances (e.g., distances with broader depth of field). Thus, the surgical imaging system 51 can be focused over an entire working range, reducing or eliminating the need to refocus the system after magnification or zoom adjustments are made.

In some embodiments, the surgical imaging system 51 includes an afocal zoom assembly to provide changes in magnification. The afocal zoom assembly comprises an afocal system that can be used to provide variations in magnification at a fixed working distance and/or to provide variations in magnification with changes in working distance. In certain embodiments, the surgical imaging system 51 includes a common objective for left and right optical paths (e.g., left and right lens systems) corresponding to left and right imaging sensors configured to produce images for the left and right eyes of the user. The left and right lens systems can each comprise one or more lenses or lens groups disposed in each of the respective left and right paths. The common objective (e.g., a single lens, compound lens, or lens group) can be configured to have a focal length corresponding to a distance to the object. The afocal zoom assembly can thus receive collimated light from the objective and produce collimated light while changing a magnification of the optical system of the surgical imaging system 51. The zoom or variable magnification can provide selectable magnification or zoom. In certain embodiments, the surgical imaging system 51 includes a variable diaphragm to adjust the aperture of the optical system. The variable diaphragm can be adjusted to increase or decrease the f-number of the optical system or the variable diaphragm can be adjusted to maintain a relatively constant f-number with changes in the magnification of the optical system.

In some embodiments, the surgical imaging system 51 includes a zoom optical system that functions to change working distance and/or magnification. The surgical imaging system 51 can also include a zoom objective lens and one or more afocal zoom assemblies.

The surgical imaging system 51 can include a gimbal system to point the camera(s), for example, objective as desired. In various embodiments, the gimbal system is configured to provide isocentric views of the worksite or surgical site. The gimbal system can be configured to change the relative position and/or orientation of imaging optics to maintain a isocentric views. In some embodiments, the gimbal system can be configured to move the imaging system (e.g., the optical assembly) while maintaining the isocentric view while also maintaining the position and/or orientation of the oculars of the surgical imaging system 51 relatively motionless.

Figure 4B:
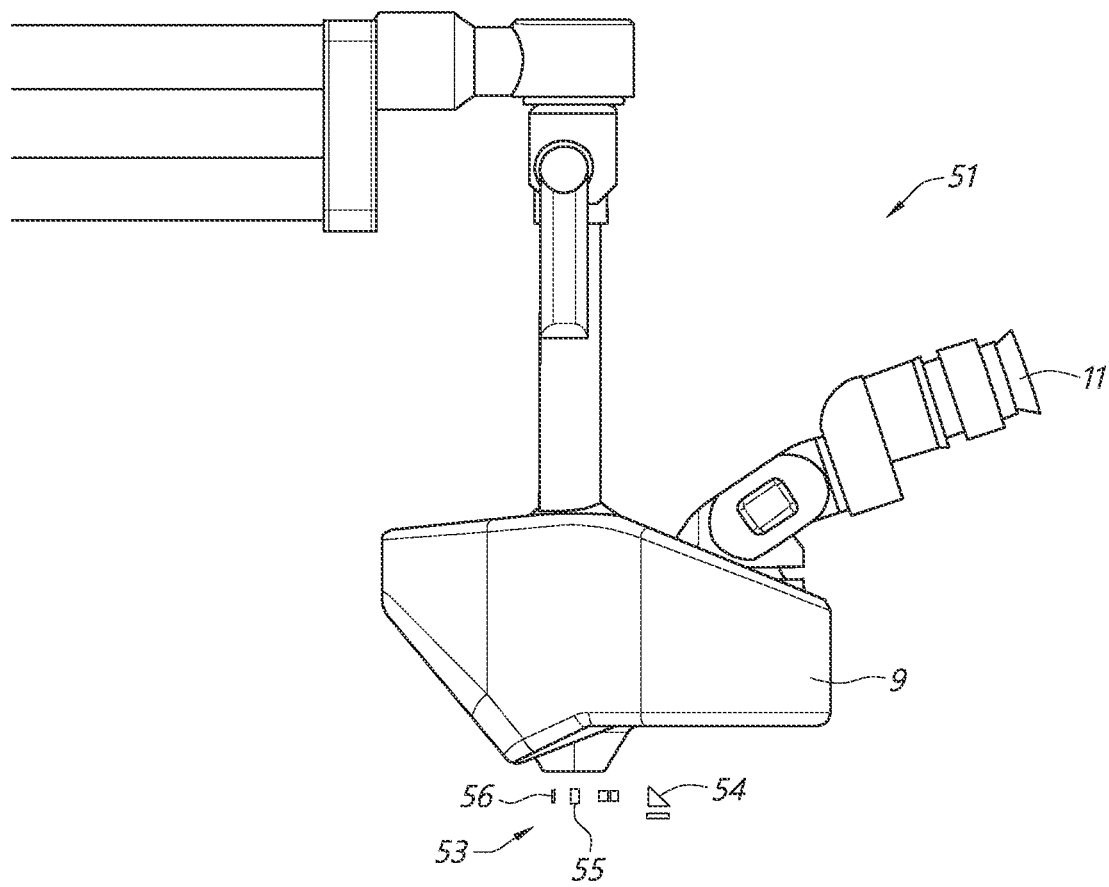

FIGS. 4A and 4B illustrate an embodiment of the surgical imaging system 51 having an optical system 53 mounted under the viewing platform 9. As illustrated, the optical components are shown as free-standing to show the structure of the components, but in practice the optical components 53 will be mounted within or on a structure attached to the viewing platform. In some embodiments, the optical system 53 and/or the cameras 18 (discussed above) can be modular and can be selected and swapped for use with the surgical imaging system 51.

The optical system 53 is configured to provide stereo image data to the imaging system 51. The optical system 53 includes a turning prism 54 to fold the optical path underneath the viewing platform 9 to decrease the physical extent (e.g., length) of the imaging system under the viewing platform 9. The turning prism 54 can be configured to fold the optical path from vertical to horizontal. This design can reduce the thickness (e.g., vertical dimension) of the optical system 53. This configuration can also reduce the size of any housing used to house the optical system 53. This approach can also reduce the size of the viewing platform 9, for example, where the optical system is incorporated into the housing of the viewing platform 9.

The optical system 53 can include, in some embodiments, an objective lens or objective lens group, an afocal zoom lens group, an imaging lens or lens group, and an image sensor or other similar detector. The afocal zoom lens group can be adjusted or manipulated to receive and produce a collimated beam wherein the adjustments alter the zoom or magnification of the optical system 53. The optical system 53 can include a common objective lens or objective lens group for both right and left optical paths (e.g., corresponding to right and left eye views for a stereoscopic display). Alternatively, the optical system 53 can include a separate objective lenses or lens groups for both right and left optical paths (e.g., corresponding to right and left eye views for a stereoscopic display). In various embodiments, the objective provides a collimated beam to the afocal zoom. The afocal zoom may also output a collimated beam in certain embodiments. In some embodiments, the optical system 53 is configured to translate the imaging lens or imaging lens group along a longitudinal axis or vertical axis (e.g., a z-axis) to change the working distance. The optical system 53 can also be configured to translate the imaging lens or imaging lens group along a transverse or horizontal axis (e.g., a x- and/or y-axis) to alter the convergence angle. In some implementations, alterations of the convergence angle correspond to changes in the working distance to maintain appropriate convergence at a targeted location or distance. For example, as the working distance decreases, the convergence angle can be made to increase. In certain embodiments, the convergence angle of the optical system 53 can be about 3 degrees at about 300 mm working distance, or between about 2 degrees and about 5 degrees at between about 150 mm and about 500 mm working distance, or between about 1 degree and about 10 degrees at between about 50 mm and about 1000 mm working distance. Values outside these ranges are also possible.

In some embodiments, the optical system 53 includes a zoom optical system that functions to change working distance and/or magnification. The optical system 53 can also include a zoom objective lens and one or more afocal zoom assemblies.

In some embodiments, the optical system 53 comprises a Greenough-style system wherein the optical paths for each eye have separate optical components. In some embodiments, the optical system 53 comprises a Galilean-style system wherein the optical paths for each eye pass through a common objective. The Greenough-style system may be preferable where imaging sensors are being used to capture and convey the image data as compared to the Galilean-style system. The Galilean system can introduce aberrations into the imagery by virtue of the rays for each eye's optical path passing through a periphery of the objective lens. This does not happen in the Greenough-style system as each optical path has its own optics. In addition, the Galilean system can be more expensive as the objective used can be relatively expensive based at least in part on the desired optical quality of the lens and its size.

The optical system 53 can include two right-angle prisms 54, two zoom systems 55, and two image sensors 56. This folding is different from a traditional operating room microscope because the optical path leads to image sensors rather than to a direct-view optical system.

In some embodiments, the optical system 53 can have a relatively constant F-number. This can be accomplished, for example, by varying the focal length and/or aperture of the system based on working distance and/or magnification. In one embodiment, as the focal length changes, the eye paths can move laterally apart (or together), the prisms 54 can rotate to provide an appropriate convergence angle, and the apertures can change their diameters to maintain the ratio of the focal length to the diameter a relatively constant value. This can produce a relatively constant brightness at the image sensor 56, which can result in a relatively constant brightness being displayed to the user. This can be advantageous in systems, such as the surgical visualization systems described herein, where multiple cameras are being used and changing an illumination to compensate for changes in focal length, magnification, working distance, and/or aperture can adversely affect imagery acquired with other cameras in the system. In some embodiments, the illumination can change to compensate for changes in the focal length and/or the aperture so as to provide a relatively constant brightness at the image sensors 56. In some embodiments, illumination can be provided through the objective lens or objective lens group of the optical assembly 53.

The optical assembly 53 can include a zoom system 55 configured to provide a variable focal distance and/or zoom capabilities. A Galilean-style stereoscopic system generally includes a common objective for the two eye paths. When this optical system is imaged with image sensors 56, it can create aberrations, wedge effects, etc. that can be difficult to compensate for. In some embodiments, the surgical imaging system 51 can include a Galilean-style optical system configured to re-center at least one of the stereo paths to a central location through the objective lens, which can be advantageous in some applications.

In some embodiments, the real-time visualization system utilizes a Greenough-style system. This can have separate optical components for each stereo path. The optical assembly 53 can be configured to provide variable magnification and/or afocal zoom and can be configured to operate in a magnification range from about 1× to about 6×, or from about 1× to about 4×, or from about 1× to about 2.5×.

The distal-most portion of the Greenough assembly 53 can be similar in functionality to an objective lens of a typical, direct-view operating room microscope with the working distance set approximately to that of the focal length. The working distance, and in some implementations the focal length, can be between about 20 cm and about 40 cm, for example. In some embodiments the work distance may be adjustable from 15 cm to 40 cm or to 45 cm. Other values outside these ranges are also possible. In some embodiments, the surgical imaging system 51 includes an opto-mechanical focus element configured to vary the focal length of a part of the optical assembly 53 or the whole optical assembly 53.

Figure 5A:
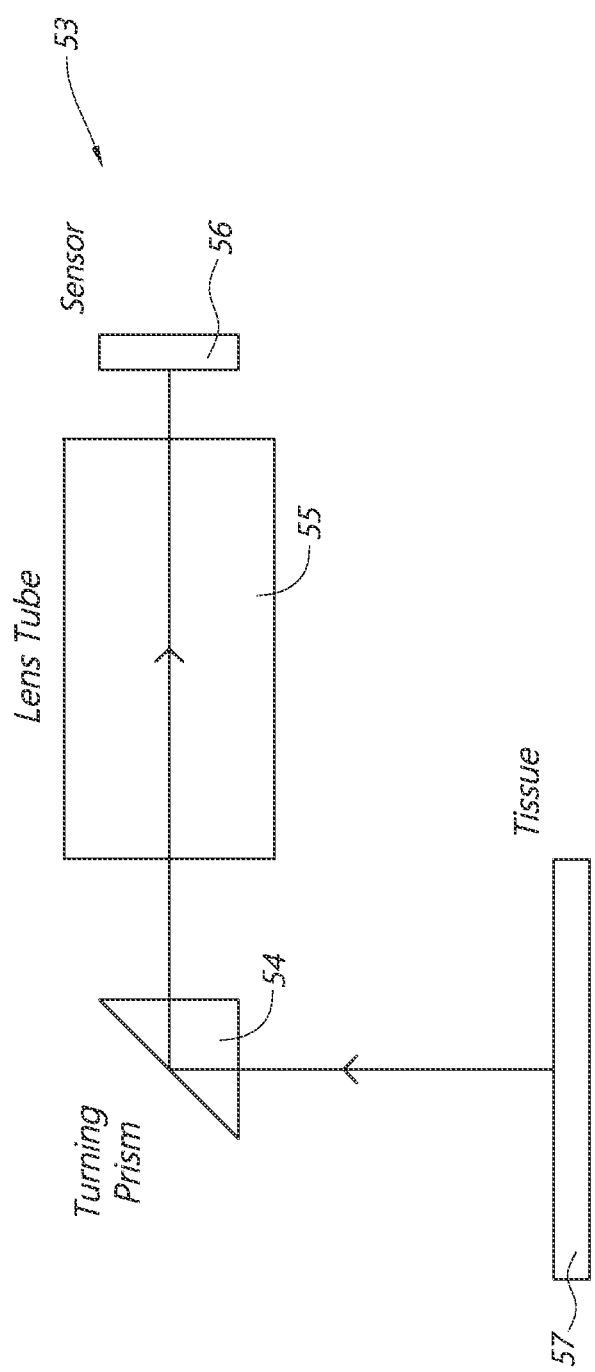
FIGS. 5A-5E illustrate embodiments of optical imaging systems for use in a stereoscopic surgical viewing system, such as those illustrated in FIGS. 4A and 4B.

FIGS. 5A-5E illustrate embodiments of optical assemblies 53 for use in a stereoscopic surgical imaging system, such as those described herein with reference to FIGS. 4A-4B. FIG. 5A illustrates a side view of an example optical assembly 53 configured to use a turning prism 54 to fold an optical path from a tissue 57 to a sensor 56 along a lens train 55 that is situated near or adjacent to a viewing platform 9. This can advantageously provide a relatively long optical path in a relatively compact distance.

Figure 5B:
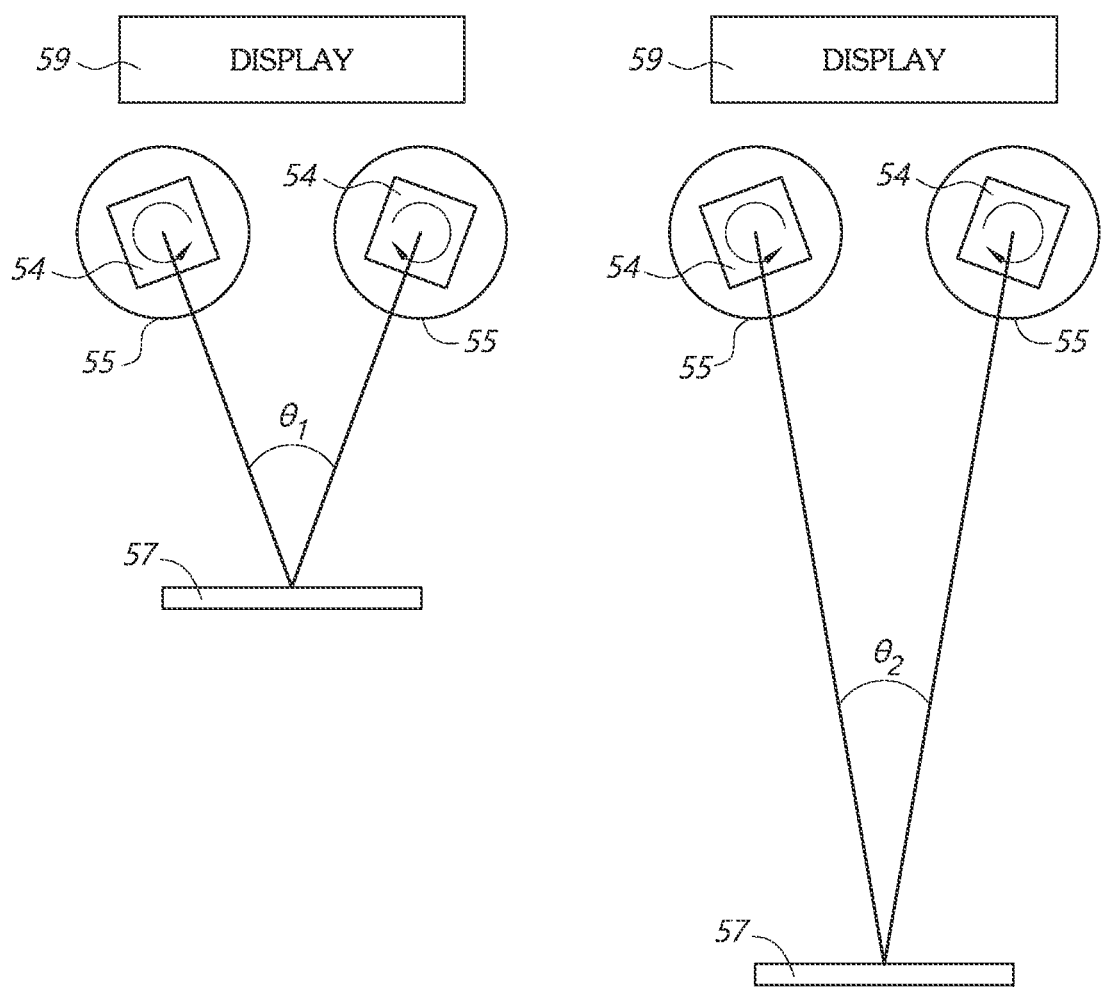

FIG. 5B illustrates a front view of an embodiment of an optical assembly configured to change a convergence angle in a stereoscopic imaging system. The prisms 54 can be the turning prism 54 illustrated in FIG. 5A. The prisms 54 can be configured to rotate to change a convergence angle, and as a result, a convergence point and/or a working distance. The working distance, which can be a distance from the prisms 54 to the target 57 (e.g., tissue), can be user-selectable or adjustable. In various embodiments, with increased working distance to the target 57, the convergence angle can decrease. Conversely, when the working distance gets smaller, the convergence angle can increase (e.g., θ1>θ2). This can be advantageous where the lens path 55 is fixed and the working distance is adjustable. The stereo imagery can then be viewed on the display 59 by a user.

Figure 5C:
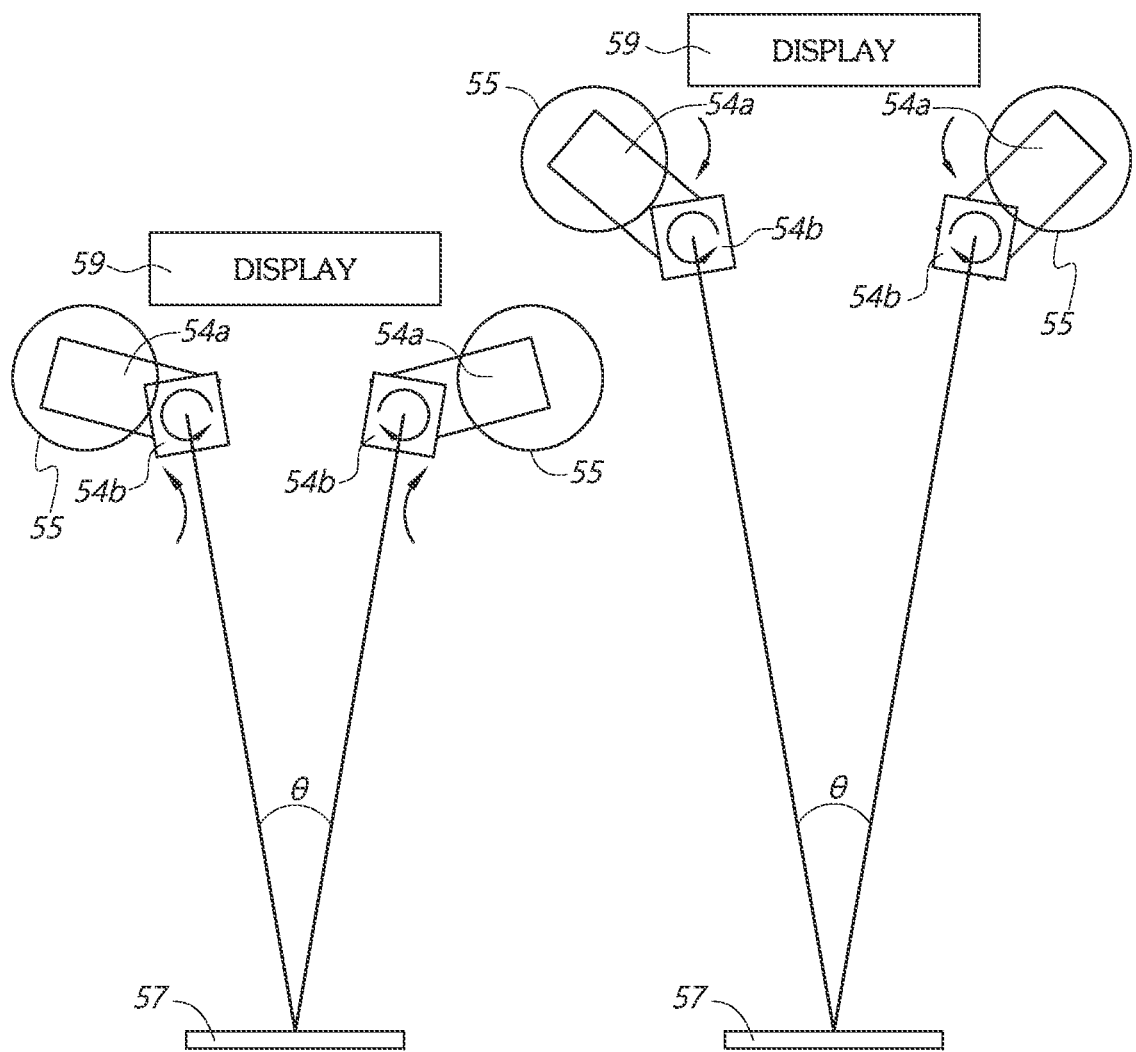

FIG. 5C illustrates a front view of an embodiment of an optical assembly 53 that is configured to maintain a substantially constant convergence angle. The optical assembly 53 can include two prisms 54a and 54b for each optical path, wherein the prisms 54a, 54b can move and/or rotate. For example, when the working distance decreases the first set of prisms 54a can rotate towards one another to decrease an effective distance between the second set of prisms 54b. The second set of prisms 54b can, in turn, rotate to compensate for the changed angle so as to converge on the common target. The second set of prisms 54b can direct the light to the first set of prisms 54a which can then direct the light down the fixed lens paths 55 (e.g., fixed in their position relative to the viewfinder). By providing a relatively fixed convergence angle, a change in working distance may not require refocusing for the user. Maintaining a constant convergence angle, especially a comfortable angle, may reduce the strain on the user such as a surgeon performing a prolonged, arduous procedure.

Figure 5D:
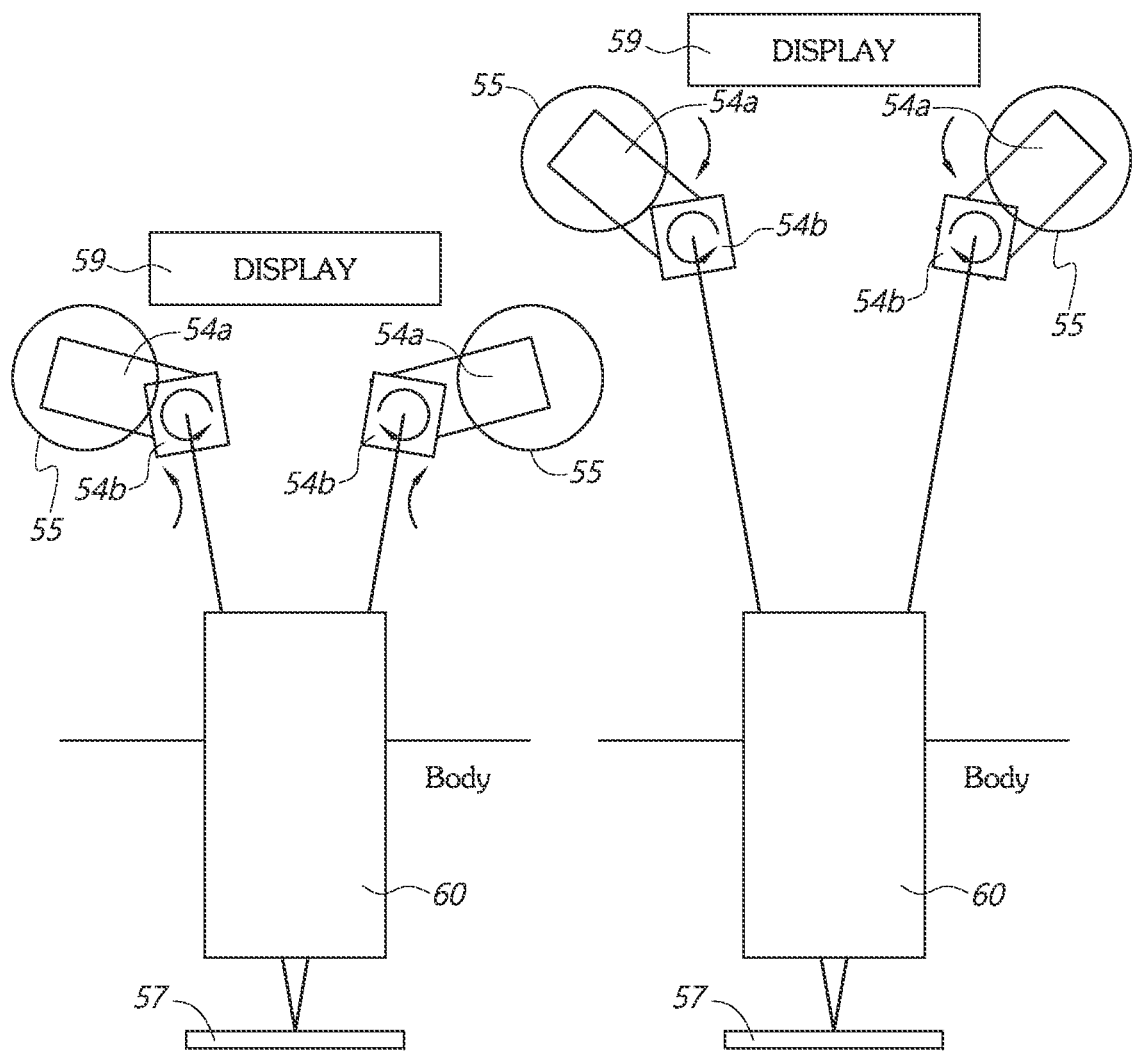

FIG. 5D illustrates a front view of an embodiment of an optical assembly 53 configured to provide a substantially narrow convergence angle to be able to view stereoscopic imagery through a narrow insertion tube 60 (e.g., a tube partially inserted into a body during a procedure). A similar assembly 53 can be used as described with reference to FIG. 5C, and the convergence angle can be maintained substantially constant or at least sufficiently narrow to view through the insertion tube 60.

Figure 5E:
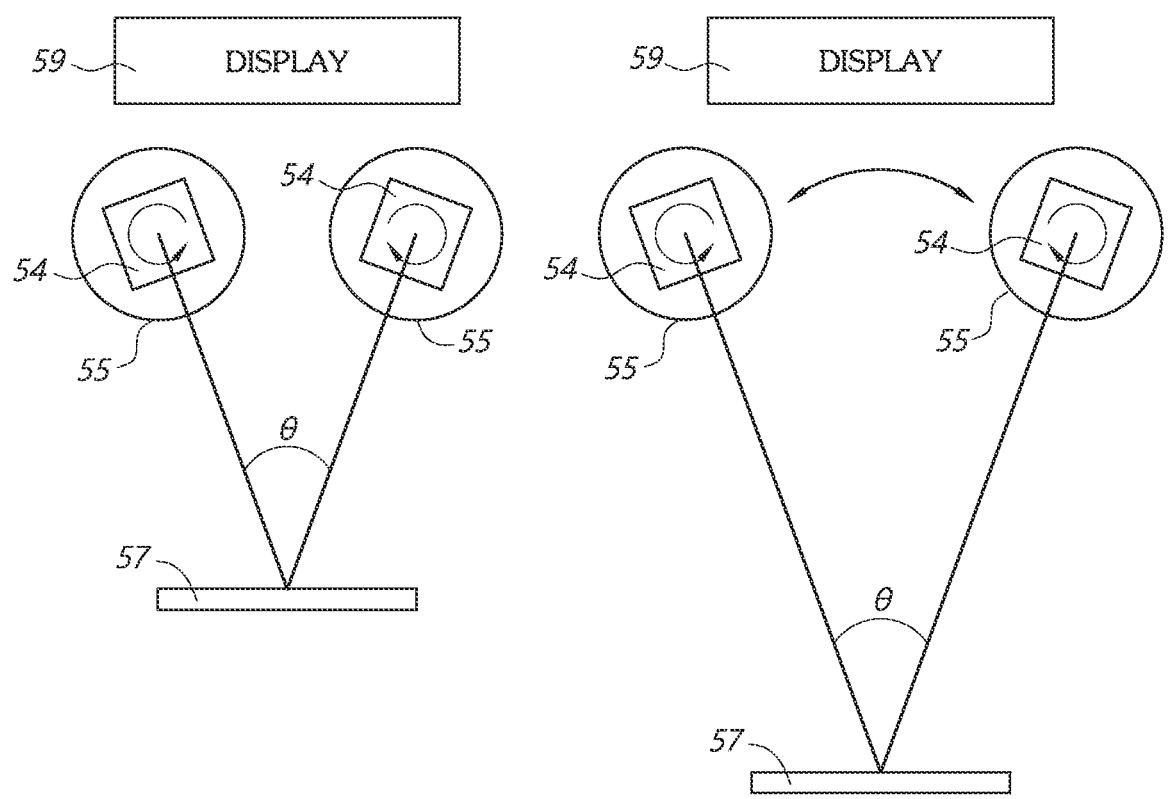

FIG. 5E illustrates a front view of an embodiment of an optical assembly 53 configured to provide a substantially constant convergence angle by moving the lens paths 55 laterally, e.g., toward or away from one another. The prisms 54 can be made to have a substantially constant orientation (e.g., no rotation for changing working distances) and compensation for changing working distance can be accomplished by translating the optical paths laterally to separate or join the optical paths. The translation of the optical paths can be accomplished using any suitable means including, for example, electro-mechanical actuators, slides, articulating arms, etc. This can simplify the optical assembly compared to the embodiments having two sets of prisms as only one set of prisms may be used when the lens paths are configured to move.

The embodiments of the optical assembly 53 which are configured to maintain a sufficiently narrow convergence angle can be advantageous as they allow stereo access to narrow surgical entries by allowing the angle to decrease and avoid clipping one of the stereo paths. For example, the left and right lens paths can move closer to one another and the prisms can adjust to the proper convergence angle for that distance. As another example, the left and right lens paths can remain fixed and there can be sets of prisms for each path configured to direct the light along the lens paths while maintaining a substantially constant convergence angle. In some embodiments, maintaining a constant convergence angle can be visually helpful to the user when zoom changes, e.g., because the changing depth cues do not confuse the user's eye and/or brain. In addition, constant convergence may induce less stress on the user. In some embodiments, the optical assembly 53 includes a source of illumination, such as a fiber optic or light emitting diode (LED) or other type of light source providing light through one or more of the optical elements of the optical assembly 53. In certain implementations, the light source (e.g., fiber optic, LED, etc.) provides illumination through the objective lens or objective lens group to provide illumination to the worksite. (A beamsplitter or beam combiner may be used to couple light into the optical path or the light source may itself be disposed in the optical path.) This arrangement can be useful as the light from the light source (e.g., fiber optic, LED, etc.) can be directed to the worksite along a similar optical path as light arriving from the worksite. This configuration can help the user to control the location and/or amount of illumination provided by the light source (e.g. fiber optic, LED, etc.). For example, the user can direct the illumination to the same location that the user is viewing. As another example, changes in the relative positions of the objective lens and light source (e.g., fiber optic, LED, etc.) can change the divergence of the light to increase or decrease the amount of light per unit area at the worksite. As another example, changes in the focal length of the objective lens group can change the divergence of the light from the light source (e.g., fiber optic, LED, etc.) to control illumination at the worksite. In some embodiments, additional optics such as beam shaping optics may be included for the light source. One or more lenses may for example be disposed forward of the fiber optic or LED or other light source and may be adjustable, to control divergence and/or beam size.

In some embodiments, the source of illumination can be controlled using a gimbal. The light source may be mounted on a gimbal or one or more other translation/rotation devices to provide the ability to controllably redirect the beam into different directions. The gimbal or other orientation control device may be moved manually or have electrically driven actuators to control movement of the system and the direction of the beam. The gimbal can be used to provide illumination with variable pitch. The gimbal can also be used to steer the illumination to provide light at a targeted location, with a targeted intensity, and/or from a desired or selected angle.

Multiple light sources may be employed. These multiple light sources may, for example, be on opposite sides of the optical path. In some embodiments, different light sources are mounted on different gimbals (or motion and/or orientation control systems) such as described above and elsewhere herein. Accordingly, a plurality of beams may be controlled so that a first beam from a first light source may be directed in a first direction (possibly using a first gimbal system) and a second beam from a second light source may be directed in a second different direction (possibly using a second gimbal system) and the first and second light sources and directions can be separately changed subsequently. In some embodiments, the size of the beam at the object is less than the field of view of the camera imaging the object. The multiple light sources can be used to fill a larger portion of that field of view that is larger than the beam from a single light source. In various embodiments, the plurality of beams from the plurality of light sources fills at least as large as the field of view of the one or more cameras imaging the object.

In various embodiments, as the optical assembly changes zoom or magnification, the illumination from the light source (e.g., fiber optic or LED) can change. For example, variable divergence of the illumination can accompany changes in zoom of the optical assembly 53 to place more light energy in an area for imaging that area. In some implementations, the fiber optic illumination source can be adjusted to maintain a relatively constant divergence with changes in zoom of the optical assembly 53 by placing the illumination at a place in the optical assembly 53 or elsewhere where the optical properties remain relatively constant with changes in zoom.

In some embodiments, the optical assembly 53 can include a common objective lens with one or more zoom lenses (e.g. Galilean configuration) or can have separate objectives for separate left and right optical paths (e.g., Greenough configurations) with the fiber optic illumination or other illumination. This arrangement can be used to transform the effective numerical aperture of the fiber optic (or other type of light source) to achieve targeted or desired illumination effects. In some embodiments, the source of illumination is remote from the optical assembly 53 and may be delivered to the worksite through the fiber optic. In other embodiments, however, as described above, instead of employing a fiber optic, a light source such as a light emitting diode (LED) or other emitter (e.g., solid state emitter), with or without beam shaping optics (e.g., one or more lenses) can be employed instead of a fiber. One or more fibers and one or more light sources (such as multiple LEDs) can be employed, for example, at different location such as on opposite sides of the optical path or surgical site. Similar combination of one or more fiber and one or more light source such as one or more LEDs can be used. As described above, these can be included in the optical system in some embodiments such that the light from the fiber or light source propagates through the camera optics used for imaging (e.g., objective, afocal zoom, and/or imaging lens) to illuminate the surgical site or a portion thereof. In various embodiments, the light from the light source propagates through the objective (and not the afocal zoom and/or imaging lens) prior to being incident on the object. Such a configuration can reduce the amount of back reflected from the optical surfaces that results in light incident on the sensor. In various embodiments, a beam splitter or beam combiner (e.g., prism) may be use to couple the illumination beam into the optical path of the camera. In other cases, the light source may be disposed itself in the optical path. In some embodiments the light source (e.g., fiber, LED, etc.) is disposed adjacent to the camera and does not couple light such that the light propagates through the camera optics prior to being incident on the surgical site.

Light sources may be used in connection with providing illumination of the object for the one or more proximal cameras disposed above the surgical site or body by, e.g., 25-40 mm, for one or more cameras mounted on a surgical tool, as well as for one or more cameras that provide a surgical microscope view, for other cameras or for any combination thereof. The light sources and illumination configurations including for example the gimbals or other positioning orientation devices may be useful for any of these applications (e.g., one or more proximal cameras, one or more cameras on a surgical tool(s), etc.) and may be used for other types of cameras (stereo or otherwise) as well. As discussed above, the cameras may have a Galilean or Greenough like configuration and illumination may be provided through at least a portion of the camera optics (e.g., one or more camera lenses) in either the left or right channels or both in the case of stereo cameras.

Movement Control System

Figure 6C:
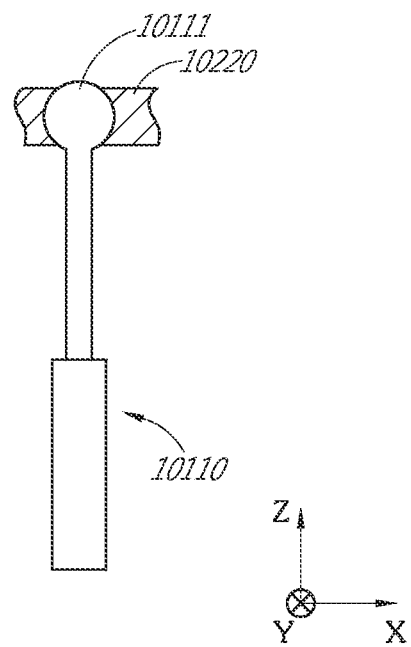
FIG. 6C is a partial section view of the embodiment of a movement control system of FIG. 6A.

FIGS. 6A-C illustrate embodiments of components of a movement control system 10100 that can be configured to allow an operator of the surgical visualization system 1, such as a medical professional or assistant, to control the movement of one or more imagers 18. Such imagers may comprise cameras that provide a surgical microscope view through the oculars 11 or eyepieces of the binocular display unit 9. In various embodiments, the movement control system can enable the imagers 18 to be moved without changing the positioning of oculars 11, and thus an operator can remain in an ergonomic position while changing the view provided by the imager 18. The imager 18 can be on the binocular display unit 9 or located elsewhere such as on a separate platform or articulated arm. Additionally, unlike conventional articulated optical systems which are generally unwieldy, complex, and have the potential for introducing optical aberrations, use of the movement control system 10100 with the surgical visualization system 1 can result in a simplified system with greater optical clarity and range of movement. It should be appreciated by one of skill in the art that, while the description of the movement control system 10100 is described herein in the context of medical procedures, the movement control system 10100 can be used for other types of visualization and imaging systems. Movement of the imagers 18 can be performed prior to and/or during the activity, such as surgical procedures, dental procedures, and the like. Movement of the imagers 18 can advantageously allow a medical professional or other operator to alter the view through oculars 11, for example, to provide different surgical microscope-like electronic visualizations which might be beneficial during the course of a medical procedure or for different surgical procedures.

In some embodiments, control of the movement of the imager 18 can be achieved using a single control member such as 10110. This provides the advantage of allowing single-handed operation of the movement control system 10100 which can, for example, allow a medical professional to move one or more imagers 18 using only one hand while using a second hand for other tasks such as performing surgical techniques. It should be appreciated by one of skill in the art that, while the description of the movement control system 10100 is described herein in the context of medical procedures, the movement control system 10100 can be used for other types of visualization and imaging systems.

Operation

As illustrated in FIGS. 6A-C, in some embodiments, the control member, such as a joystick, 10110 can be used to translate the imager 18, adjust the pitch, yaw, and/or roll of the imager 18, and/or adjust the working distance of the imager 18. In some embodiments, the oculars 11 can remain immobile when translating the imager 18, adjusting the pitch, yaw, and/or roll of the imager 18, and/or adjusting the working distance of the imager 18. The ability for a single control member 10110 to control translation, adjustments to pitch and/or yaw, and/or adjustments to the working distance can beneficially simplify operation of the device as an operator need not release the control member 10110 to control multiple aspects of its operation. For example, an operator can translate the imager 18 and subsequently adjust the pitch and/or yaw without having to release the control member 10110 thereby increasing ease-of-use of the system and enhancing efficiency when using this system.

As shown in FIG. 6C, one or more control members of the movement control system 10100, such as control member 10110, and/or one or more imager arms (see FIG. 7) can be attached to a component of the movement control system 10100 using various types of joints and/or can be remote from the movement control system 10100 such as a remote joystick or toggle. In some embodiments, the control member 10110 can include a joint for attachment to the movement control system 10100. For example, as shown in the illustrated embodiment, control member 10110 can include joint 10111. In some embodiments, one or more of the joints can include components for detecting movement of the control member and/or an imager arm. For example, one or more of the joints can include one or more sensors for detecting rotation and/or translation of the control member and/or the imager arm about the joint. The signals from these sensors can be used to control other components of the movement control system, such as one or more electromechanical components.

For purposes of this disclosure, rotation about joints, such as joint 10111, around the x-axis is hereinafter termed "pitch" or "tilt" and rotation about joints, such as joint 10111, around the y-axis is hereinafter termed "yaw" or "pan."

As shown in the illustrated embodiment, the joint 10111 can be spherical joints received in a socket formed in the member 10220 thereby forming a ball-and-socket attachment. As should be apparent to one of ordinary skill in the art, other types of mounting mechanisms may be used for attaching control member 10110 as well as an imager arm to components of the movement control system 10100. For example, joints such as gimbals can be used which limit the rotational degrees of freedom about the gimbal. Other types of joint can be used depending on the types of movement the movement control system is designed to allow. For example, if only pitch is needed without yaw, one can use a joint having a single rotational degree of freedom. In some embodiments, the control member 10110 can be positioned remotely from the movement control system 10100.

General Embodiment

With continued reference to FIGS. 6A and 6B, in some embodiments, the movement control system 10100 can be attached to an attachment structure, such as binocular display unit 9, and support one or more imagers 18. As shown in the illustrated embodiment, the movement control system 10100 can be oriented generally underneath the binocular display unit 9 and in some embodiments can be sized such that the movement control system 10100 does not extend significantly beyond the outer housing of the binocular display unit 9. This can advantageously provide a smaller form factor thereby reducing the likelihood that the movement control system 10100 will interfere with the medical professionals and assistants during a medical procedure. In other embodiments, the attachment structure can be other components of the surgical visualization system 1 such as, but not limited to, a dedicated articulating arm or a display arm. In some embodiments, the movement control system 10100 can extend significantly beyond the outer housing of the binocular display unit 9 or any other platform to which it is attached. This can be advantageous in situations where a greater degree of movement of the imagers 18 is desired or in embodiments where the control member 10110 is located above the attachment point between the movement control system 10100 and binocular display unit 9.

With continued reference to FIGS. 6A and 6B, as discussed in part above, the movement control system 10100 can be configured to allow translation of one or more attached imagers 18 along a plane relative to the binocular display unit 9. In some embodiments, the binocular display unit 9 can be immobile while the one or more imagers 18 are translated. For example, when attached to the binocular display unit 9 with the movement control mechanism 10100 parallel to an operating table 10101, the one or more imagers 18 can be translated along a plane parallel to the operating table 10101. As shown in the illustrated embodiment, the movement control system 10100 can be translated along both the x-axis and the y-axis (which projects perpendicularly through the sheet). This can advantageously allow the medical professional to position the view of oculars 11 for comfortable viewing by the surgeon thereby reducing physical strain on the surgeon during long procedures.

In some embodiments, defining an imager 18 centered on the movement control system 10100 (as shown in FIG. 6A) as having an x-axis, y-axis, and z-axis coordinate of zero, the movement control system 10100 can have a range of translation relative to the binocular display unit 9, of approximately ±500 mm along the x-axis and y-axis at full extension, approximately ±400 mm along the x-axis and y-axis at full extension, approximately ±300 mm along the x-axis and y-axis at full extension, approximately ±200 mm along the x-axis and y-axis at full extension, or approximately ±100 mm along the x-axis and y-axis at full extension. In some embodiments, full extension along one axis can be greater than full extension along the other axis. For example, in some embodiments, full extension along the x-axis may be approximately ±175 mm whereas the y-axis extension can be three-quarters full extension of the x-axis, one-half full extension of the x-axis, one-quarter full extension of the x-axis, or any other ratio between unity and zero. In some embodiments, the range of translation relative to the binocular display unit 9 along the y-axis can be approximately ±87.5 mm. This can be advantageous in cases where allowing the y-axis to have a full range of motion may interfere with the medical professional and/or assistants.

These ratios can be reversed such that the range of translation of the x-axis can be three-quarters full extension of the y-axis, one-half full extension of the y-axis, one-quarter full extension of the y-axis, or any ratio between unity and zero. Additionally, in some embodiments, the imager 18 can translate further in the "positive" direction than the "negative" direction. For example, along the x-axis, the imager 18 may move from −100 mm to 500 mm. Ranges of motion outside these ranges are also possible. As should be apparent to one of ordinary skill in the art, the maximum translation relative to the binocular display unit 9 along the x-axis and y-axis can be chosen to provide a balance between greater maneuverability, the yaw and/or pitch angles, working distances, size constraints, and other such factors.

As described in part above and as will be discussed in greater detail below, in some embodiments, translation of the imagers 18 can be performed by translating one or more control members, such as control member 10110, in the desired direction. In some embodiments, the control member 10110 can be electrically coupled to the movement control system 10100 to provide translation via an electromechanical system utilizing stepper motors, linear motors, or the like. For example, a joint of the control member 10110 can include components for detecting translation of the control member 10110. The signals from these sensors can be used to control other components of the movement control system, such as one or more electromechanical components such as stepper motors, linear motors, or the like to translate the imager 18. The electromechanical components can be coupled to a moveable platform to which the imager 18 can be attached. In some embodiments, the control member 10110 can be physically connected to the movement control system 10100 without any electromechanical assistance.

As should be appreciated by one of ordinary skill in the art, the movement control system 10100 need not translate solely along a plane parallel to the operating table 10101 or the x-y plane as set forth in the illustrated embodiment. In some embodiments, the plane of translation can be defined by the orientation of the mount to which the movement control system 10100 is connected. In some embodiments, the movement control system 10100 can be configured for non-planar translation and/or translation along more than one plane. In some embodiments, for example, a tip and tilt stage provides angular motion. A rotary stage can also be used to provide rotary motion.

With continued reference to FIGS. 6A and 6B, as described in part above, the movement control system 10100 can be configured to allow rotation of the one or more attached imagers 18 about a joint which can be attached to components of the movement control system 10100 and/or remotely from the movement control system 10100. In some embodiments, the movement control system 10100 can be designed to allow the control member, such as control member 10110, as well as the imager 18 and/or imager armto "pitch" or "tilt" and "yaw" or "pan" relative to the binocular display unit 9. In some embodiments, the binocular display unit 9 can be immobile while the "tilt" and "yaw" or "pan" of the one or more imagers 18 are adjusted. Pitch or yaw can allow the imager 18 to have a line of sight that is centered (e.g., focused) on the surgical site after the imager 18 is translated. This can advantageously allow the medical professional or assistant to adjust the viewing angle during a medical procedure. This can be beneficial in circumstances where a medical professional is unable to adequately view an object due to another element obstructing the view. Under such circumstances, a medical professional can translate the imager 18 and adjust the viewing angle of the imager 18 such that the same general area is viewed from a different angle.

In some embodiments, defining an imager 18 in a perpendicular orientation to the movement control system 10100 (as shown in FIG. 6A) as having an a pitch and yaw of zero (i.e., as shown in FIG. 6A), the movement control system 10100 can allow both pitch and yaw adjustments relative to the binocular display unit 9 within the range of approximately ±60 degrees each, by approximately ±50 degrees each, by approximately ±40 degrees each, by approximately ±30 degrees each, by approximately ±20 degrees each, or approximately ±10 degrees each. In some embodiments, the pitch and yaw can have different adjustment ranges. For example, in some embodiments, the yaw can have an adjustment range of approximately ±40 degrees whereas the pitch can have an adjustment range of approximately three-quarters that of the yaw, one-half that of the yaw, one-quarter that of the yaw, or any other ratio between unity and zero. In some embodiments, the pitch can have an adjustment range of approximately ±20 degrees.

The adjustment range of yaw and pitch can correspond to the distance at full extension along both the x-axis and the y-axis. For example, in some embodiments, the pitch and yaw can be chosen such that the imager 18 can remain centered on the surgical site when the movement control system 10100 is fully extended in any direction. In some embodiments, the working distance between the imager 18 and the surgical site can be approximately 200 mm, with a range of translation along the x-axis of approximately ±175 mm, and a range of translation along the y-axis of approximately ±87.5 mm. In order to remain centered on the surgical site, the pitch adjustment range can be ±20 degrees and the yaw adjustment range can be ±40 degrees. As such, because the full extension need not be the same in both directions, the pitch and yaw adjustment ranges can also be different to match the differences in extension. In other embodiments, such as those in which the working distance can be adjusted, the pitch and yaw adjustment range can be chosen such that the imager 18 can remain centered on the surgical site when the movement control system 10100 is fully extended in any direction at least one working distance. For example, in embodiments where the working distance can be adjusted between approximately 200 mm and 400 mm, the pitch and yaw adjustment range can be approximately ±20 degrees and approximately ±10 degrees respectively to allow centering at a working distance of 400 mm.

Additionally, in some embodiments, the imager 18 can adjust further in a "positive" angle than a "negative" angle. For example, the yaw may range from −5 degrees to 15 degrees.

As described in part above and as will be discussed in greater detail below, in some embodiments, increasing or decreasing the pitch and/or yaw of the imagers 18 relative to the binocular display unit 9 can be achieved by increasing or decreasing the pitch and/or yaw of the one or more control members, such as control member 10110. In some embodiments, the control member 10110 can be electrically coupled to the movement control system 10100 to provide pitch and yaw via an electromechanical system utilizing stepper motors, linear motors, or the like. For example, a joint of the control member 10110 can include components for detecting pitch and/or yaw of the control member 10110. In some embodiments, the joint of the control member 10110 can be gimbals which can detect pitch and/or yaw of the control member 10110. The signals from these sensors can be used to control other components of the movement control system, such as one or more electromechanical components such as stepper motors, linear motors, or the like to adjust the pitch and/or yaw of the imager 18. As should be appreciated by one of ordinary skill in the art, in some embodiments, the movement control system 10100 can be configured to allow rotation along other axes such as the z-axis. In some embodiments, the control member 10110 can be physically connected to the movement control system 10100 without any electromechanical assistance.

Additionally, in some embodiments, the movement control system 10100 can be configured to adjust the working distance between the imagers 18 and the surgical site. In some embodiments, the binocular display unit 9 can remain immobile while the working distance of the imagers 18 is adjusted. In some embodiments, the working distance can range from between approximately 1 m to approximately 10 mm, from between approximately 800 mm to approximately 50 mm, from between approximately 600 mm to approximately 100 mm, or from between approximately 400 mm to approximately 200 mm. In some embodiments, the control member 10110 can be electrically coupled to the movement control system 10100 to provide working distance adjustment via an electromechanical system utilizing stepper motors, linear motors, or the like. For example, a joint of the control member 10110 can include components for detecting rotation of the control member 10110 about the longitudinal axis. The signals from these sensors can be used to control other components of the movement control system, such as one or more electromechanical components such as stepper motors, linear motors, or the like to adjust the pitch and/or yaw of the imager 18. In some embodiments, the control member 10110 can be physically connected to the movement control system 10100 without any electromechanical assistance.

In some embodiments, the movement control system 10100 can include a translation system for translating an imager 18 and/or an imager arm, a pitch-yaw adjustment system for adjusting the pitch and/or yaw of the imager 18 and/or an imager arm, a control member, such as control member 10110, and one or more imager arms to which the imager 18 can be attached. In some embodiments, a working distance adjustment system can be included which can allow adjustments in working distance of the imager 18 and/or an imager arm. It should be appreciated by one of ordinary skill in the art that the translation system, the pitch-yaw adjustment system, and/or the working distance adjustment system can be used separately or in any combination.

Operation of the translation, pitch-yaw adjustment, and/or working distance adjustment systems can be performed using a control member, such as control member 10110. In some embodiments, control member 10110 can be operatively coupled to the translation, pitch-yaw adjustment, and/or working distance adjustment systems. For example, as described above, in some embodiments, the control member can be coupled to an electromechanical system for controlling the translation, pitch-yaw adjustment, and/or working distance adjustment systems. The control member can be directly attached to a component of the movement control system 10100 or can be remotely positioned (e.g., a toggle or joystick on a separate module). In some embodiments, the control member can be coupled directly to the translation, pitch-yaw adjustment, and/or working distance adjustment systems such that no electromechanical devices are used. In some embodiments, the operator can be given the option of controlling the translation, pitch-yaw adjustment, and/or working distance adjustment systems with or without electromechanical devices. For example, the operator can control the translation, pitch-yaw adjustment, and/or working distance adjustment systems without electromechanical devices for certain portions of a procedure and use such electromechanical devices for controlling the translation, pitch-yaw adjustment, and/or working distance adjustment systems during other portions of a procedure. As another example, in some embodiments coarse control of the movement control system 10100 can be achieved without use of electromechanical devices whereas fine control of the movement control system 10100 can be achieve with use of electromechanical devices, vice-versa, or a combination of the two.

In some embodiments, the movement control system 10100 can include a control system which controls functions of the electromechanical devices. In some embodiments, the electromechanical components can be programmed such that the electromechanical components can orient the translation, pitch-yaw adjustment, and/or working distance adjustment systems in certain positions based on the operator's input. For example, the electromechanical components can be programmed such that it goes to reverts back to a pre-set or previous position upon receiving a command from the operator. As another example, the electromechanical components can be programmed such that an operator can specify a desired position for the imager 18 and the control system can control the electromechanical devices coupled to the translation, pitch-yaw adjustment, and/or working distance adjustment systems orient the imager 18 in the desired position.

Figure 7:
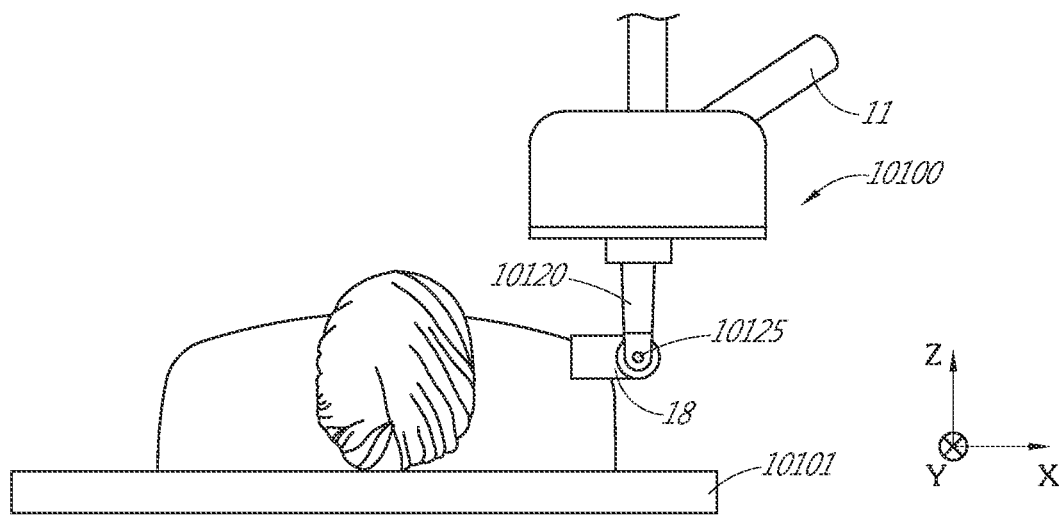
FIG. 7 is a side view of an embodiment of a surgical visualization system, a movement control system, and an imager.

With reference to FIG. 7, in some embodiments, the imager arm 10120 and the imager 18 can be attached such that the imager 18 can be directed towards the side of the head of a patient. For example, in some embodiments, the imager 18 can be attached to the imager arm 10120 using a yoke 10125 which can be designed to allow for coarse and/or fine control of pitch, yaw, and/or roll of the imager 18. In some embodiments, the yoke 10125 can have one or more pivots which can be configured to allow the imager 18 to have a viewing angle parallel to the operating room floor such that an operator can view the side of the head. In some embodiments, the yoke 10125 can be configured to allow the imager 18 to rotate such that the imager can be directed to a portion of the back of the head.

Figure 8:
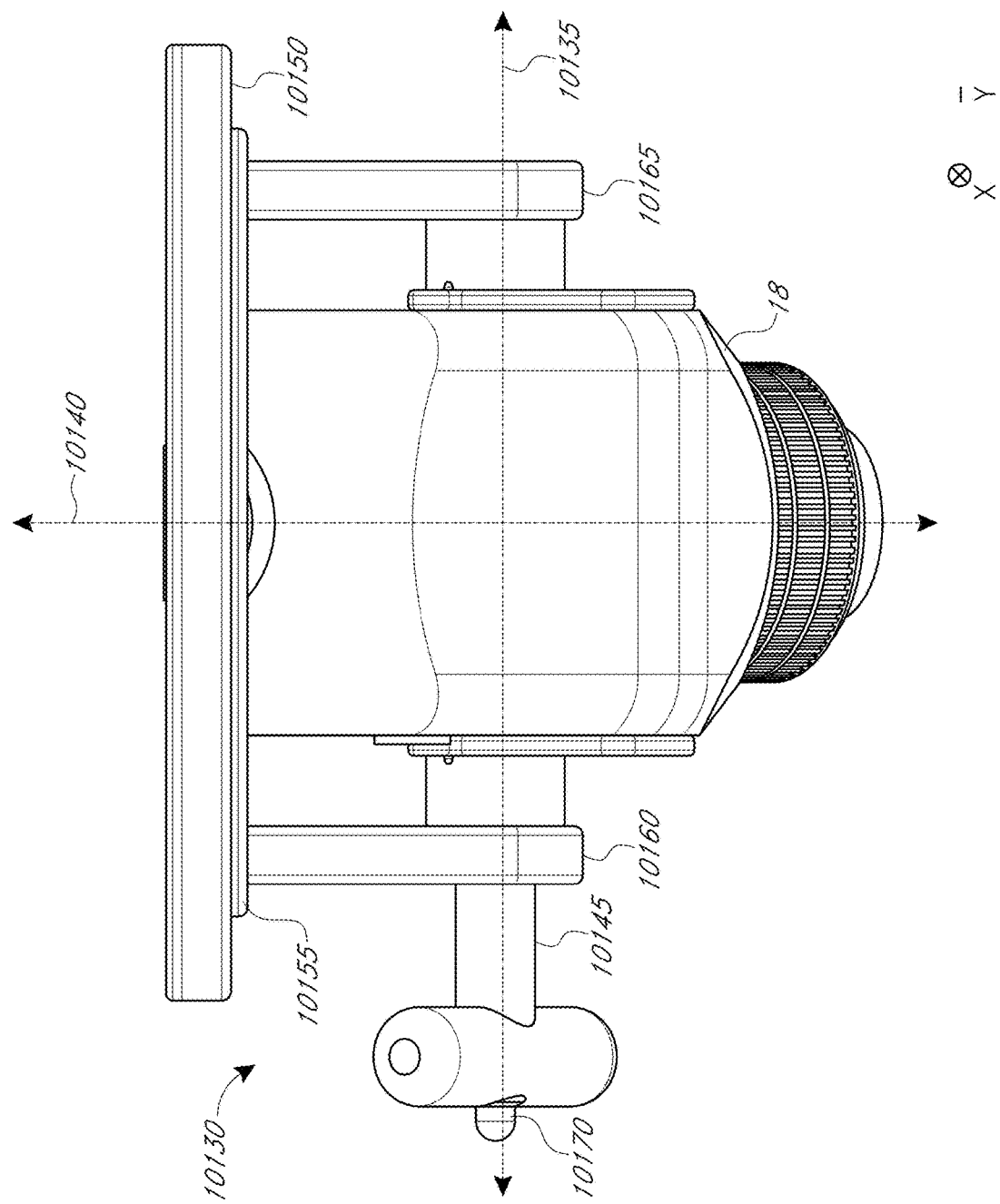
FIG. 8 is a rear view of an embodiment of an embodiment of a movement control system.

In some embodiments, the imager 18 can be positioned on a movement control system 10130 providing at least two rotational degrees of freedom and/or at least one translational degree of freedom. In some embodiments, movement control system 10130 can provide two rotational degrees of freedom and at least two translation degrees of freedom. For example, as shown in FIG. 8, the movement control system 10130 can allow for rotation along axis 10135 of the movement control system 10130 and/or along axis 10140 (which can be parallel with the z-axis). Moreover, as shown in the illustrated embodiment, the movement control system can allow translation along both the x-axis and y-axis. In some embodiments, apparatus 10130 can provide at least one translational degree of freedom.

As shown in the illustrated embodiment, the movement control system 10130 can include a one or more control members, such as control member 10145. Control member 10145 can be positioned such that the longitudinal axis of the control member 10145 is parallel with and/or collinear with axis 10135. This can advantageously allow the imager 18 to be rotated about axis 10135 by rotating the control member 10145. In some embodiments, the control member 10145 can be mechanically coupled to the imager 18. In some embodiments, the control member 10145 can be coupled to the imager 18 via an electromechanical system. For example, the control member 10145 can include sensors for detecting rotation of the control member 10145 and use data received from the sensors to rotate the imager 18 via electromechanical components such as stepper motors, linear motors, or the like.

As shown in the illustrated embodiment, the movement control system 10130 can include a first plate element 10150 and a second plate element 10155 which can be rotatable coupled. The second plate element 10155 can include first and second supports 10160, 10165 to which the imager 18 can be attached. In some embodiments, the first and second plate elements 10150, 10155 can be rotatable coupled such that the axis of rotation of the two plate elements 10150, 10155 is parallel and/or collinear with axis 10140.

In various embodiments, the gimbal advantageously allows movement of the camera without movement of the display such as the binocular display. Such movement can include pitch or yaw, as well as possibly, x, y, or z motion or any combination thereof. Despite such movement of the camera that provides surgical microscope views, the binocular display need not move similarly. Accordingly, in various embodiments a joint is provided between the camera and binocular display that permits pitch or yaw, as well as possibly, x, y, or z or any combination thereof of the stereo surgical microscope view camera without requiring the same motion (include pitch or yaw, as well as possibly, x, y, or z or any combination thereof) of the binocular display. The binocular display is thus decoupled from the camera. Such a decoupling of motion is possible, even if the camera is connected to the binocular display. For example, the camera may move laterally in the x direction and or up and down in the y direction or may be rotated about the x or y axis to introduce yaw and/or to introduce pitch, however, the binocular display (and the oculars) need not move similarly or need not move at all such that the surgeon need not reorient his or her head to view the images on the display. Movement and/or positioning and/or orientation control systems, other than gimbal systems may be employed as well. By decoupling the movement of the camera from that of the binocular display, even for camera's mounted on or connected to the binocular display, ergonomic benefits can be achieved. For example, the surgeon need not contort their neck in positions that are uncomfortable for long surgical procedures.

In various embodiments, the gimbal does not provide roll of the camera(s), for example, about the axis 10140. If for example the camera comprises a stereo camera with separate left and right cameras, such roll would raise the left channel above the right or vice versa. A horizontal line through the line of sight of the left and right channels might not therefore be parallel with the floor (perpendicular to the gravity vector). This roll might therefore cause disorientation and/or discomfort for the viewer. Accordingly, various embodiments of the gimbal or other positioning/orientation system for the camera's that provide surgical microscope views are configured not to such roll. Substantially reducing or eliminating roll might apply to use for the camera for surgery either or both in the downward view (for example, for spine surgery) as well as the oblique view (for temporal approach into the skull). Such configurations that substantially reduce or eliminate roll may be applicable for gimbal systems for other cameras including one or more proximal cameras disposed outside the surgical site a distance from the patient's body but in close proximity thereto (for example on a stereotactic frame, etc.), such as for example, a distance of between 5 mm and 50 mm, between about 20 mm and 40 mm (e.g., between 10 mm to 25 mm) from the patient's body and/or surgical site. A plurality of cameras including possibly a plurality of stereo cameras and possibly one or more mono-cameras (for example at 3, 6, 9, and 12 o'clock positions) can be repositioned and/or reoriented using positioning and orientations devices potentially in x, y, and z directions as well as in pitch and yaw and any combination thereof. However, in various embodiments such positioning and/or orientation devices do not permit the amount of roll to exceed that which would cause disorientation or do not provide for roll of the left and right channels of the stereo cameras altogether so as to reduce disorientation for the viewer.

In some embodiments, the control member 10145 can include one or more switches and/or actuators 10170 for controlling movement of the device. For example, the actuator 10170 can be coupled to mechanisms which can unlock the apparatus 10130 such that the movement control system 10130 can be manipulated to rotate and/or translate the imager 18. In some embodiments, the switches and/or actuators can be coupled to an electromechanical system to rotate and/or translate the movement control system 10130.

Figure 8A:
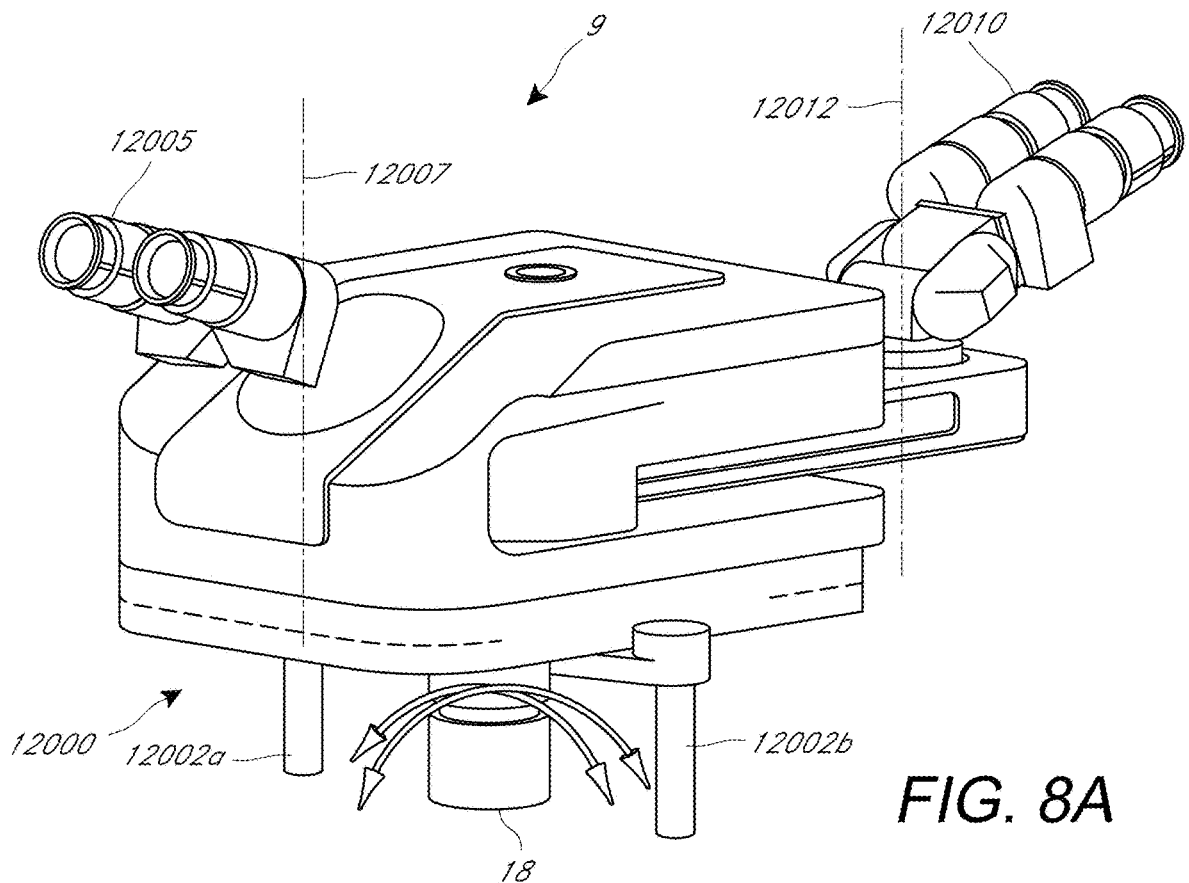
FIG. 8A illustrates a perspective view of an example gimbal system for an imager, the gimbal system coupled to a viewing assembly comprising two pairs of oculars.

FIG. 8A illustrates a perspective view of an example gimbal system 12000 for an imager 18, the gimbal system 12000 coupled to a viewing assembly 9 comprising 2 pairs of oculars, 12005, 12010. The first pair of oculars 12005 is configured to adjust its orientation about an axis 12007. The second pair of oculars 12010 is configured to adjust its orientation relative to an axis 12012 as well as relative to the first pair of oculars 12005. For example, the second pair of oculars 12010 can be oriented such that users of the two pairs of oculars face one another when using the viewing assembly 9, such as when a doctor and an assistant are on opposite sides of a patient. The second pair of oculars 12010 can also be oriented such that it is at about 90 degrees relative to the first pair of oculars 12005. Other relative orientations are also available, such as any value between about 15 degrees to about 180 degrees between the first and second pairs of oculars 12005, 12010.

The gimbal system 12000 can include a pair of handles 12002a, 12002b to allow a user to change the orientation of the imager 18. As illustrated, the user can adjust the pitch and yaw of the imager 18 using the handles 12002a, 12002b.

Figure 8B:
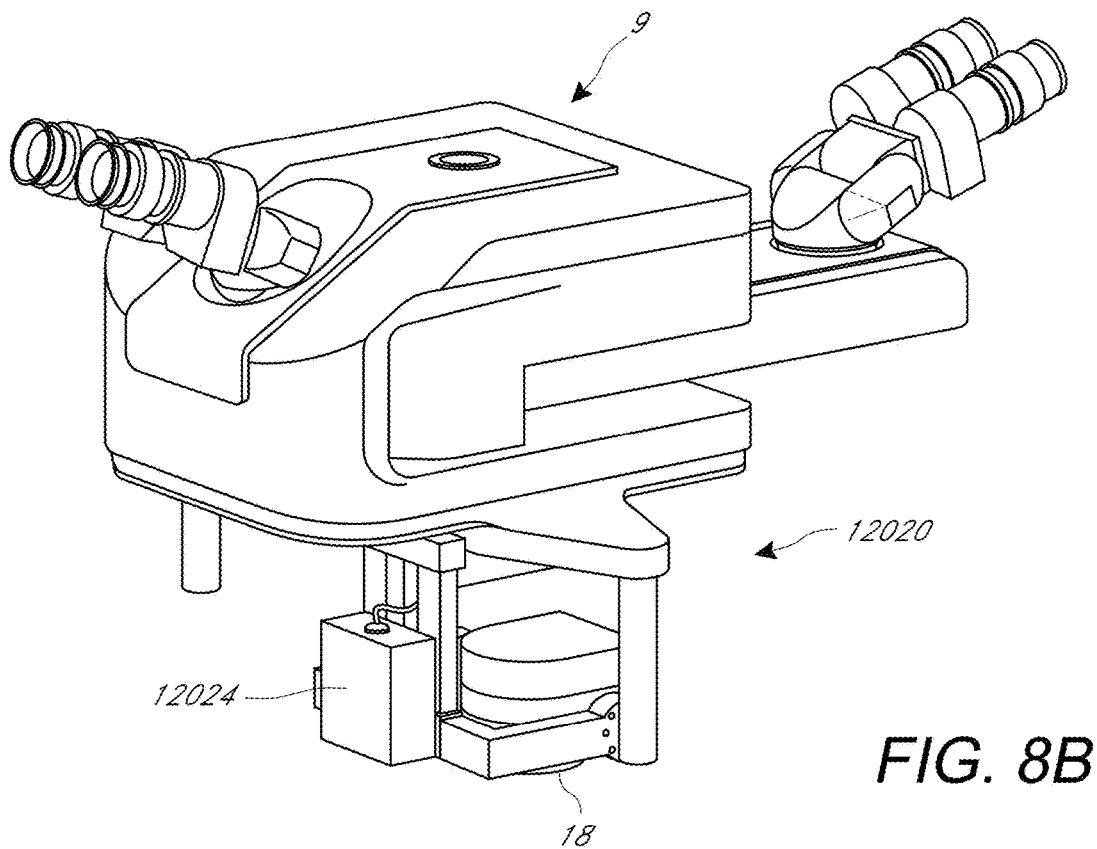
FIG. 8B illustrates a perspective view of a second example gimbal system for an imager, the gimbal system coupled to a viewing assembly.

FIG. 8B illustrates a perspective view of a second example gimbal system 12020 for an imager 18, the gimbal system 12020 coupled to a viewing assembly 9. The support structure 12024 for the imager 18 is configured to allow a user to change the orientation and position of the imager 18.

Figure 8C:
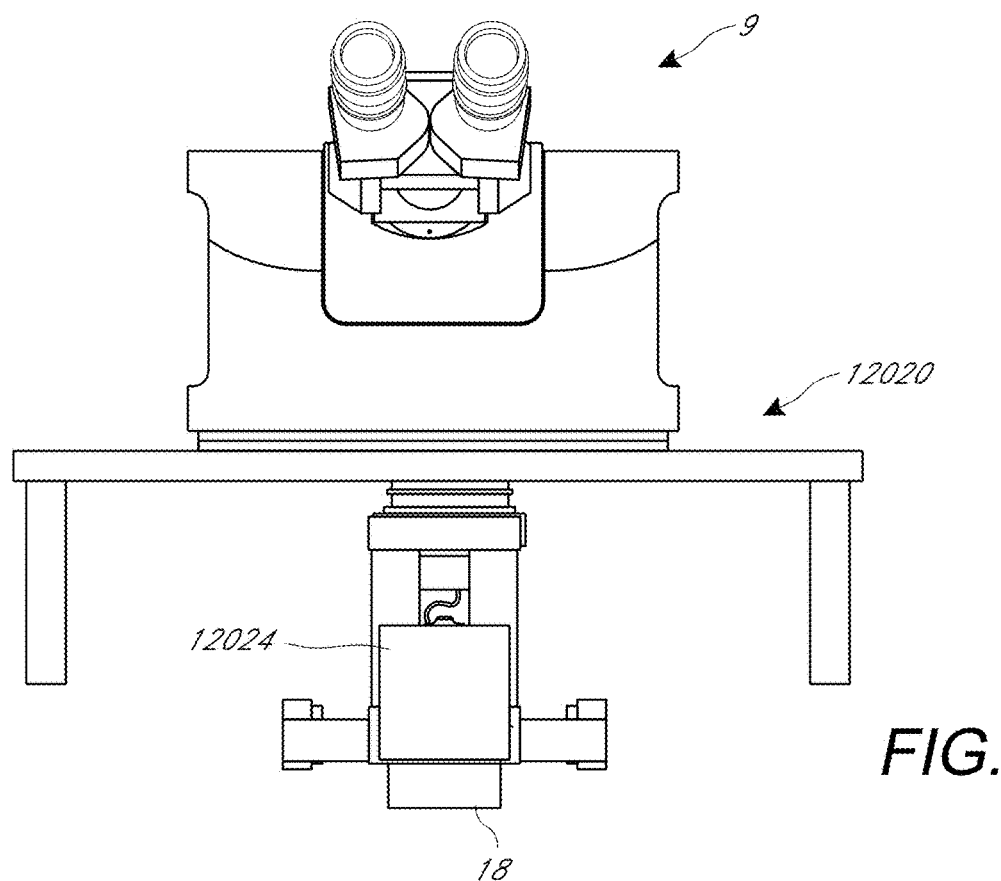
FIGS. 8C-E illustrate various views of the second example gimbal system.
Figure 8D:
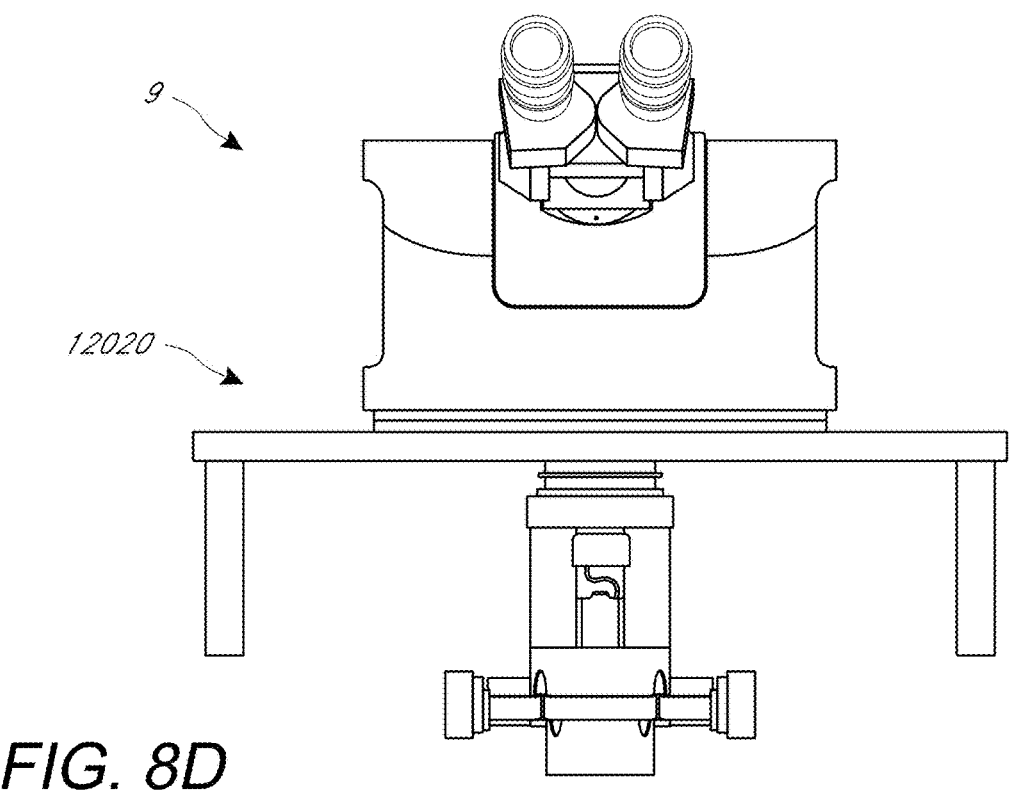

FIG. 8C illustrates a front view of a second example gimbal system 12020 attached to the viewing assembly 9. The imager 18 includes a support structure 12024 that orients the imager 18 as well as provides for electrical connections between the viewing assembly 9 and the imager 18. As described herein, in some embodiments, the viewing assembly 9 does not provide an optical path to the worksite that passes from the oculars through the viewing assembly 9 to the worksite or surgical site. FIG. 8D illustrates a back view of the example gimbal system 12020 attached to the viewing assembly 9.

Figure 8E:
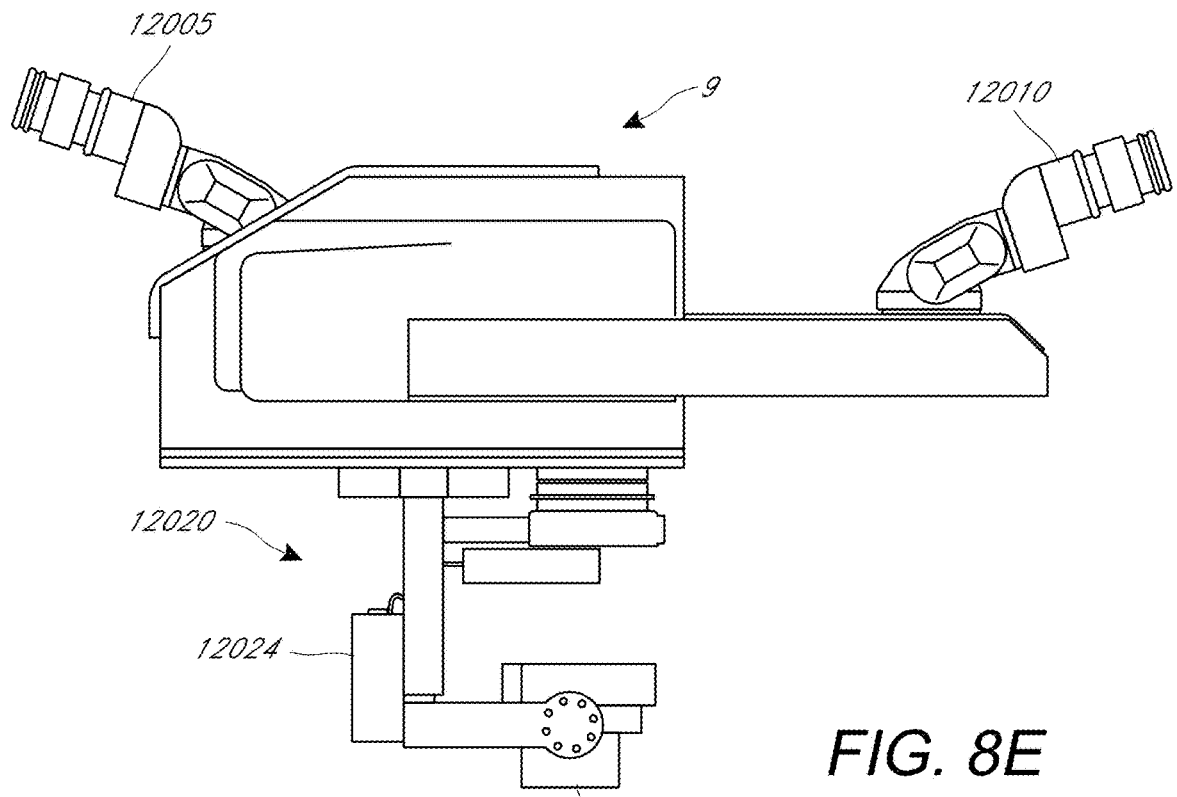

FIG. 8E illustrates a side view of the example gimbal system 12020 attached to the viewing assembly 9, with the two pairs of oculars 12005, 12010 oriented with a relative angle of about 180 degrees between them. The support structure 12024 is configured to change the orientation of the imager 18, allowing it to rotate about an axis that is perpendicular to the page and vary the pitch of the imager.

Figure 8F:
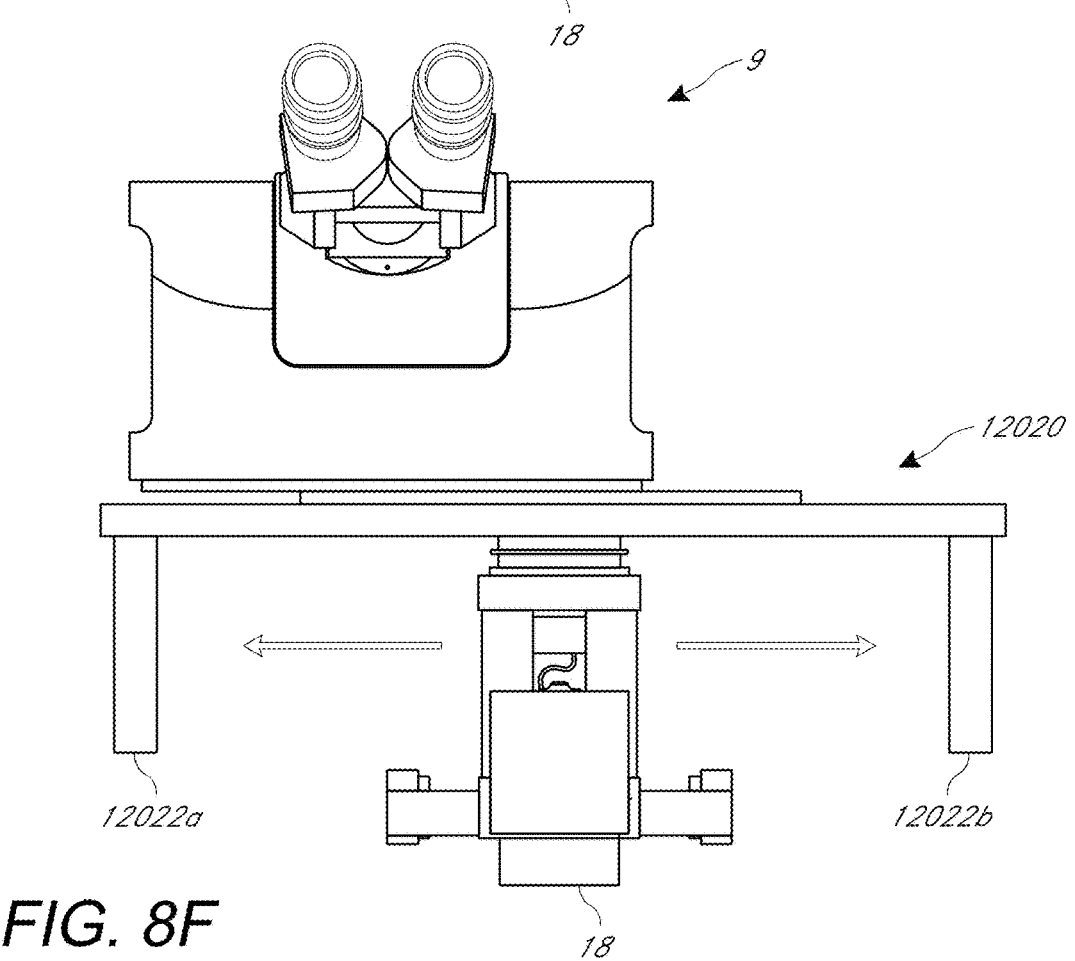
FIGS. 8F and 8G illustrate examples of translating the imager using the second example gimbal system.
Figure 8G:
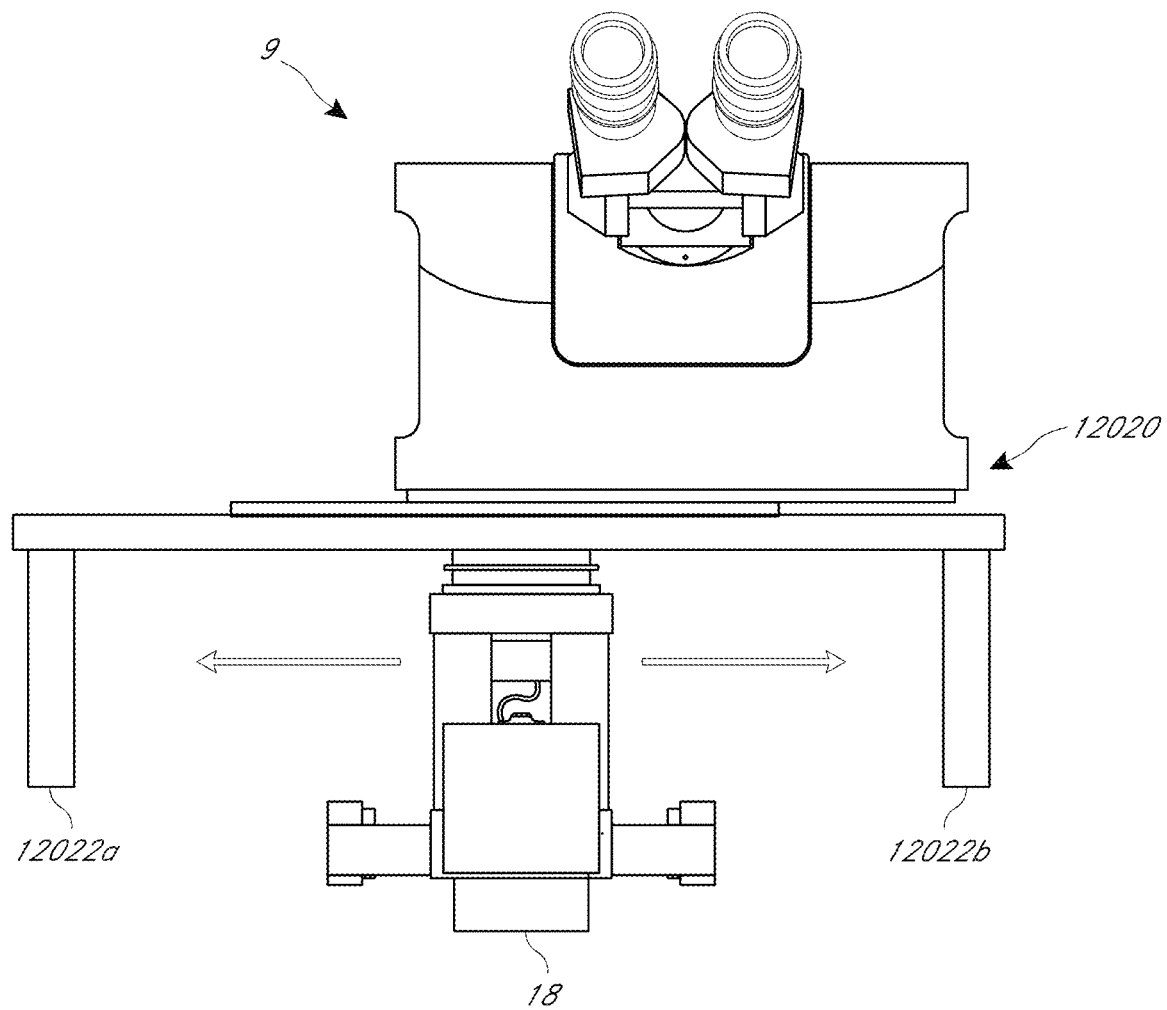
Figure 8H:
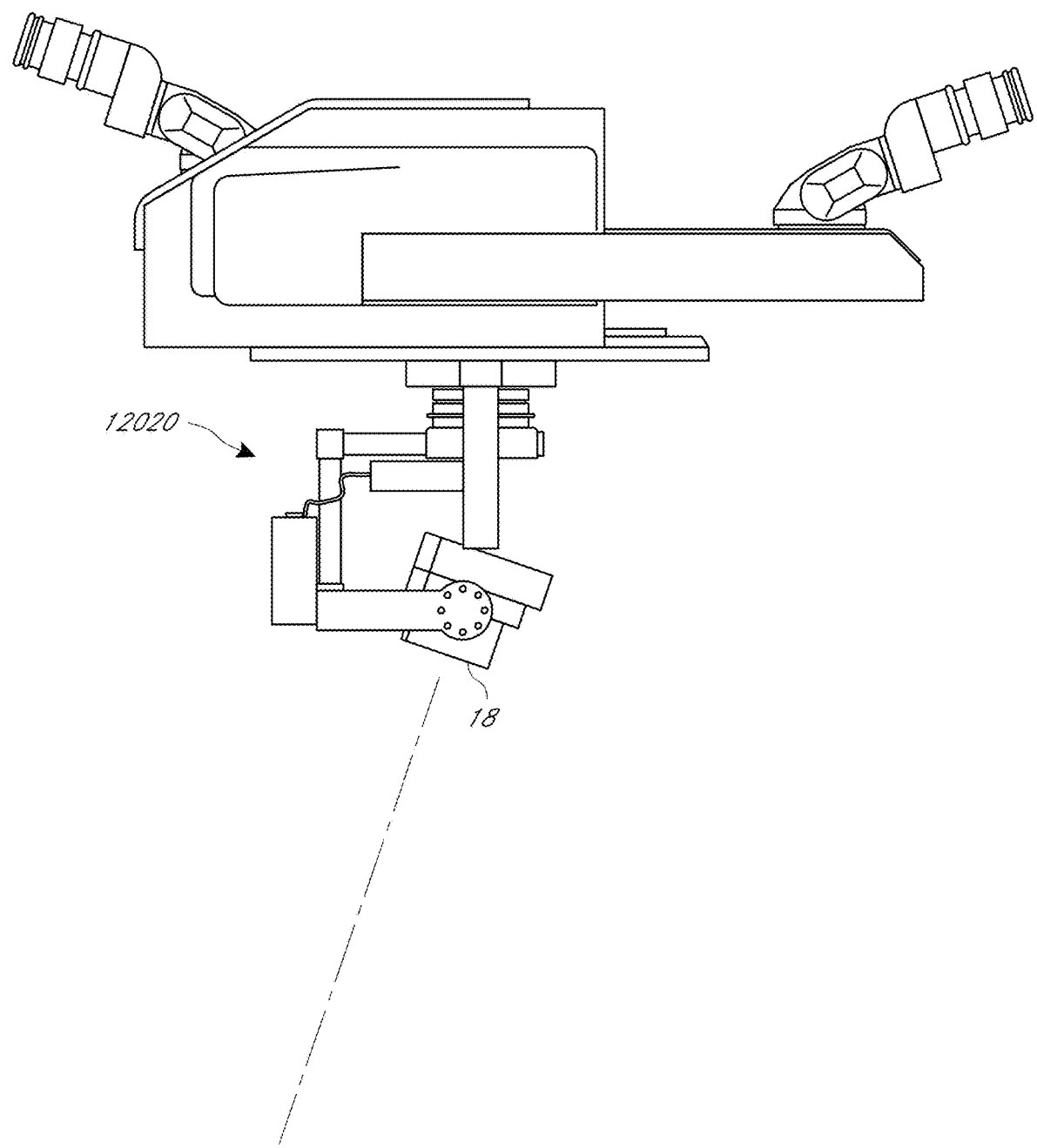
FIGS. 8H-8J illustrate that the second example gimbal can be configured to allow the imager to change its orientation to achieve a relatively wide range of orientations relative to the viewing assembly, from a vertical orientation to a near horizontal orientation.
Figure 8I:
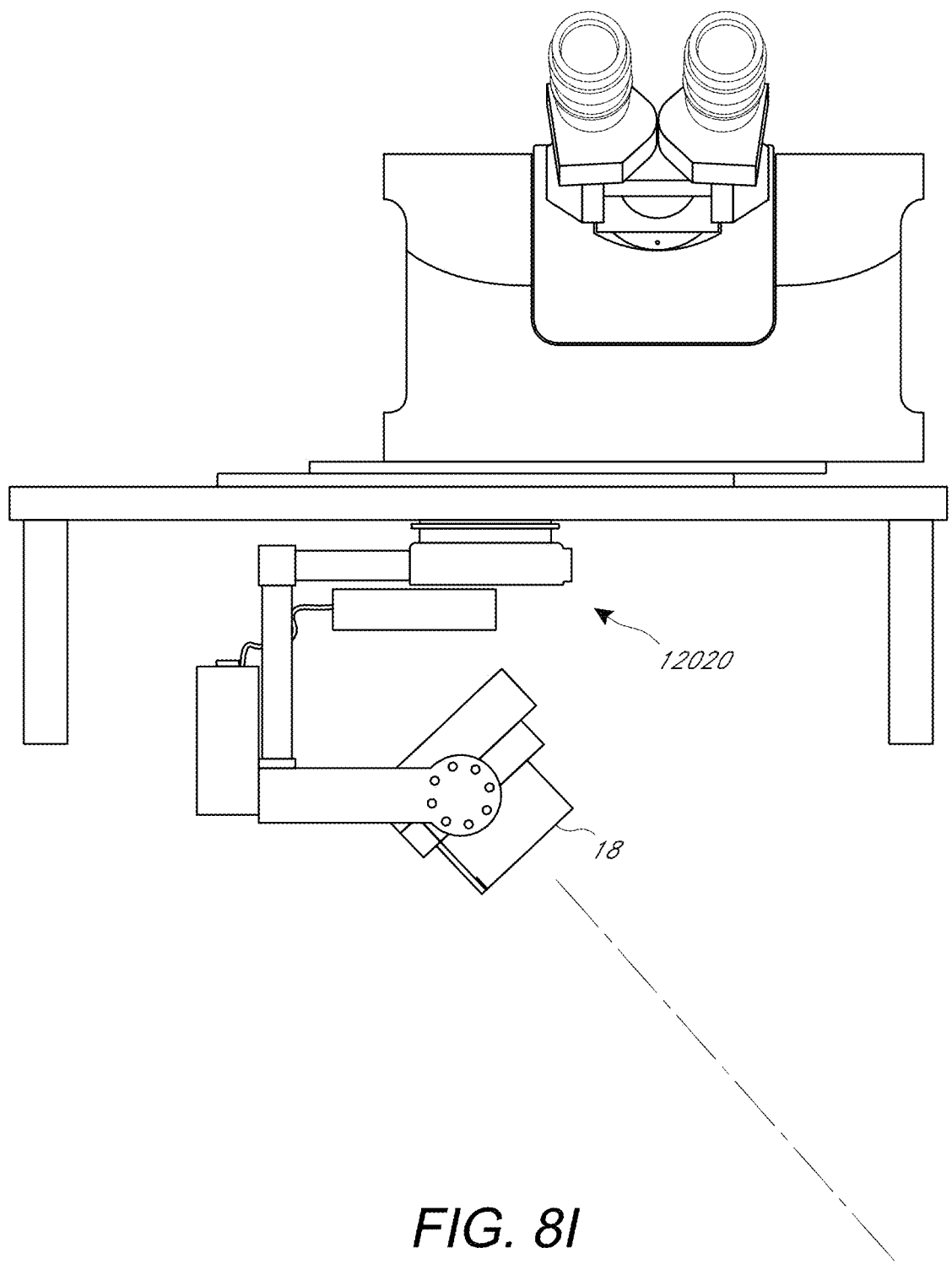
Figure 8J:
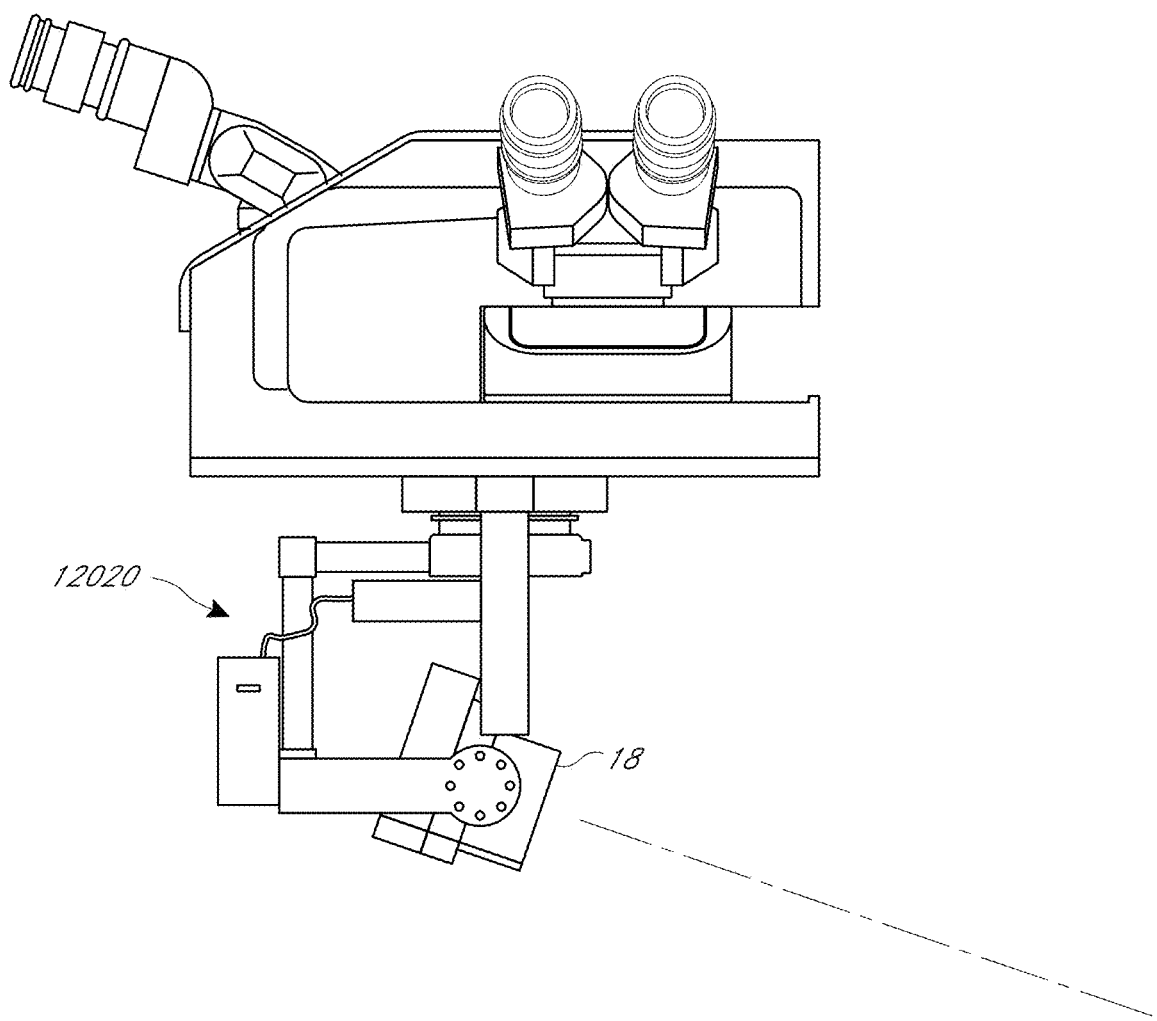

FIGS. 8F and 8G illustrate examples of translating the imager 18 using the gimbal system 12020. In use, the handles 12022a, 12022b can be used to slide the imager 18 laterally (e.g., in the x- and/or y-directions), for example, with respect to the oculars. The handles 12022a, 12022b can also be used to change the orientation of the imager 18 in addition to or instead of changing the position of the imager 18, as illustrated in FIGS. 8H-8J. FIGS. 8H-8J illustrate that the gimbal 12020 can be configured to allow the imager 18 to change its orientation to achieve a relatively wide range of orientations relative to the viewing assembly, from a vertical orientation to a near horizontal orientation.

Figure 8K:
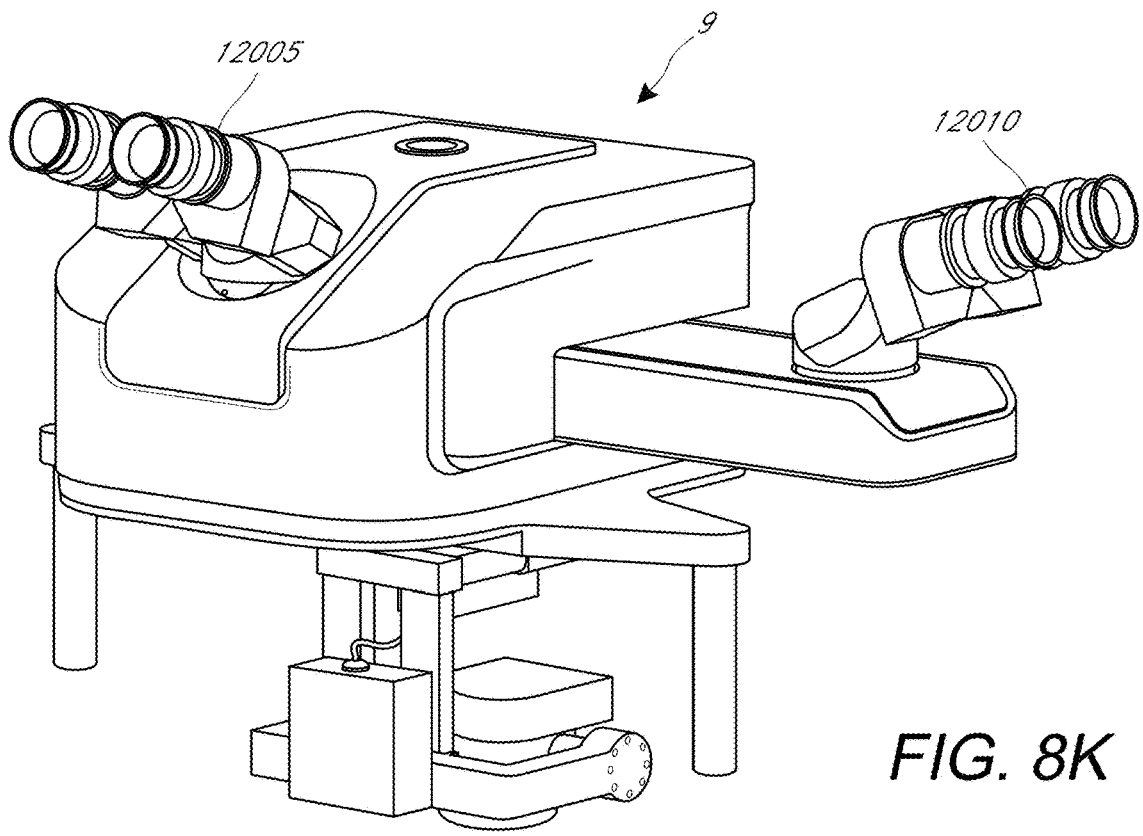
FIGS. 8K-8L illustrate views of the viewing assembly with the two pairs of oculars oriented orthogonal to one another.
Figure 8L:
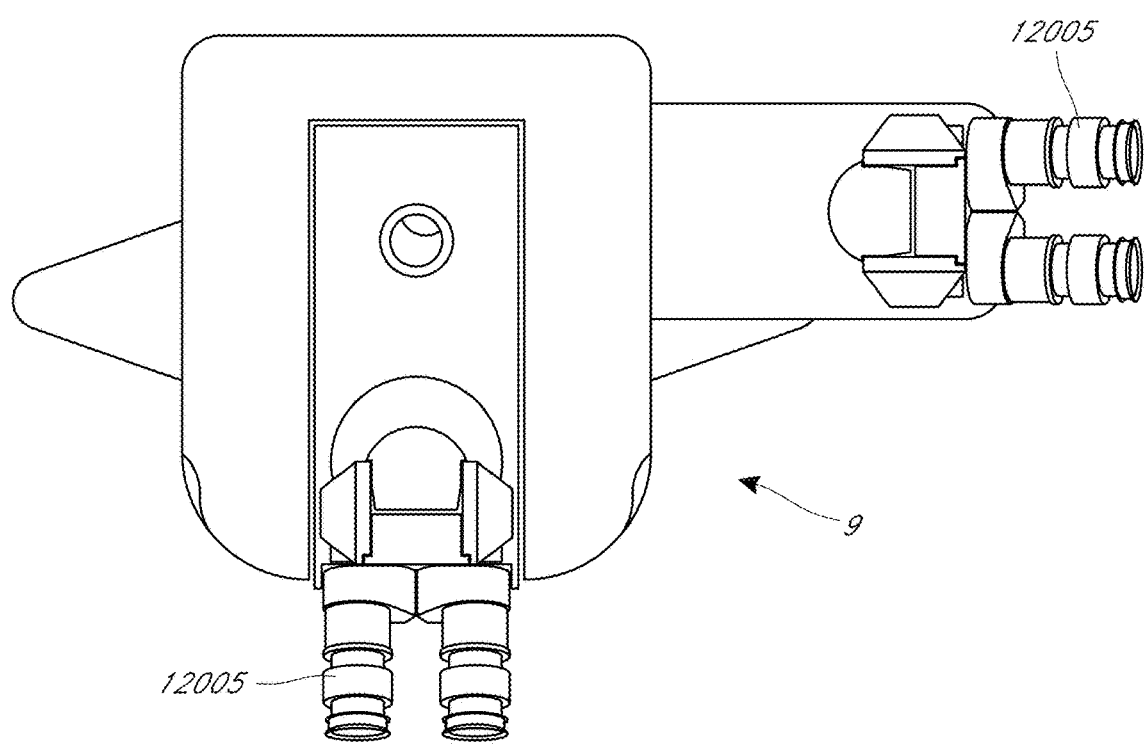
Figure 8M:
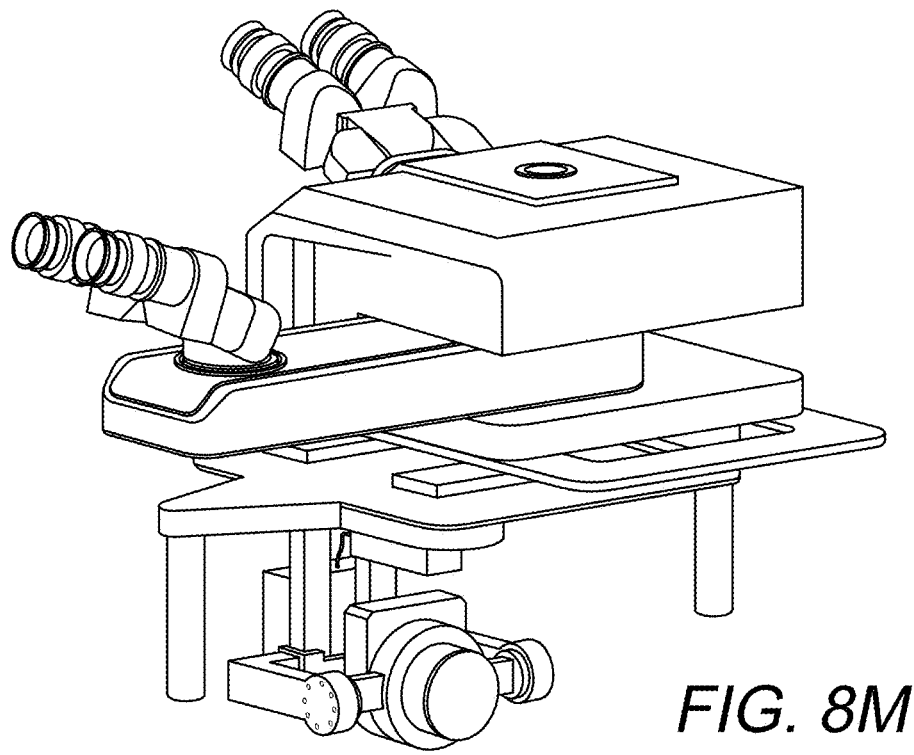
FIGS. 8M-8P illustrate movement of a gimbal system for a camera system providing a surgical microscope view, the camera system movable independent of the two pairs of oculars.
Figure 8N:
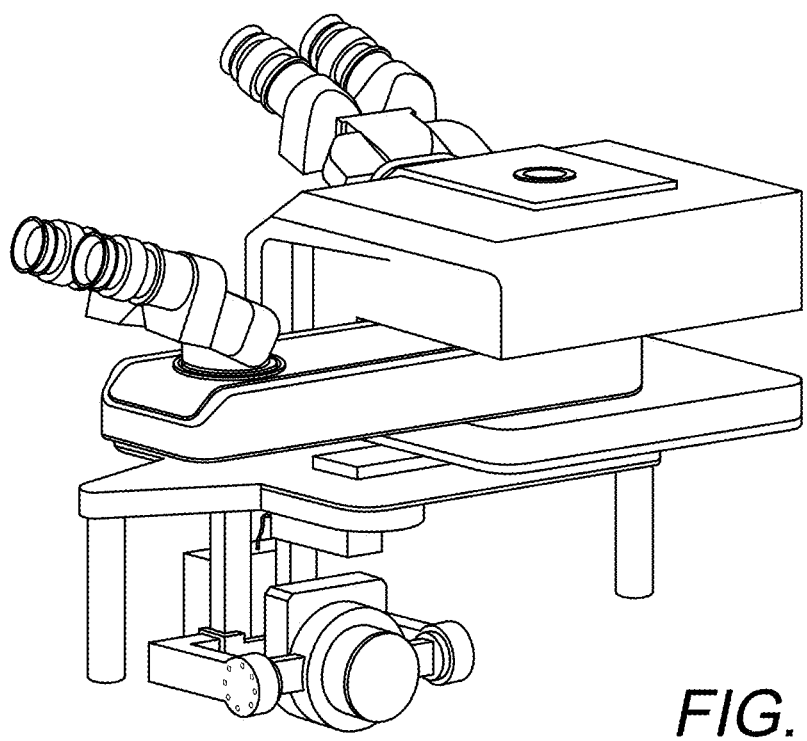

FIG. 8K illustrates a perspective view of the viewing assembly 9 with the two pairs of oculars 12005, 12010 oriented orthogonal to one another. This is also illustrated in FIG. 8L that shows a top view of the viewing assembly 9 with the oculars 12005, 12010 in this orientation.

In some embodiments, the handles 12022a, 12022b are used to mechanically alter the position and/or orientation of the imager 18. In certain embodiments, the handles 12022a, 12022b are used as electronic controls to control one or more motor systems to orient and position the imager 18. In some embodiments, the handles 12022a, 12022b are a convenience or comfort for a user, and other separate controls are used to control the position and/or orientation of the imager 18 relative to the viewing assembly 9.

In some embodiments, one or more handles 12022 can include controls for controlling features of the overall system. For example the handle can include one or more controls, e.g., button(s), for altering the illumination, zoom, focus, work distance, camera view provided, arrangement of camera views or any combination of these feature or other features in the alternative or in addition.

Although a gimbal system is shown, other types of systems for position (e.g., x, y, and/or z) and orienting (e.g., pitch, yaw, and possibly roll), may be employed. In some embodiments, encoders or sensors provide signals with regard to the position and/or orientation of the camera. In some embodiments, the gimbal or positioning and/or orientation system may include motors or actuators that can be controlled by control electronics. In some embodiments the control electronics can be configured to cause to gimbal or other positioning and/or orientation system to return to a preset position and orientation. Memory, may for example be included that record certain preset positions and/or orientations. Such preset positions and/or orientations may be positions and/or orientations for certain types of surgical procedures, for certain surgeons, or combinations of both. Selection of the particular procedure or indication of the particular surgeon may cause the gimbal or position/orientation system to go to the appropriate preset position stored in memory. Such preset positions and/or orientations may also include a storage position.

Other types of positioning and/or orientation systems may include a hexapod and/or an articulated arm.

In some embodiments, light weight material may be used to form the display and/or console such as the housing. A honeycomb structure may for example be employed as a housing or cover.

The discussions above or elsewhere herein may be applicable to other types of cameras and positioning and/or orientation systems for other types of cameras including but not limited to one or more cameras on a surgical tool(s), one or more proximal cameras disposed outside a patient but within a close proximity to the patient and/or surgical site, such as 5 mm, 10 mm, 20 mm, 25 mm to 30 mm, 40 mm, 45 mm or any ranges therebetween. The distance of the proximal cameras to the patient's body and or surgical site may be greater or less than these values recited above.

Optical Systems for Displays

FIGS. 9A-9D illustrate example display optical systems 11005 configured to provide a view of displays 11010 through oculars (not shown) that receive light from the last lens 11015 in the display optical system 11005. The display optical system 11005 forms an exit pupil at or near the entrance pupil of the surgeon binoculars. These pupils are closely matched, for example, in size and shape. In some embodiments, the exit pupil of the display optical system 11005 can be the same size or smaller than the entrance pupil of oculars used to view the display. The oculars form an exit pupil that is matched (e.g., in size and shape) to the entrance pupil of the surgeon's eye(s). In some embodiments, the display optical system 11005 is configured to produce a beam that has a relatively constant cross-section between the first lens element 11012 and the last lens element 11015, where the cross-section is relatively small. Advantageously, this allows the display optical system 11005 to be included in a relatively small or compact package and use relatively small optical elements. In some embodiments, the last lens 11015 collimates the beam leaving the display optical system 11005. The termination of the rays shown in FIG. 11A to the left of lens 11015 is the exit pupil of the display optical system 11005. In some embodiments, the exit pupil of the display optical system 11005 is configured to be the same size or smaller than, and positioned at the same location, as an entrance pupil of a binocular viewing assembly configured to allow a user to view the display 11010.

The lenses in the display optical system 11005 form a highly color-corrected view of the display by forming the exit pupil in a position favorably disposed for the user and the binoculars. A combination of singlets and bonded lenses provide such correction. The display optical system 11005 may be designed to provide such correction while keeping a small beam column or ray bundle, which permits adding mirrors and obtaining a compact package. In various embodiments, producing an undistorted image can be difficult without such a group of lenses designed properly to provide such correction. This correction includes both color correction as well as distortion correction.

The display optical system 11005 advantageously allows a relatively small, compact lens assembly to provide a view of a relatively large display 11010. The display optical system 11005 can be configured to work with displays 11010 of varying sizes, including, without limitation, displays with a diagonal that is less than or equal to about 0.86 in. (22 mm), at least about 0.86 in. (22 mm) and/or less than or equal to about 10 in., at least about 1 in. and/or less than or equal to about 9 in., at least about 2 in. and/or less than or equal to about 8 in., or at least about 4 in. and/or less than or equal to about 6 in. The display may, for example, have a diagonal of about 5 inches or about 8 inches in some embodiments. The display can be configured to have a relatively high pixel count (e.g., 1920×1080 pixels, 1280× 720 pixels, 3840×2160 pixels, etc.). The total optical path length of the display optical system 11005 can be less than or equal to about 9 in., at least about 9 in. and/or less than or equal to about 20 in., at least about 10 in. and/or less than or equal to about 19 in., at least about 14 in. and/or less than or equal to about 18 in. The display optical system 11005 can include lenses, mirrors, prisms, and other optical elements configured to direct and manipulate light along an optical path. The display optical system 11005 can be used in conjunction with a primary display, a surgeon display, an assistant display, possibly other displays, or any combination of these.

Figure 9A:
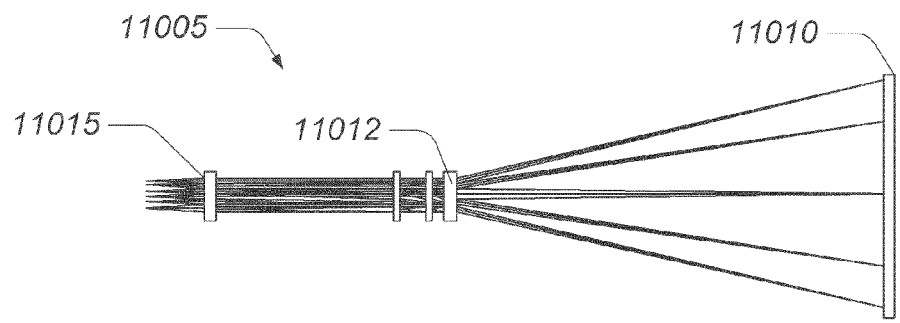
FIGS. 9A-9D illustrate example display optical systems configured to provide a view of a display or a pair of displays through oculars.

The example display optical system 11005 illustrated in FIG. 9A has a total optical path length of about 16.2 in. (412 mm). It is configured to provide an image of a 5 in. display 11010. The display optical system 11005 can include a lens 11012 configured to direct the light from the display 11010 along a path wherein light from the display 11010 is directed along a path with a relatively narrow cross-section. In various embodiments, the light received from the display is initially substantially reduced in beam size for example by the lens 11012 or lenses closest to the display and a more narrow beam is produced. In certain embodiments, for example, the lens 11012 or lenses closest to the display collect light at an angle (half angle) in excess of 20°, 25°, 30° and reduce the beam size of the light. This design is advantageous because it allows for the elements in the display optical system 11005 to be relatively small and compact. In some embodiments, the cross-section of the optical beam after the lens 11012 in the display optical system 11005 can be configured to be relatively constant. This configuration allows folding or redirecting mirrors present in the optical path to remain small.

Figure 9B:
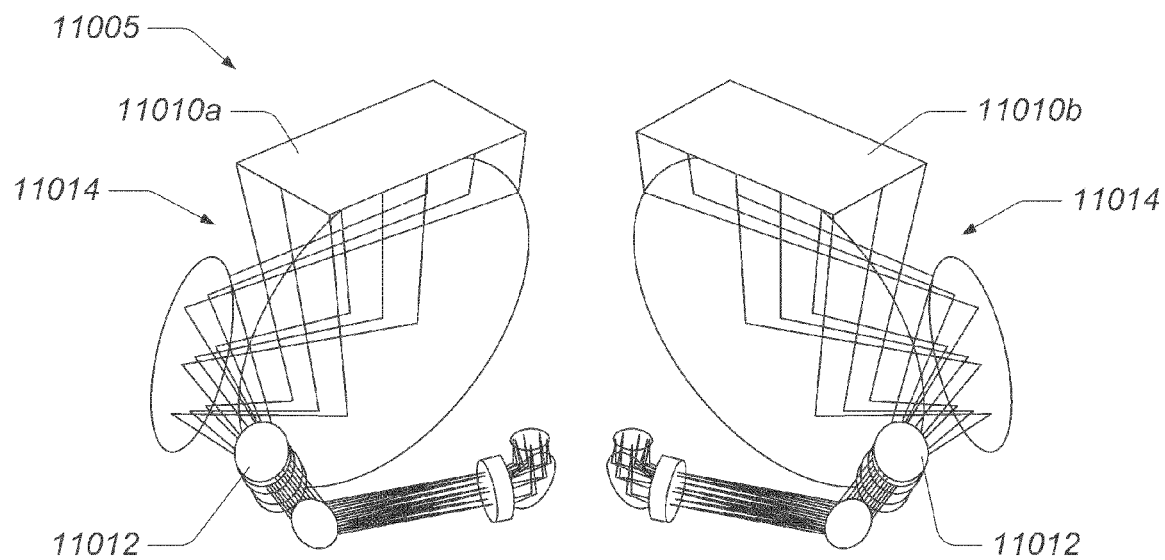

FIG. 9B illustrates a binocular display optical system 11005 configured to provide a view of stereo displays 11010a, 11010b through a pair of oculars. The binocular display optical system 11005 can be based on the optical design illustrated in FIG. 9A, and can include one or more elements 11014 in the optical path before the lens 11012 to reduce the physical size of the optical system while maintaining the length of the optical path. These elements can include mirrors, prisms, and/or other optical elements configured to redirect the light from the displays 11010a, 11010b to the lens 11012. In some embodiments, the elements 11014 include curved mirrors which redirect the optical path and converge the rays from the displays 11010a, 11010b. In some embodiments, the elements 11014 include mirrors or prisms (for example that may have planar reflecting surface) that do not substantially affect the convergence of the light rays, but redirect the optical path. In some embodiments, because of the shape of the beam incident on the reflective surface, for example, mirror, the reflective surface or cross-section of the mirror is non-circular, and is, for example, elliptical. Accordingly, in various embodiments the cross-section of the mirror or other reflective surface is possibly being longer in one direction than in another, for example, orthogonal direction. These elements may fold the optical path to provide for a more compact system. Such a system may therefore have an optical path length from display to ocular that is longer than the length and/or width of the viewing platform of the combination thereof.

In some embodiments, the display optical system 11005 can include at least four mirrors, or less than or equal to four mirrors. In certain implementations, two mirrors can be used to fold the optical path from the display 11010 to the exit pupil, the two mirrors positioned between the first lens 11012 and the display 11010. In some embodiments, the display optical system 11005 includes at least four lenses or less than or equal to four lenses.

Figure 9C:
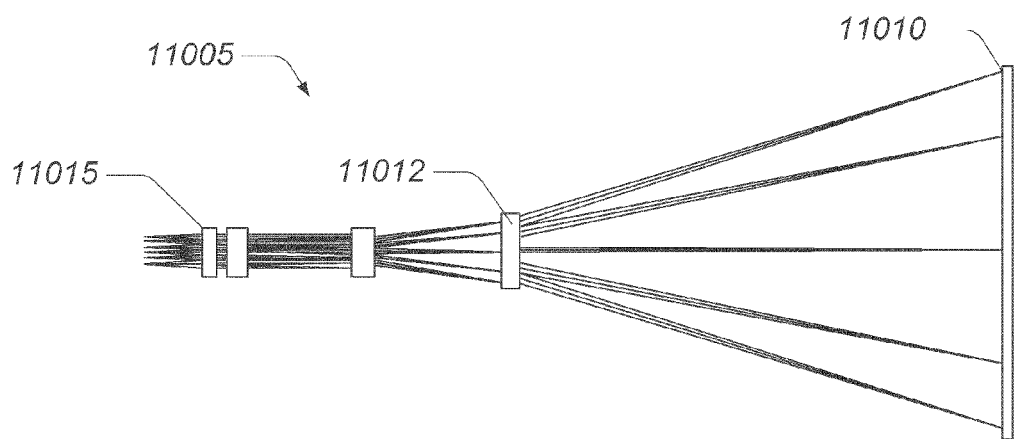

The example display optical system 11005 illustrated in FIG. 9C has a total optical path length of about 18.7 in. (475 mm). It is configured to provide an image of an 8 in. display 11010. The display optical system 11005 can include a lens 11012 configured to direct the light from the display 11010 along a path wherein light from the display 11010 is directed along a path with a relatively narrow cross-section, allowing for the display optical system 11005 to be relatively small and compact. In some embodiments, the cross-section of the optical beam after the lens 11012 in the display optical system 11005 (e.g., to the exit pupil prior to the entrance to a binocular viewing assembly) can be configured to be relatively constant. This configuration allows folding or redirecting mirrors present in the optical path to remain small. The display optical system 11005 can be configured to be used in conjunction with a display 11010 with a relatively high resolution.

Figure 9D:
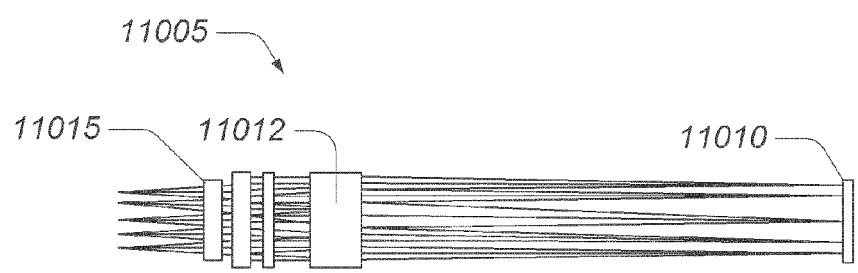

The example display optical system 11005 illustrated in FIG. 9D has a total optical path length of about 9.3 in. (237 mm). It is configured to provide an image of a smaller display, in this case a 0.9 in. (22 mm) display 11010. Because the display is much smaller than the display in the embodiments described in connection with FIGS. 9A-9C, the optical path can be much shorter and may fit into a smaller space. The display optical system 11005 can include a lens 11012 configured to direct the light from the display 11010 along a path wherein light from the display 11010 is directed along a path with a relatively narrow cross-section, allowing for the display optical system 11005 to be relatively small and compact. In some embodiments, the cross-section of the optical path after the lens 11012 in the display optical system 11005 can be configured to be relatively constant. This configuration allows folding or redirecting mirrors present in the optical path to remain small. Based at least in part on the relatively short optical path length, the display optical system 11005 can be configured to be used in conjunction with a secondary display or an assistant display.

Figure 10A:
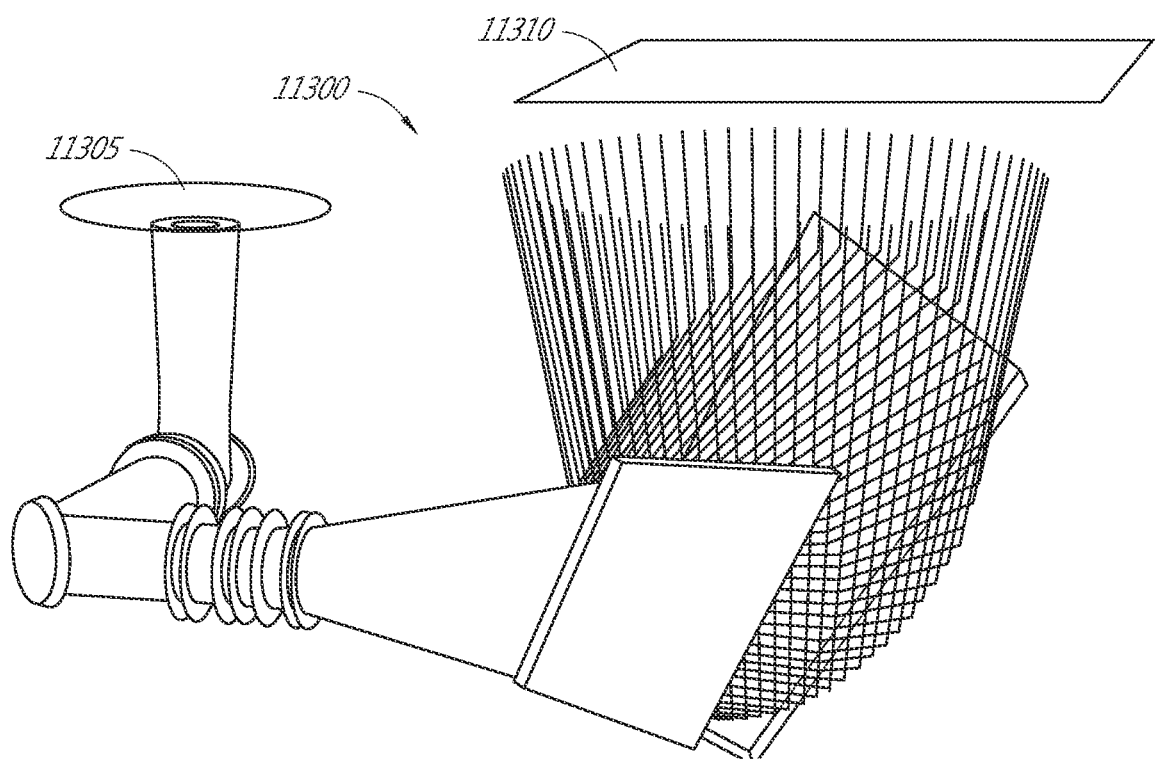
FIGS. 10A-10G illustrate example display optical systems configured to deliver to oculars images of a display wherein light paths that would intersect a viewing assembly are reduced or eliminated through baffles.
Figure 10B:
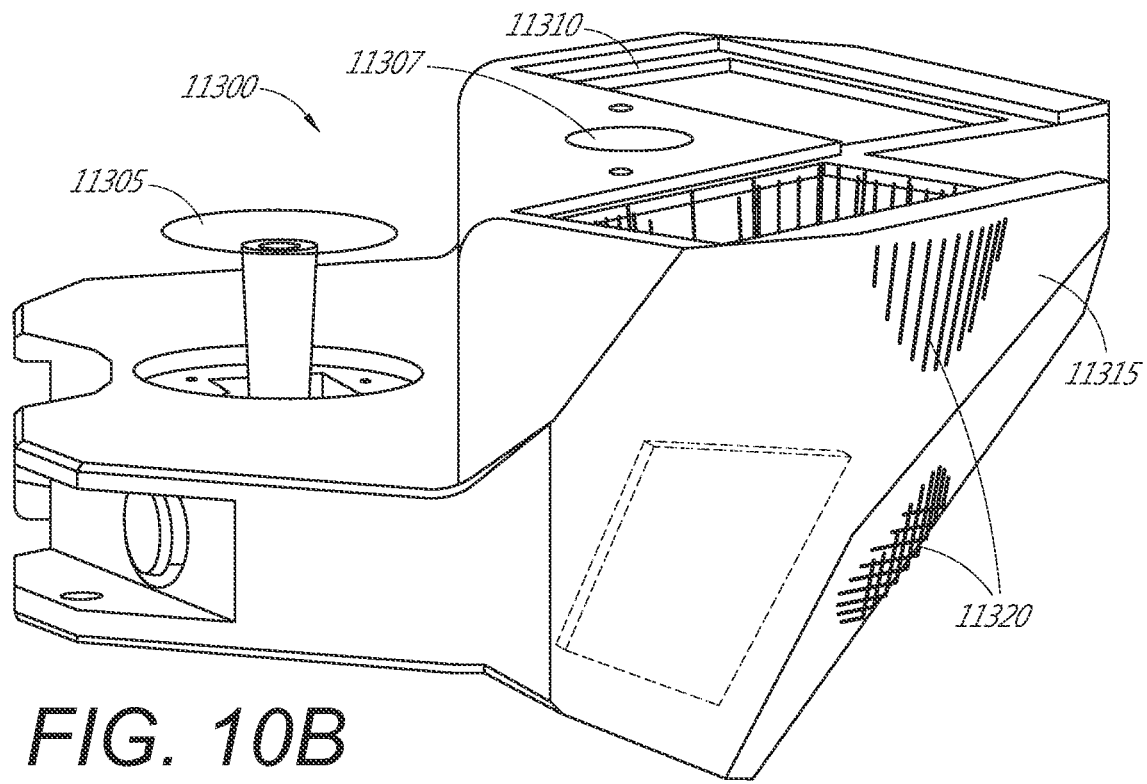

FIGS. 10A-10G illustrate example display optical systems 11300 configured to provide a view of a display 11310, the display optical system 11300 having an exit pupil 11305 wherein light paths that would intersect a viewing assembly housing 11315 are reduced or eliminated through baffles or apertures 11320, where a baffle includes a panel with an aperture. FIG. 10A illustrates an example embodiment of a display optical system 11300 comprising a display 11310, with other optical components configured to direct the light from the display 11310 to the exit pupil 11305. The light paths are traced with black lines to show the periphery of the bundle of light paths from the display 11310 to the exit pupil 11305. FIG. 10B shows this same display optical system 11300 as situated in an example viewing assembly housing 11315. When the display optical system 11300 is configured in this way, portions of the light 11320 from the display 11310 are outside of the housing 11315, which leads to light being reflected and/or scattered off the sidewalls of the housing along the path to the exit pupil 11305. This can lead to undesirable results, such as degradation in the quality of the image of the display 11310 viewed with an ocular, for example, by reducing contrast. The display optical systems 11300 can be configured to provide a collimated beam at the exit pupil 11305 such that a binocular viewing assembly comprising an objective and oculars can mate to the viewing assembly housing 11315 and view the display 11310.

Figure 10C:
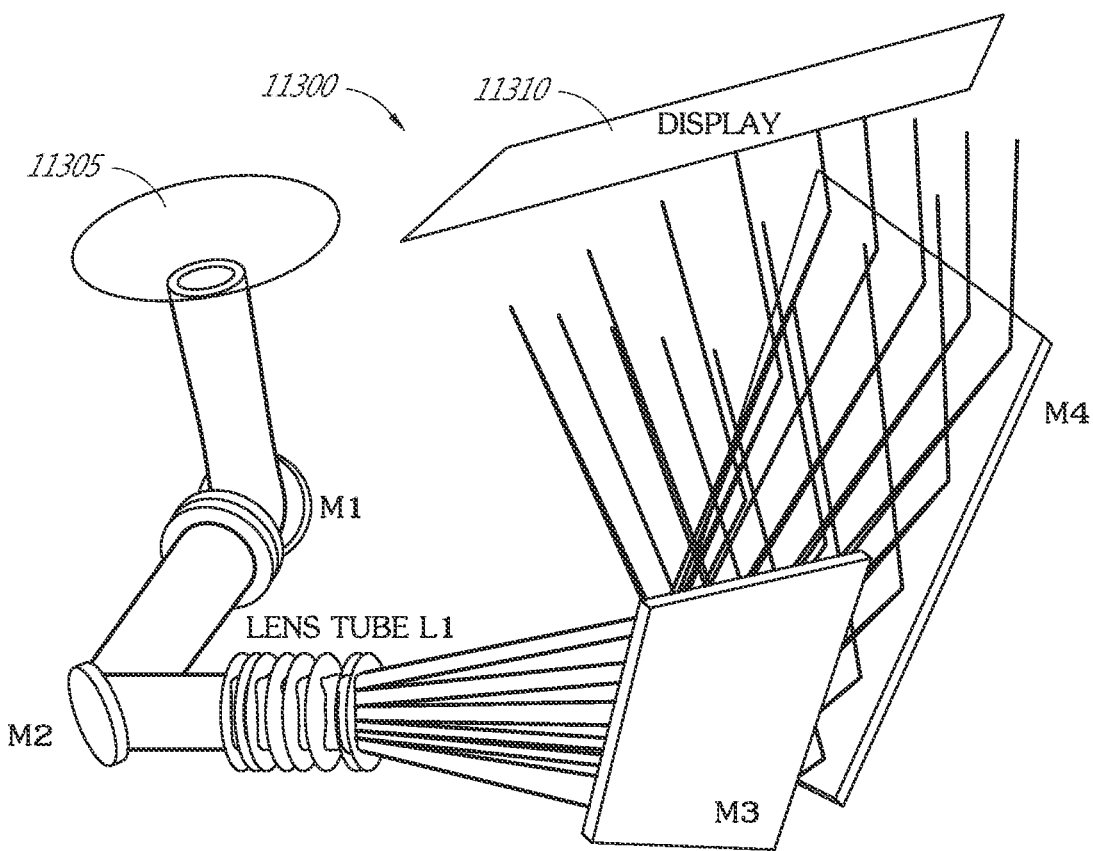
Figure 10D:
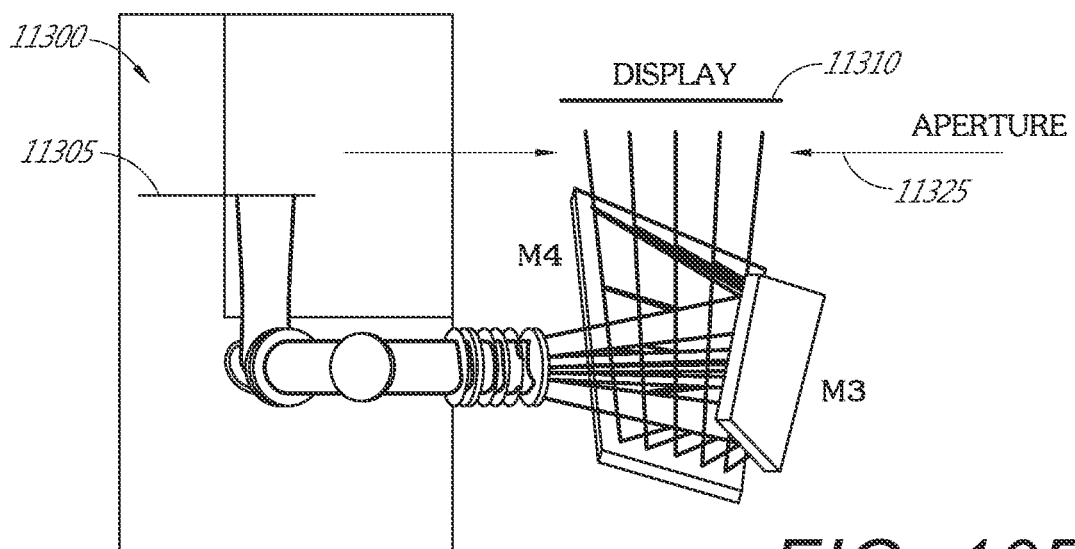
Figure 10E:
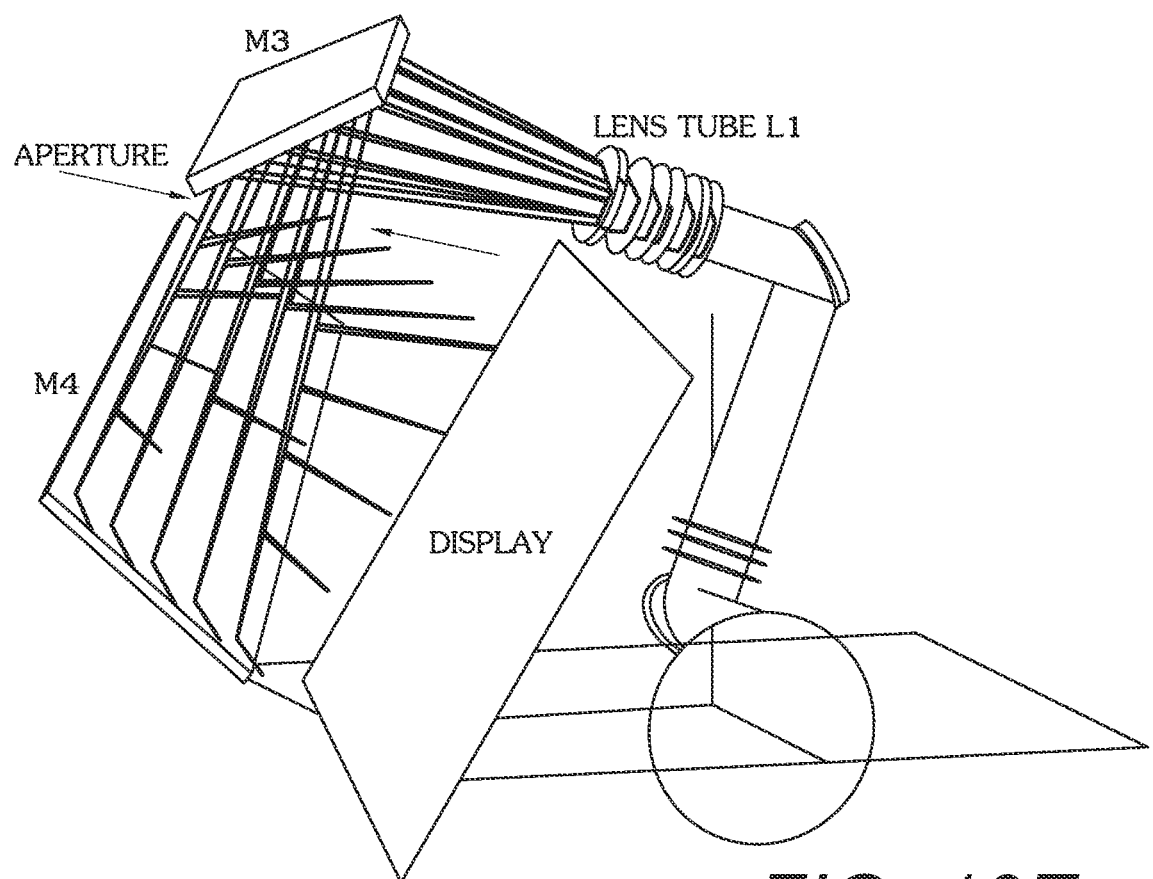
Figure 10F:
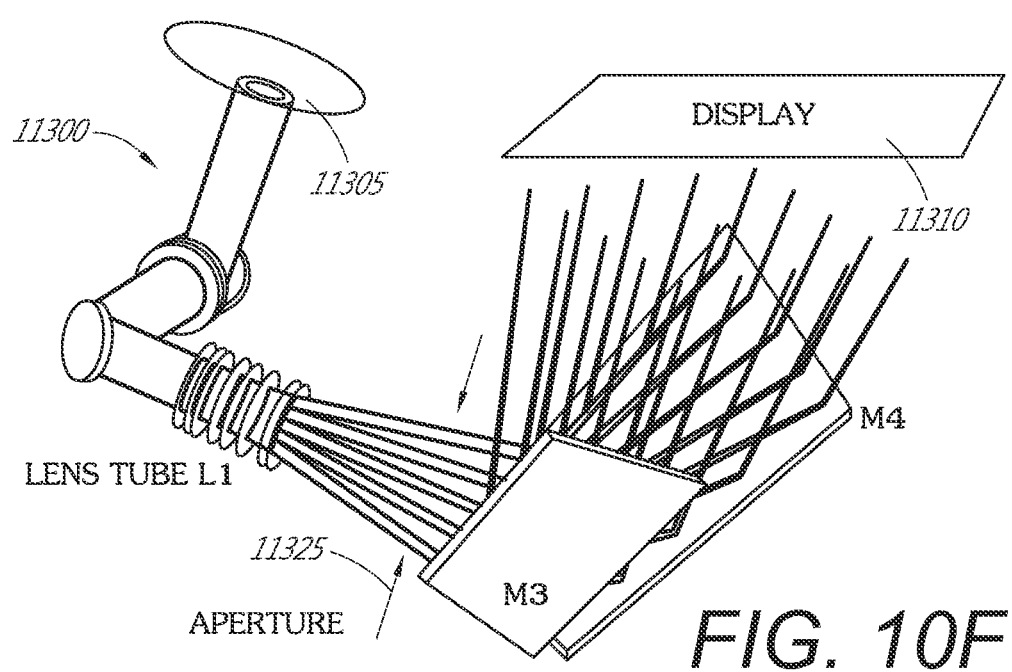

In some embodiments, one or more baffles or apertures 11325 can be incorporated into the display optical system 11300 to reduce or eliminate the amount of light that intersects with the housing 11315. The apertures may be disposed to reduce the view of the sidewalls by the ocular, thereby reducing the light collected that is reflected off the sidewalls. FIG. 10C illustrates an example embodiment of the display optical system 11300 without any apertures. The display optical system includes mirrors M1, M2, M3, and M4 to redirect the light path within the viewing assembly. The mirrors M1, M2, M3, and M4 fold the optical path such that the display optical system 11300 can be contained in a more compact housing having a smaller footprint. Additionally in various embodiments, the mirrors M1, M2, M3, and M4 fold the optical path wraps around a supporting column configured to support the housing on an arm. In various embodiments the column is a conduit for electrical signals, power, and illumination fibers. Electronics boards, for example, with FPGAs, etc., can be disposed on the top of the display. Such a configuration may be useful because signal integrity (e.g. of MIPI2 signal) can be preserved with short cable routing. An opening 11307 for the support column about which the optical path is wrapped is visible in FIG. 10B. The display optical system includes lenses in lens tube L1 to shape (e.g., collimate) the light path along the path from the display 11310 to the exit pupil 11305. The lens tube L1 can be used to maintain a relatively narrow optical passageway that contains substantially all of the light travelling from the display 11310 to the exit pupil 11305. FIG. 10D illustrates the example embodiment of the display optical system 11300 from FIG. 10C with an aperture 11325 added between the mirror M4 and the display 11310. FIG. 10E illustrates the example embodiment of the display optical system 11300 from FIG. 10C with an aperture 11325 added between the mirror M3 and the final mirror M4. FIG. 10F illustrates the example embodiment of the display optical system 11300 from FIG. 10C with an aperture 11325 added between the lens tube L1 and the mirror M3.

Figure 10G:
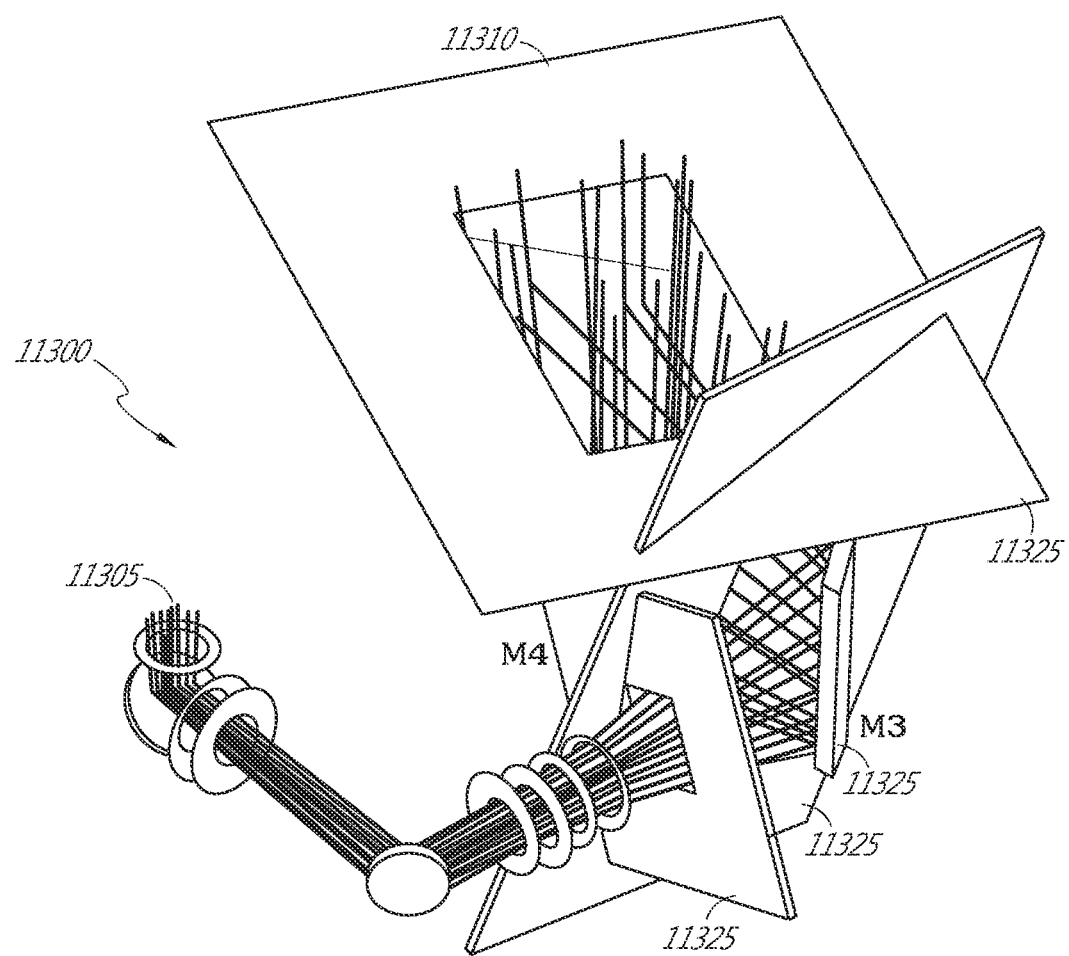

FIG. 10G illustrates the example embodiment of the display optical system 11300 from FIG. 10C, with apertures 11325 added at all the locations illustrated in FIGS. 10D to 10F, between the lens tube L1 and the mirror M3, between the mirror M3 and the mirror M4, and between the mirror M4 and the display 11310. Simulations of the performance of this configuration have shown that the radiant intensity of unwanted light, e.g., light that arrives after being reflected or scattered from the inner housing of the housing 11315, have been reduced by about 3.6× while the radiant intensity at the exit pupil 11305 from the display 11310 has been substantially held constant which substantially means that there is less than a 10% change in the radiant intensity.

In some embodiments, the display optical system 11300 can include at least four baffles or less than or equal to four baffles. In certain implementations, four baffles can be included in the optical path between the first lens and the display 11310. In some implementations, two mirrors can be included in the optical path between the first lens and the display 11310. In some embodiments, the optical path can include, in order from the display 11310, a first baffle, a first mirror, a second baffle, a second mirror, and a third baffle prior to the first lens.

In some embodiments, the display optical system can include binoculars having an optical power of about 10×. The binoculars can have a field of view of about 80 degrees to about 90 degrees. The binoculars can be configured to provide a field of view that is relatively wide (e.g., panoramic) without producing a noticeable "kidney bean effect." The binoculars can also be configured to provide a view of the display without viewing the field stop. In some embodiments, the binoculars have a focal length of about 10 mm. The display optical system can include a field stop in the oculars. The display optical system can include a circular exit pupil with rectangular baffles.

The optics of the display optical system can include one or more optical elements configured to output collimated rays. In some embodiments, the optical elements, however, can be configured to not produce collimated light within the lens train of the display optical system. By incorporating a converging lens near the display in the display optical system, the light tube can be configured to be relatively small compared to the size of the display. This can allow the size of the viewing assembly to be relatively compact.

In some embodiments, the display can be a curved surface, for example either a projection display or recent generation of flexible LCD or OLED displays having high-resolution (e.g., in excess of 300 ppi). A curved display may provide two advantages: the imaging optics for the display can be less complex than for flat panels, and the cone or numerical aperture of each picture element in the display can be directed towards the viewing optics and in the periphery of the display, thereby providing a brighter image less subject to vignetting.

In some embodiments, the display can be a volumetric display comprising two or more transmissive display panels having a single backlight wherein the transmissive display panels are stacked to provide different planes of focus for a surgeon. The transmissive displays can be active matrix liquid crystal displays ("AMLCD") or other types of transmissive displays. The backlight can be a fluorescent lamp, LEDs, or other suitable light source. By having displays positioned in different focal planes, image data from different focal planes may be presented to the surgeon with relatively less image processing and/or compression compared to a system which combines data from multiple focal planes into a single image. In some embodiments, a number of cameras can be positioned at varying depths or having varying focal distances such that the displays at different focal planes are configured to display image data from cameras positioned or focused at different depths to create a display that assists the surgeon in identifying positions of features within displayed images.

The display can show, as an overlay, pre-operative CT, MR, or other 3D image datasets from, for example, conventional surgical navigation systems (e.g., the Medtronic StealthStation or Treon, Stryker Surgical Navigation System, or Brainlab, among others). In various embodiments, in addition to images, the display can additionally provide numerical data and/or text. For example, in various embodiments, the display can overlay information such as distance or tool measurements, transparent tool renderings, camera identification information (e.g., the portion of the composite image attributable to a specific optical sensor may generate an identifying border around that portion), up/down orientation, elapsed time, and/or one or more still images captured from one or more optical sensors from a previous time in the operation The tracking system can provide 5-DOF (degrees of freedom) or 6-DOF position and orientation information to conventional surgical navigation systems. Other information, graphic, alpha numeric, or otherwise, can be provided.

The tool image can be magnified with respect to the wide-field view image, and change in image scaling will occur as the tool is moved in and out. In some embodiments, a visual metaphor for embodiments of the display is that of a hand-held magnifying glass for inspecting and doing work on a smaller region of a larger workpiece, while seeing the larger workpiece with lower magnification (if any) in more peripheral regions of the visual field to provide situational awareness. Tool images, for example, can be superimposed on the background image thereby blocking that portion of the background image. In various embodiments, the tool images may be stereo.

In some embodiments fluorescence information can be displayed. Cameras that image in different wavelengths, such as infrared, could image the surgical site or objects contained therein. In some embodiments, features could be made to fluoresce, for example, by injecting fluorescent chemical and illuminating the area with light the will induce fluorescence. Such a technique may be useful to identify and/or highlight the location and/or boundaries of specific features of interest such as tumors, etc. The fluorescence or other wavelength of interest may be detected by the one or more cameras imaging the surgical field such as one or more camera providing a surgical microscope view. In some embodiments, images produced by fluorescence or other wavelengths of interest are superimposed on one or more images from other camera(s). Filtering could be provided to remove unwanted wavelengths and possibly increase contrast. The filter can remove excitation illumination. In some embodiments emission image content, (e.g., fluorescing tissue) can be parsed and superimposed on image content that is not emitting (e.g., tissue that is not fluorescing), or vice versa. In various embodiments, such as where the fluorescing wavelength is not visible (e.g., for fluorescence in the infrared), an artificial color rendition of the fluorescing content can be used in place of the actual fluorescing color so as to enable the fluorescing tissue to be visible.

Figure 11:
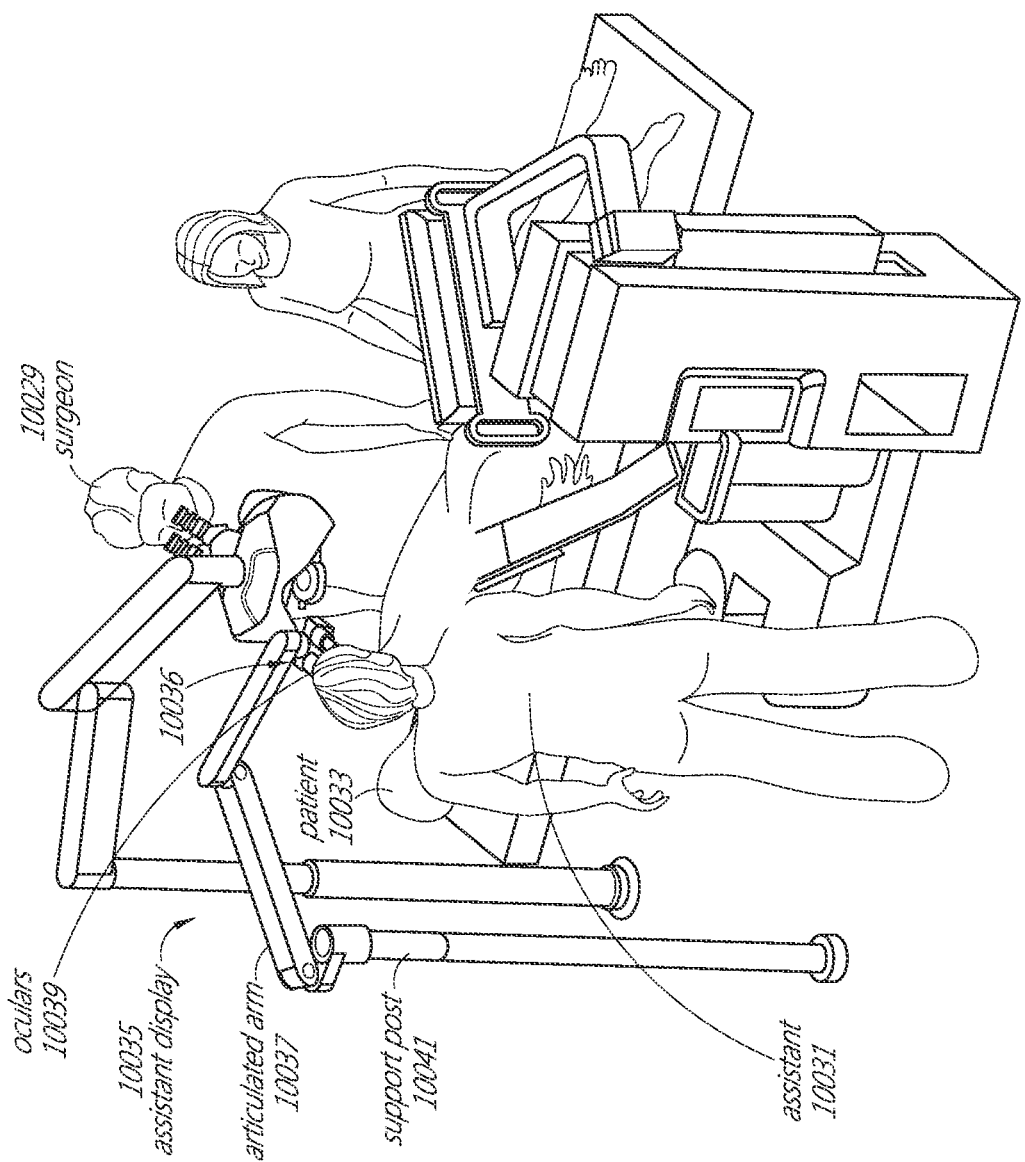
FIG. 11 is a schematic illustration of a surgical visualization system including an assistant display.

FIG. 11 is a schematic illustration of a surgical visualization system and an assistant display. In some embodiments, a separate assistant display may be provided for use by a surgical assistant or observer. As illustrated in FIG. 11, the assistant display 10035 comprises a binocular viewing platform 10036 for the assistant that includes oculars 10039 mounted on a lockable articulated arm 10037, which extends from a support post 10041. For example, the assistant 10031 and surgeon 10029 may be positioned on opposite sides of the patient 10033, as in the illustrated arrangement. In such an arrangement, the image provided in the assistant display 10035 may be rotated 180 degrees with respect to that provided to the surgeon 10029. The assistant may be at other locations, for example, in other procedures. The assistant may, for example, be located at a location 90 degrees with respect to the surgeon, as opposed to 180 degrees with respect to the surgeon. Likewise, the image provided in the assistant display 10035 may be rotated 90 degrees with respect to that provided to the surgeon 10029. Similarly the image may be reoriented as needed, possibly based on the location/position and perspective of the assistant. Additionally, the assistant display can be provided with any of the features described elsewhere herein.

In some embodiments fluorescence images can be collected and displayed. These fluorescence images may be viewed superimposed on images of the surgical site not based on fluorescence. Cameras that image in different wavelengths, such as infrared, could image the surgical site or objects contained therein. In some embodiments, features could be made to fluoresce, for example, by injecting fluorescent chemical and illuminating the area with light that will induce fluorescence. For example, in certain embodiments anatomical features may contain fluorescent dye that fluoresces, for example, when exposed to short wavelength radiation such as UV radiation. Such a technique may be useful to identify and/or highlight the location and/or boundaries of specific features of interest such as tumors, etc. The fluorescence or other wavelength of interest may be detected by the one or more cameras imaging the surgical field such as one or more camera providing a surgical microscope view or one or more cameras on a surgical tool providing a surgical tool view. For example, an optical detector that is sensitive to the wavelength of the fluorescent emission may be employed to view the fluorescent image. In some embodiments, the wavelength of fluorescent emission is in the infrared. In certain embodiments sensors sensitive to different wavelengths may be employed. In particular, one or more sensors sensitive to the fluorescing wavelength (e.g., IR) may be used in conjunction with one or more sensors not sensitive or less sensitive to the fluorescing wavelength but sensitive or more sensitive to other useful wavelengths (e.g. visible light). Light can be collected and distributed to both types of detectors for example using a beamsplitter such as a wavelength dependent beamsplitter that reflects one wavelength and passes another. The fluorescent and non-fluorescent images can be recorded by the respective sensors. In some embodiments, the fluorescent and non-fluorescent images can be superimposed when displayed on electronic displays that receive image data from both types of sensors. In various embodiments, the cameras, including fluorescent and/or non-fluorescent cameras, that provide a surgical microscope view, a surgical tool view (e.g., from a camera on a tool), or other view of the surgical site, may comprises stereo cameras and the displays may comprise stereo displays.

In some embodiments, images produced by fluorescence or other wavelengths of interest are superimposed on one or more images from other camera(s). Filtering could be provided to remove unwanted wavelengths and possibly increase contrast. For example, the filter can be used to remove excitation illumination. In some embodiments, emission image content, (e.g., fluorescing tissue) can be parsed and superimposed on image content that is not emitting (e.g., tissue that is not fluorescing), or vice versa.

In some embodiments, IR fluorescence images are superimposed over non-IR (e.g. visible) images. Other wavelengths such as other fluorescence wavelengths may be employed. In various embodiments, such as where the fluorescing wavelength is not visible (e.g., for fluorescence in the infrared), an artificial color rendition of the fluorescing content can be used in place of the actual fluorescing color so as to enable the fluorescing tissue to be visible.

Figure 12:
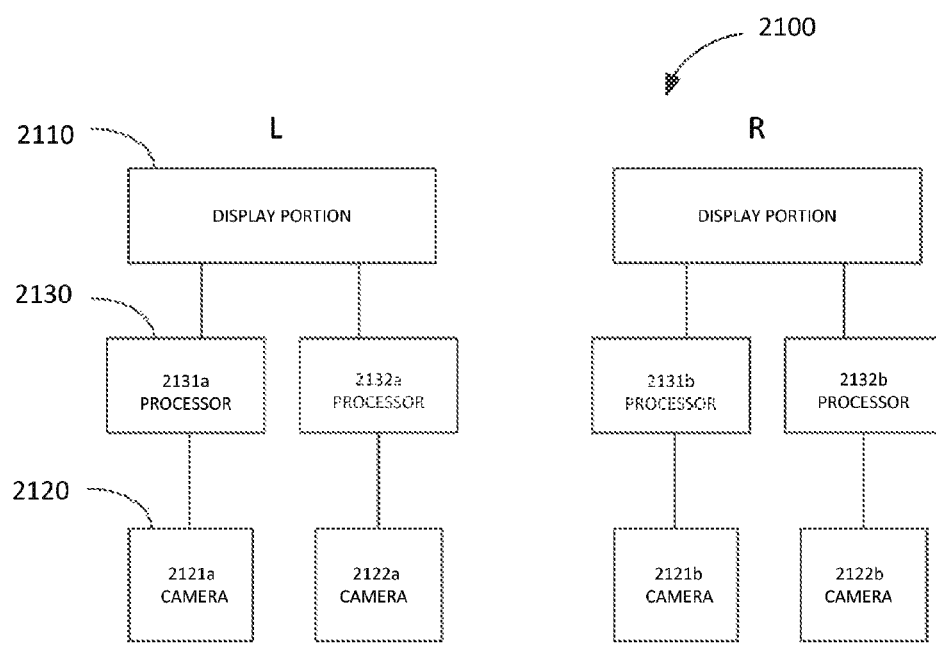
FIG. 12 schematically illustrates an example medical apparatus in accordance with certain embodiments described herein.

FIG. 12 schematically illustrates an example medical apparatus in accordance with certain embodiments described herein. The medical apparatus 2100 can comprise a display (or display portion) 2110, a plurality of cameras 2120, and one or more processors 2130. The plurality of cameras 2120 can include at least one first camera 2121*a* configured to image fluorescence in a surgical field, and at least one second camera 2122*a* configured to produce a non-fluorescence image of the surgical field. The processor 2130 can be configured to receive images from the plurality of cameras 2121*a*, 2122*a*, and to display on the display 2110 a fluorescence image from the at least one first camera 2121*a* and to display on the display 2110 the non-fluorescence image from the at least one second camera 2122*a*. As shown in FIG. 12, the processor 2130 can advantageously include a plurality of processors 2131*a*, 2132*a*, e.g., a separate processor for each camera within the plurality of cameras 2120. For example, at least one first processor 2131*a* can be configured to receive an image from at least one first camera 2121*a* and to display on the display 2110 a fluorescence image. In addition, at least one second processor 2132*a* can be configured to receive an image from at least one second camera 2122*a* and to display on the display 2110 the non-fluorescence image.

The display 2110 can be a primary display, a surgeon display, an assistant display, possibly other displays, or any combination of these. The display 2110 can include a display portion, a display, or display device as described herein. For example, in some embodiments, the display 2110 can include a display (or display portion) to be viewed through one or more oculars, e.g., a display within the viewing platform 9 of the surgical viewing system 1 shown in FIGS. 1, 2, 3A, 4A and 4B. The display (or display portion) could be within a housing. In other embodiments, the display 2110 can include a display mounted on a display arm from the ceiling or on a post, e.g., a display device 13 on display arm 5 of the surgical viewing system 1 shown in FIG. 1 or be mounted on the wall. In various embodiments, such displays comprise panel displays having a length of, for example, be between 15-70 inches, or larger or smaller. In some embodiments, the display 2110 can comprise a head mounted display (e.g., eyewear, googles, a mask etc.), for example, as described herein.

In various embodiments, the plurality of cameras 2120 can include a camera to provide a surgical microscope view of the surgical field. In some embodiments, the plurality of cameras 2120 can include a camera disposed on a surgical tool or on another medical device. The plurality of cameras 2120 can include at least one first camera 2121*a* and at least one second camera 2122*a* configured to form a left-eye view of the surgical field. The plurality of cameras 2120 can also include at least one first camera 2121*b* and at least one second camera 2122*b* configured to form a right-eye view of the surgical field. In some embodiments, the left and right-eye views are for stereoscopic viewing of the surgical field and the cameras can be angled to provide desired convergence mimicking the human eye. One or more cameras 2121*a*, 2121*b*, 2122*a*, and/or 2122*b* of the plurality of cameras 2120 can include optical assemblies as described herein. For example, one or more cameras 2121*a*, 2121*b*, 2122*a*, and/or 2122*b* can include a turning prism 54, a lens train 55, and/or a sensor 56 as shown in FIG. 5A.

As described herein, for the left-eye view, the at least one first camera 2121*a* can be configured to image fluorescence in a surgical field, and the at least one second camera 2122*a* can be configured to produce a non-fluorescence image of the surgical field. Similarly, for the right-eye view, the at least one first camera 2121*b* can be configured to image fluorescence in a surgical field, and the at least one second camera 2122b can be configured to produce a non-fluorescence image of the surgical field.

In some embodiments, the first camera 2121a and/or 2121b can be sensitive to infrared wavelengths, ultraviolet wavelengths, or other fluorescence wavelengths. For example, an optical detector, e.g., sensor 56 or an array of sensors, of the first camera 2121a and/or 2121b can be sensitive to fluorescence wavelengths. In some embodiments, the first camera 2121a and/or 2121b sensitive to fluorescence wavelengths can include an infrared, ultraviolet, or other fluorescence light source. In some embodiments, illumination using an optical fiber can be used to provide pump radiation to induce fluorescence. In some embodiments, a filter may be used to selectively direct fluorescence wavelengths to the first camera 2121a and/or 2121b sensitive to fluorescence wavelengths. In some embodiments, the second camera 2122a and/or 2122b may not be sensitive to fluorescence wavelengths.

In some embodiments, the processor 2130 can be configured to superimpose the fluorescence image over the non-fluorescence image. In other embodiments, the processor 2130 can be configured to superimpose the non-fluorescence image over the fluorescence image. In various embodiments, the processor 2130 can electronically process and synchronize the fluorescence and non-fluorescence images together. For example, the processor 2130 can read, align, and combine together the images.

The processor 2130 can include a general all-purpose computer and in some embodiments, a single processor may drive both the left and right display portions 2110. However, various embodiments of the medical apparatus 2100 can include separate processing electronics for the left-eye and right-eye views. Such separate processing for the left and right channels can be advantageous over a processor with single processing electronics or the general all-purpose computer since time is critical in surgical procedures. For example, in some embodiments, having separate dedicated processing electronics for each channel can provide pure parallel processing, which results in faster processing of images, thereby reducing latency. In addition, addressing a failure of a general all-purpose computer may entail rebooting of the computer and involve some downtime. Furthermore, with separate processing electronics in left-eye and right-eye view channels, if one of the processing electronics were to fail, the processing electronics in the other channel can continue to provide images to the surgeon. Such redundancy can also be incorporated into a monocular viewing system. For example, in some embodiments of a monocular viewing system, two channels similar to a binocular viewing system can be provided. Images for the monocular viewing system can be split into each channel, with each channel having its own processing electronics.

Furthermore, in some even more advantageous embodiments, as shown in FIG. 12, the medical apparatus 2100 can include separate processing for each camera within each channel to further increase processing of images and reduce latency. For example, for the left-eye view, processor 2131a can be configured to receive an image from camera 2121a and to display on the display 2110 a fluorescence image from camera 2121a. Processor 2132a can be configured to receive an image from camera 2122a and to display on the display 2110 the non-fluorescence image from camera 2122a. The fluorescence and non-fluorescence images can be superimposed optically on the display 2110. Similarly, for the right-eye view, processor 2131b can be configured to receive images from camera 2121b and to display on the display 2110 a fluorescence image from camera 2121b. Processor 2132b can be configured to receive images from camera 2122b and to display on the display 2110 the non-fluorescence image from camera 2122b. The fluorescence and non-fluorescence images can be superimposed optically on the display 2110.

In certain embodiments, each of the separate processing electronics can be configured for image manipulation, e.g., to receive image data, process the image data, and output the images for display. For example, each of the processing electronics can be configured to receive one or more user inputs, receive one or more input signals corresponding to images from one or more cameras, and/or select which image to display. Each of the processing electronics can also resize, rotate, or reposition the selected image based at least in part on one or more user inputs or provide any combination of these operations. The processing electronics can also produce one or more output signals to drive one or more displays to produce one or more images. For example, each processing electronics can include a microprocessor, a field programmable gate array (FPGA), or an application specific integrated circuit (ASIC). Each processing electronics can also include a graphics processing unit (GPU) and random access memory (RAM). The processing electronics can also control the color balance, brightness, contrast, etc. of the one or more images or provide any combination of these operations.

In some embodiments, instead of superimposing fluorescence and non-fluorescence images, an image at a first wavelength range can be superimposed with an image at a second wavelength range. For example, one or more sensors can capture a first image at a first wavelength range, and one or more sensors can capture a second image at a second wavelength range. The first and second images can be superimposed optically as disclosed herein. As another example, the image at a first wavelength can be provided by narrow band imaging instead of fluorescence imaging. For example, a filter in some embodiments can allow imaging with the use of ambient light at blue (about 440 to about 460 nm) and/or green (about 540 to about 560 nm) wavelengths for the image at the first wavelength. Imaging at or near these wavelengths can improve visibility of features since the peak light absorption of hemoglobin occurs at these wavelengths. The image at the second wavelength can be provided without narrow band imaging (e.g., use of ambient light without a filter).

In further embodiments, the plurality of cameras 2120 can include different cameras for multiple views of the surgical site instead of or in addition to cameras mainly for imaging at different wavelengths. For example, in some embodiments, the plurality of cameras 2120 can include a camera providing a surgical microscope view, a camera disposed on a surgical tool (e.g. cutting tool), and a camera disposed on another medical device to provide different views of the surgical site or any combination thereof. Some embodiments can also include a switch or switching module to determine which views are to be displayed, for example, as superimposed, overlapping, adjacent, stereo or as a monocular view, etc. One or more image could also be from other sources, e.g., a data file, a computed tomography (CT) scan, a computer aided tomography (CAT) scan, magnetic resonance imaging (MRI), an x-ray, ultrasound imaging instrument, etc.

Figure 13A:
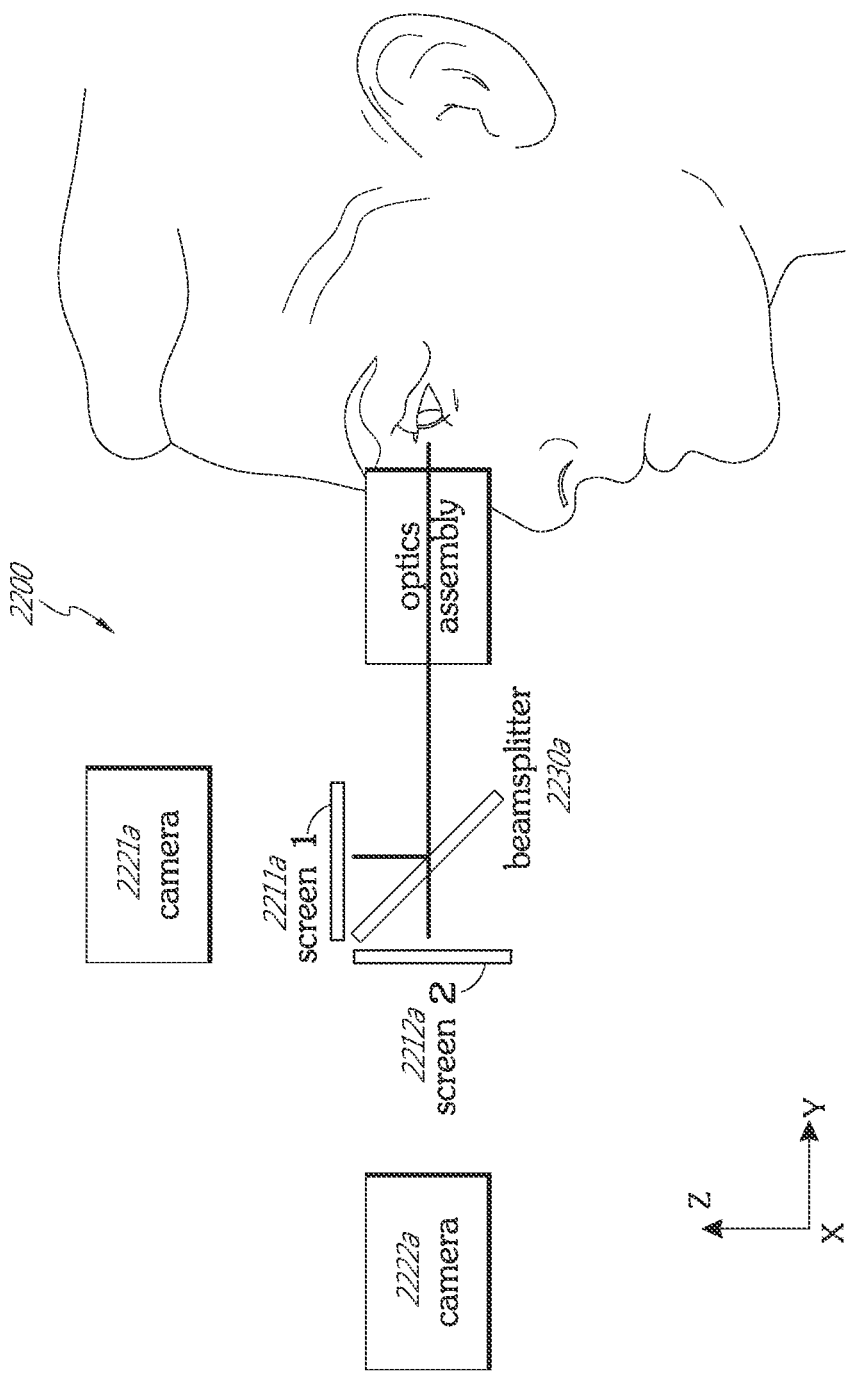
FIG. 13A-13C schematically illustrate another example medical apparatus in accordance with certain embodiments described herein.

FIG. 13A schematically illustrates another example medical apparatus in accordance with certain embodiments described herein. Some such embodiments can also advantageously decrease the time to produce an image for viewing, which can be important in certain surgical procedures.

For example, the medical apparatus 2200 can include a plurality of displays (or display portions), a plurality of cameras, and one or more beam combiners. As shown in FIG. 13A, to form a left-eye view, the plurality of cameras can include at least one first camera 2221a configured to produce a fluorescence image onto a first display 2211a and at least one second camera 2222a configured to produce a non-fluorescence image onto a second display 2212a. In some embodiments, the cameras 2221a, 2222a can produce the images onto the plurality of displays 2211a, 2212a, e.g., with a processor. However, in such embodiments, an electronic processor need not perform the combining of images. A beam combiner 2230a can be configured to receive the fluorescence and non-fluorescence images from the first 2211a and second 2212a displays and to combine or superimpose optically the fluorescence and non-fluorescence images for left-eye viewing, e.g., within a housing through an ocular or on a display device.

Figure 13B:
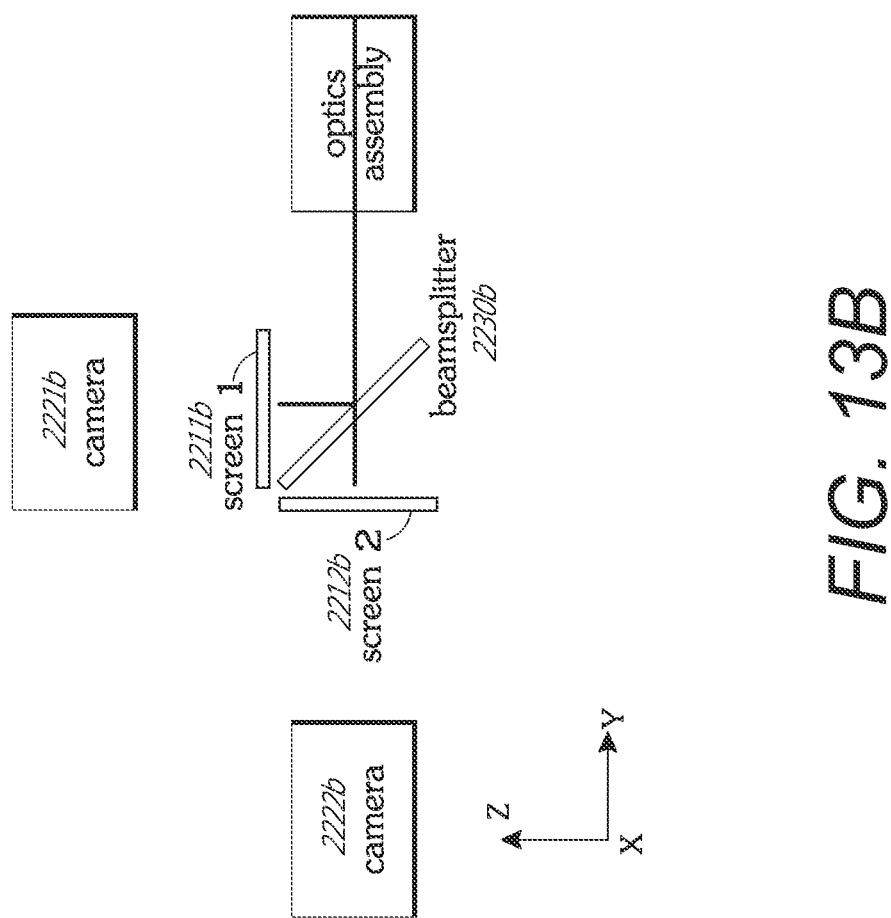

As shown in FIG. 13B, to form a right-eye view, the plurality of cameras can also include another first camera 2221b configured to produce a fluorescence image onto another first display 2211b and another second camera 2222b configured to produce a non-fluorescence image onto another second display 2212b. In some embodiments, the cameras 2221b, 2222b can obtain images that can be viewed on the plurality of displays 2211b, 2212b, for example, using processing electronics. However, in such embodiments, an electronic processor need not perform the combining of images. A beam combiner 2230b can be configured to receive the fluorescence and non-fluorescence images from the first 2211b and second 2212b displays and to superimpose the fluorescence and non-fluorescence images for right-eye viewing, e.g., within a housing through an ocular or on a display device.

Figure 13C:
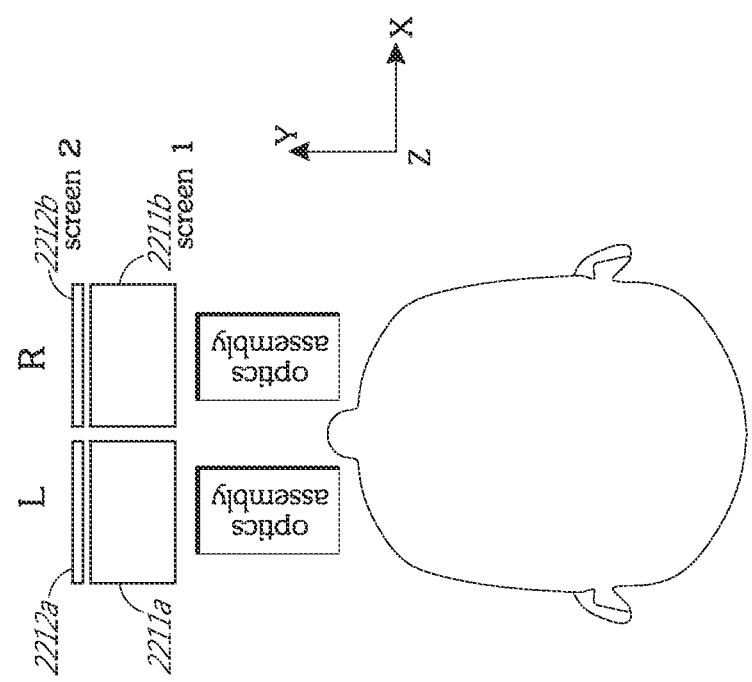

In various embodiments, the beam combiner 2230 can include a beamsplitter (e.g., a 45 degree or other angle splitter used in reverse), a dichroic beamsplitter, a prism, or other optical structure to combine the beams. As an example, a beam combiner 2230a can be placed within the left-eye optical path to receive the fluorescence and non-fluorescence images from the first 2211a and second 2212a displays and to superimpose the fluorescence and non-fluorescence images for left-eye viewing, e.g., within a housing through an ocular or on a display device. Similarly, another beam combiner 2230b can be placed in the right-eye optical path to receive the fluorescence and non-fluorescence images from the first 2211b and second 2212b displays and to superimpose the fluorescence and non-fluorescence images for right-eye viewing. Some embodiments can further include imaging optics (e.g., an optics assembly) disposed to collect light from the displays to enable the images to overlap. The imaging optics can be configured to form images at infinity. FIG. 13C schematically illustrates a top view of an embodiment of a medical apparatus incorporating the example left and right assemblies from FIGS. 13A and 13B.

In some embodiments, instead of superimposing fluorescence and non-fluorescence images, an image at a first wavelength range can be superimposed with an image at a second wavelength range. For example, a first camera 2221a can produce a first image at a first wavelength range onto a first display 2211a, and a second camera 2222a can produce a second image at a second wavelength range onto a second display 2212a. The beam combiner 2230a can optically superimpose the first and second images. As another example, the image at a first wavelength can be provided by narrow band imaging instead of fluorescence imaging, and the image at the second wavelength can be provided without narrow band imaging as described herein.

Figure 14A:
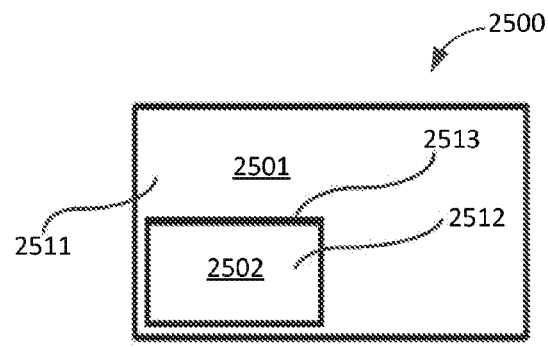
FIG. 14A illustrates a schematic of an example of a composite image with a picture-in-picture (PIP) view of a surgical field.
Figure 14B:
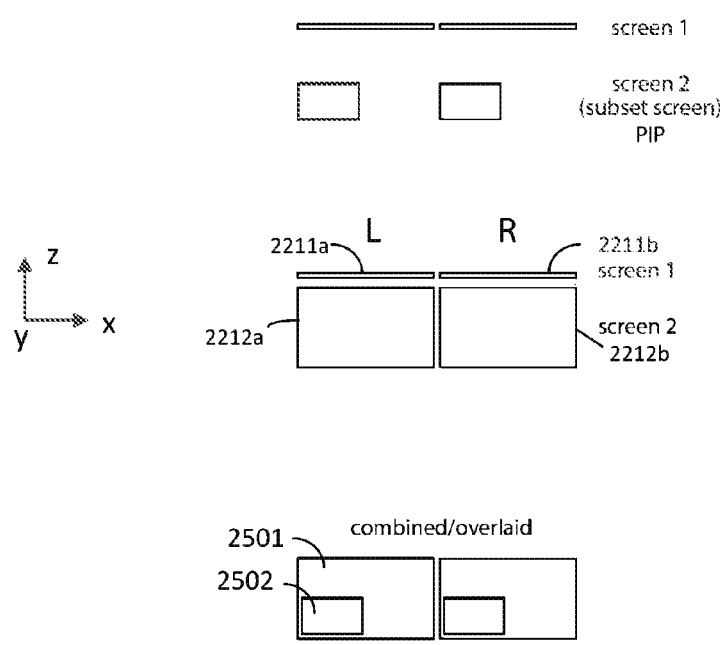
FIG. 14B schematically illustrates a front view of an embodiment of a medical apparatus incorporating left and right assemblies to produce a composite image of two or more images for both left and right eyes.

In addition, images from two different cameras of the same or substantially the same wavelength, but having other properties can be superimposed. For example, one image could be a natural image of tissue, and another view could be an unnatural image (e.g., an image with false color or an image with exaggerated or extreme contrast). In some embodiments, such superimposed images can advantageously show margins between healthy and unhealthy tissue. The example embodiments of the medical apparatuses shown in FIGS. 12 and 13A-13C can also be modified to produce a composite image of two or more images. FIG. 14A illustrates a schematic of an example composite image 2500, where a first (e.g., a background) image 2501 is produced on a first portion 2511 of the composite image 2500, and a second (e.g., a picture-in-picture (PIP)) image 2502 is produced on a second portion 2512 of the composite image 2500. In some embodiments, the images can include a fluorescence image and a non-fluorescence image. However, in other embodiments, the images are not necessarily fluorescence and non-fluorescence images. For example, one image can be a surgical microscope view of the surgical field from a camera producing the surgical microscope view. The other image can be the image of the surgical field from a camera disposed on a surgical tool (e.g. cutting tool) or other medical device. One or more image could also be from sources other than cameras, e.g., a data file, a computed tomography (CT) scan, a computer aided tomography (CAT) scan, magnetic resonance imaging (MRI), an x-ray, ultrasound imaging instrument, etc. FIG. 14B schematically illustrates a front view of an embodiment of a medical apparatus incorporating the example left and right assemblies from FIG. 12 or 13A-13C to produce a composite image of two or more images for both left and right eyes.

Referring to the example embodiment shown in FIG. 12, for the left-eye view, the first camera 2121a can be a camera producing a surgical microscope view, and the second camera 2122a can be a camera disposed on a surgical tool (e.g. cutting tool) or other medical device. Similarly, for the right-eye view, the first camera 2121b can be another camera producing a surgical microscope view, and the second camera 2122b can be another camera disposed on a surgical tool (e.g. cutting tool) or other medical device. For each eye's view, the first camera 2121a, 2121b can produce the background image 2501 of the composite image 2500, and the second camera 2122a, 2122b can produce the PIP image 2502 in the composite image 2500. For the left-eye view, the processor 2131a can be configured to receive an image from the first camera 2121a and to display on the display 2110 the image as the background image 2501 of the composite image 2500. In addition, the processor 2132a can be configured to receive an image from the second camera 2122a and to display on the display 2110 the image as the PIP image 2502 of the composite image 2500. For the right-eye view, the processor 2131b can be configured to receive an image from the first camera 2121b and to display on the display 2110 the image as the background image 2501 of the composite image 2500. In addition, the processor 2132b can be configured to receive an image from the second camera 2122b and to display on the display 2110 the image as the PIP image 2502 of the composite image 2500. As shown in FIG. 14B, the position of the PIP image 2502 in the composite image 2500 can be in the same or different location from that illustrated in the figures. Additional cameras or sources can also be used to produce a multiple PIP images.

Referring to the example embodiment shown in FIGS. 13A-13C, a beam combiner 2230a, 2230b can be placed within each eye's optical path to produce the composite image 2500. In some embodiments, the background image from a camera can be resized or the row count of pixels of the background image can be reduced. For example, the background image can be resized from the full frame to the size of the first portion 2511 (e.g., about ½, ⅔, ¾, etc., or any range therebetween) of the composite image 2500. The beam combiner 2230a, 2230b in each eye's optical path between the viewer and the displays can superimpose the background image with a PIP image such that the background image appears on the first portion 2511 of the composite image 2500, and the PIP image forms within the remaining portion 2512 (e.g., about ½, ⅓, ¼, etc., or any range therebetween) of the composite image 2500. In some embodiments, the remaining portion 2512 can include a border 2513 having a thickness (e.g., 1%, 2%, 3%, 5%, 10%, or 15%, of the width of the image, or any range therebetween) surrounding the PIP image 2502 to help prevent the viewer from seeing similar types of images as being falsely contiguous (e.g., similar types of tissues from multiple sources).

With reference to FIG. 13A, an example illustration using the left-eye view will be provided. The example illustration can also apply to the right-eye view in certain embodiments. For example, a first camera 2221a for providing a surgical microscope view can provide the background image on a first display 2211a, and a second camera 2222a disposed on a surgical tool or other medical device can provide the smaller image on a second display 2212a. The beam combiner 2230a can produce the background image from the first display 2211a as the first portion 2511 (e.g., about ⅔) of the composite image 2500. The beam combiner 2230a can also combine the PIP image from the second display 2212a as part of a second portion 2512 (e.g., about ⅓) of the composite image 2500. As shown in FIG. 14A, the background image 2501 can be produced in the majority (e.g., about ⅔) of the composite image 2500. The PIP image 2502 can be produced as part of, e.g., within the remaining portion 2512 (e.g., about ⅓) of the composite image 2500.

The display 2211a for the background image can be a 5" display. The smaller PIP image from the second camera 2222a can be displayed on a smaller panel viewed off from the beam combiner 2230a, or could be displayed on a 5" display using only a portion of the display (e.g., about ⅓ of the display or about part of ⅓ of the display). After properly baffling the optical pathways, the viewer can see the smaller image 2502 adjacent the background image 2501 as though it were a picture-in-picture.

The beam combiner 2230 can also produce additional PIP images from other displays as part of the composite image 2500. For example, multiple images (e.g., two, three, four, five, six, nine, twelve, etc., or any range therebetween) from multiple displays (e.g., two, three, four, five, six, nine, twelve, etc., or any range therebetween) can be viewed for each eye's view by using one or more beam combiners 2230.

In some embodiments, the smaller images can be superimposed with a dark (e.g., black) or light (e.g., clear) border to prevent the viewer from seeing similar images as being falsely contiguous (e.g., similar types of tissues from multiple sources). For example, after resizing the background image (e.g., to about ⅔ size), the remaining portion (e.g., about ⅓) of the image can be left black. The smaller images from other displays can be superimposed onto the black portion of the background image such that the images do not appear falsely contiguous. In addition, the border can help facilitate the beam combiner 2230 arrangement, making the alignment less critical in some embodiments. In various embodiments, the border to can have a thickness of between of 2% to 5% or 3% to 10% of the width of the images or larger. In some embodiments, the smaller images could be superimposed onto the background image. For example, the background image could include additional superimposed or overlapping images. Some embodiments can include a switch or switching module to determine which image to be displayed. For example, the background image could be switched off and not be displayed so that a different image(s) can be displayed in the first portion 2511 of the view 2500.

As described herein, two images can form a composite image. For example, two non-latent images, e.g., two real-time images of the surgical field, can form a composite image. In various embodiments, when the horizontal line of sight is maintained, merging of images is possible. In addition, one non-latent image (e.g., a real-time image of the surgical field) and one latent image (e.g., a data file, a CT scan, a CAT scan, an MRI, an x-ray, ultrasound image, etc.) can form a composite image. In various embodiments, the latent and/or non-latent images can be seen individually by both eyes; and one or more of the images can have convergence information for a stereo or 3D effect. For example, the images can be displayed on 2D displays that represent 2D images from the input cameras. However, with convergence information, the brain can allow the eyes to see a 3D image.

FIG. 14B1 shows an illustration of an example medical apparatus according to certain embodiments described herein. FIG. 14B1-a shows a larger view of the side view of FIG. 14B1; and FIG. 14B1-b shows a larger view of the front view of FIG. 14B1. Example dimensional (e.g., in millimeters) values are provided. However, the dimensions are not particularly limited. As shown in FIG. 14B1-a, the example embodiment of the medical apparatus 3000 includes an imaging optics assembly 3003, a beam combiner 3004, a first display 3005a, and a second display 3006a. In some embodiments, the first display 3005a can be the same size as the second display 3006a. In some embodiments, one of the displays 3005a can be a combination of smaller displays with a corresponding outer dimension equal to the other display 3006a. In some other embodiments, the first display 3005a can have a different size than the second display 3006a. In some embodiments, the imaging optics assembly 3003 can include a mirror 3007 to relocate the optical path from the viewing oculars, chambers, ports or portals to a direction upwards (e.g. vertically) to the displays 3005a, 3006a. This can allow for the optical path from the viewing oculars, chambers, ports or portals to be of a suitable length without moving the oculars, chambers, ports or portals further (e.g., horizontally) from the surgical site. In some embodiments, the imaging optics assembly 3003 can have a periscope design with a first mirror or reflector configured to direct the optical path from the ocular or portal upward or vertically and another reflector, possibly a partially reflecting partially transmitting beamsplitter to reflect at least a portion of the optical path horizontally similar to a periscope. In some embodiments, the surgeon can advantageously be positioned to view the surgical site and to manipulate tools in an ergonomic way with the surgeon's arms sufficiently close to the surgical site so as not to need to stretch his or her arms, which can be especially uncomfortable for long surgical procedures. Accordingly, in some embodiments, 70% to 95% (e.g., 75% to 90%) of the height of the viewing assembly 3000 can be located above the viewing oculars, chambers, or ports. In some embodiments, the horizontal distance from the entrance of the ocular or portal to the display is not larger than the vertical distance from the entrance of the ocular or portal to the display 3005*a*.

As illustrated in the example embodiments, the distance between the ocular or eye portal optics and the display where the distance is the vertical distance or the distance along an axis perpendicular to the optical axis of the ocular or eye portal can be about 173 mm or between about 100 mm and about 250 mm, between about 120 mm and about 225 mm, or between about 140 mm and about 200 mm or any range between any of these values. The distance between the ocular or eye portal optics and the display where the distance is the horizontal distance or the distance along an axis parallel to the optical axis of the ocular or eye portal can be less than the vertical distance. In some embodiments, the horizontal distance is about 100 mm or between about 50 mm and about 200 mm, between about 75 mm and about 150 mm, or between about 90 mm and about 125 mm or any range between any of these values. In some embodiments, the horizontal distance is about 50% of the vertical distance, or between about 40% and about 90% of the vertical distance, between about 50% and about 80% of the vertical distance, or between about 60% and about 70% of the vertical distance or any range between any of these values. In some embodiments, the display housing of the medical apparatus has greater than or equal to about 50% of the display housing volume above the oculars or eye portals. In some embodiments, the display housing of the medical apparatus has greater than or equal to about 60% of the display housing volume above the oculars or eye portals, greater than or equal to about 70% of the display housing volume above the oculars or eye portals, greater than or equal to about 80% of the display housing volume above the oculars or eye portals, or greater than or equal to about 90% of the display housing volume above the oculars or eye portals, or greater than or equal to about 70% and/or less than or equal to about 95% of the display housing volume above the oculars or eye portals. As described herein, the displays can be positioned above the center of the oculars or eye portals where above the center of the oculars or eye portals can be any position above a plane defined by the optical axis at the exit window (e.g., lens or transparent window) from the display to the eye of the user in the ocular or eye portal. When the plane defined by the optical axis at the exit window is horizontal (e.g., perpendicular to gravity), then an object is above that plane when it is displaced along an axis perpendicular to the defined plane in a direction opposite the direction of gravity. If the display unit rotates to change the orientation of the defined plane, then, in some instances, the relative orientation of the components remains substantially fixed.

FIG. 14B1-*c* shows the example medical apparatus of FIG. 14B1 with an eye 3001 viewing into an ocular 3002. The medical apparatus includes an imaging optics assembly 3003, a beam combiner 3004, and first and second displays 3005*a*, 3006*a*. As described herein, the first display 3005*a* can display an image with a portion (e.g., bottom ¼ of the display) left black. The second display 3006*a* can display another image with a portion (e.g., top ¾ of the display) left black. FIG. 14B1-*c* also shows an alternative example of a first display 3015*a* with a ¼ corner left black, and a second display 3016*a* with the remaining ¾ portion left black. Other examples are possible.

As described herein, each eye can merge the two images together such that the two displays appear as one. For example, the eye can form a composite image including a background image and a PIP image. In various embodiments, the predominant image (e.g., from the first display 3005*a*) can be a non-latent image (e.g., a surgical microscope view of the surgical field), while the supplementary view, supplementary information, supplementary text, and/or supplementary overlays (e.g., from the second display 3006*a*) can be another non-latent image (e.g., an image of the surgical field from a surgical tool) or a latent image (e.g., a data file, a CT scan, a CAT scan, an MRI, an x-ray, an ultrasound image, etc.). In some embodiments, the two images can be separated from each other by a black bar or the two images can substantially overlap (e.g., in the form of a fluorescence image or a near IR image that goes through a processing box).

FIG. 14B1-*d* shows an illustration of a beam combiner arrangement 3004, a first camera 3008*a*, and a second camera 3009*a*. The first camera 3008*a* is in communication with a first camera controller 3010*a*, and the second camera 3009*a* is in communication with a second camera controller 3011*a*. The first camera controller 3010*a* can receive signals from the first camera 3008*a*, and the second camera controller 3011*a* can receive signals from the second camera 3009*a*. A graphical user interface (GUI) controller 3012 and switcher 3013 can communicate how to produce the images on the displays 3005*a*, 3006*a* (e.g., which portions to leave black) with the first and second camera controllers 3010*a*, 3011*a*. In certain embodiments of the medical apparatus, such processing does not introduce latency for real-time images because such resizing is not a latency-causing activity or function. For example, in some embodiments, the processing can be performed by a video switcher and/or controller and not by a single central processing unit. In various embodiments, the first and/or second camera controllers 3010*a*, 3011*a* can include image processors and/or camera control units. In some embodiments, the first and/or second camera controllers 3010*a*, 3011*a* can have modest functions. For example, in some embodiments, the first and/or second camera controllers 3010*a*, 3011*a* do not have to include computers. As an example, some embodiments include two non-latent lines, signals, or channels.

Certain embodiments of the medical apparatus can receive and display images based on the request from the GUI. For example, upon request, some embodiments can receive a latent image to be displayed. As an example, a static image of an x-ray, a CAT scan, an MRI, or an image from a computer can be received from a source, such as in a format like DICOM (Digital Imaging and Communications in Medicine). A non-latent image can also be received from another source. In some embodiments, the predominant image can be the non-latent image. However, in some instances, the predominant image can be the latent image. For example, a surgeon may wish to view the MRI. The surgeon would know that the MRI is not in real-time. However, the surgeon may wish to have the real-time image of the surgical site in view. In some such instances, the surgeon can switch, via the GUI, the predominant image to the MRI and keep the image of the surgical site as a PIP image. Various embodiments of the medical apparatus do not include a direct optical connection between the two displays (e.g., a decoupled display system) and are not configured in the same way as an operating room microscope.

Certain embodiments of the medical apparatus can include four displays (e.g., two displays for each eye). As disclosed herein, some embodiments can include three or more displays for at least one eye. For example, instead of the second display being as equal to the first, the second display could be a matrix of four smaller screens from four source channels. From a processor standpoint, a section of the display can be designed as non-latent, and can receive a non-latent image from another portion of the display or from another source. In some embodiments, two non-latent real-time images can be imposed as a PIP view in one display, and the transformation can be performed by either the camera or the display system, by multiple cameras or the display system, or by a controller. In some embodiments, when two non-latent images are superimposed and/or overlaid, there can be varying degrees of transparency. In addition, in some embodiments, the images can be registered with both the left and right eyes. For example, the PIP images for the left and right eyes can be placed in the same relative space (e.g., upper right hand corner for both left and right eyes).

In some embodiments, a latent image can be displayed on one display and the non-latent image on another display. In some embodiments, a latent image can be inserted into a non-latent image. For example, the images can be processed through a computer or a computer-like device (e.g., a same computer with the same display). Certain embodiments of the medical apparatus can include two or more displays to provide images (latent and/or non-latent) overlaid or integrated and merged in each eye. The advantage of certain embodiments is the ability to view images (latent and/or non-latent) from multiple sources, e.g., distal cameras, proximal cameras, external sources, etc.

In addition, sources with different formats can be combined. For example, one display can include an image from a digital source and the other display can include an image from an analog source. As one example, one camera can be a digital 3G SDI camera and the other camera can be an analog camera. If one of the displays was set up for an analog format and the other display was set up for a digital format, certain embodiments of a medical apparatus can mix formats without having to convert them into a common format. Accordingly, certain embodiments of a medical apparatus can provide a way of merging digital and analog formats in the same view without translation. In various embodiments, dissimilar and/or incompatible imaging sources can be combined by the user in each eye. In some embodiments, each eye's combined view might differ only by virtue of the convergence angle at the source. As an example, a near IR image can allow one to see within the tissue, e.g., within 1 cm in some cases from the surface. The convergence angles can be parallel, but lie outside the convergence angle of the visible image. The images on the display can be overlaid and displaced to match the convergence depth.

Figure 14C:
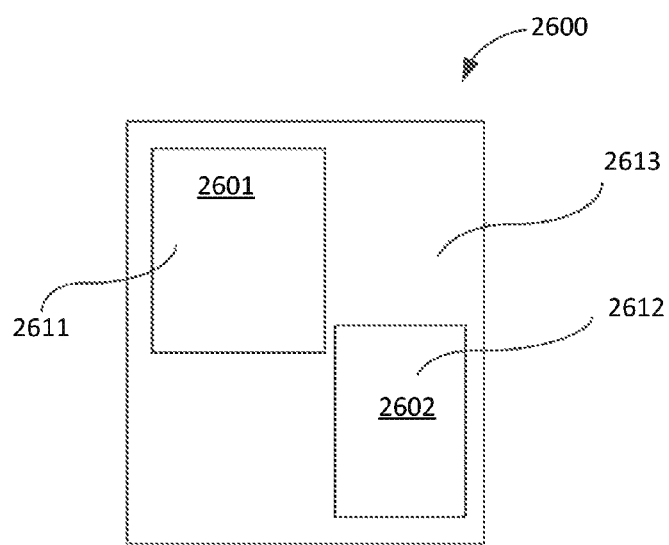
FIG. 14C illustrates a schematic of an example view of multiple images of a surgical field combined adjacent to one another.

FIG. 14C illustrates that the images are not restricted to PIP images. FIG. 14C shows, for example, a schematic of an example view 2600 of multiple images (e.g., from multiple sources) of the surgical field disposed adjacent to one another. For example, a first (e.g., a background) image 2601 is produced on a first portion 2611 of the view 2600, and a second (e.g., a smaller or of similar size) image 2602 is produced on a second portion 2612 of the view 2600 such that the images do not necessarily overlap one another or do not need to substantially overlap, or one image does not need to be substantially contained within the other images. In such embodiments, the images can appear adjacent to one another or tiles in a manner that is not restricted to a PIP arrangement. As described above, more than two images may be included, for example, tiled with respect to each other. Additionally, more than one beam combiner and more than two displays may be employed in various embodiments to combine images, for example, for the left eye (or for the right eye).

As described herein, some embodiments as shown in FIG. 13A-13C can, by the use of beam combiners 2230, advantageously can reduce latency by decreasing the time to produce an image for viewing. For example, multiple images can be tiled to view the multiple images from a variety of sources as opposed to being aligned and combined using an image processing technique that consumes computing power. In addition, an advantage of additional displays in each eye's path in certain embodiments can present to the viewer superimposed images without the complexity of electrical registration and timing issues. In some such embodiments, the brain can also merge the images if the additional displays are reasonably aligned optically.

Head Mounted Display

In various embodiments, a binocular head mounted display may be employed to view images, for example, from the camera's that provide a surgical microscope view or from a camera on a surgical tool (e.g., cutting tool). In particular, the head mounted display may have left and right display portions that display images from an image processing system. The images may come from a stereo optical assembly comprising one or more stereo cameras that provides surgical microscope views of a surgical site, from one or more surgical tool cameras that provides views of the surgical site from a surgical tool, or other cameras that provides views of the surgical site. Such cameras may be stereo cameras or may be monocular cameras or combinations thereof.

Such head mounted displays may provide ergonomic benefits for the surgeon and/or assistant as the wearer can view images of the surgical site without needing to situate themselves in awkward or tiring positions for long times during the surgical procedure. Various embodiments of the head mounted displays may be configured to reduce nausea and/or disorientation by providing the wearer with a view of the surrounding room while the wearer views camera images of the surgical site or when the surgeon looks away from the surgical site. Accordingly, in various embodiments, the head mounted display provides a binocular display of the surgical area similar to as described above while allowing the surgeon to maintain their head at the natural viewing angle and position.

Figure 16:
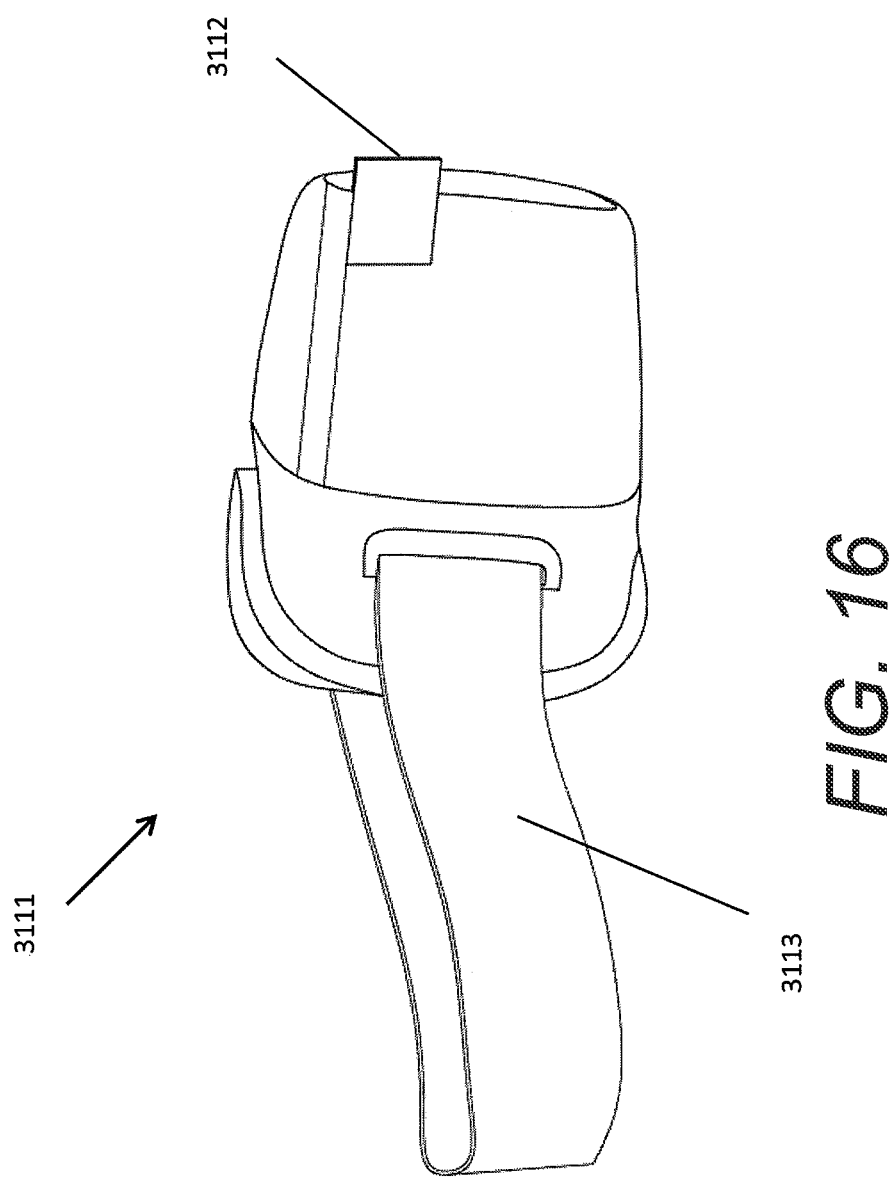
Figure 17:
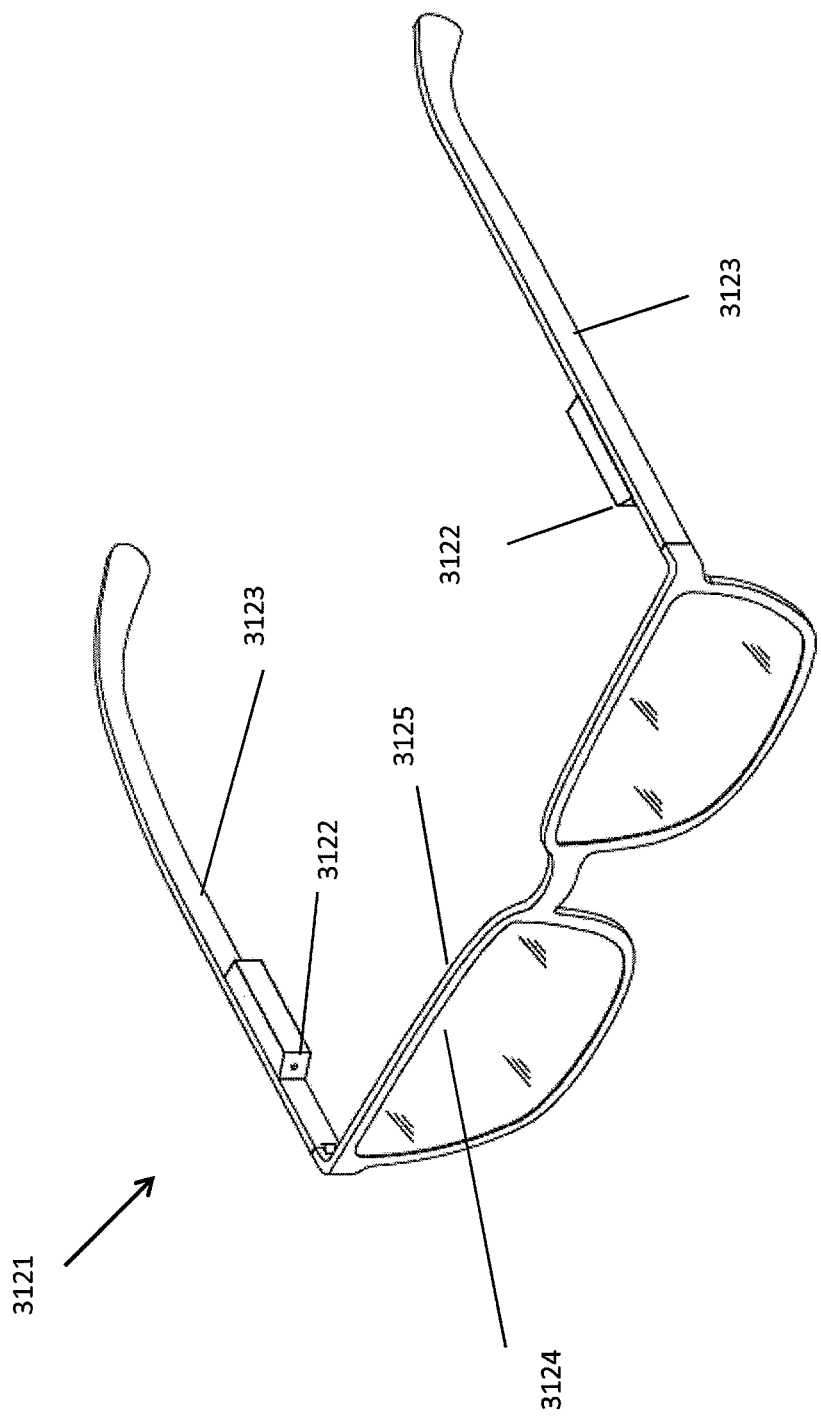
FIG. 17 illustrates a head mounted display that comprises an optically transparent medium such as a glass or plastic window or lens.

FIGS. 15-17 illustrate some example embodiments of head mounted displays that may be used to display images including stereo images configured to provide 3D. The head mounted display includes eyewear that can be worn by the surgeon or the surgeon's assistant, a primary surgeon, secondary surgeon, nurse, technician, students, observers, or others. Some head mounted display can allow the wearer to view at least two views. The views can include a view of the surgical area in microscopic, zoomed in, or a normal view. The views can also include a view of the surrounding environments such as a view of the surgeon's hand grasping an instrument or tool or moving on the outer ends of the surgical area, a large portion (at least half, two-thirds, or three-fours) of the whole patient, the room (e.g., at least an eighth, a quarter, half, three fourths, etc. of the room or any range therebetween), the staff, etc. The different views can help the surgeon, assistant, or other user avoid becoming disoriented. For example, the surgeon can become disoriented or nauseous when looking solely at a surgical microscope while moving about the room or turning his or her head quickly in different directions. In contrast, the head mounted display may be configured to provide the wearer with both a surgical microscope view and a view of the operating room at the appropriate time and allow the wearer to easily adjust between the surgical microscopic view and view of the room or possibly a broader view of the area surrounding the surgical site.

The multiple views (e.g., a surgical microscope view, an area surrounding the surgical site, a view of the room, etc.) can be provided by the head mounted display in various ways. A view of the surgical area as well as a view of the surrounding area can be presented and displayed within the head mounted display at different times or at the same or similar time through a picture-in-picture. Alternatively, the head mounted display can provide one view displayed in the head mounted display and provide a second view through a transparent or partially transparent view through the display for viewing of the surrounding environment. The head mounted display can switch between the various views based on inputs from the user including defined movements of the users head and/or a switch or touch sensor.

In certain embodiments, to provide the at least two views, the head mounted display can provide a camera or possibly one or more pairs of cameras on the head mounted display. The cameras can provide a view of the surrounding environment including the surroundings in the room or the surgeon's hands or instruments as they move around the surgical area. This view may be an unmagnified view. Additionally, the cameras can provide a surgical microscope view or a view from a camera on a surgical tool (e.g., cutting tool) or other input as described herein. The cameras can be mounted on various positions of the head mounted displays depending on the view to be provided. In certain embodiments, the cameras can be stereo cameras that provide a substantially similar view and convergence angle as provided by the eyes.

FIGS. 15-16 illustrate a design incorporating a pair of cameras 3112 on the head mounted display 3111. The pair of cameras 3112 can provide video images of the room that are displayed on the left and right display portions of the head mounted display 3111. The pair of cameras can provide a view of the room similar to that seen by a person's eyes gazing outward into the room. The pair of cameras 3112 can, for example, be generally oriented in a direction similar or parallel to the optical axis or line of light of the surgeon's eyes. In some embodiments, the fields of view of the cameras can be substantially similar to the field of view of the eyes. By these arrangements, the pair of cameras 3112 can simulate the natural view of the surgeon with the display corresponding to what the surgeon/assistant see beyond the head mounted display. For example, the pair of cameras may have lines of sight or optical axes that are slightly converging with respect to each other. In some embodiments, the display portions of the head mounted display can display a view from cameras on the head mounted display or possibly another platform. In such designs, the wearer can see the view beyond the head mounted display even if the head mounted display is opaque and obstructs the wears normal line of sight.

The head mounted display can include an orientation sensing system to determine where the wearer is located and/or how the wearer's head is oriented and where the wearer's eyes are directed, so as to control the wearer's view that is provided through the head mounted display. The image presented on the head mounted display can be dependent on the tracked location or orientation obtained from the orientation sensing system. The head mounted display can present images that correspond to the tracked location or orientation of the head mounted display relative to the wearer/user. The head mounted display can provide different images for the different locations. For example, if the wearer is looking down into the surgical area the display can be adjusted to provide a surgical microscope view the surgical area. When the wearer looks up at the surgical room or other surroundings in the room, the display can be adjusted to allow the wearer to view the surroundings in the room, for example, without magnification. The head mounted display can provide a view of the surgical site when the wearer looks down toward the surgical area and the head mounted display can provide a view of the surrounding room when the wearer looks away from the patient. The head mounted display can present various camera views. Moving the head at a fast rate in comparison to other movements may trigger a change in the views presented by the head mounted display. For example, a view of the room may be provided if the wearer quickly looks up.

To determine the general line of sight of the wearer or orientation of the head mounted display and wearer's head, the orientation sensing system may comprise fiducial markers disposed on the head mounted display. An optical imaging system can be used to track the fiducial markers to determine the line of sight of the wearer and the orientation and/or position of the wearer's head. The fiducial markers can be located on the head mounted display, for example, on the left and right sides of the head mounted display. The fiducial markers can be a marking or pattern on the surface of the head mounted display, for example, the fiducial markers can be a mark, a line, a set of marks, a set of lines, barcode, image, and/or set of images. Other known points or features may be used as the fiducial markers as well. The optical imaging system for tracking the fiducial markers can be located on an assembly remote from the head mounted display. This assembly may comprise for example the binocular display assembly or unit 9 or console 3 discuss elsewhere herein such as shown, for example in FIGS. 1-4, 6, 7, and 9-11. The optical imaging system can detect the orientation or position/locations of the fiducial markers and thereby correlate the view of the marker (or overall image including the markers) or change in view of the markers (or overall image including the markers) with the orientation or position of the head mounted display.

In some embodiments, the head mounted display can dock with a docking station when not in use. This docking station may be on the binocular display unit or console, for example, or may be a separate unit. In some embodiments, this docking station includes the optical tracking system for tracking the fiducials or other known points or features on the head mounted display. In various embodiments, calibration is performed when the head mounted display is docking in the docking station. Cameras may locate the fiducial markers or other calibration pattern on the head mounted display when the head mounted display is docked in the docking station and in a known position and/or orientation. The cameras may correspond to the cameras used in the optical system for tracking the location of the fiducials during usage of the head mounted display when worn by the users or can comprise one or more other cameras. Other sensors can be used for calibrating. Additionally, other methods of calibrating the orientation sensing system may be employed.

The orientation sensing system may also comprise sensors such as gyroscopes, accelerometers, inertial measurement units (IMUs), MEMS devices, or other sensors that can be used to detect the position and/or orientation or change in position and/or orientation of the head mounted display. The sensors can be located in the head mounted display.

In some embodiments, the head mounted display can have transmitters located thereon. The transmitters can be in communication with a receiver system. The receiver system can be located on a remote location such as on the binocular display assembly or unit, console, and/or the docking station or other location. The receiver system is in communication with the transmitters to determine orientation and/or position of the head mounted display, head of the surgeon or assistant, line of sight of the surgeon or assistant, etc., by receiving a signals from the transmitters. In various embodiments, as the head mounted display is moved or reoriented, the receiver system recognizes the position and/or orientation and/or the change in position and/or orientation. In some embodiments, the receiver system is located on the head mounted display and communicates with a transmitting system located on a remote location such as the binocular display unit, console, or docking station. The receivers on the head mounted display can be configured to receive signals from the transmitters to determine orientation of the head mounted display, the head of the wearer and/or the generally line of sight of the wearer.

In other embodiments, other tracking devices such as EM tracking devices can be used to track the orientation and/or position of the head mounted display. The EM tracking device can detect the orientation and position of the head mounted display when the wearer is looking down at the surgical area and the head mounted display can provide a view of the surgical area. The EM tracking device can detect when the wearer looks away from the surgical area and the head mounted display can display or provide for a view of the surrounding environment.

Sensors, transmitters, receivers, elsewhere in the room, for example, on the patient, on the gurney, or elsewhere may be used to ascertain the direction of the gaze of the wearer (e.g., surgeon and/or assistant).

The head mounted display of FIGS. 15-16 may comprises opaque display portions that prevent the left and right eyes from viewing through the head mounted display. The display portions may comprises one or more display, such as a LCD or LED display that is not transmissive on which an image is projected or transmitted. The head mounted display may be included in a housing or frame that does not provide an optical path through the head mounted display in the forward direction thereby blocking the view of the left and right eye of the region forward the display portions of the head mounted display.

The display portions however can provide views of the surgical site and/or the surrounding environment, such as a view of the surgeon's hand grasping an instrument or tool or moving on the outer ends of the surgical area, a large portion (at least half, two-thirds, or three-fours) of the whole patent, the room (e.g., at least an eighth, a quarter, half, three fourths, etc. of the room or any range therebetween), the staff, etc. The video images provided on the display can be predefined views from the cameras for different orientations and/or locations of the head mounted display. For example, if the wearer (e.g., surgeon) gazes at a wound or surgical area, the main view that appears in the display can correspond to the surgical microscope view. The display of the surgical area can also vary in zoom or magnification. The display of the surgical area can be a surgical microscope view, a zoomed-in view of the surgical site or wound area, or an unmagnified view of the surgical area to allow the surgeon to view the surgical area as if the head mounted display was not being worn or used. The surgeon can switch between these different zooms or magnifications through a mechanical control, such as a button or other tactile input, a keyboard, mouse, touch screen, graphic user interface, foot pedal, as well as possibly voice command recognition, sensed hand or tool motions, or other input from the user. Additionally, the head mounted display can automatically change views, for example, with the movement of the wearer's (e.g., surgeon's) head, for example, using an orientation sensing system comprising, e.g., the tracking devices and/or sensors. In some embodiments, a combination of an orientation sensing system (e.g., sensors or tracking devices) and manual input, commands, or control can be employed to cause the head mounted display to switch between the multiple views.

The ability to switch easily between the view (possibly magnified) of the surgical site and the room view allows the wearer (e.g., surgeon) to comfortably transition between tasks and reduces or avoids disorientation or discomfort associated with such movement. In various embodiments, the surgical microscope view may be displayed in a picture-in-picture view while the room view is also provided. This additional view of the surgical area while looking away from the surgical area can allow the surgeon to continue to monitor the surgical or wound area while performing other tasks. In various embodiments, the relative size or percentage of the display portion showing the respective video images or views, can be varied depending on the orientation of the head mounted display. For example, when the wearer (e.g., surgeon or assistant) is gazing outward into the room as opposed to downward onto the patient, the surgical microscope view may be smaller than the room view and possible contain therein in picture-in-picture format or otherwise tiled with respect to each other. Similarly, if the surgeon's line of sight is directed downward toward the patient, a surgical microscope view may be enlarged. In various embodiments, additional sensors, transmitters, and or receivers may be disposed about the room, for example, on the patient, or elsewhere to assist in determine the gaze direction of the wearer (e.g., surgeon or assistant) and the orientation of the head mounted display.

In some embodiments, the head mounted display can be used during surgical procedures where the surgical area is not presented on the top surface of the patient. For example, the surgical area can be at an extreme oblique angle. The surgical access area can be a temporal access to the brain through the ear or a portion of the brain instead of on a top surface (front or back of patient lying on his/her back or front, respectively). Traditionally, the surgeon would have to tilt and/or rotate his or her head and/or bend his or her neck and/or back for long periods of time to view the surgical area at an extreme oblique angle or from a side perspective. Various embodiments of the head mounted display described herein allow the surgeon to view at such different angles without the need to rotate or tilt their head in an extreme manner during the surgery and thereby reduces discomfort that would traditionally occur. The oblique view or temporal view of the surgical area can be displayed in the head mounted display providing a view of the surgical area while the surgeon's head is not required to be disposed at an extreme angle. Various embodiments of the head mounted display described herein reduced disorientation and/or nausea of the surgeon.

In some embodiments, providing different views when the wearer's (e.g., surgeon's) head is oriented differently can help reduce the disorientation and nausea. The transition between the view of the wound area and the view of the surroundings or room can be accomplished by tracking or detecting the orientation or movement of the wearer and the wearer's head during use. The tracking system or sensor as described herein can differentiate between looking downward at the surgical area or wound and if the wearer is looking upward at the room. Additionally, the tracking system or sensors can differentiate between larger motions verses smaller motions. For example, if the wearer simply gazes away from the surgical area slightly, the head mounted display can display the room and surroundings but also maintain the surgical area in the display as a picture-in-picture view. Alternatively, a larger motion or movement of the wearer or wearer's head can switch the display from the surgical microscope view to the room view mostly (e.g., using a PIP for the other view) or only the room view. The size of the picture-in-picture view relative to the entire viewing area of the display can vary from greater than or equal to 90% to less than or equal to 5% of the display viewing area. The size of the PIP may be for example, 10%, 20%, 30%, 40%, 50%, 60%, 70%, 80%, of the size of the entire viewing area of the display or any range between these values. In some embodiments, the size of the picture-in-picture window can be related to the amount of movement, with a larger movement corresponding to a smaller picture-in-picture window and a smaller movement corresponding to a larger picture-in-picture window or vice versa, for example, for the surgical microscope view, surgical tool view, or room view. Additionally, in other embodiments, the surgical microscope view, surgical tool view, or zoomed view of the surgical area can be projected on the view of the natural surroundings video or the line of sight or gaze direction of the surgeon while the surgeon is looking up or around the room or can be a picture-in-picture image within the natural surroundings image. This approach allow the surgeon to see the zoomed view on a large section of the display portion, however, the natural surroundings can be present and visible on the outer edges of the display. For example, the surgeon could be zoomed in on the surgical area and the display could display mostly the surgical microscopic view and the surgeon can reach for or be handed an instrument and the surgeon can see a natural view of their hand or the surgical assistants hand to assist the surgeon in handling the instrument and prevent disorientation.

FIG. 17 illustrate a head mounted display 3121 that comprises an optically transparent medium such as glass or plastic window or lens 3124. The transparent head mounted display 3121 can comprise a projection system 3122 mounted on the inside of the head mounted display that projects an image into the eye of the wearer possibly by reflecting light off the optical transparent window. In this embodiment, the display portion can be transparent as illustrated in FIG. 17 and allow the surgeon to see the surgical area or the surrounding area via direct view and not using a camera. When an image of the magnified or surgical microscopic view of the surgical area is useful, the image can be projected toward the partially reflective display surface 3125 and into the wearer's eye. The projection system can project light onto the transparent window, which then reflects the light back into the wearer's (e.g., surgeon's) eye forming an image therein. In various embodiments, the projection system is configured such that light reflected off the transparent window and into the eye is collimated. Thus, the wearer can focus at infinity thereby reducing eye strain and possible discomfort. If the surgeon/assistant wears prescription glasses, the glasses can possibly be worn under the head mounted display. This configuration can allow the reflected image to be passed through the prescription glasses and the correction of the prescription lenses can be applied to create a clear image for the user.

In some such embodiments, the head mounted display may be larger to fit the glasses underneath and may more resemble a design such as shown in FIGS. 15-16, however, where the head mounted display has display portions that are transparent instead of opaque. Other configurations are possible. Likewise, the various embodiments described herein may comprise goggles, glasses, other types of eyewear, masks, etc. A wide range of combinations of features are possible.

In some embodiments, the display portion can be selectively transparent. For example, the head mounted display may be selectively opaque and selectively transmissive. The controllably transmissive head mounted display can allow the wearer to view the surroundings through the lenses of the eyewear at certain times but can obscure the view through the lenses are other times. Similar to the eyewear described with reference to FIG. 17, the head mounted display can provide an image of the surgical area from the surgical microscope or surgical tool that is magnified to the desired amount while the surgeon is viewing the surgical area or wound. Additionally, as the wearer looks away from the wound area, the projection of the video images can be attenuated or turned off and the wearer can look through the display with no other image in view. Alternatively, the video of the surgical microscope view or surgical tool view can be reduced in size and/or moved out of the center of the line of sight of the surgeon. For example, as described above, the projection can appear as a picture-in-picture view or as a percentage of the display while allowing the surgeon to continue to view through the transparent material.

As described above, the transparent eyewear or head mounted display utilize the orientation sensing system described above which may include for example, optical tracking with fiducial markers, sensors, gyroscopes, accelerometers, IMUs, EM tracking, or other techniques to determine the size or appearance of the video image as described herein.

Figure 18:
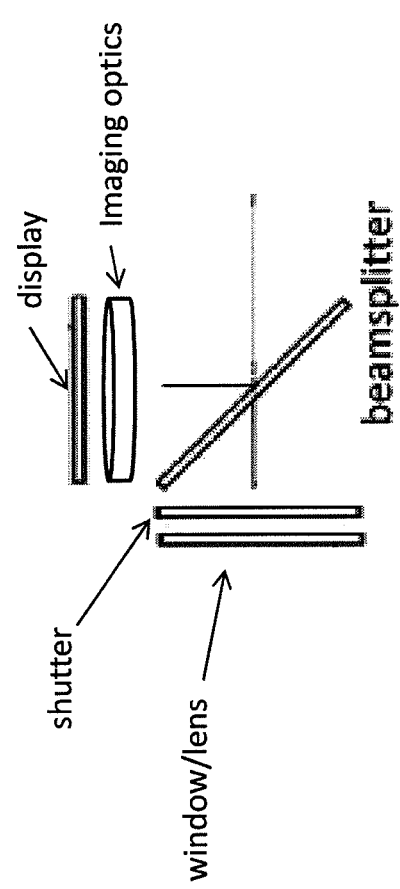
FIG. 18 schematically illustrates another example medical apparatus in accordance with certain embodiments described herein.

In various embodiments the head mounted display can comprise a display, a spatial light modulator, and a beam combiner (also referred to as a beamsplitter) as illustrated in FIG. 18. The beam combiner and the spatial light modulator may form a first optical path and the display and the beam combiner forming a second optical path. The line of sight of the surgeon is directed through the beam combiner and the spatial light modulator along the first path. As depicted in FIG. 18, the spatial light modulator may operate as a shutter and can be configured to provide selected transmission therethrough. The spatial light modulator may comprises, for example, a liquid crystal spatial light modulator configured to control the amount of light permitted to pass therethrough. The display is disposed with respect to the beam combiner to reflect light from the display into the eye such that output video images displayed on the display are viewable by the eye. The display may comprise, for example, and light emitting diode (e.g., organic LED) display, an LCD, or other type of display.

The wearer (e.g., surgeon) can view the room, staff, etc. through the selectively transmissive spatial light modulator when the spatial light modulator is transmissive. The surgeon can also view separate video images, for example, surgical microscope view video images can be displayed. The relative strength of the direct view versus the image projected into the eye can be varied by increasing or decreasing the transmission through the spatial light modulator. In some embodiments, for example, the spatial light modulator can be between 5% to 50% transparent or 50% to 95% transparent or outside these ranges.

Similar to the eyewear described above, the head mounted display can provide an image of the surgical area from the surgical microscope that is magnified to the desired amount while the wearer is viewing the surgical area or wound. Additionally, as the wearer looks away from the wound area or surgical area the display of the image can be turned off increasing the transparency of the spatial light modulator or shutter and/or control of the display. The wearer can look through the display portion (transparent window) with no video image form the display in his or her view and the wearer can thus view through the head mounted display. In other situations, video images from the display may be projected into the eye using the beam combiner to reflect light from the display. The video images from the display, however, can be reduced in size and/or moved out of the central line of sight of the surgeon as desired. For example, as described above, the video images can appear as an offset picture-in-picture view or as an areal percentage of the display portion while allowing the wearer to continue to view the images in his direct line of sight through the transparent material. Similarly, the relative intensity and/or transparency of the video images compared to the view through the display portion can be selected. For example, the video images from the display can be made more intense by reducing the transmission of light through the spatial light modulator. Conversely, the video images from the display can be weakened relative to the direct view through the spatial light modulator by passing more light through the spatial light modulator from the scene forward the display portion of the head mounted display. Control of the intensity of the (e.g., LED) display can also be used.

These embodiments of the head mounted display can vary the size and/or appearance of the video image by utilizing the orientation sensing system described above, which may include for example, optical tracking with fiducial markers, sensors, gyroscopes, accelerometers, IMUs, EM tracking, or other techniques to determine the size or appearance of the video image as described herein.

Figure 19:
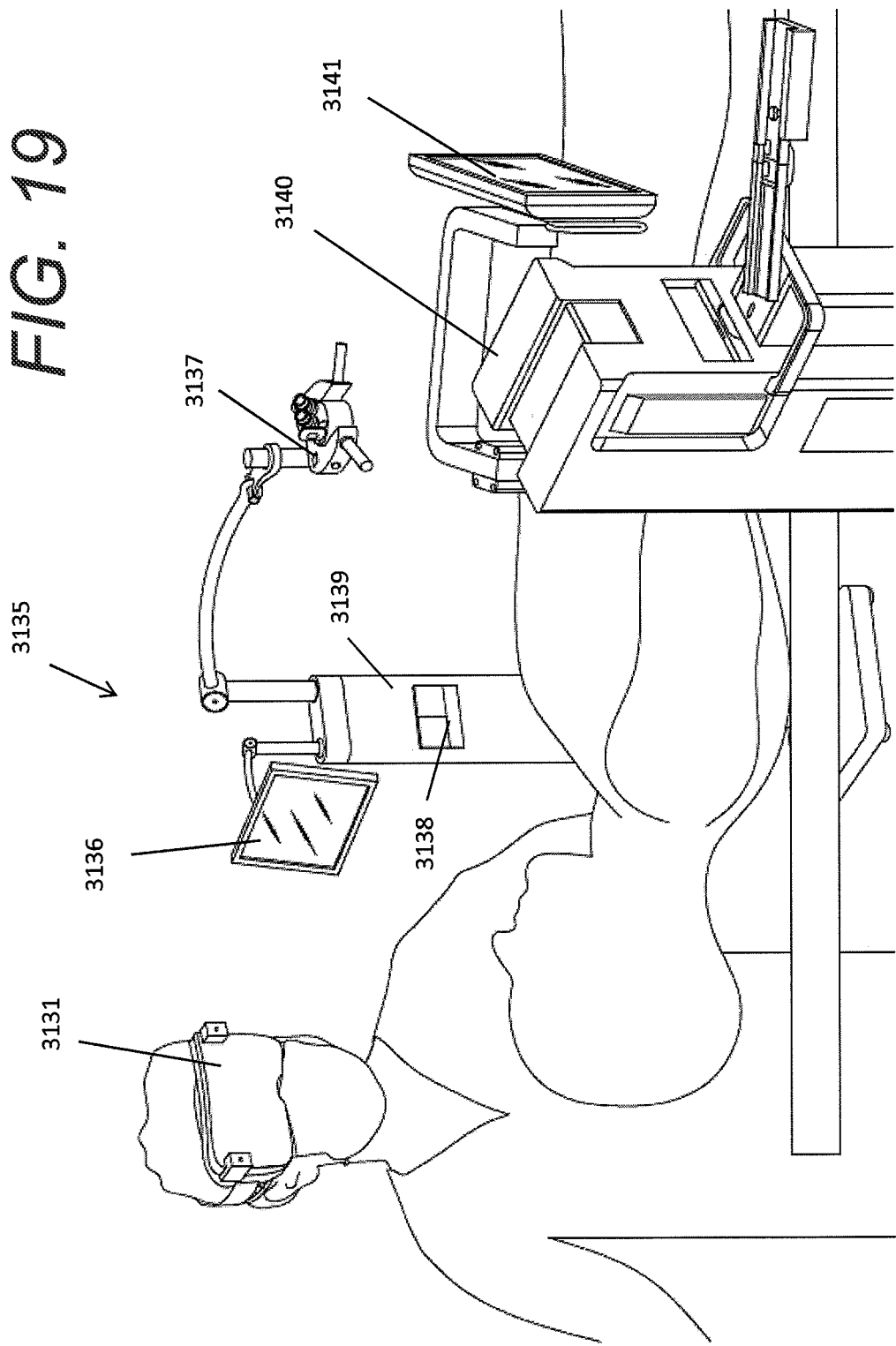
FIG. 19 illustrates a head mounted display worn by a surgeon in a surgical area.

FIG. 19 illustrates a head mounted display worn by a surgeon in a surgical area. The head mounted display illustrated in FIG. 19 may be similar to the head mounted display described with reference to FIGS. 15-16 and may include cameras disposed thereon. However, the head mounted display can be similar to the transmissive head mounted displays described above as well. The surgical imaging equipment can include a panel display 3136 and a binocular viewing unit 3137 that is not a head mounted display. The binocular display unit 3137 can be connected to the console 3139. The head mounted display can be configured to dock with console 3139 and a camera providing a surgical microscope view can be mounted on the plane below the binocular display unit 3139 or elsewhere. The head mounted display 3131 can dock on the console 3139 when not in use and can communicate with the console when in use. A docking station 3138 can be on console 3139, on binocular viewing assembly 3137 or elsewhere.

A combination of displays types can be used throughout the surgical procedure. For example, the head mounted display 3131, the panel display 3136, and the binocular viewing assembly 3137 can be used in combination to provide the surgeon different options for viewing the surgical area. The different displays can provide the surgeon with additional information in some embodiments. In further embodiments, the surgeon can use a combination of binocular display unit 3137, the panel display 3136, and the head mounted display 3131. The surgeon can have the option to switch between the various displays. Similarly, the assistant can have a binocular display unit or a head mounted display also. In some embodiments, the surgeon may employ the binocular display unit 3137 and the assistant may use head mounted displays. In some cases, the binocular display unit 3137 provides a higher quality image than the head mounted displays.

In some embodiments, the binocular display assembly 3137 can be detachable. For example, if the head mounted display 3131 and/or panel display 3136 are preferred over the binocular display unit 3137, and then the binocular display 3137 can be removed or detached. In some situations, removing the binocular display unit 3137 can provide additional clearance for the surgeon to operate. Even when the binocular display unit 3137 is removed, the camera providing the surgical microscope views can remain on the binocular display unit 3137. Alternatively, the surgical microscope view camera may be at a different location.

As described above, the assistant can have a binocular display or a head mounted display also. Additionally, an assistant display unit 3140 can be used to provide a separate panel display 3141. The additional assistant displays can provide the assistant the multiple views available to the surgeon in the various displays as well as more or less views.

Cooperative Surgical Display Systems

As part of the surgical visualization systems described herein, a surgical display system can be configured to provide advantageous viewing features to a surgeon, assistant, or other operator of the surgical visualization system. A surgical display system can be configured to provide displays and optical components to view the displays. These displays can be configured to provide views of video captured with one or more cameras of the surgical visualization system. These displays can also be configured to provide views of other information, such as text data, images, or the like provided by another electronic device. A surgical display system can provide ports, portals, or oculars, transparent plates, lenses, prisms, mirrors, chambers, baffles, and the like to provide optical paths for a viewer to view the displays of the surgical display system.

In some embodiments, a surgical display system includes one or more displays (e.g., flat panel displays or FPDs) that are configured to be viewed by a surgeon. In the surgical display system, the optical paths to each eye include a combination of lenses configured to provide a view along a right eye optical path and a left eye optical path. Each optical path can be directed to the same display (e.g., to different parts of a single display) or to different displays, for example and without limitation. On the one or more displays, video images can be displayed from a collection of sources. Sources can include camera systems of a surgical visualization system. Examples of sources include one or more cameras on endoscopes, one or more cameras providing surgical microscope views of a surgical site, one or more proximal cameras mounted on a frame near or adjacent to the surgical site, one or more cameras on a surgical tool, and the like.

In some embodiments, a surgical display system includes one or more displays that are viewable in a particular optical path for an eye. For example, the right eye optical path can lead to one or more displays and the left eye optical path can lead to one or more separate displays. In such embodiments, each image acquisition camera system can be registered and aligned to produce a substantially identical view of a scene differing only in waveband selection. The images can be processed to enhance distinctive features or to differentiate between the images provided in the different wavebands. In some implementations, insertion and registration of presurgical information produced by an external source can be included on the one or more displays.

In some embodiments, a surgical display system includes one or more displays per eye optical path, wherein a display of information or image in a first display corresponds to a black area in a second display. This can allow the displays to combine to create a seemingly unitary image without ghosting or visual overlapping of different images. The black portion of the screen can be advantageous as it emits little to no light to reduce the contrast of the image provided on the first display.

In some embodiments, a surgical display system is provided that includes one or more displays per eye optical path. In such embodiments, a second image or portion of a second image can be registered to a first image on a first display. In this way, the first and second images can be combined visually to produce a coherent image.

In some embodiments, the surgical display systems disclosed herein are configured so that the right eye path (or right eye view) and the left eye path (or left eye view) provide different perspectives of the same image or images. The surgical display systems can be configured so that the exit pupil produced by the system for each eye path is nominally about 2-9 mm. The surgical display systems can be configured so that the field stop produced by the system for each eye is between about 18 mm and about 28 mm. The surgical display systems can be configured so that the apparent field of view associated with the exit pupil is between about 45 degrees and about 100 degrees. The surgical display systems can be configured so that the eye relief for each eye path is nominally between about 15 mm and about 30 mm. The surgical display systems can be configured so that the total path or track length of the optical path between any display and the viewer's eye (or exit pupil) is at least about 50 mm and/or less than or equal to about 400 mm. The surgical display systems can be configured so that the total track or path length of the optical path between any display and the viewer's eye (or exit pupil) contains one or more reflecting surfaces. The surgical display systems can be configured so that the total path length of the optical path between any display and the viewer's eye (or exit pupil) contains one or more prisms, for example, utilizing total internal reflection. The surgical display systems can be configured so that the one or more displays include more than one display per eye path and two or more displays are combined with a pellicle or thin glass mounted beamsplitter or combiner coating comprising one or more layers. In such embodiments, a thin glass mounted beamsplitter or combiner can be utilized and the ratio of diameter to substrate thickness can be less than about 100 to 1. In such embodiments, the beamsplitter or combiner coating can for example be made of a metalized layer, a patterned layer, or dielectric coating that has multiple layers.

Binocular Display Unit

Various embodiments include a binocular display unit including a pair of oculars that produces (for example, for each eye) an exit pupil in space. This can be a small zone where the marginal rays of the corners of the field of view cross the optical axis. A person's eye naturally chooses this spot when viewing scenes. At this position, a person sees a black margin around the field of view. For a modified Wheatstone configuration, the binocular display unit can be configured to utilize a rectangular display to take advantage of the natural tendencies of the viewer's vision.

Some embodiments employ a display with an exit pupil (as opposed to a large eye box). A rectangular field stop can be included in the ocular. In some implementations, rectangular baffles can be included in the display for rejection of stray light. These features can be combined with a rectangular panel display for each eye wherein the rectangular panel displays its half of a stereo image. The display can be positioned at a conjugate position with the field stop in the ocular. A near-eye display places the display at the field stop of the ocular.

The eye relief, e.g., the position of the exit pupil relative to the last surface of the ocular, is a factor that determines how close a viewer is to the device when viewing the displays. When the eye relief is greater than about 15 mm to about 20 mm, the observer can comfortably wear spectacles during use of the device.

The oculars of the binocular display unit can be used to provide a view with a larger apparent field of view. The ocular can be configured to provide the power and magnification to produce an exit pupil at a desired or targeted location thereby providing desired or targeted eye relief from a field stop. This can produce this apparent field of view.

Beyond a certain field of view (where field of view is inversely proportional to the focal length of the ocular), the output of the ocular does not generally couple with the pupil of an eye and a viewer typically fails to see part of the field. This effect can be referred to as a kidney bean effect, as the portion not seen has a kidney bean shape. A 10× magnification operating room microscope ocular, for example, has a wide field of view and comfortable exit pupil position. In the binocular display unit, the last components of the display system (e.g., the oculars), enable the apparent field of view.

Another consideration when designing a display unit that uses an eye box rather than an exit pupil is illumination. As the apparent field of view increases, the relative brightness of the display decreases. So, as the exit pupil grows until it becomes an eye box, the display panels decrease in apparent brightness because the area (of the eye box) is larger. Accordingly, the disclosed binocular display units put a significant amount of the total illumination into a useful sized exit pupil (as opposed to an eye box). This facilitates interoperability and integration into a surgical environment as the exit pupil of operating room microscopes is a well-established and accepted size.

Various embodiments of the binocular display unit provide a compact unit with ergonomic adjustments at or near the oculars. These display units can be configured to be less massive than other display units meaning that it can be easier to move and adjust.

In some embodiments, a display unit can include a display housing, an opening in the display housing, at least two chambers within the display housing (one for the left eye and one for the right eye), and at least one electronic display disposed the display housing, each of the at least one electronic display comprising a plurality of pixels configured to produce a two-dimensional image. The separate left and right optical paths together provide stereo viewing. The display housing is further configured to separate a right eye path from a left eye path to the at least one electronic display so that light intended to be viewed with a right eye from the at least one electronic display does not travel down the left eye path and vice versa. The medical apparatus includes an imaging system disposed on the display housing, the imaging system configured to generate images of a surgical site from outside the surgical site. The view of the display within the housing can be configured to provide a stereoscopic image to a viewer, as discussed above. In some embodiments, the housing further includes lenses and/or a transparent plate between the eyes of a viewer and the at least one electronic display. In some embodiments, the housing further includes a baffle or other structure to separate the left eye path and the right eye path. In some embodiments, each chamber is baffled to prevent light from one channel to communicate to the other eye path. In some embodiments, at least a portion of the chambers comprise oculars.

In certain implementations, the display unit can be baffled to prevent light communication between the left and right eye channels. To adjust for different accommodations, the displays within the display system can be configured to move toward and/or away from the viewer along the optical path. This can have an effect similar to varying focal lengths of lenses in an ocular system. In some embodiments, the display housing with the electronic displays can change to move the displays closer or further from the viewer along the optical path. In some embodiments, both the display housing and the electronic displays are configured to be adjustable along the optical path to adjust for accommodation.

In certain implementations, the binocular display unit can be configured to receive video images acquired with an endoscope and display these video images within the unit. These images can be combined (e.g., stitched, tiled, switched, etc.) with video from other sources by an operator so that video images from one or more sources, including the endoscope video images, can be viewed with the binocular display unit.

Display Unit with Folded Optical Path

Various embodiments include a display unit including optical elements configured to redirect an optical path from a viewer's eye to a display such that the display is positioned above the viewer's eye when the viewer is looking substantially horizontally (e.g., where horizontal is perpendicular to gravity which is vertical) into the display unit. FIG. 14B1-*a* illustrates an example of such a configuration for a display unit wherein optical components direct and focus images from displays 3005*a* and 3006*a* to the viewer using a beamsplitter/combiner 3004 and mirror or reflector 3007. This allows the displays 3005*a* and 3006*a* to be positioned above the level of the eye when the viewer is looking substantially horizontally (e.g., with gravity vertical) into the display unit. This may also be the case where the majority or all of the optical components are not above the level of the eye when the viewer is looking substantially horizontally into the display unit.

In some embodiments, the display unit includes oculars through which the viewer looks to view images provided by the displays 3005*a*, 3006*a*. In some embodiments, the display unit includes eye portals through which the viewer looks to view images provided by the displays 3005*a*, 3006*a*. In either of these embodiments, the oculars or eye portals and the display unit can include optical components configured to direct the optical path from the displays to the oculars or eye portals as well as to provide imaging functionality. In some embodiments, dimensions of the display housing include the oculars or eye portals and in some embodiments, dimensions of the display housing exclude the oculars or eye portals.

To facilitate the description of the configuration of the display unit, a coordinate system will be adopted that is fixed to the display unit. The coordinate system will take the optical axis through the oculars or eye portals as the x-axis (an example of which is illustrated in FIGS. 14B1-*e* and 14B1-*f*) and the optical axis after the redirection optical component (e.g., the mirror or reflector 3007 in FIG. 14B1-*a*) as the y-axis (an example of which is illustrated in FIGS. 14B1-*e* and 14B1-*f*), the x-axis being perpendicular to the y-axis. The physical distance along the x-axis from the display to the oculars can be a fraction of the distance along the y-axis from the display to the oculars. For example, the distance along the x-axis to the display can be less than or equal to 90% of the distance along the y-axis to the display, less than or equal to 80% of the distance along the y-axis to the display, less than or equal to 70% of the distance along the y-axis to the display, less than or equal to 60% of the distance along the y-axis to the display, or less than or equal to 50% of the distance along the y-axis to the display or any ranges therebetween. In some embodiments, after the optics of the oculars or eye portals, the majority of the optical components can be positioned above (e.g., in a positive direction along the y-axis as defined) the oculars or eye portals. In some embodiments, a majority of the length of the optical path can be positioned above the oculars or eye portals. For example, the total length of the optical path can be taken as the distance from a first optical component (e.g., window where a window may be a lens or planar transparent plate) of the oculars or eye portal to the display 3005*a* or 3006*a*. In some embodiments described herein, less than 50% of that total length is the length of the optical path before the mirror 3007 or the optical component that redirects the optical path from being substantially along the x-axis to being substantially along the y-axis. In some embodiments, the optical axis does not travel downward along the y-axis. In some embodiments, the optical axis does not travel downward along the y-axis prior to being redirected upward along the y-axis toward the displays. These features can allow for a display unit that is larger in height than in depth. This may be advantageous to allow for a display unit that can be moved around in an operating room environment without substantially interfering with the positioning of other display units, camera assemblies, and/or personnel.

To further describe the configuration of the display unit, the coordinate system defined above can include a plane that is perpendicular to the y-axis, referred to as the viewing plane, where the viewing plane intersects the optical axis at the oculars or eye portals. In some embodiments, the display unit can be configured so that a majority of the optical path is not below this viewing plane. In some embodiments, the display unit can be configured so that a majority of the optical path is above this viewing plane. In some embodiments, the display unit can be configured so that at least 40%, at least 50%, at least 60%, at least 70%, at least 80%, or at least 90% of the optical path is above the viewing plane or any value therebetween. In some embodiments, the display unit can be configured so that at least 40% and/or less than or equal to about 99%, at least 50% and/or less than or equal to about 95%, at least 60% and/or less than or equal to about 90%, or at least 70% and/or less than or equal to about 85% of the optical path is above the viewing plane. In some embodiments, the display unit can be configured so that a majority of the optical components are above the viewing plane. In some embodiments, the display unit can be configured so that the displays are above the viewing plane. In some embodiments, the display unit can be configured so that a majority of the display housing volume is above the viewing plane. In some embodiments, the display unit can be configured so that at least 40%, at least 50%, at least 60%, at least 70%, at least 80%, or at least 90% of the display housing volume is above the viewing plane. In some embodiments, the display unit can be configured so that at least 40% and/or less than or equal to about 99%, at least 50% and/or less than or equal to about 95%, at least 60% and/or less than or equal to about 90%, or at least 70% and/or less than or equal to about 85% of the display housing volume is above the viewing plane.

In some embodiments, the display units can be positioned so that their display panels are substantially perpendicular to one another, as illustrated in FIG. 14B1-*e*. In some embodiments, the display units can be positioned so that their display panels are substantially parallel to one another, as illustrated in FIG. 14B1-*f*. In such an embodiment, an additional mirror 3004*b* can be included above the beamsplitter/combiner 3004 to redirect the optical axis to the other display.

The display unit can have a depth, d, (e.g., the extent of the display unit housing along the x-axis) and a height, h, (e.g., the extent of the display unit housing along the y-axis) that forms an aspect ratio (d:h) that is less than 1. The aspect ratio of the depth to height can be less than or equal to about 0.95, 0.9, 0.85, 0.8, 0.75, 0.7, 0.65, 0.6, 0.55, 0.5, 0.45, or 0.4 or ranges therebetween any of these values (e.g., 0.95-0.6 or 0.9-0.65).

To facilitate the description of other configurations of the display unit, another coordinate system will be adopted that is fixed relative to gravity. The coordinate system will take gravity as the y-axis and the x-axis lies within the horizontal plane perpendicular to gravity, the x-axis being the projection of the optical axis at the exit window (e.g., final lens element of the oculars or eye portal) on the horizontal plane. In this coordinate system, the height of the display unit can be taken as the dimension of the display housing along the y-axis (e.g., the direction parallel to gravity) and the depth can be the dimension taken along the x-axis (e.g., the direction perpendicular to gravity and parallel to the projected optical path at the ocular or eye portal). With this convention, the display unit can have a depth, d, (e.g., the extent of the display unit housing along the x-axis) and a height, h, (e.g., the extent of the display unit housing along the y-axis) that forms an aspect ratio (d:h) that is less than 1. The aspect ratio of the depth to height can be less than or equal to about 0.95, 0.9, 0.85, 0.8, 0.75, 0.7, 0.65, 0.6, 0.55, 0.5, 0.45, or 0.4 or ranges therebetween any of these values (e.g., 0.95-0.6 or 0.9-0.65). In some implementations, the optical path of the oculars or eye portals can form an angle that is less than or equal to about 30 degrees with the horizontal plane, less than or equal to about 15 degrees with the horizontal plane, less than or equal to about 10 degrees with the horizontal plane, less than or equal to about 5 degrees with the horizontal plane, or less than or equal to about 0 degrees with the horizontal plane.

In some embodiments, the display housing can have a height that is larger than its depth. For example, the depth can be less than or equal to about 90% of the height, less than or equal to about 80% of the height, less than or equal to about 70% of the height, less than or equal to about 60% of the height, less than or equal to about 50% of the height, or less than or equal to about 40% of the height. In some embodiments, the display housing can be longer than it is deep. For example, the display housing can be at least 10% longer than it is deep, at least 25% longer than it is deep, at least 50% longer than it is deep, or at least 100% longer than it is deep. In some implementations, the optical path within the display housing can be longer along its height than along its depth. For example, the optical path along the height can be at least 10% longer than along its depth, at least 25% longer than along its depth, at least 50% longer than along its depth, or at least 100% longer than along its depth or any range of values therebetween.

In some embodiments, the display unit can include an optical system (e.g., lenses) with one or more two-dimensional displays and illumination sources, the optical system configured to direct rays from the displays and illumination sources towards the eyes of a viewer, the optical system configured to produce a collimated virtual image of the one or more displays for each eye. A majority or all of the optical system of the display unit can be near or above a plane that is parallel to the viewer's line of site when looking through oculars or eye portals into the display unit to see the displays. In certain implementations, the collimated rays can be disposed at an angle relative to a vertical plane that is substantially perpendicular to the plane parallel to the viewer's line of site. In some implementations, the display unit includes one or more fold mirrors or prisms or reflectors that are positioned between the displays and the optical system enabling the use of displays that are wider than the center-to-center spacing of the ocular or eye portals or the viewer's eyes, an example of which is illustrated in FIGS. 14B1 and 14B1-*b*. In some implementations, the one or more fold mirrors or prisms or reflectors lie within the optical system rather than between the optical system and the displays. In some implementations, the optical system includes one or more fold mirrors or prisms or reflectors configured to permit displacement (e.g., in the z-direction) of each eye's opto-mechanical axis to permit a compact overall design and ergonomic adjustment. In some implementations, one or more fold mirrors or prisms or reflectors are positioned between the displays and the optical system, the one or more fold mirrors or prisms configured to permit displacement (e.g., in the z-direction) of each eye's opto-mechanical axis to permit a compact overall design and ergonomic adjustment.

Accommodation Differences

In some embodiments, a display unit can include a display housing, an opening in the display housing, at least two chambers within the display housing, and at least one electronic display disposed in the display housing, each of the at least one electronic display comprising a plurality of pixels configured to produce a two-dimensional image. The display housing is further configured to separate a right eye path from a left eye path to the at least one electronic display so that light intended to be viewed with a right eye from the at least one electronic display does not travel down the left eye path and vice versa. The medical apparatus includes an imaging system disposed on the display housing, the imaging system configured to generate images of a surgical site from outside the surgical site. The view of the display within the housing can be configured to provide a stereoscopic image to a viewer. In some embodiments, the housing further includes lenses and/or a transparent plate between the eyes of a viewer and the at least one electronic display. In some embodiments, the housing further includes a baffle or other structure to separate the left eye path and the right eye path. In some embodiments, each chamber is baffled to prevent light from one channel to communicate to the other eye path. In some embodiments, at least a portion of the chambers comprise oculars.

In certain implementations, the display unit can be baffled to prevent light communication between the left and right eye channels. To adjust for different accommodations, the displays within the display system can be configured to move toward and/or away from the viewer along the optical path. This can have an effect similar to varying focal lengths of lenses in an ocular system. Similarly, lenses or other optical components can be moved in the system to provide for different accommodations. In some embodiments, accommodation adjustment can be made by moving the screens relative to the lenses inside the display unit. In certain implementations, by lengthening the housing with the screens attached, or by moving the screens within a fixed housing relative to the lenses and user, or by moving the position and/or the separation of lenses or groups of lenses, accommodation can be adjusted. Additional adjustments between the two chambers can be accomplished by physically moving the two chambers laterally, e.g., by separating or moving the chambers closer together to adjust for inter pupillary distance differences between users.

In some embodiments, the display housing with the electronic displays can change to move the displays closer or further from the viewer along the optical path. In some embodiments, both the display housing and the electronic displays are configured to be adjustable along the optical path to adjust for accommodation.

In certain implementations, the binocular display unit can be configured to receive video images acquired with an endoscope and display these video images within the unit. These images can be combined (e.g., stitched, tiled, switched, etc.) with video from other sources by an operator so that video images from one or more sources, including the endoscope video images, can be viewed with the binocular display unit.

Camera Providing Surgical Microscope Views

The beginning, middle and end of a surgical case may involve differing visualization goals. As the case begins, the surgeon may be interested in surveying and viewing the area for the surgery. At skin level the surgeon may use surgical tools and the operating room microscope to guide their progress into the body to the surgical site. This means what is desirable is an image acquisition system functioning like an operating room microscope (OR scope) until such time as they choose to use views from other cameras (e.g., one or more cameras on a surgical tool(s), endoscope(s), one or more proximal cameras, etc.).

With this display design a number of surgical microscope camera functions are enabled. As described herein, the difference between using an exit pupil versus using an eye box results in differing apparent fields of view. Similarly, the choice of an electronic acquisition system that is not optically connected to the displays, as is the case in typical OR microscopy, makes many features possible.

An optically coupled microscope may have huge arms and complicated motions to position the microscope in positions required for surgery, in particular for neurosurgery. Some stands give the operating room microscopes a wide range of counterbalanced motions. Decoupling the optical system acquisition from the display, allows for a far greater range of motion, and this motion is closer to the optical elements of the system rather than the stand. Such a decoupled optical system can enable a compact system that can eliminate most or all counterbalancing efforts due at least in part to the reduced size and mass. Similarly, decoupling image acquisition of the surgical microscope view and providing an electronic display with no direct optical path from the oculars to the surgical site affords the opportunity to make a compact and ergonomic system.

Oblique surgical microscope views are useful, for example, for neurosurgery. One challenge to overcome in such systems is if there is a rotation of the surgical microscope views for oblique views there may be a roll component with the following result. The surgeon's eyes are in a plane parallel with the horizon and parallel with the display. Adding an oblique view in the right eye and left eye path's rolling, meaning the right eye and left eye may rock up and down with respect to one another as the mechanism is repositioned.

If the pitch is in a line coincident with the primary surgeon's gaze, from vertical to oblique, yaw around a central axis position-able in x and y, a collar to rotate surgical microscope cameras to switch views between the pairs of optics or alternatively the upper gimbal can be rotated 90 degrees and the view through the right eye left eye pairs can be switched electronically to give a roll motion in a vertical position. The pitch and yaw and collar gimbals are can be motor driven controlled by a joystick on one of the handles that manually control x and y of the assembly. A fine focus z adjustment can be manual or motor driven from controls or mechanisms on one handle or on one of the 2 handles on either side of the assembly. Zoom functions, illumination controls, fixing gaze position etc. can be controlled from the handles as well. The one handle or the 2 handles can reposition the entire mechanism under the display in x and y without disturbing the position of the display.

This assembly does not introduce roll in an oblique view, but could be positioned in a vertical position to have some roll if that is desired. For example, if one wants to roll the view slightly to one side or another so one or the other eye's view is not obstructed by tool use in the surgical opening when the surgical microscope camera is used in a substantially vertical position.

In some embodiments, an electronic surgical microscope for one or more surgeons to view a stereo pair of images in an electronic display from a surgical site is provided that includes a right eye path and a left eye path through a common objective. The electronic surgical microscope can be configured to be used at the focal length of the objective.

In a further embodiment, the electronic surgical microscope can include a right eye path comprising a view through a common objective and an afocal zoom assembly as well as a left eye path comprising a view through a common objective and an afocal zoom assembly.

In a further embodiment, the electronic surgical microscope can include a right eye path comprising a view through a common objective and an afocal zoom assembly and an adjustable diaphragm as well as a left eye path comprising a view through a common objective and an afocal zoom assembly and an adjustable diaphragm.

In a further embodiment, the electronic surgical microscope can include a right eye path comprising a view through a common objective and an afocal zoom assembly and an adjustable diaphragm and a focusing lens assembly as well as a left eye path comprising a view through a common objective and an afocal zoom assembly and an adjustable diaphragm and a focusing lens assembly.

In a further embodiment, the electronic surgical microscope can include a right eye path comprising a view through a common objective and an afocal zoom assembly and an adjustable diaphragm and a focusing lens assembly forming an image on a detector. In a further embodiment, the electronic surgical microscope can include a left eye path comprising a view through a common objective and an afocal zoom assembly and an adjustable diaphragm and a focusing lens assembly forming an image on a detector.

In a further embodiment, the electronic surgical microscope can include 2 or more real time video camera systems coupled to the right eye and left eye paths for processing signals from the right eye and left eye detectors, wherein electronic signals of each eye path produce resolution compatible with HD displays, e.g. 720i, 720p, 1080i, 1080p, and 4k.

In a further embodiment, the electronic surgical microscope can be configured so that neither eye path produces an aerial image suitable for direct viewing.

In a further embodiment, the electronic surgical microscope can include a system to divide the output of each detector, right and left eye, and vertically flip the images to a second right eye and left eye display for an assistant surgeon at 180 degrees to the primary surgeon.

In a further embodiment, the electronic surgical microscope can include a second pair of stereo paths that include a right eye path comprising a view through a common objective and an afocal zoom assembly and an adjustable diaphragm and a focusing lens assembly forming an image on a detector, a left eye path comprising of a view through a common objective and an afocal zoom assembly and an adjustable diaphragm and a focusing lens assembly forming an image on a detector, where both stereo paths are rotated 90 degrees from the first stereo pair paths to permit a second surgeon to view through the common objective and sit at 90 degrees to the primary surgeon. In addition, it can be configured so that neither eye path produces an aerial image suitable for direct viewing. In yet a further embodiment, the right eye path and the left eye path to their respective detectors permit an assistant surgeon to sit at right angles to the primary surgeon. Similarly, the output of the right eye and left eye detector of the assistant surgeon's detector may be vertically flipped to display the stereo scenes appropriately whether the assistant surgeon sits on the right or left side of the primary surgeon. Likewise, the surgical microscope can include a collar to support the stereomicroscope permitting the 4 eye paths to be rotated around the line of sight within the collar plus or minus 90 degrees or more and a system to switch stereo pairs displayed in the viewer from assistant surgeon to primary surgeon.

In some embodiments, a surgical microscope image acquisition system can be provided for acquiring stereo images of a surgical site to be displayed for one or more surgeons without a direct path optically between the lens elements of the acquiring system and surgeon's eyes. In a further embodiment, the surgical microscope image acquisition system can be suspended below an electronic display system for surgery and attached to a plane parallel with the horizon. The plane is the bottom surface of an electronic display for viewing the output of the stereomicroscope image acquisition system. In some embodiments, the plane is integral with a proximal column providing rotation, yaw, for integral displays and one or more stereomicroscope image acquisition systems. In a further embodiment, the column attaches to an arm which provides x y and z positioning movement for entire acquisition and display system at, over or adjacent to the patient. In a further embodiment, the arm attaches to a vertical column supporting all of the above which provides z, rotation and yaw. In some embodiments, the column can provide gross positioning and focusing without the need of counter balance measures as seen in operating room microscope stands, due to the lack of a directly optical pathway from the surgical site to the doctor's eyes.

Decoupling image acquisition from display in a Wheatstone like stereo display results in less mass and less movement of the display(s) that can result in an ergonomic viewing position for long cases. The primary positioning of a surgical view can be by the gimbaled image acquisition system. The positioning elements can be moved from adjacent to column in competing solutions to adjacent to the image acquisition system described herein that provides surgical microscope views.

In some embodiments, a surgical microscope image acquisition system whose stereo pair eye paths view a surgical site through a common objective contains one or more zoom (or just 'lens') assemblies to transform the numerical aperture of one or more fiber cccoptic cables from a remote source(s) also functioning through a common objective. By this means the divergence of the illumination light may be altered to illuminate a scene as either the imaging zoom changes, or to place more energy in an area.

In some embodiments, a surgical microscope image acquisition system is provided where the fiber optic illumination zoom functioning through a common objective has a gimbal mechanism so that the illumination may be steered within the surgical opening, or on the patient.

In some embodiments, a surgical microscope image acquisition system is provided wherein one or more surgical cameras are suspended below an electronic display system for surgery and attached to a plane parallel with the horizon. The plane can be the integral to a docking station for one or more head mounted electronic stereo displays for viewing the output of the stereomicroscope image acquisition system.

In some embodiments, a surgical microscope image acquisition system is provided that includes a pair of cameras mounted on each surgeon's head mounted display which face outward more or less on the same axis as the surgeon's on eyes, providing a right eye or left eye equivalent view of the room, or patient, or staff, or wherever his/her gaze directs his/her head controllable from a central processing unit.

A pair of fiducial markers, or known points can be located at respective positions (e.g., on the right side and left side) on a head mounted display worn by a surgeon in surgery, the arrangement including an imaging system to view the markers located on the plane or docking station. This information can be used to determine the line of sight of the surgeon.

One or more transmitters, can be located at respective positions (e.g., on the right side and left side) on a head mounted display worn by a surgeon in surgery, the arrangement including a receiving system to view the transmitters located on the plane, or docking station. This information can be used to determine the line of sight of the surgeon.

In some embodiments, the plane includes two or more cameras for locating the head mounted displays worn by the surgeons. The cameras can be calibrated using a calibration pattern(s) mounted on the head mounted displays. Then the unknown transformation from the image acquisition system's line of sight coordinates to the calibration pattern coordinate system as well as the transformation from the surgeon's new gaze to the coordinate system can be estimated simultaneously in a processing unit. With these estimates, the processing unit can calculate a difference between surgeon gaze positions. A central processing unit or processing electronics can be used for registering or calculating and selecting the main gaze. If, for example, a surgeon is looking into the wound in the display then the display can be at least mostly filled with the surgical view. If, for example, the surgeon shifts his/her gaze to the other side of the room the processing unit scales the surgical view to a picture in picture view, small relative to the room view. The picture in picture scaling can be configurable so that small movements of the surgeon's gaze can have little or no effect on the relative sizes of the room view and the surgical site view. Larger motions can be configured to select mostly the room view. The location of the picture in picture can be positionable within the main view and can be parked in a corner or centrally as appropriate.

A head mounted display can be configured to include two liquid crystal elements controlling the amount of light and corresponding scene allowed to pass to each eye. When the surgeon is gazing in a selected manner, e.g., at the surgical site, the liquid crystal, or other shutter, stops the pass-through room view and shows images originating from the image acquisition system. The displayed image can be viewed from a beamsplitter placed in the line of sight originating from a right eye and left eye LCD or OLED panels in the head mounted display. The size and location of the displayed image may be scaled and relocated to a corner of the field of view of the wearer. This allows the surgeon to see the patient or room, when desired, all the while maintaining a view of the surgical site; or a semitransparent view of the surgical scene with a modulated view of the room, which are configurable.

In some embodiments, tethered or wireless transmission from cameras on image acquisition systems to head mounted displays is provided.

A pair of fiducial markers, or known points can be located at respective positions (e.g., on the right side and left side) on a head mounted display with liquid crystal shutters worn by a surgeon in surgery, the arrangement including an imaging system to view the markers located on the plane, or docking station. These can be used to determine line of sight of the surgeon.

One or more transmitters, can be located at respective positions (e.g., on the right side and left side) on a head mounted display worn by a surgeon in surgery, the arrangement including a receiving system to view the transmitters located on the plane, or docking station. These can be used to determine line of sight of the surgeon.

One or more sensors, can be located at respective positions (e.g., on the right side and left side) on a head mounted display worn by a surgeon in surgery, the arrangement including a transmitting system to view or locate the sensors located on the plane, or docking station. These can be used to determine line of sight of the surgeon.

Various embodiments include a gimbaled image acquisition system, which has a working distance range and stereo separation of an operating room microscope, without an optical through path to the surgeon's eyes. The acquisition system is mounted in a collar (described above) in a gimbal system so that four zoom paths can be rotated 90 degrees around the line of sight to switch stereo paths between assistant surgeon and primary surgeon.

The acquisition system and collar attach to a yoke, which allows the surgical microscope image acquisition system to pitch, e.g., view closer to or further away from the surgeon.

An electronic stereomicroscope for one or more surgeons is provided to view a stereo pair of images in an electronic display from a surgical site having separate right eye and left eye paths (e.g., a Greenough configuration) with a variable convergence. In some embodiments, the electronic stereomicroscope can include a right eye path comprising tilted afocal zoom assembly providing variable convergence angle option as well as a left eye path comprising tilted afocal zoom assembly providing variable convergence angle option.

Figure 8O:
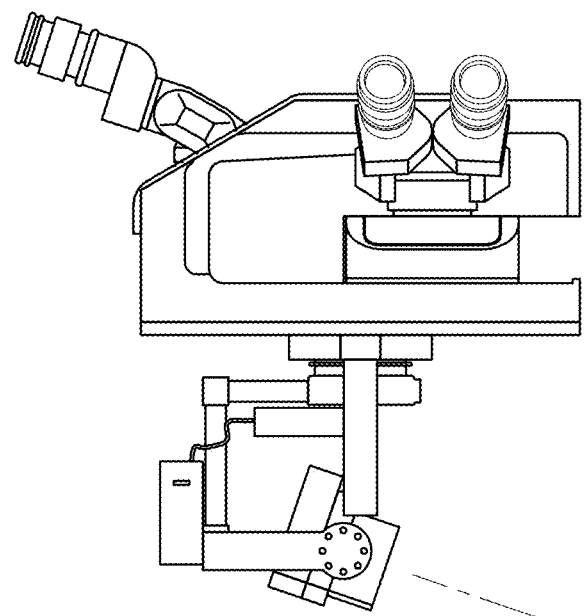
Figure 8P:
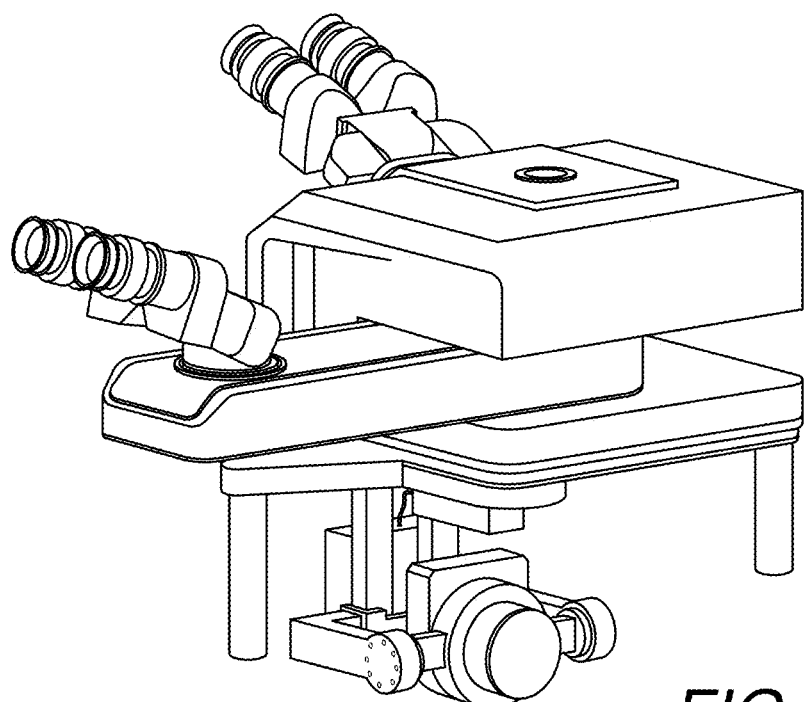
Figure 8Q:
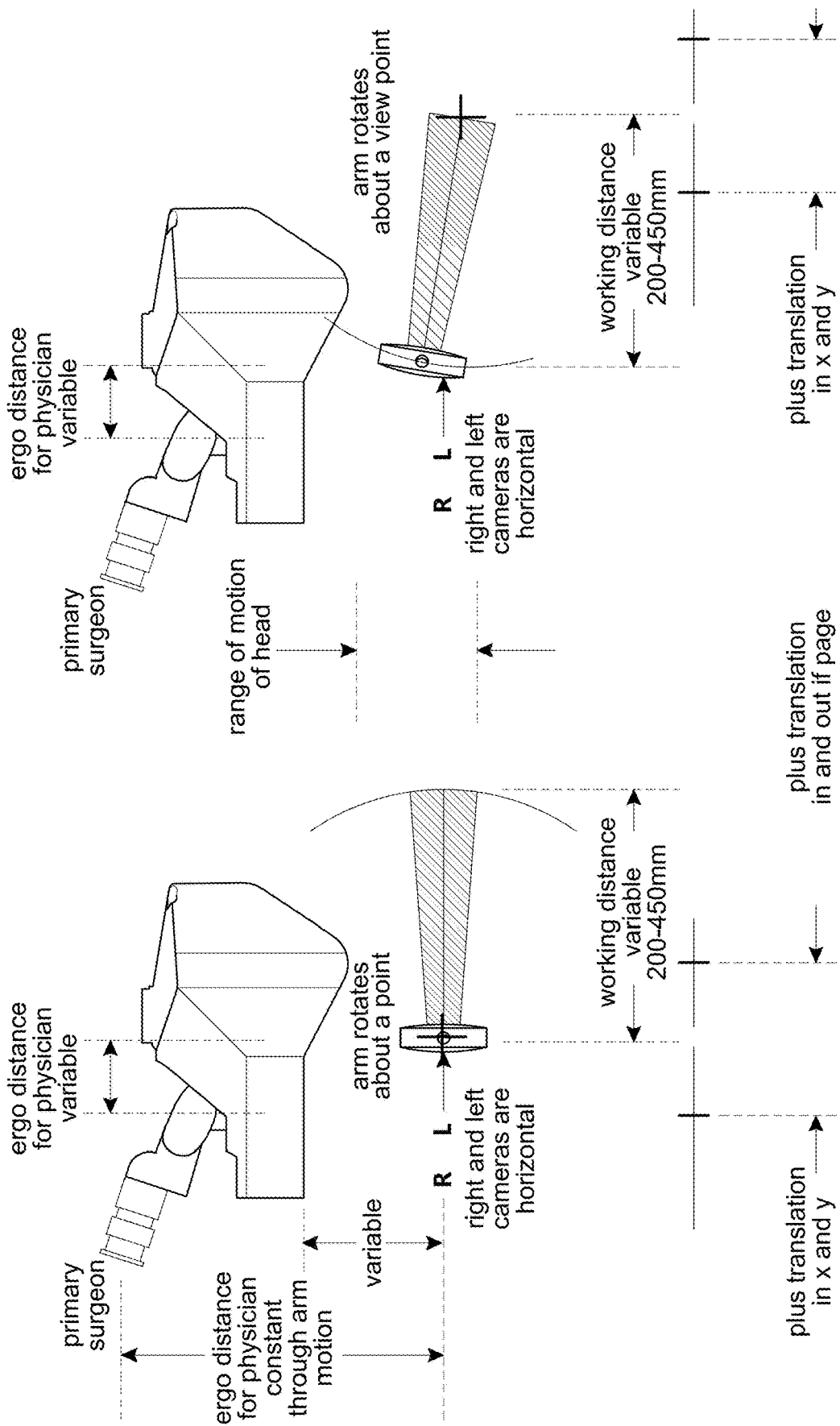
FIG. 8Q illustrates potential movement of a camera system providing a surgical microscope view wherein the camera system can be rotated about a point or about a viewpoint while the oculars remain stationary.

FIGS. 8A-8O illustrate views of a camera providing a surgical microscope view rotated around a central axis from the point of view of the primary surgeon. The x y stage under the display allows the surgical camera view mechanism to be shifted from one side to another giving the surgeon better access to the surgical site for tool use. The assistant scope can be moved from one side of the device to the other, e.g., +/−90 degrees, from the position of the primary surgeon.

The surgical microscope view camera system is shown in a vertical, i.e. top down viewing. The gimbal on the yoke allows the device to see retrograde from vertical. The gimbal system can be positioned for an oblique side view. The device can be configured for oblique views which may be particularly advantageous for neurosurgery.

Frame and Proximal Cameras

Certain embodiments include a medical apparatus comprising one or more proximal and/or distal cameras. In some cases (e.g., in some cases of brain surgery), minimal retraction and/or momentary retraction may be desired. Accordingly, certain embodiments of a medical apparatus comprising a frame, which is not a retractor, can be beneficial. Accordingly, various embodiments of a medical apparatus can comprise a frame that is not a retractor. The frame may be configured to be disposed above a surgical site of a patient. The frame can be mounted to a bed or to the patient and in some embodiments, anchored outside the surgical site of the patient. The medical apparatus can also include one or more cameras (e.g., a stereo camera, a mono camera, a camera providing a surgical microscope view, etc.) mounted to the frame. The one or more cameras can be configured to image the surgical site.

Figure 20A:
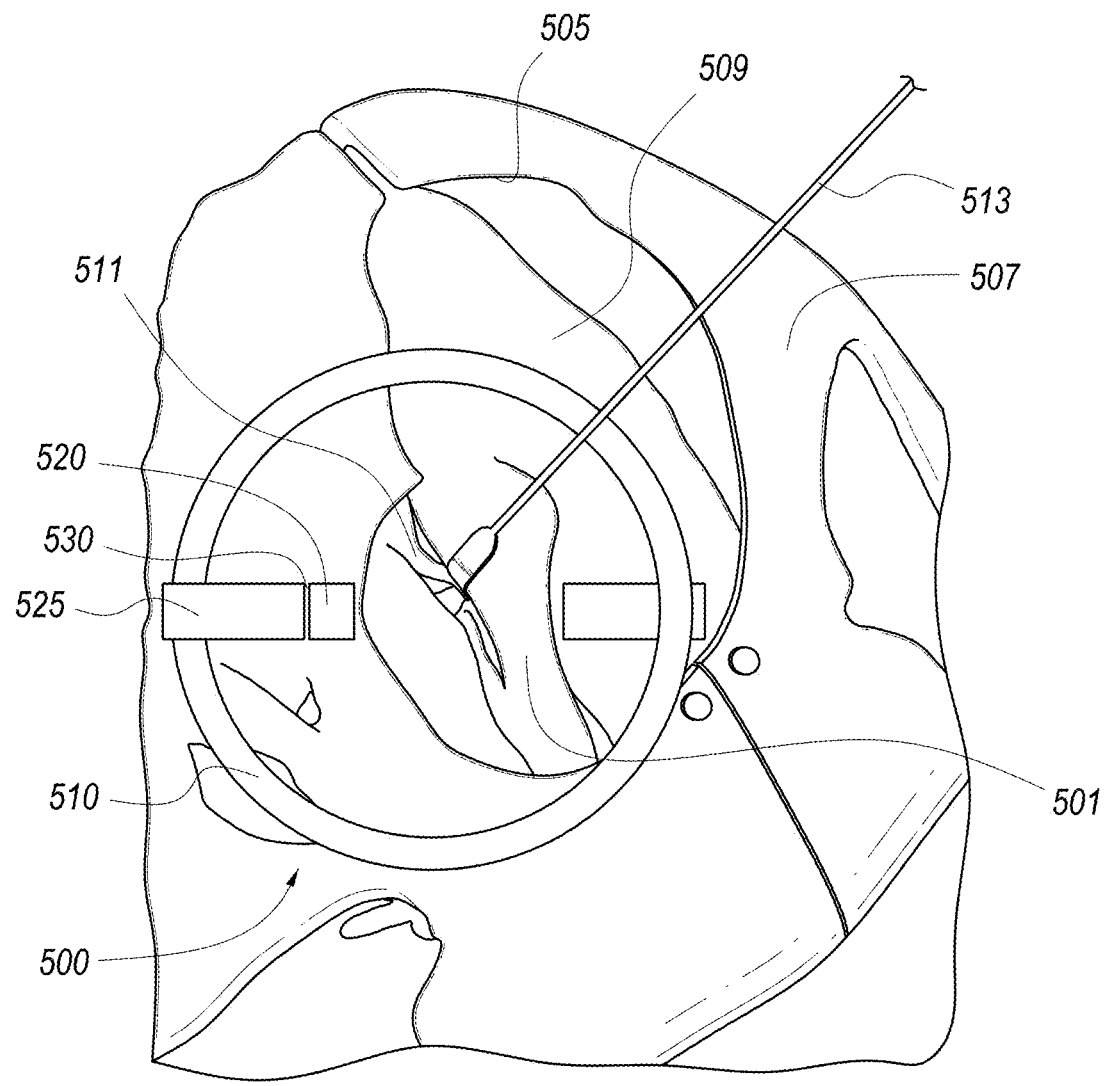
FIG. 20A shows a schematic of an example medical apparatus comprising a frame 510 disposed above a surgical site of a mock patient.

FIG. 20A shows a schematic of an example of such a medical apparatus 500 comprising a frame 510 disposed above a surgical site 501 of mock patient. The mock patient includes an opening 505 in the skull 507, material 509 representing brain, and material 511 representing white tissue. A hand retractor 513 is shown as lifting the material 509 representing brain to show the skull base tissue 511. The frame 510 can be configured to be disposed above the surgical site 501 of the patient. One or more cameras 520 can be mounted to the frame 510. For example, referring to FIG. 20A, one or more cameras 520 can be mounted to the frame 510 via mounts, clamps, and/or fingers 525 (with or without gimbals 530).

In various embodiments, the frame 510 can be configured to be mounted to a bed (e.g., to a gurney) or to the patient. For example, the frame 510 can be configured to be mounted to the bed (e.g., to the bed rail) and/or to the patient via a Mayfield clamp or a Mayfield mount. The frame 510 can be configured to be disposed outside the patient but within a close proximity to the patient and/or surgical site 501. For example, the frame 510 can be configured to be disposed above the surgical site 501 and/or above the patient by a distance of 1 mm, 5 mm, 10 mm, 15 mm, 20 mm, 25 mm, 30 mm, 35 mm, 40 mm, 45 mm, 50 mm, 75 mm, 100 mm, 120 mm, 130 mm, 140 mm, 150 mm, 175 mm, 200 mm, 250 mm, 300 mm or any value in between these values. Accordingly, in various embodiments, the frame 510 can be configured to be disposed, for example, 1 mm to 50 mm, 5 mm to 40 mm, 5 mm to 50 mm, 10 mm to 25 mm, 10 mm to 40 mm, 10 mm to 50 mm, 50 mm to 75 mm, 50 mm to 100 mm, 50 mm to 120 mm, 50 mm to 130 mm, 50 mm to 140 mm, 50 mm to 150 mm, 100 mm to 200 mm, (or any range formed by any of the values from 1 mm to 300 mm) above the surgical site 501 and/or above the patient. In various embodiments, the camera location can be configured to be disposed above the surgical site 501 and/or above the patient by a distance of 1 mm, 5 mm, 10 mm, 15 mm, 20 mm, 25 mm, 30 mm, 35 mm, 40 mm, 45 mm, 50 mm, 75 mm, 100 mm, 120 mm, 130 mm, 140 mm, 150 mm, 175 mm, 200 mm, 250 mm, 300 mm or any value in between these values. Accordingly, in various embodiments, the frame 510 can be configured to be disposed, for example, 1 mm to 50 mm, 5 mm to 40 mm, 5 mm to 50 mm, 10 mm to 25 mm, 10 mm to 40 mm, 10 mm to 50 mm, 50 mm to 75 mm, 50 mm to 100 mm, 50 mm to 120 mm, 50 mm to 130 mm, 50 mm to 140 mm, 50 mm to 150 mm, 100 mm to 200 mm, (or any range formed by any of the values from 1 mm to 300 mm) above the surgical site 501 and/or above the patient. In some embodiments, the camera can extend close to and/or inside the surgical site even if the frame 510 is located above the surgical site.

The one or more cameras 520 can include any of the cameras described herein. For example, the one or more cameras 520 can include a mono view camera, e.g., a single camera with one field of view with a circular, rectangular, or square image output. In various embodiments, the one or more cameras 520 can provide a left-eye view and a right-eye view. In some such embodiments, the one or more cameras 520 can be configured to provide stereo imaging. For example, the one or more cameras 520 can include a stereo view camera, stereo assemblies, a pair of cameras, or a split sensor with one-half providing the right-eye view and the other half providing the left-eye view. The one or more cameras 520 can include one or more illumination sources.

Various embodiments of the medical apparatus 500 include a frame 510 for the purpose, partially or predominantly, of holding one or more cameras 520 (e.g., one or more cameras as described herein). Because the frame 510 is not a retractor and does not move or retract tissue, a hand retractor 513 can be used to move tissue in the surgical site 501. In various embodiments, one or more cameras 520 can be configured to be mounted to the frame 510. In some embodiments, the one or more cameras 520 can face inwardly and/or downwardly into the surgical site. The size of the frame 510 is not particularly limited and can depend on the size of the surgical site 501 and/or the type of surgical procedure. The shape of the frame 510 is also not particularly limited. As some examples, the frame 510 can have a cross-sectional shape comprising a round shape (e.g., a circle, an oval, etc.), a regular polygon (e.g., a square, a rectangle, a hexagon, an octagon, etc.), or an irregular polygon (e.g., an L-type shape). FIGS. 20A1-*a*, 20A1-*b*, and 20A1-*c* schematically illustrate an example circular frame 510*a*, an example square frame 510*b*, and an example L-shaped frame 510*c* respectively.

Various embodiments of the medical apparatus 500 can include one or more cameras 520 mounted to the frame 510 to provide one or more perspectives of the surgical site 501. In some embodiments, proximal cameras can be mounted to the frame 510 providing at least two or at least four different perspectives. As one example, four cameras 520 can be mounted to the frame 510 at 3 o'clock, 6 o'clock, 9 o'clock, and 12 o'clock positions. As shown in FIGS. 20A1-*a*, cameras 520*a* are mounted to frame 510*a* at 3, 6, 9, and 12 o'clock positions. In addition, as shown in FIGS. 20A1-*b*, cameras 520*b* are mounted to frame 510*b* at 3, 6, 9, and 12 o'clock positions. In various embodiments, referring to FIG. 20A, the cameras 520 can be positioned 90 degrees (or other angles) apart from each other. Accordingly, referring to FIG. 20A, the cameras 520 can be positionable around the frame 510, for example, around a ring or around a square. In some instances, the cameras 520 can be symmetrically positioned around the frame 510. In other instances, the cameras 520 can be asymmetrically positioned around the frame 510. As additional examples, cameras 520 can be mounted to an L shape of one kind or another. In FIGS. 20A1-*c*, cameras 520*c* are mounted to the L-shaped frame 510*c*.

By being mounted to the frame 510, the one or more cameras 520 can image the surgical site 501. Certain embodiments described herein can include one or more mounts (or clamps or fingers) 525 connecting the one or more cameras 520 to the frame 510. Although the cross-sectional shape of the mounts 525 in FIG. 20A is schematically shown as rectangular, the shape of one or more mounts 525 is not particularly limited.

Various embodiments of the medical apparatus 500 can include one or more gimbals 530 and/or movement control systems (e.g., other positioning and/or orientation systems similar to any of those described herein) to couple a camera 520 to the frame 510 and to change the positioning and/or orientation of the camera 520. In some embodiments, the one or more gimbals 530 can provide gimballing motions similar to those described for cameras providing a surgical microscope view underneath a display. For example, various embodiments utilize a gimbal system similar to those from under the camera providing a surgical microscope view, yet can be relatively smaller and disposed on mounts, clamps, or fingers 525. As will be described herein, various embodiments can include attachment points 515 for four-bar or other x-y-z mechanisms (see, e.g., FIGS. 20A1-*a*, 20A1-*b*, and 20A1-*c*).

Accordingly, in various embodiments, one or more cameras 520 can include first and second cameras configured to move relative to the surgical site 501. For example, certain embodiments of the medical apparatus 500 include one or more gimbals 530 mounted to one or more mounts 525. The one or more gimbals 530 can be configured to allow positioning of one or more proximal cameras 520, such as those not inside the surgical site 501 but viewing into it. Such embodiments can have some advantageous positions. Thus, in various embodiments, one or more gimbals 530 can be configured to move the one or more cameras 520 relative to the frame 510. Some embodiments can include knobs or heads to turn one or more cameras 520 in and out. Some embodiments can also include some features to drive one or more cameras 520 in a precise manner (e.g., sub-millimeter range of motions). In some embodiments, three, four, or more knobs can be provided on either side on the external side (e.g., the outboard side) of the frame 510. By turning the knobs, one or more gimbals 530 can be oriented to move in one axis or the other axis, or move in an x axis or move in a y axis, or move in a z axis, which can be a very advantageous situation. In some embodiments, one or more cameras 520 can be configured to move electronically.

As described herein, the one or more cameras 520 can include any of the cameras described herein. For example, the one or more cameras 520 can include a stereo view camera, stereo assemblies, a pair of cameras, or a split sensor with one-half providing the right-eye view and the other half providing the left-eye view.

One of the advantages of stereo imaging is the ability to provide great depth perception. One of the downsides of any kind of surgery inside the body is becoming disoriented. To give an orientation of location inside the body, surgeons can look at surgical landmarks, the direction of a light source, an external part of an endoscope (e.g., outside the body), and/or a cable coming out of the scope. Additionally, an anatomical landmark relative to others can also be used. However, tissue with very different functions can look very similar, thus resulting in disorientation. Stereo imaging, while it can give great depth perception, can actually add to confusion. If surgeons can be certain that they are always in a horizontal orientation, it can be an extremely advantageous feature, because at least surgeons can know they were not rotated. For example, surgeons may still have some orientation issue about location. However, knowing that the right eye and left eye are seeing things as though standing on the floor and upright, with the right eye and left eye in the same plane, can be extremely advantageous to avoid becoming disoriented.

Utilizing one or more gimbals 530 (and/or other positioning and/or orientation systems), e.g., including those having six degrees of freedom, can allow the horizontal line of sight, e.g., right eye and left eye, to have the same orientation as the viewer. For example, certain embodiments can maintain the horizontal in a way that does not allow any other motion other than keeping the right eye and left eye horizontal orientation, whether looking straight down or in an oblique situation. As described herein, this can be advantageous in some instances. If a surgeon has an obstruction, it may be desired to angle the surgeon's view to see around the distraction, but to maintain a horizontal line of sight or at least not to introduce roll.

Accordingly, in certain embodiments, the one or more cameras 520 can include first and second cameras configured to move relative to the surgical site 501 and to maintain a same horizontal orientation with respect to each other. For example, referring to FIG. 20A, the mounts 525 can hold the six degrees of freedom (or however many degrees of freedom desired) to create a gimbal that moves around (e.g., to allow a gimbal 530 to move around) but, can in various embodiments, maintain the horizontal orientation of right eye and left eye in the same plane or allow the viewer to not feel the right eye or left eye higher than or lower than the other eye. With continued reference to FIG. 20A, in certain embodiments, a camera 520 can be relatively smaller than the mount 525. The gimbal 530 can have a relatively small pitch yaw rotation structure that can move the camera 520 to direct its line of sight in six degrees of freedom. Certain embodiments provide x-y-z and pitch, yaw, and roll mainly both to position the camera 520 but also to maintain the horizontal axis of the two eye views. For example, in various embodiments, the one or more gimbals 530 can be configured to potentially allow for repositioning in (transverse) x, y, or (longitudinal) z direction as well as pitch or yaw (rotation), or any combination thereof. Various embodiments, however, might not enable roll so as to reduce the disorientation that may result when the left and right channels of a stereo camera are rolled (e.g., the horizontal line through the left and right channels are not parallel to the ground). Accordingly, the one or more cameras 520 can be configured to move with respect to an x direction, a y direction, or a z direction. In some embodiments, one or more cameras 520 can be configured to move with respect to a pitch or yaw. For example, one or more cameras 520 can be configured to move with respect to a pitch and/or yaw, and without roll.

As described herein, in various embodiments, the frame 510 can be configured to be mounted (directly or indirectly) to a bed (e.g., a gurney) and/or to the patient and anchored outside the surgical site of the patient. In some embodiments, the frame 510 can be configured to be mounted to the bed (e.g., to the bed rail) and/or to the patient via a Mayfield clamp or a Mayfield mount. In some embodiments, the frame 510 can be configured to provide a stereotactic planning system. For example, a system that provides a frame of reference, e.g., a coordinate system associated with many positions in that region can be used. Certain embodiments can be drilled right into or otherwise attached to a patient (e.g., skull for brain surgery). If the patient moves (e.g., coughs), the whole device moves. Accordingly, in certain embodiments, the frame of reference may not get disoriented by involuntary or voluntary movement of the patient. In various embodiments, the frame 510 can be a stereotactic frame. In various embodiments, the frame 510 can be mounted to a stereotactic system. In various embodiments, the frame 510 can be mounted to the patient and connected indirectly to a stereotactic system.

Certain embodiments of the medical apparatus 500 can be supported by the bed, by a Mayfield clamp, by a Mayfield mount, or by the frame 510 (e.g., a stereotactic frame). For example, in certain embodiments, a stereotactic frame or the bed provides a supporting structure. In some embodiments, a stereotactic frame can mount on the patient's skull, and some other support mechanism can mount to the bed.

Certain embodiments of the medical apparatus 500 can include more distal cameras than the proximal cameras 520. For example, a more distal camera than the proximal camera 520 can be mounted to the frame 510, e.g., on a finger 525 that goes down into the surgical site 501. The cameras 520 can be mounted to face inward with respect to each other (and/or possibly downward into the surgical site). Various embodiments including cameras 520 on a frame 510, such as a stereotactic frame or a bed-mounted frame, can include features applicable to other technology including but not limited to distal and proximal cameras.

In certain embodiments of proximal cameras 520 on frames 510, the proximal cameras 520 can be positioned just outside and adjacent to the surgical site 501 (e.g., between 5 mm and 50 mm, between 10 mm and 25 mm above the patient, between 10 and 40 mm above the patient, between 10 and 50 mm above the patient, between 50 mm and 75 mm, between 50 mm and 100 mm, between 50 mm and 120 mm, between 50 mm and 130 mm, between 50 mm and 140 mm, between 50 mm and 150 mm, between 100 mm and 200 mm, etc.). Accordingly, the field of view for various embodiments of proximal cameras 520 on frames 510 can be different than the field of view of distal cameras within a surgical site (e.g., distal cameras on a surgical tool). For example, for a distal camera within a surgical site, in order to provide an image from within a surgical site, a wide as possible field of view is desired even if not in the center of field. Whereas for certain embodiments having a proximal camera 520 on a frame 510, the field of view can be narrower because the camera 520 may not be in the surgical site 501.

Accordingly, certain embodiments of a proximal camera 520 on a frame 510 can have a different optical function than a distal camera (e.g., a distal camera on a surgical tool). Some such embodiments of a proximal camera 520 can be relatively small like an endoscope but behave structurally like certain embodiments of a gimbal camera as described herein for a surgical microscope view camera. In certain embodiments, the proximal camera 520 can be used with a camera providing a surgical microscope view, such as for example described elsewhere in this application. Accordingly, a distal camera can be useful for endoscopic procedures. However, certain embodiments having a camera (e.g., a proximal camera and/or a more distal camera than a proximal camera) mounted to a frame 510 can be useful for procedures that are endoscopic, as well as those that are not critically endoscopic, but that are microscopic-like, such as for some brain surgical procedures.

In some instances, cameras positioned within the surgical site may compromise the cameras' imaging ability, e.g., being in the wrong position. For proximal cameras 520 mounted to a frame 510 being just outside and adjacent to the surgical site 501, certain embodiments can include precision controls on the proximal cameras 520 that may not be placed on small distal cameras inside the surgical site 501. For various embodiments including a proximal camera 520, the frame 510 and mount 525 (or clamp or finger) may remain still with only the gimbal 530 being adjusted.

FIG. 20B1-*a* shows an illustration of an imaging system 540 comprising a camera 541, fiber optics 542 and a laparoscope 545 (which can also be representative of an endoscope) going inside the abdomen 546 through the abdominal wall 547 at a port 548 of entry (e.g., a trocar or cannula insertion point). The laparoscope 545 can have a field of view 549 of the area 550 of interest. Because the laparoscope 545 goes inside the body some distance, the port 548 of entry can become a rotation point around that fulcrum (e.g., at the insertion point). Whether the laparoscope 545 is going through a single port, a laparoscope 545 and tools going through the same port, or the laparoscope 545 and tools going through different ports, a lever arm on the laparoscope 545 and/or tools from the point 548 of entry in the imaging system 540 can create disadvantageous imaging issues. Thus, having a lever arm from the port 548 of entry can be an optical disadvantage for endoscopes and laparoscopes. Further, a laparoscope 545 used through the abdominal wall 547 is typically positioned at zero degree, with spin not desired. For example, rotation of the horizon with the laparoscope 545 is typically not desired. Because of the entry point 548 of the abdominal wall 547, a gimbal system and/or imaging movement may generally be not possible in certain embodiments.

FIG. 20B1-*b* shows an illustration of certain embodiments of a medical apparatus having one or more proximal cameras D on a frame G. Some such embodiments can be useful where the surgical site opening is bigger and not similar to an opening through an abdominal wall 547. Certain such embodiments can have an optical advantage of no lever arm from an entry point of the body. Other optical advantages of some such embodiments include the ability to use gimbals F similar to one's own vision (e.g., eye, head, neck combination), a stationary ergonomic display, gimbals for stereo cameras, and/or planar four-bar mechanisms for positioning without disturbing horizontal positions of right and left eye acquisition for horizontal viewing in display.

When not going through the abdominal wall 547, skull-based surgery, sinus surgery, knee surgery, or surgery in various other constrained body passages can be performed without a trocar opening. Often, such surgery (e.g., sinus surgery, neurosurgery, laparosurgery, or orthopedic surgery) can involve rotation and result in disorientation. With such rotation, the surgeon may have to keep the eye/brain combination working to know one's location in space. Thus, in various instances, maintaining the horizon without roll is desired.

In FIG. 20B1-*a*, when viewing the area 550 of interest with a laparoscope 545, a surgeon may be restricted by the port 548 of entry through the abdomen 546. In FIG. 20B1-*b*, when viewing the area E of interest, a medical apparatus 600 including one or more proximal cameras D on a frame G, a gimbal system F can allow maintenance of the horizontal right eye/left eye configuration. A surgeon C can view through an ocular B to view an inside view of the body on the display A. The gimbal system F can comprise a mechanism configured to provide movement of the proximal cameras D while maintaining the horizon (e.g., right eye/left eye parallel with the right eye/left eye in the display).

FIG. 20B2-*a* schematically illustrates imaging optics of an example imaging system compatible with certain embodiments of cameras as described herein. FIG. 20B2-*b* shows an illustration of an example top-down view of certain embodiments disclosed herein. In certain such embodiments, the center I of rotation is at the end of the gimbal of the proximal camera D instead of at the abdomen wall 547. In certain embodiments, such movement H can be analogous to rotating one's eyes in their socket or rotating one's head around the axis of the neck. Movement laterally and longitudinally of the gimbal mechanism can occur at the center I of rotation. The rotation H around the center I (e.g., side-to-side movement) can maintain the horizon in some embodiments. FIG. 20B2-*c* shows an illustration of an example side view of one optical channel of the apparatus shown in FIG. 20B2-*b*. In the example side view, the proximal camera D can rotate around J. Such movement can be analogous to the head-and-neck combination (e.g., up-and-down movement).

FIG. 20B2-*d* shows an illustration of an example proximal camera arrangement. Two proximal cameras D are shown here, e.g., at 12 o'clock and 6 o'clock on a plane of the frame G. There could be four cameras, e.g., also in an orientation of 3 o'clock and 6 o'clock and still maintain their stereo movement. FIG. 20B2-*e* shows an illustration of a display A viewable through portals (e.g., oculars B) by a surgeon C. FIG. 20B2-*f* illustrates a top-view of a left proximal camera $D_L$ providing a left line $L_L$ of sight and a right proximal camera $D_R$ providing a right line $L_R$ of sight. FIG. 20B2-*f* also illustrates an example planar four-bar mechanism K that can allow movement of proximal cameras $D_L$, $D_R$ in one orientation and then tip and turn without inducing roll. For example, yaw (movement around I), pitch (movement around J), and the motion (from the four-bar mechanism K) that can represent the lateral movement around in space are shown. In certain embodiments, motion for the proximal cameras $D_L$, $D_R$ can include pitch and yaw, but not roll. If there were roll on the acquisition cameras, the line-of-sight of the right eye and left eye in the display can be different from the right eye and left eye of the acquisition system. FIG. 20B2-*g* shows an illustration of the side view of FIG. 20B2-*f*. FIG. 20B2-*g* shows pivots P of the four-bar mechanism K and mount M to the frame.

Some embodiments can include sensors and cameras that can be automatically rotated if the right eye and left eye of the display system is rotated (e.g., roll). In some such embodiments, if a camera tipped, the display can follow the camera up to a certain point. For example, if a camera tipped at 15 degrees, the display can tip 15 degrees. If roll were induced in the acquisition system in the proximal cameras and the display were to follow the roll, the cameras providing a surgical microscope view underneath the display can stay constant in certain embodiments (or might roll as well). In some embodiments, the surgical microscope cameras can roll with roll of the display (as may potentially the proximal cameras). However, in many embodiments, the ability for the proximal cameras (and/or the surgical microscope view cameras) to roll may not be provided or may be limited to reduce disorientation.

FIG. 20B3 is an illustration of certain embodiments described herein showing an oblique camera orientation. The motion F can allow one or more proximal cameras D to image from multiple views. In some embodiments, unlike the endoscope or laparoscope 545 where pitch can be typically dictated by the port 548 of entry, the pitch is about the point J of rotation at a proximal camera D. Such motion F can be similar to an eye locating in a socket. Motion F can represent the ability of a proximal camera D to move around its own axis, supported by the frame G (e.g., on a non-laparoscopic device). The one or more proximal cameras D can include a relatively small pair of cameras such as stereo cameras. Providing only yaw, only pitch, a four-bar mechanism, and a z motion can maintain the horizontal line through the lines of sight of the left and right cameras, eliminating roll in some embodiments.

As described herein, certain embodiments can include the x and y motion of a four-bar mechanism. In other embodiments, other x-y-z mechanisms besides a four-bar mechanism can be used. In some embodiments, the pitch and yaw can be moved to a proximal camera on a frame independent of a display. By providing one or more proximal cameras with gimballing motion, and in some embodiments, with all motions except roll, near the opening of the body, various embodiments can be different than endoscopes and not comparable with microscopes.

An endoscope typically can have a 50 degree field of view to 110 degree field of view. An operating room microscope (e.g., a camera providing a surgical microscope view) can have typically a smaller field of view, for example, the area of interest can be 50 mm in diameter and 300 mm away from the vertex of the acquisition system.

In some embodiments, a proximal camera as described herein can be in between those two ranges. Thus, some embodiments of a proximal camera can be described as being sometimes endoscope-like and sometimes microscope-like. Some such proximal cameras can have a narrower field of view than an endoscope and a wider field of view than a microscope. Some such proximal cameras can also be positioned closer to the patient than a surgical microscope because the sensors and cameras can be much smaller. In addition, compared to loupes, various embodiments of proximal camera and display can be more advantageous by having the opportunity to be in an ergonomic position and the ability to see additional views.

An endoscope, sinus scope, neuro scope, and/or laparoscope might have a working distance from 10 mm to 100 mm, and might have a field of view between 50 degrees and 110 degrees. An operating room microscope might have a field of view as seen on the patient (e.g., not in an angled space) from 35 mm to 200 mm, and at a working distance of 200 mm to 450 mm. In various embodiments, proximal cameras can be from 10 degree field of view to 50 degree field of view with working distances of 5 mm to 50 mm, 40 mm to 100 mm, 40 mm to 150 mm, 50 mm to 100 mm, 50 mm to 150 mm, 100 mm to 200 mm (e.g., something that allows you to be close to the patient). In some embodiments, the workspace can be determined by the opening into the body, the depth of the wound or the surgical passageway, and the surgeon's hands and tools. Surgeons typically may not take a tool like forceps with scissor action in their hand, but may take a tool like pistol grips. In addition, surgeons typically may not run their hands into the body. Accordingly, there may be a standoff working distance, e.g., a 150 mm tool, at a minimum, for a 100 mm passage. In addition, there may be some surplus of space between the surgeon's hand and the opening of the body, e.g., to accommodate a drape for example. The frame (e.g., 125 mm in diameter) can be positioned above this working distance, e.g., within 10 mm, 25 mm, 40 mm, 50 mm, 75 mm, 100 mm, 130 mm, 140 mm, 150 mm, 175 mm, or 200 mm in some instances, above the surgical opening to have this proximal camera. Thus, certain embodiments of proximal cameras can be disposed at the opening of the passageway and view down in the surgical opening, with a narrower field of view than an endoscope, but a closer working distance than a microscope. In some embodiments, the working distance can be between 1 mm to 50 mm, 5 mm to 40 mm, 5 mm to 50 mm, 10 mm to 25 mm, 10 mm to 40 mm, 10 mm to 50 mm, 50 mm to 75 mm, 50 mm to 100 mm, 50 mm to 120 mm, 50 mm to 130 mm, 50 mm to 140 mm, 50 mm to 150 mm, 100 mm to 200 mm, 100 mm to 300 mm (or any ranges formed by any values between 1 mm and 300 mm). In addition, in some embodiments, the field in the object plane can be between 25 mm to 200 mm or between 25 mm to 250 mm (or any ranges formed by any values between 25 mm and 250 mm).

Additionally, any of the features or embodiments described in connection with the surgical tools, surgical visualization systems and components thereof, may be used with, combined with, incorporated into, be applicable to, and/or are otherwise compatible with one or more embodiments of a medical apparatus including one or more proximal cameras mounted to a frame disposed above the patient and/or surgical site as described herein.

For example, in various embodiments of a medical apparatus can include one or more cameras. At least one of the cameras can include a surgical microscope camera configured to provide a surgical microscope view of the surgical site. In various embodiments, the surgical microscope camera is not coupled to a direct view surgical microscope. As also described herein, the medical apparatus can include a binocular viewing assembly comprising a housing and a plurality of portals (e.g. oculars). The plurality of portals or oculars (e.g., separated left and right portals or oculars) can be configured to provide views of at least one display disposed in the housing. The left and right portals (e.g. oculars) can be separated by sidewalls, baffling, tubing, etc. that reduces optical cross-talk therebetween. For example, light from a display or display portion associated with the left portal or ocular is blocked so as to not propagate into the right portal or ocular, and vice versa. Similarly, light from a display or display portion associated with the right portal or ocular is blocked so as to not propagate into the left portal or ocular. The medical apparatus can further include an image processing system (e.g., comprising processing electronics) in communication with the camera (e.g., the camera including the surgical microscope camera) and the one or more displays. As also described herein, the image processing system can be configured to receive images acquired by the camera (e.g., the camera including the surgical microscope camera), and to present output images based on the received images on the one or more displays so that the output images are viewable through the plurality of oculars.

Numbered Example Embodiments

The following is a numbered list of example embodiments that are within the scope of this disclosure. The example embodiments that are listed should in no way be interpreted as limiting the scope of the embodiments. Various features of the example embodiments that are listed can be removed, added, or combined to form additional embodiments, which are part of this disclosure:

1. A medical apparatus comprising:
   a first display portion configured to display a first image;
   a second display portion configured to display a second image;
   electronics configured to receive one or more signals corresponding to images from a plurality of sources and to drive said first and second display portions to produce said first and second images based at least in part on said images from said plurality of sources; and
   a first beam combiner configured to receive said first and second images from said first and second display portions and to combine said first and second images for viewing.

2. The medical apparatus of Embodiment 1, wherein said first and second display portions comprise first and second displays.

3. The medical apparatus of Embodiment 1 or 2, further comprising a housing and a first ocular for viewing the combined first and second images within said housing.

4. The medical apparatus of Embodiment 3, further comprising a second ocular for viewing an additional image within said housing.

5. The medical apparatus of any of the preceding embodiments, further comprising imaging optics disposed to collect light from both said first and second display portions.

6. The medical apparatus of Embodiment 5, wherein said imaging optics are configured to form images at infinity.

7. The medical apparatus of any of the preceding embodiments, wherein said plurality of sources comprises at least one camera providing a surgical microscope view.

8. The medical apparatus of Embodiment 7, further comprising said at least one camera providing said surgical microscope view.

9. The medical apparatus of any of the preceding embodiments, wherein said plurality of sources comprises at least one camera disposed on a surgical tool.

10. The medical apparatus of Embodiment 9, further comprising said at least one camera disposed on said surgical tool.

11. The medical apparatus of any of the preceding embodiments, wherein said plurality of sources comprises at least one source providing data, a computed tomography scan, a computer aided tomography scan, magnetic resonance imaging, an x-ray, or ultrasound imaging.

12. The medical apparatus of Embodiment 11, further comprising said at least one source providing said data, computed tomography scan, computer aided tomography scan, magnetic resonance imaging, x-ray, or ultrasound imaging.

13. The medical apparatus of any of the preceding embodiments, wherein said first image comprises a fluorescence image and said second image comprises a non-fluorescence image.

14. The medical apparatus of Embodiment 1, further comprising:
   a third display portion configured to display a third image;
   a fourth display portion configured to display a fourth image; and
   a second beam combiner configured to receive said third and fourth images from said third and fourth display portions and to combine said third and fourth images for viewing.

15. The medical apparatus of Embodiment 14, wherein said third and fourth display portions comprise third and fourth displays.

16. The medical apparatus of Embodiment 14 or 15, further comprising a housing, a first ocular for viewing the combined first and second images within said housing, and a second ocular for viewing the combined third and fourth images within said housing.

17. The medical apparatus of any of Embodiments 14-16, further comprising additional electronics configured to receive one or more signals corresponding to images from another plurality of sources and to drive said third and fourth display portions to produce said third and fourth images based at least in part on said images from said another plurality of sources.

18. The medical apparatus of any of Embodiments 14-17, further comprising imaging optics disposed to collect light from both said third and fourth display portions.

19. The medical apparatus of Embodiment 18, wherein said imaging optics are configured to form images at infinity.

20. The medical apparatus of any of Embodiments 17-19, wherein said another plurality of sources comprises at least one camera providing a surgical microscope view.

21. The medical apparatus of Embodiment 20, further comprising said at least one camera providing said surgical microscope view.

22. The medical apparatus of any of Embodiments 17-21, wherein said another plurality of sources comprises at least one camera disposed on a surgical tool.

23. The medical apparatus of Embodiment 22, further comprising said at least one camera disposed on said surgical tool.

24. The medical apparatus of any of Embodiments 17-23, wherein said another plurality of sources comprises at least one source providing data, a computed tomography scan, a computer aided tomography scan, magnetic resonance imaging, an x-ray, or ultrasound imaging.

25. The medical apparatus of Embodiment 24, further comprising said at least one source providing said data, computed tomography scan, computer aided tomography scan, magnetic resonance imaging, x-ray, or ultrasound imaging.

26. The medical apparatus of any of Embodiments 14-25, wherein said third image comprises a fluorescence image and said fourth image comprises a non-fluorescence image.

27. The medical apparatus of any of the preceding embodiments, wherein said medical apparatus provides 3D viewing of a surgical field.

28. The medical apparatus of any of the preceding embodiments, wherein the combined first and second images for viewing comprises a composite image of said first and second images, wherein said first beam combiner is configured to produce said first image as a background image of said composite image, and to produce said second image as a picture-in-picture (PIP) of said composite image.

29. The medical apparatus of any of Embodiments 14-28, wherein the combined third and fourth images for viewing comprises a composite image of said third and fourth images, wherein said second beam combiner is configured to produce said third image as a background image of said composite image, and to produce said fourth image as a picture-in-picture (PIP) of said composite image.

30. A binocular display for viewing a surgical field, said binocular display comprising:
   one or more cameras configured to produce images of said surgical field;
   a left-eye view channel comprising:
      a first display configured to display a left-eye view image of said surgical field; and
      one or more first processing electronics; and
   a right-eye view channel comprising:
      a second display configured to display a right-eye view image of said surgical field; and
      one or more second processing electronics;
   wherein each of said first and second processing electronics is configured to receive one or more user inputs, receive one or more input signals corresponding to said images from said one or more cameras, select which image of said images from said one or more cameras to display, resize, rotate, or reposition the selected image based at least in part on said one or more user inputs, and produce one or more output signals to drive said first or second display to produce said left-eye or right-eye image.

31. The binocular display of Embodiment 30, wherein each of said first and second processing electronics comprises a microprocessor, a field programmable gate array (FPGA), or an application specific integrated circuit (ASIC).

32. The binocular display of Embodiment 30 or 31, wherein said one or more cameras comprises at least one camera providing a surgical microscope view.

33. The binocular display of any of Embodiments 30-32, wherein said one or more cameras comprises at least one camera disposed on a surgical tool.

34. The binocular display of any of Embodiments 30-33, wherein said one or more cameras comprises a camera configured to produce a fluorescence image and a camera configured to produce a non-fluorescence image.

35. The binocular display of any of Embodiments 30-34, further comprising one or more sources providing data, a computed tomography scan, a computer aided tomography scan, magnetic resonance imaging, an x-ray, or ultrasound imaging.

36. The binocular display of any of Embodiments 30-35, wherein said binocular display provides 3D viewing of said surgical field.

37. The binocular display of any of Embodiments 30-36, wherein said one or more first processing electronics comprises separate processing electronics for each of said one or more cameras configured to produce images on said first display.

38. The binocular display of any of Embodiments 30-37, wherein said one or more second processing electronics comprises separate processing electronics for each of said one or more cameras configured to produce images on said second display.

39. A surgical visualization system comprising:
a stereo optical assembly comprising a stereo camera configured to provide a stereo surgical microscope view of a surgical site;
a binocular head mounted display viewing assembly configured to be worn by a user having left and right eyes, said binocular head mounted display comprising left and right display portions for displaying images viewable by said left and right eyes, respectively; and
an image processing system in communication with the stereo optical assembly and the display portions, the image processing system comprising processing electronics,
wherein the image processing system is configured to:
receive video images acquired by the stereo camera,
provide output video images based on the received video images, and
present the output video images on the display portions so that the output video images are viewable on said display portions of said head mounted display.

40. A surgical visualization system of Embodiment 39, wherein the head mounted display comprises eyewear, eyeglasses, goggles, or a mask.

41. A surgical visualization system of Embodiment 39 or 40, further comprising an orientation sensing system configured to provide orientation information regarding the orientation of the head mounted display with movement of the head mounted display, the image processing system configured to alter the output video images on the display portions based on orientation information sensed by the orientation sensing system.

42. The surgical visualization system of Embodiment 41, wherein said orientation sensing system comprises one or more of the following: one or more gyroscopes, one or more accelerometers, one or more inertial measurement units (IMUs), or a tracking system.

43. The surgical visualization system of Embodiment 42, wherein the orientation sensing system comprises one or more accelerometers, gyroscopes, inertial measurement units (IMUs) or combinations thereof.

44. The surgical visualization system of Embodiment 42, wherein the orientation sensing system comprises a tracking system.

45. The surgical visualization system of Embodiment 44, wherein the tracking system comprises fiducial markers on the head mounted display and an optical imaging system for imaging said fiducial markers.

46. The surgical visualization system of Embodiment 44, wherein the tracking system comprises a transmitter on the head mounted display and a receiver on a remote display assembly.

47. The surgical visualization system of Embodiment 44, wherein the tracking system comprises a receiver on the head mounted display and a transmitter on a remote display assembly.

48. The surgical visualization system of any of Embodiments 39-47, wherein the binocular head mounted display is opaque so as to block the view of the left and right eyes along the line of sight of the respective left and right eyes through the head mounted display.

49. The surgical visualization system of any of Embodiments 39-48, further comprising one or more cameras disposed on the head mounted display.

50. The surgical visualization system of any of Embodiments 1-48, further comprising one or more cameras having a field of view that moves with movement head mounted display.

51. The surgical visualization system of any of Embodiments 1-50, wherein the image processing system is configured to replace output video images of the surgical microscope view with output video images from one or more cameras on the head mounted display based on orientation information.

52. The surgical visualization system of any of Embodiments 1-50, wherein the image processing system is configured to replace output video images of the surgical microscope view with an unmagnified view forward the head mounted display.

53. The surgical visualization system of any of Embodiments 41-52, wherein the output video images of the surgical microscope view are presented on the display portions together with output video images from at least one camera on the head mounted display.

54. The surgical visualization system of Embodiment 53, wherein the orientation sensing system is configured to control the relative sizes of (i) the output video images of a surgical microscope view and (ii) the output video image from the at least one camera on the head mounted display that are presented on the display portions.

55. The surgical visualization system of any of Embodiments 41-47, wherein the output video images of the surgical microscope view are presented on the display portions together with an unmagnified view forward the head mounted display.

56. The surgical visualization system of Embodiment 55, wherein the orientation sensing system is configured to control the size and percentage of the output video images of a surgical microscope view with respect to the size and percentage of the view forward the head mounted display that are presented on the display portions.

57. The surgical visualization system of any of Embodiments 1-47, wherein the head mounted display is at least partially transparent along the line of sight of the respective left and right eyes such that the left and right eyes can see through the head mounted display along the line of site of the left and right eyes when the head mounted display is worn by the user.

58. The surgical visualization system of Embodiment 57, wherein the display portions comprises a transparent material configured to provide a view therethrough along the line of sight of the left and right eyes.

59. The surgical visualization system of Embodiment 57, wherein the display portions comprises at least one heads-up projection display comprising an at least partially transparent window and at least one projector configured to project an image into the left and right eyes such that a view through the window and said projected image are viewable by said left and right eyes.

60. The surgical visualization system of Embodiment 59, wherein the image processing system is configured to attenuate output video images of the surgical microscope view on the head mounted display with respect to the view through the transparent window along the line of sight of the left and right eyes.

61. The surgical visualization system of any of Embodiments 1-60, wherein the image processing system is configured to attenuate output video images of the surgical microscope view such that said output video images of the surgical microscope view are not visible while the view forward the head mounted display is visible.

62. The surgical visualization system of any of Embodiments 1-47, wherein the output video images of the surgical microscope view and a view forward the head mounted display are visible at the same time by user.

63. The surgical visualization system of Embodiment 62, wherein the orientation sensing system is configured to control the relative sizes with respect to each other of (i) the output video images of a surgical microscope view and (ii) the view forward the head mounted display.

64. The surgical visualization system of Embodiment 1, wherein the output video images of the surgical microscope view are visible together with a view along the line of sight of the left and right eyes.

65. The surgical visualization system of Embodiment 59, wherein an orientation sensing system is configured to control the size and percentage of the output video images of a surgical microscope view with respect to the size and percentage of the view through the window along the line of sight of the left and right eyes of the user of the head mounted display.

66. The surgical visualization system of Embodiment 65, wherein the orientation sensing system is configured to control the amount of transparency of the display portions.

67. The surgical visualization system of any of Embodiments 1-47, 65 or 66, wherein the display portion for the right eye comprises a display, a spatial light modulator, and a beam combiner, said beam combiner and said spatial light modulator forming a first optical path and said display and said beam combiner forming a second optical path.

68. The surgical visualization system of Embodiment 67, wherein the line of sight is directed through the beam combiner and the spatial light modulator along the first path, said spatial light modulator being configured to provide selected transmission therethrough.

69. The surgical visualization system of Embodiment 67 or 68, wherein the beam combiner and display are disposed with respect to each other and the line of sight of the right eye such that output video images displayed on the display are viewable by the right eye.

70. The surgical visualization system of any of Embodiments 67-69, wherein said spatial light modulator comprises a liquid crystal spatial light modulator configured to control the amount of light permitted to pass therethrough.

71. The surgical visualization system of any of Embodiments 67-70, wherein said display comprises a light emitting diode display or a liquid crystal display.

72. The surgical visualization system of any of Embodiments 67-71, wherein an orientation sensing system is configured to control the amount of light passing through the spatial light modulator.

73. The surgical visualization system of any of Embodiments 1-72, further comprising a camera configured to provide a surgical tool view.

74. The surgical visualization system of Embodiment 73, further comprising a surgical tool.

75. The surgical visualization system of any of Embodiments 1-74, further comprising additional cameras configured to provide view of the surgical site.

76. A surgical visualization system comprising:
a stereo optical assembly comprising a stereo camera configured to provide a surgical tool view of a surgical site;
a binocular head mounted display viewing assembly configured to be worn by a user having left and right eyes, said binocular head mounted display comprising left and right display portions for displaying images viewable by said left and right eyes, respectively; and
an image processing system in communication with the stereo optical assembly and the display portions, the image processing system comprising processing electronics,
wherein the image processing system is configured to:
receive video images acquired by the stereo camera,
provide output video images based on the received video images, and
present the output video images on the display portions so that the output video images are viewable on said display portions of said head mounted display.

77. A surgical visualization system of Embodiment 76, wherein the head mounted display comprise eyewear, eyeglasses, goggles, or a mask.

78. A surgical visualization system of Embodiment 76 or 77, further comprising an orientation sensing system configured to provide orientation information regarding the orientation of the head mounted display with movement of the head mounted display, the image processing system configured to alter the output video images on the display portions based on orientation information sensed by the orientation sensing system.

79. The surgical visualization system of Embodiment 78, wherein said orientation sensing system comprises one or more of the following: one or more gyroscopes, one or more accelerometers, one or more inertial measurement units (IMUs), or a tracking system.

80. The surgical visualization system of Embodiment 79, wherein the orientation sensing system comprises one or more accelerometers, gyroscopes, inertial measurement units (IMUs) or combinations thereof.

81. The surgical visualization system of Embodiment 79, wherein the orientation sensing system comprises a tracking system.

82. The surgical visualization system of Embodiment 81, wherein the tracking system comprises fiducial markers on the head mounted display and an optical imaging system for imaging said fiducial markers.

83. The surgical visualization system of Embodiment 81, wherein the tracking system comprises a transmitter on the head mounted display and a receiver on a remote display assembly.

84. The surgical visualization system of Embodiment 81, wherein the tracking system comprises a receiver on the head mounted display and a transmitter on a remote display assembly.

85. The surgical visualization system of any of Embodiments 76-84, wherein the binocular head mounted display is opaque so as to block the view of the left and right eyes along the line of sight of the respective left and right eyes through the head mounted display.

86. The surgical visualization system of any of Embodiments 76-84, further comprising one or more cameras disposed on the head mounted display.

87. The surgical visualization system of any of Embodiments 76-86, further comprising one or more cameras having a field of view that moves with movement head mounted display.

88. The surgical visualization system of any of Embodiments 76-87, wherein the image processing system is configured to replace output video images of the surgical tool view with output video images from one or more cameras on the head mounted display based on orientation information.

89. The surgical visualization system of any of Embodiments 76-87, wherein the image processing system is configured to replace output video images of the surgical tool view with an unmagnified view forward the head mounted display.

90. The surgical visualization system of any of Embodiments 78-87, wherein the output video images of the surgical tool view are presented on the display portions together with output video images from at least one camera on the head mounted display.

91. The surgical visualization system of Embodiment 90, wherein the orientation sensing system is configured to control the relative sizes of (i) the output video images of a surgical tool view and (ii) the output video image from the at least one camera on the head mounted display that are presented on the display portions.

92. The surgical visualization system of any of Embodiments 78-84, wherein the output video images of the surgical tool view are presented on the display portions together with an unmagnified view forward the head mounted display.

93. The surgical visualization system of Embodiment 92, wherein the orientation sensing system is configured to control the size and percentage of the output video images of a surgical tool view with respect to the size and percentage of the view forward the head mounted display that are presented on the display portions.

94. The surgical visualization system of any of Embodiments 76-84, wherein the head mounted display is at least partially transparent along the line of sight of the respective left and right eyes such that the left and right eyes can see through the head mounted display along the line of site of the left and right eyes when the head mounted display is worn by the user.

95. The surgical visualization system of Embodiment 94, wherein the display portions comprises a transparent material configured to provide a view therethrough along the line of sight of the left and right eyes.

96. The surgical visualization system of Embodiment 94, wherein the display portions comprises at least one heads-up projection display comprising an at least partially transparent window and at least one projector configured to project an image into the left and right eyes such that a view through the window and said projected image are viewable by said left and right eyes.

97. The surgical visualization system of Embodiment 96, wherein the image processing system is configured to attenuate output video images of the surgical tool view on the head mounted display with respect to the view through the transparent window along the line of sight of the left and right eyes.

98. The surgical visualization system of any of Embodiments 35-97, wherein the image processing system is configured to attenuate output video images of the surgical tool view such that said output video images of the surgical tool view are not visible while the view forward the head mounted display is visible.

99. The surgical visualization system of any of Embodiments 76-84, wherein the output video images of the surgical tool view and a view forward the head mounted display are visible at the same time by user.

100. The surgical visualization system of Embodiment 99, wherein the orientation sensing system is configured to control the relative sizes with respect to each other of (i) the output video images of a surgical tool view and (ii) the view forward the head mounted display.

101. The surgical visualization system of Embodiment 76, wherein the output video images of the surgical tool view are visible together a view along the line of sight of the left and right eyes.

102. The surgical visualization system of Embodiment 96, wherein an orientation sensing system is configured to control the size and percentage of the output video images of a surgical tool view with respect to the size and percentage of the view through the window along the line of sight of the left and right eyes of the user of the head mounted display.

103. The surgical visualization system of Embodiment 102, wherein the orientation sensing system is configured to control the amount of transparency of the display portions.

104. The surgical visualization system of any of Embodiments 76-84, 102 or 103, wherein the display portion for the right eye comprises a display, a spatial light modulator, and a beam combiner, said beam combiner and said spatial light modulator forming a first optical path and said display and said beam combiner forming a second optical path.

105. The surgical visualization system of Embodiment 104, wherein the line of sight is directed through the beam combiner and the spatial light modulator along the first path, said spatial light modulator being configured to provide selected transmission therethrough.

106. The surgical visualization system of Embodiment 104 or 105, wherein the beam combiner and display are disposed with respect to each other and the line of sight of the right eye such that output video images displayed on the display are viewable by the right eye.

107. The surgical visualization system of any of Embodiments 104-106, wherein said spatial light modulator comprises a liquid crystal spatial light modulator configured to control the amount of light permitted to pass therethrough.

108. The surgical visualization system of any of Embodiments 104-107, wherein said display comprises a light emitting diode display or a liquid crystal display.

109. The surgical visualization system of any of Embodiments 104-108, wherein an orientation sensing system is configured to control the amount of light passing through the spatial light modulator.

110. The surgical visualization system of any of Embodiments 76-109, further comprising a surgical tool.

111. The medical apparatus of any of Embodiments 1-29, wherein said first display portion, second display portion, and first beam combiner are included in an assistant display.

112. The medical apparatus of Embodiment 111, further comprising a primary surgeon display.

113. The medical apparatus of any of Embodiments 30-38, wherein said left-eye and right eye view channels are included in an assistant display.

114. The medical apparatus of Embodiment 113, further comprising a primary surgeon display.

115. The surgical visualization system of any of Embodiments 39-110, wherein said binocular head mounted display viewing assembly comprises an assistant display.

116. The surgical visualization system of Embodiment 115, further comprising a primary surgeon display.

117. The surgical visualization system of Embodiment 116, wherein the primary surgeon display comprises a binocular display unit comprising at least one display disposed in a housing and a pair of oculars.

118. The surgical visualization system of Embodiment 116, wherein the primary surgeon display does not comprise a head mounted display.

119. The surgical visualization system of any of Embodiments 46, 47, 83, or 84, wherein the remote display assembly comprises a binocular display unit comprising at least one display disposed in a housing and a pair of oculars.

120. The surgical visualization system of Embodiment 119, wherein the at least one display of the binocular display unit is configured to provide a 3D view.

121. A medical apparatus comprising:
a display housing;
an opening in the display housing;
an electronic display disposed within the display housing, the electronic display comprising a plurality of pixels configured to produce a two-dimensional image; and
a display optical system disposed within the display housing, the display optical system comprising a plurality of lens elements disposed along an optical path, wherein the display optical system is configured to:
receive the two-dimensional image from the electronic display;
produce a beam with a cross-section that remains substantially constant along the optical path; and
produce a collimated beam exiting the opening in the display housing.

122. The medical apparatus of Embodiment 121, wherein the display optical system further comprises an optical redirection element configured to fold the optical path.

123. The medical apparatus of Embodiment 122, wherein the optical redirection element comprises a mirror.

124. The medical apparatus of Embodiment 122, wherein the optical redirection element comprises a prism.

125. The medical apparatus of Embodiment 122, wherein the display optical system is configured to direct light received from the electronic display to the opening in the display housing while reducing stray light.

126. The medical apparatus of Embodiment 121, wherein the display optical system further comprises a baffle configured to reduce stray light.

127. The medical apparatus of Embodiment 126, wherein the display optical system comprises less than or equal to four baffles.

128. The medical apparatus of Embodiment 127, wherein the display optical system comprises less than or equal to four mirrors.

129. The medical apparatus of Embodiment 128, wherein a first baffle is positioned between the electronic display and a first baffle along the optical path, the first mirror positioned prior to the plurality of lens elements along the optical path from the display to the opening.

130. The medical apparatus of Embodiment 129, wherein at least three baffles are positioned prior to the plurality of lens elements along the optical path from the display to the opening.

131. The medical apparatus of Embodiment 129, wherein at least two mirrors are positioned prior to the plurality of lens elements along the optical path from the display to the opening.

132. The medical apparatus of Embodiment 121, wherein the display optical system has an exit pupil and the electronic display is not parallel to the exit pupil.

133. The medical apparatus of Embodiment 121, wherein the opening in the display housing comprises a mounting interface configured to mate with a binocular assembly for a surgical microscope.

134. The medical apparatus of Embodiment 133, wherein an exit pupil of the display optical system is of a same size or smaller than an entrance pupil of oculars in the binocular assembly.

135. The medical apparatus of Embodiment 121, further comprising a second electronic display and a second display optical system configured to provide a stereo view.

136. The medical apparatus of Embodiment 121, further comprising processing electronics configured to communicate with the electronic display to provide images for the electronic display.

137. The medical apparatus of Embodiment 136, wherein the processing electronics are configured to receive images from one or more cameras on a surgical device.

138. The medical apparatus of Embodiment 136, wherein the processing electronics are configured to receive images from one or more cameras that provide a surgical microscope view.

139. The medical apparatus of Embodiment 121, wherein the optical path is less than or equal to 16.2 inches and a light-emitting portion of the electronic display has a diagonal measurement that is greater than or equal to 5 inches.

140. The medical apparatus of Embodiment 121, wherein the optical path is less than or equal to 18.7 inches and a light-emitting portion of the electronic display has a diagonal measurement that is greater than or equal to 8 inches.

141. The medical apparatus of Embodiment 121, wherein the display optical system further comprises a converging mirror.

142. The medical apparatus of Embodiment 121, further comprising a viewing assembly comprising an objective lens, beam positioning optics, and an ocular, the viewing assembly configured to receive the collimated beam exiting the opening in the display housing.

143. The medical apparatus of Embodiment 121, wherein the electronic display has a diagonal light-emitting portion between 4 inches and 9 inches.

144. The medical apparatus of Embodiment 121, wherein an optical path length from the electronic display to a last element of the display optical system is at least 9 inches.

145. The medical apparatus of Embodiment 144, wherein the optical path length from the electronic display to the last element of the display optical system is less than 20 inches.

146. A medical apparatus comprising:
a viewing assembly comprising a housing and an ocular, the ocular configured to provide a view an electronic display disposed in the housing;

an optical assembly disposed on the viewing assembly, the optical assembly configured to provide a surgical microscope view of a surgical site, the optical assembly comprising:
an auxiliary video camera; and
a gimbal configured to couple the auxiliary video camera to the viewing assembly and configured to change an orientation of the auxiliary video camera relative to the viewing assembly; and
an image processing system in communication with the optical assembly and the electronic display, the image processing system comprising at least one physical processor,
wherein the image processing system is configured to:
receive video images acquired by the auxiliary video camera,
provide output video images based on the received video images, and
present the output video images on the electronic display so that the output video images are viewable through the ocular,
wherein the gimbal is configured to adjust a pitch of the auxiliary video camera between a first position and a second position, wherein the auxiliary video camera has a first viewing angle perpendicular to a floor in the first position and a second viewing angle that is within about 10 degrees of parallel to the floor in the second position.

147. The medical apparatus of Embodiment 146, wherein the gimbal comprises two pivots.

148. The medical apparatus of Embodiment 147, wherein a first pivot is configured to adjust a pitch of the auxiliary video camera and a second pivot is configured to rotate the auxiliary video camera around an axis perpendicular to the floor.

149. The medical apparatus of Embodiment 146, wherein the gimbal is configured to adjust a pitch of the auxiliary video camera between the first position and a third position, wherein the auxiliary video camera has a third viewing angle in the third position that is less than or equal to 180 degrees from the first viewing angle.

150. The medical apparatus of Embodiment 146, wherein the gimbal is electronically controlled.

151. The medical apparatus of Embodiment 146, wherein the optical assembly is configured to provide an oblique view of a portion of a patient.

152. The medical apparatus of Embodiment 151, wherein an orientation of the ocular of the viewing assembly is configured to remain stationary when an orientation of the auxiliary video camera changes to provide the oblique view of the portion of the patient.

153. The medical apparatus of Embodiment 146, wherein the gimbal is configured to smoothly adjust the viewing angle of the auxiliary video camera between the first position and the second position.

154. The medical apparatus of Embodiment 146, wherein the auxiliary video camera comprises a stereo video camera and the ocular comprises a pair of oculars.

155. The medical apparatus of Embodiment 146, further comprising a camera arm attached to the viewing assembly.

156. A medical apparatus comprising:
a camera having a field of view that can be configured to include a surgical site, wherein the camera is configured to provide a surgical microscope view of the surgical site;
a binocular viewing assembly comprising a housing and a plurality of oculars, the plurality of oculars configured to provide views of at least one display disposed in the housing;
an image processing system configured to receive images acquired by the camera and present the output video images on the at least one display; and
a movement control system configured to move the camera relative to the binocular viewing assembly, the movement control system comprising a control member operatively coupled to the movement control system to translate the camera relative to the binocular viewing assembly along at least a first axis and a second axis and to rotate the camera relative to the binocular viewing assembly.

157. The medical apparatus of Embodiment 156, wherein the movement control system comprises a translation system comprising a moveable platform to which the camera is attached, the moveable platform being positioned between the binocular viewing assembly and the camera and being moveable relative to the binocular viewing assembly along at least a first axis and a second axis.

158. The medical apparatus of Embodiment 157, wherein the translation system further comprises an electromechanical device operatively coupled to the moveable platform.

159. The medical apparatus of Embodiment 156, wherein the movement control system comprises a pitch-yaw adjustment system comprising an electromechanical device to which the camera is attached, the pitch-yaw adjustment system configured to rotate the camera relative to the binocular viewing assembly around an axis parallel to the first axis and rotate the camera around an axis parallel to the second axis.

160. The medical apparatus of Embodiment 156, wherein the control member is operatively coupled to the movement control system via sensors configured to detect movement of the control member, the sensors in communication with one or more components of the movement control system.

161. The medical apparatus of Embodiment 156, wherein the control member is operatively coupled to the movement control system via a gimbal having one or more sensors configured to detect movement of the control member, the sensors in communication with one or more components of the movement control system.

162. The medical apparatus of Embodiment 156, wherein the movement control system is attached to the binocular viewing assembly.

163. The medical apparatus of Embodiment 156, wherein the movement control system is attached to an articulated arm.

164. The medical apparatus of Embodiment 156, wherein the camera is attached to the movement control system via an arm.

165. The medical apparatus of Embodiments 156, wherein the medical apparatus comprises a control system for controlling one or more electromechanical devices operatively coupled to the movement control system.

166. The medical apparatus of Embodiment 165, wherein the control system includes one or more pre-set positions for the movement control system.

167. A medical apparatus comprising:
a display housing; and
a plurality of electronic displays disposed within the display housing, each of the plurality of electronic displays comprising a plurality of pixels configured to produce a two-dimensional image, wherein the plurality of electronic displays are configured to present superimposed images in a field of view of a person's eye.

168. The medical apparatus of Embodiment 167, further comprising a binocular viewing assembly coupled to the display housing.

169. The medical apparatus of Embodiment 167, wherein at least one of the plurality of electronic displays comprises a transmissive display panel.

170. The medical apparatus of Embodiment 167, wherein the superimposed images comprise a video of a first portion of a surgery site that is superimposed on a video of a second portion of the surgery site, the first portion contained within the second portion.

171. The medical apparatus of Embodiment 170, wherein the video of the first portion is magnified relative to the video of the second portion.

172. A medical apparatus comprising:
a display housing;
an opening in the display housing;
at least one electronic display disposed within the display housing, the at least one electronic display comprising a plurality of pixels configured to produce a two-dimensional image; and
a display optical system disposed within the display housing, the display optical system comprising a left eye path and a right eye path to the at least one electronic display, wherein the display optical system includes a baffle to optically separate the left eye path and the right eye path.

173. A medical apparatus comprising:
a camera having a field of view that can be configured to include a surgical site, wherein the camera is configured to provide a surgical microscope view of the surgical site;
a viewing assembly comprising a housing and at least one display disposed in the housing;
an image processing system configured to receive images acquired by the camera and at least one other camera and present the output video images on the at least one display,
wherein the image processing system is configured to provide views of one or more received images or to provide views of received images from a selected source; and
wherein potential sources of video images include the camera providing the surgical microscope view, one or more proximal cameras mounted on a frame mounted near or adjacent to the surgical site, a camera on an endoscope, or a video coupler camera configured to acquire images from an external imager.

174. A medical apparatus comprising:
a camera having a field of view that can be configured to include a surgical site, wherein the camera is configured to provide a surgical microscope view of the surgical site;
a video coupler comprising an optical system and a camera, the optical system configured to form an entrance pupil and to form an image of light received at the entrance pupil on the camera;
a viewing assembly comprising a housing and at least one display disposed in the housing; and
an image processing system configured to receive images acquired by the camera and the video coupler camera and to present the output video images on the at least one display,
wherein the image processing system is configured to provide views of one or more received images or to provide views of received images from a selected source, and
wherein the video coupler is configured to receive images from an endoscope.

175. A medical apparatus comprising:
a camera having a field of view that can be configured to include a surgical site, wherein the camera is configured to provide a surgical microscope view of the surgical site;
an endoscope comprising an endoscope camera;
one or more proximal cameras mounted on a frame near or adjacent to the surgical site;
a viewing assembly comprising a housing and at least one display disposed in the housing; and
an image processing system configured to receive images acquired by the camera providing the surgical microscope view, the endoscope camera, and the one or more proximal cameras and to present output video images on the at least one display based on the received images.

176. A medical apparatus comprising:
a frame configured to be disposed above a surgical site of a patient, said frame configured to be mounted to a bed or to said patient and anchored outside said surgical site of said patient;
one or more cameras mounted to said frame, said one or more cameras configured to image said surgical site;
a surgical microscope camera configured to provide a surgical microscope view of said surgical site, said surgical microscope camera not coupled to a direct view surgical microscope;
a viewing assembly comprising a housing and separate left and right eye portals for left and right eyes of a viewer, said left and right eye portals configured to provide views of at least one display disposed in said housing; and
an image processing system in communication with said one or more cameras, said surgical microscope camera, and said at least one display, said image processing system comprising processing electronics,
wherein said image processing system is configured to:
receive images acquired by said one or more cameras and said surgical microscope camera, and
present output images based on said received images on said at least one display so that said output images are viewable through said separate left and right eye portals.

177. The medical apparatus of Embodiment 176, wherein said one or more cameras comprise first and second cameras configured to move relative to said surgical site and to maintain a same horizontal orientation with respect to each other.

178. The medical apparatus of Embodiment 176 or 177, further comprising one or more gimbals connecting said one or more cameras to said frame, said one or more gimbals configured to move said one or more cameras relative to said frame.

179. The medical apparatus of any of Embodiments 176-178, wherein said one or more cameras are configured to move electronically.

180. The medical apparatus of any of Embodiments 176-179, wherein said one or more cameras are configured to move with respect to an x direction, a y direction, or a z direction.

181. The medical apparatus of any of Embodiments 176-180, wherein said one or more cameras are configured to move with respect to a pitch or yaw.

182. The medical apparatus of any of Embodiments 176-181, wherein said one or more cameras are configured to move with respect to a pitch and/or yaw, and without roll.

183. The medical apparatus of any of Embodiments 176-182, wherein said one or more cameras comprise cameras to provide a left-eye view and a right-eye view.

184. The medical apparatus of Embodiment 183, wherein said cameras are configured to provide stereo imaging.

185. The medical apparatus of any of Embodiments 176-184, wherein said one or more cameras comprise four cameras mounted to said frame at 3 o'clock, 6 o'clock, 9 o'clock, and 12 o'clock positions.

186. The medical apparatus of any of Embodiments 176-185, wherein said frame has a cross-sectional shape comprising a circle, a square, or an L-shape.

187. The medical apparatus of any of Embodiments 176-186, wherein said frame is configured to be disposed 10 to 50 mm above said surgical site.

188. The medical apparatus of any of Embodiments 176-187, wherein said frame is configured to be disposed 10 to 50 mm above said patient.

189. The medical apparatus of any of Embodiments 176-186, wherein said frame is configured to be disposed 50 to 150 mm above said surgical site.

190. The medical apparatus of any of Embodiments 176-186, wherein said frame is configured to be disposed 50 to 150 mm above said patient.

191. The medical apparatus of any of Embodiments 176-186, wherein said frame is configured to be disposed 100 to 200 mm above said surgical site.

192. The medical apparatus of any of Embodiments 176-186, wherein said frame is configured to be disposed 100 to 200 mm above said patient.

193. The medical apparatus of any of Embodiments 176-192, wherein said frame is configured to provide a stereotactic planning system.

194. The medical apparatus of any of Embodiments 176-193, wherein said frame is configured to be mounted to a gurney.

195. The medical apparatus of any of Embodiments 176-194, wherein said frame is configured to be mounted to a bed rail.

196. The medical apparatus of any of Embodiments 176-195, wherein said frame is configured to be mounted to said bed or to said patient via a Mayfield clamp.

197. The medical apparatus of any of Embodiments 176-196, wherein said separate left and right eye portals comprise a plurality of oculars.

198. The medical apparatus of any of Embodiments 176-197, wherein at least one of said one or more cameras comprise a stereo camera and said separate left and right eye portals provide a stereo view providing 3D visualization.

199. The medical apparatus of any embodiment having a surgical microscope image acquisition system, further comprising a fiber optic illumination zoom functioning through a common objective, wherein the fiber optic illumination has a gimbal mechanism so that the illumination may be steered within the surgical opening, or on the patient.

200. The medical apparatus of any of Embodiments 173-176 wherein the image processing system comprises independent processing systems, processors, or controllers for individual cameras in the medical apparatus.

201. The medical apparatus of any of Embodiments 176-198, wherein said image processing system comprises separate electronics for each of said one or more cameras.

202. The medical apparatus of any of Embodiments 176-198 or 201, wherein said at least one display comprises:
a first display configured to display a first image from a first camera of said one or more cameras; and
a second display configured to display a second image from said surgical microscope camera, wherein said medical apparatus further comprises a beam combiner configured to receive said first and said second images from said first and second displays and to combine said first and second images for viewing.

CONCLUSION

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A medical apparatus comprising:
a camera having a field of view that can be configured to include a surgical site, wherein the camera is configured to provide a surgical microscope view of the surgical site;
a display housing comprising an eye portal;
an electronic display disposed within the display housing, the electronic display comprising a plurality of pixels configured to produce a two-dimensional image, an optical path extending from said electronic display to said eye portal;
a display optical system disposed within the display housing, the display optical system comprising a plurality of optical elements disposed along said optical path from said electronic display to said eye portal configured to direct images from the electronic display to the eye portal; and
an image processing system configured to receive images acquired by the camera providing the surgical microscope view and to present output video images on the electronic display based on the received images,
wherein the plurality of optical elements comprises a redirection element configured to redirect the optical path from said electronic display to said eye portal such that at least 40% and less than or equal to 95% of the total length of the optical path from said electronic display to said eye portal in the display housing is above the eye portal when the display housing is oriented such that the portion of the optical path through the eye portal is horizontal, and wherein the electronic display disposed within the display housing is decoupled from movement of the camera.

2. The medical apparatus of claim 1, wherein the display housing has a depth to height ratio that is from 0.4 and less than 1.

3. The medical apparatus of claim 2, wherein the display housing has a depth to height ratio that is from 0.4 and less than 0.7.

4. The medical apparatus of claim 1, wherein a distance from the eye portal to the electronic display along a direction parallel to the optical path at the eye portal is less than or equal to the distance from the eye portal to the electronic display along a direction orthogonal to the optical path at the eye portal.

5. The medical apparatus of claim 4, wherein a distance from the eye portal to the electronic display along a direction parallel to the optical path at the eye portal is less than or equal to 70% of the distance from the eye portal to the electronic display along a direction orthogonal to the optical path at the eye portal.

6. The medical apparatus of claim 1, wherein the electronic display is positioned above the eye portal when the eye portal is positioned such that the portion of the optical path of the eye portal is horizontal.

7. The medical apparatus of claim 1, wherein at least 50% and less than or equal to 95% of the plurality of optical elements of the display optical system are positioned above the eye portal when the eye portal is positioned such that the portion of the optical path of the eye portal is horizontal.

8. A medical apparatus comprising:
a camera having a field of view that can be configured to include a surgical site, wherein the camera is configured to provide a surgical microscope view of the surgical site;
a display housing comprising an eye portal;
an electronic display disposed within the display housing, the electronic display comprising a plurality of pixels configured to produce a two-dimensional image, an optical path extending from said electronic display to said eye portal;
a display optical system disposed within the display housing, the display optical system comprising a plurality of optical elements disposed along said optical path configured to direct images from the electronic display to the eye portal; and
an image processing system configured to receive images acquired by the camera providing the surgical microscope view and to present output video images on the electronic display based on the received images,
wherein the display housing has a height that is larger than its depth, and
wherein the electronic display disposed within the display housing is decoupled from movement of the camera.

9. The medical apparatus of claim 8, wherein the optical path is longer along the height of the display housing than along the depth of the display housing.

10. The medical apparatus of claim 8, wherein at least 50% and less than or equal to 95% of the volume of the display housing is above an axis through the optical path at the eye portal.

11. The medical apparatus of claim 8, wherein at least 50% and less than or equal to 95% of the optical path lies above an axis through the optical path at the eye portal.

12. The medical apparatus of claim 8, wherein the height of the display housing is at least 25% longer than its depth.

13. The medical apparatus of claim 8, wherein at least 50% and less than or equal to 95% of the optical components lies above an axis through the optical path at the eye portal.

14. The medical apparatus of claim 8, wherein the electronic display lies above a plane defined by an axis through the optical path at the eye portal.

15. The medical apparatus of claim 8, wherein the optical path does not travel downward between the eye portal and the electronic display.

16. The medical apparatus of claim 8, wherein the optical path does not travel downward prior to being redirected upward by a redirection element toward the electronic display.

17. A medical apparatus comprising:
a camera having a field of view that can be configured to include a surgical site, wherein the camera is configured to provide a surgical microscope view of the surgical site;
a display housing comprising an ocular;
an electronic display disposed within the display housing, the electronic display comprising a plurality of pixels configured to produce a two-dimensional image, an optical path extending from said electronic display to said ocular;
a display optical system disposed within the display housing, the display optical system comprising a plurality of optical elements disposed along said optical path configured to direct images from the electronic display to the ocular; and
an image processing system configured to receive images acquired by the camera providing the surgical microscope view and to present output video images on the electronic display based on the received images,
wherein the plurality of optical elements comprises a redirection element configured to redirect the optical path such that at least 40% and less than or equal to 95% of the total length of the optical path from said electronic display to said ocular in the display housing is above the ocular when the ocular is positioned such that the portion of the optical path of the ocular is horizontal, and
wherein the electronic display disposed within the display housing is decoupled from movement of the camera.

18. The medical apparatus of claim 1, wherein at least 50% of the total length of the optical path is above the eye portal when the display housing is oriented such that the portion of the optical path through the eye portal is horizontal.

19. The medical apparatus of claim 1, wherein at least 70% of the total length of the optical path is above the eye portal when the display housing is oriented such that the portion of the optical path through the eye portal is horizontal.

20. The medical apparatus of claim 1, wherein at least 90% of the total length of the optical path is above the eye portal when the display housing is oriented such that the portion of the optical path through the eye portal is horizontal.

21. The medical apparatus of claim 1, wherein the eye portal comprises a right eye portal.

22. The medical apparatus of claim 21, further comprising a left eye portal.

23. The medical apparatus of claim 1, wherein the eye portal comprises an ocular.

24. The medical apparatus of claim 17, wherein the ocular comprises a right ocular.

25. The medical apparatus of claim 24, further comprising a left ocular.

26. The medical apparatus of claim 1, wherein the camera is not coupled to a direct view surgical microscope.

27. The medical apparatus of claim 8, wherein the camera is not coupled to a direct view surgical microscope.

28. The medical apparatus of claim 17, wherein the camera is not coupled to a direct view surgical microscope.

29. The medical apparatus of claim 1, wherein the electronic display disposed within the display housing comprises a liquid crystal or light emitting diode display.

30. The medical apparatus of claim 8, wherein the electronic display disposed within the display housing comprises a liquid crystal or light emitting diode display.

31. The medical apparatus of claim 17, wherein the electronic display disposed within the display housing comprises a liquid crystal or light emitting diode display.

\* \* \* \* \*